US007452678B2

(12) United States Patent
Durham et al.

(10) Patent No.: US 7,452,678 B2
(45) Date of Patent: Nov. 18, 2008

(54) IDENTIFICATION OF BIOMARKERS FOR LIVER TOXICITY

(75) Inventors: Stephen K. Durham, Manlius, NY (US); Donna Dambach, Wyncote, PA (US); Stanley Hefta, Pennington, NJ (US); Frederic Moulin, Newtown, PA (US); Ji Gao, Cranbury, NJ (US); Gregory Opiteck, Lawrenceville, NJ (US); Stephen M. Storm, Richboro, PA (US); Leah Ann Garulacan, King of Prussia, PA (US); Jun-Hsiang Lin, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 456 days.

(21) Appl. No.: 10/873,595

(22) Filed: Jun. 22, 2004

(65) Prior Publication Data

US 2004/0265889 A1 Dec. 30, 2004

Related U.S. Application Data

(60) Provisional application No. 60/480,964, filed on Jun. 24, 2003, provisional application No. 60/529,806, filed on Dec. 16, 2003.

(51) Int. Cl.
*G01N 33/53* (2006.01)

(52) U.S. Cl. ........................ 435/7.1; 435/7.2; 435/7.91; 435/7.92

(58) Field of Classification Search .................. 455/7.1, 455/7.2, 7.91, 7.92
See application file for complete search history.

(56) References Cited

U.S. PATENT DOCUMENTS

| | | | | |
|---|---|---|---|---|
| 5,279,957 | A | 1/1994 | Gross | |
| 5,817,475 | A * | 10/1998 | Gibbs et al. | 435/29 |
| 6,083,763 | A * | 7/2000 | Balch | 436/518 |
| 6,215,894 | B1 | 4/2001 | Zeleny et al. | |
| 2003/0113708 | A1 | 6/2003 | Flint et al. | |
| 2004/0101874 | A1* | 5/2004 | Ghosh et al. | 435/6 |

FOREIGN PATENT DOCUMENTS

WO WO2004030615 A2 4/2004

OTHER PUBLICATIONS

Adamus, et al., "Anti-Enolase-α Autoantibodies in Cancer-Associated Retinopathy: Epitope Mapping and Cytotoxicity on Retinal Cells", J. Autoimmunity, vol. 11, pp. 671-677 (1998).

Al-Mulla, et al., "Raf Kinase Inhibitor Protein Expression in a Survival Analysis of Colorectal Cancer Patients", J. Clin. Oncol., vol. 24, pp. 5672-5679 (2006).

Andrews, et al., "Exon Skipping in Purine Nucleoside Phosphorylase mRNA Processing Leading to Serve Immunodeficiency", J. Biol. Chem., vol. 267(11), pp. 7834-7838 (1992).

Aust, et al., "Molecular Analysis of Mutations in a Patient with Purine Nucleoside Phosphorylase Deficiency", Am. J. Hum. Genet., vol. 51, pp. 763-772 (1992).

Babia, et al., "Modulation of carcinoembryonic artigen release by glucosylceramide Implications for HT29 cell differentiation", Eur. J. Biochem., vol. 258, pp. 233-242 (1998).

Barnidge, et al., "Extraction Method for Analysis of Detergent-Solubilized Bacetiorhodopsin and Hydrophobic Peptides by Electrospray Ionization Mass Spectrometry", Anal. Biochem., vol. 269, pp. 1-9 (1999).

Bernhagen, et al., "Regulation of the immune response by macrophage migration inhibitory factor: biological and structural features", J. Mol. Med., vol. 76, pp. 151-161 (1998).

Bernhage, et al., "MIF is a pituitary-derived cytokine that potentiates lethal endotoxaemia", Nature, vol. 365, pp. 756-759 (1993).

Borgers, et al., Purine Nucleoside Phosphorylase in Chronic Lymphocytic Leukemia (CLL), Blood, vol. 52(5), pp. 886-895 (1978).

Bourdi, et al., "Macrophage migration inhibitory factor in drug-induced liver injury: a role in susceptibility and stree responsiveness", Biochem. Biophys. Res. Comm., vol. 294, pp. 225-230 (2002).

Brock, et al., "Co-localization of Leukotrience $A_4$ Hydrolase with 5-Lipoxygenase in Nuclei of Alveolar Maceophages and Rat Basophilic Leukemia Cells but Not Neutrophils", J. Biol. Chem., vol. 276(37), pp. 35071-35077 (2001).

Calandra, et al., "Macrophage Migration Inhibitory Factor (MIF): A Glucocorticoid County-Regulator within the Immune System", Critical Rev. Immunolgy, vol. 17, pp. 77-88 (1997).

Canduri, et al., "Structures of human purine nucleoside phosphorylase complexed with inosine and ddl", Biochem. Biophys. Res. Comm., vol. 313, pp. 907-914 (2004).

Canduri, et al., "Crystal structure of human PNP complexed with hypoxanthine and sulfate ion", Biochem. Biophys. Comm., vol. 326, pp. 335-338 (2005).

Chapman, John R., "Mass Spectrometry of Poteins and Peptides", Methods in Molecular Biology, Humana Press, Totowa, New Jersey, vol. 146 (2000), Table of Contents.

Chaudhri, et al., "Mammalian and yeast 14-3-3 isoforms form patterns of dimmers in vivo", Biochem. Biophys. Res. Comm., vol. 300, pp. 679-685 (2003).

(Continued)

*Primary Examiner*—Long V. Le
*Assistant Examiner*—Jacob Cheu
(74) *Attorney, Agent, or Firm*—Stephen C. D'Amico

(57) ABSTRACT

The present invention relates to biomarker polypeptides, polynucleotides, and antibodies that have utility in predicting in vitro and/or in vivo hepatotoxicity of various drugs, compounds, or other therapeutic agents (i.e., test substances). Also related are screens, kits, microarrays, and cell culture systems that employ the polypeptides, polynucleotides, and/or antibodies of the invention. The reagents and methods of the invention are useful for predicting hepatotoxic effects resulting from treatment with one or more test substances, and can be utilized before, after, or concurrently with pre-clinical, clinical, and/or post-clinical testing. In this way, the reagents and methods of the invention can be used to identify test substances or combinations of test substances that cause hepatic injury, including idiosyncratic hepatotoxicity, and thereby prevent medical complications (e.g., liver failure) resulting from such injury.

6 Claims, 29 Drawing Sheets

OTHER PUBLICATIONS

Chen, et al., "Mammalian Polynucleotide Phosphorylase Is an Intermembrane Space RNase That Maintains Mitochondrial Homeostasis", Molec. Cell. Biol., pp. 8475-8487 (2006).
Chen, et al., "Identification and characterization of PEBP as a calpain substrate", J. Neurochem., vol. 99, pp. 1133-1141 (2006).
Corbit, et al., "Activation of Raf-1 Signaling by Protein Kinase C through a Mechanism Involving Raf Kinase Inhibitory Protein", J. Biol. Chem., vol. 278(15), pp. 13061-13068 (2003).
Crouch, et al., "The use of ATP bioluminescence as a measure of cell proliferatin and cytotoxicity", J. Immunol. Methods, vol. 160, pp. 81-88 (1993).
Donnelly, et al., "Macrophage migration inhibitory factor: a regulator of glucocorticoid activity with a critical role in inflammatory disease", Molec. Med. Today (Reviews), vol. 3, pp. 502-507 (1997).
Eddes, et al., "Chomper: A bioinformatics tool for rapid validation of tandem mass spectrometry search results associated with high-throughput proteomic strategies", Proteomics, vol. 2, pp. 1097-1103 (2002).
Eng, et al., "An Approach to Correlate Tandem Mass Spectral Data of Peptides with Amino Acid Sequences in a Protein Database", J. Am Soc. Mass Spectrum, vol. 5, pp. 976-989 (1994).
Evans, et al., "Pharmacogenomics: Translating Functional Genomics into Ratinal Therapeutics", Science, vol. 286, pp. 487-491 (1999).
Fabre, et al., "Human hepatocytes as a key in vitro model to improve preclinical drug development", Eur. J. Drug Metabolism Pharmacokinetics, vol. 15(2), pp. 165-171 (1990).
Fach, et al., "In Vitro Biomarker Discovery for Atherosclerosis by Proteomics", Mol. Cell Proteomics, vol. 3, pp. 1200-1210 (2004).
Feo, S. et al. ENO1 gene product binds to the c-*myc* promoter and acts as a transcriptional repressor: relationship with Myc promoter-binding protein 1(MBP-1), FEBS Letters, vol. 473, pp. 47-52 (2000).
Frank, R et al., "Clinical Biomarkers in Drug Discovery and Development", Nature, vol. 2, pp. 566-580 (2003).
Fretland, A. et al., "Epoxide hydrolases: biochemistry and molecular biology", Chemico-Biology Interactions, vol. 129, pp. 41-59 (2000).
Funk, C. et al., "Molecular cloning and amino acid sequence of leukotriene $A_4$ hydrolase", PNAS, vol. 84, pp. 6677-6681 (1987).
Gao, J. et al., "Changes in the Protein Expression of Yeast as a Function of Carbon Source", J. of Proteome Research, vol. 2, pp. 643-649 (2003).
Gao, J. et al., "Identification of in vitro protein biomarkers of idiosyncratic liver toxicity", Toxicology in Vitro, vol. 18, pp. 533-541 (2004).
Gatlin, C. et al., "Automated Identification of Amino Acid Sequence Variations in Proteins by HPLC/Microspray Tandem Mass Spectrometry", Anal. Chem., vol. 72, pp. 757-763 (2000).
Gerhard, D. et al., The Status, Quality, and Expansion of the NIH Full-Length cDNDA Project: The Mammalian Gene Collection (MGC), Genome Research, vol. 14, pp. 2121-2127 (2004).
Ghosh, A. et al., "A Novel 16-Kilodalton Cellular Protein Physically interacts with and Antagonizes the Functional Activity of c-*myc* Promoter-binding Protein 1", Molecular and Cellular Biology, vol. 21(2), pp. 655-662 (2001).
Ghosh, A. et al., "Functional Domains of c-myc Promoter Binding Protein 1 Involved in Transcriptional Repression and Cell Growth Regulation", Molecular & Cell. Biology, vol. 19(4), pp. 2880-2886 (1999).
Giallongo, A. et al., "Structure of the human gene for α-enolase", Eur. J. Biochem., vol. 190, pp. 567-573 (1990).
Giallongo, A. et al., "Molecular cloning and nucleotide sequence of a full-length cDNA for human α enolase", PNAS, vol. 83, pp. 6741-6745 (1986).
Green, A. J., "Cerebrospinal fluid brain-derived proteins in the diagnosis of Alzheimer's disease and Creutzfeldt-Jakob disease", Neuropathology and Applied Neurobiology, vol. 28, pp. 427-440 (2002).
Green, J.E. et al., "14-3-3 in the cerebrospinal fluid of patients with variant and sporadic Creutzfeldt-Jakob disease measured using capture assay able to detect low levels of 14-3-3 protein", Neuroscience Letters, vol. 324, pp. 57-60 (2002).
Gregory, S. et al., "The DNA sequence and biological annotation of human chromosome 1", Nature, vol. 441, pp. 315-321 (2006).
Grunebaum, E. et al., "Novel Mutations and Hot-Spots in Patients with Purine Nucleoside Phosphorylase Deficiency", Nucleosides, Nucleotides & Nucleic Acids, vol. 23(8&9) pp. 1411-1415 (2004).
Häne, B. et al., "The Pearson product-moment correlation coefficient is better suited for identification of DNA fingerprint profiles than band matching algorithms", Electrophoresis, vol. 14, pp. 967-972 (1993).
Helgadottir, A, et al., "A variant of the gene encoding leukotriene A4 hydrolase confers ethnicity-specific risk of myocardial infarction", Nature Genetics, vol. 38(1), pp. 68-74 (2006).
Hori, N. et al., "A human cDNA sequence homologue of bovine phosphatidylethanolamine-binding protein", Gene, vol. 140, pp. 293-294 (1994).
Ji, H. et al., "A two-dimensional gel database of human colon carcinoma proteins", Electrophoresis, vol. 18, pp. 605-613 (1997).
Jonsson, J. et al., "Sequence and functional characterization of the human purine nucleoside phosphorylase promoter", Nucleic Acids Research, vol. 19(18), pp. 5015-5020 (1991).
Kim, S. C. et al., "Substrate and Functional Diversity of Lysine Acetylation Revealed by a Proteomics Survey", Molecular Cell, vol. 23, pp. 607-618 (2006).
Krauskopf, a. et al., "Cyclosporin A-induced free radical generation is not mediated by cytochrome P-450", British J. of Pharmacology, vol. 135, pp. 977-986 (2002).
Lebovitz, H., "Differentiating members of the thiazolidinedione class: a focus on safety", Diabetes Metab Res. Rev., vol. 18, pp. S23-S29 (2002).
Lee, H.C. et al., "Basic-Liver, Pancreas, and Biliary Tract", Gastroenterology, vol. 131, pp. 1208-1217 (2006).
Lin, J. et al., "The Role of Absorption, Distribution, Metabolism, Excretion and Toxicity in Drug Discovery", Current Topics in Medicinal Chemistry, vol. 3, pp. 1125-1154 (2003).
Link, A., "2-D Proteome Analysis Protocols", Methods in Molecular Biology, vol. 112, Table of Contents Dept of Molecular Biotechnology, University of Washington, Seattle, WA. (1999).
Link, A., et al., "Direct analysis of protein complexes using mass spectrometry", Nature Biotechnology, vol. 17, pp. 676-682 (1999).
Link, A., "Multidimensional peptide separations in proteomics", Trends in Biotechnology, vol. 20(12 Suppl.) pp. S8-S13 (2002).
Liu, T. et al., "Human Plasma *N*-Glycoproteome Analysis by Immunoaffinity Subtraction, Hydrazide Chemistry, and Mass Spectrometry", J. of Proteome Research, vol. 4, pp. 2070-2080 (2005).
Lopez-Alemany, R. et al., "Inhibition of Cell Surface Mediated Plasminogen Activation by a Monoclonal Antibody Against α-Enolase", American J. of Hematology, vol. 72, pp. 234-242 (2003).
Lorenz, K. et al., "Protein kinase C switches the Raf kinase inhibitor from Raf-1 to GRK-2", Nature, vol. 426, pp. 574-579 (2003).
Lubetsky, J. et al., "The Tautomerase Active Site of Macrophage Migration Inhibitory Factor is a Potential Target for Discovery of Novel Anti-inflammatory Agents", The J. of Biological Chemistry, vol. 277(2), pp. 24976-24982 (2002).
Lue, H. et al., "Macrophage migration inhibitory factor (MIF): mechanisms of action and role in disease", Microbes and Infection, vol. 4, pp. 449-460 (2002).
Mace, K. et al., "Aflatoxin $B_1$-induced DNA adduct formation and p53 mutations in CYP450-expressing human liver cell lines", Carcinogenesis, vol. 18(7), pp. 1291-1297 (1997).
Markert, M. L., "Purine Nucleoside Phosphorylase Deficiency", PNP Deficiency Reviews, vol. 3, pp. 45-81 (1991).
McDonald, W. et al., "Shotgun proteomics and biomarker discovery", Disease Markers, vol. 18, pp. 99-105 (2002).
Meadows, M., "Why Drugs get pulled off the Market", US FDA Consumer magazine, Jan.-Feb. 2002 pp. 1-7.
Medina, J. et al., "Leukotriene $A_4$ hydrolase: Determination of the three zinc-binding ligands by site-directed mutagenesis and zinc analysis", PNAS, vol. 88, pp. 7620-7624 (1991).
Minami, M. et al., "Molecular Cloning of a cDNA Coding for Human Leukotriene $A_4$ Hydrolase", The J. of Biological Chemistry, vol. 262(29), pp. 13873-13876 (1987).

Mitchell, R. et al., "Macrophage migration inhibitory factor (MIF) sustains macrophage proinflammatory function by inhibiting p53: Regulatory role in the innate immune response", PNAS, vol. 99(1), pp. 345-350 (2002).

Mohammad, R. et al., "Induced Expression of Alpha-Enolase in Differentiated Diffuse Large Cell Lymphoma", Enzyme Protein, vol. 48, pp. 37-44 (1994-1995).

Molinaro, R. et al., "Selection and cloning of poly(rC)-binding protein 2 and Raf kinase inhibitor protein RNA activators of 2', 5'-oligoadenylate synthetase from prostate cancer cells", Nucleic Acids Research, vol. 37(22), pp. 6684-6695 (2006).

Ochi, H. et al., "Proteomic analysis of human brain identifies α-enolase as a novel autoantigen in Hashimoto's encephalopathy", FEBS Letters, vol. 528, pp. 197-202 (2002).

Ohishi, N. et al., "Leukotriene $A_4$ Hydrolase in the Human Lung", The J. of Biological Chemistry, vol. 262(21), pp. 10200-10205 (1987).

Onyango, P. et al., "Molecular Cloning and Expression Analysis of Five Novel Genes in Chromosome 1p36", Genomics, vol. 50, pp. 187-198 (1998).

Pancholi, V., "Multifunctional α-enolase: its role in diseases", Cellular and Molecular Life Sciences, vol. 58, pp. 902-920 (2001).

Pang, J. et al., "Biomarker Discovery in Urine by Proteomics", J. of Proteome Research, vol. 1, pp. 161-169 (2002).

Pappas, Jr. N., "Source of increased serum aspartate and alanine aminotransferase: cycloheximide effect on carbon tetrachloride hepatotoxicity", Clinica Chimica Acta, vol. 154, pp. 181-190 (1986).

Park, S. et al., "Regulation of RKIP binding to the N-region of the Raf-1 kinase", FEBS Letters, vol. 580, pp. 6405-6412 (2006).

Petty, R. et al., "Comparison of MTT and ATP-Based Assays for the Measurement of Viable Cell Number", J. Biolumin Chemilumin, vol. 10, pp. 29-34 (1995).

Pfeifer, AMA. et al., "Simian virus 40 large tumor antigen-immortalized normal human liver epithelial cells express hepatocyte characteristics and metabolize chemical carcinogens", PNAS, vol. 90, pp. 5123-5127 (1993).

Qiu, H. et al., "Expression of 5-lipoxygenase and leukotriene $A_4$ hydrolase in human atherosclerotic lesions correlates with symptoms of plaque instability", PNAS, vol. 103(21), pp. 8161-8166 (2006).

Rådmark, O. et al., "Cloning of leukotriene $A_4$ Hydrolase cDNA", Molecular Biology, vol. 187, pp. 486-491 (1990).

Ray, R. et al., "Cloning and Characterization of a Human c-*myc* Promoter-Binding Protein", Molecular and Cellular Biology, vol. 11(4), pp. 2154-2161 (1991).

Rittinger, K. et al., "Structural Analysis of 14-3-3 Phosphopeptide Complexes Identifies a Dual Role for the Nuclear Export Signal of 14-3-3 in Ligand Binding", Molecular Cell, vol. 4, pp. 153-166 (1999).

Rundell, K. et al., "The role of the SV40 ST antigen in cell growth promotion and transfrmation", Cancer Biology, vol. 11, pp. 5-13 (2001).

Rush, J. et al., "Immunoaffinity profiling of tyrosine phosphorylation in cancer cells", Nature Biotechnology, vol. 23(1), pp. 94-101 (2005).

Rybina, I. et al., "Regulation of Leukotriene $A_4$ Hydrolase Activity in Endothelial Cells by Phosphorylation", The J. of Biological Chemistry, vol. 272(50), pp. 31865-31871 (1997).

Schoentgen, F. et al., "From structure to function: possible biological roles of a new widespread protein family finding hydrophobic ligands and displaying a nucleotide binding site", FEBS Letters, vol. 369, pp. 22-26 (1995).

Seddiq, N. et al., "Amino Acid Sequence of the *Homo sapiens* Brain 21-23-kDa Protein (Neuropolypeptide h3), Comparison with Its Counterparts from *Rattus norvegicus* and *Bos Taurus* Species, and Expression of Its mRNA in Difference Tissues", J. Mol. Evol., vol. 39, pp. 655-660 (1994).

Skonier, J. et al., "Recognition of Diverse Proteins by Members of the Immunogloblin Superfamily: Delineation of the Receptor Binding Site in the Human CD6 Ligand ALCAM", Biochemistry, vol. 35, pp. 12287-12291 (1996).

Smith, P.K. et al., "Measurement of Protein Using Bicinchoninic Acid", Analytical Biochemistry, vol. 150, pp. 76-85 (1985).

Stelzl, U. et al., "A Human Protein-Protein Interaction Network: A Resource for Annotating the Proteome", Cell, vol. 122, pp. 957-968 (2005)

Subramanian, A. et al., "Structural Analysis of α-Enolase", The J. of Biological Chemistry, vol. 275(8), pp. 5958-5965 (2000).

Swanson, B., "Delivery of high-quality biomarker assays", Disease Markers, vol. 18, pp. 47-56 (2002).

Tabb, D. et al., "DTASelect and Contrast: Tools for Assembling and Comparing Protein Identification from Shotgun Proteomics", J. of Proteome Research, vol. 1, pp. 21-26 (2002).

Takahashi, Y., "The 14-3-3 Proteins: Gene, Gene Expression, and Function", Neurochemical Research, vol. 28(8), pp. 1265-1273 (2003).

Thunnissen, M. et al., "Crystal structure of human leukotriene $A_4$ hydrolase, a bifunctional enzyme in inflammation", Nature structural biology, vol. 8(2), pp. 131-135 (2001).

Tohdoh, N. et al., "Sequence homology of rat and human HCNP precursor proteins, bovine phosphatidylethanolamine-binding protein and rat 23-kDa protein associated with the opioid-binding", Molecular Brain Research, vol. 30, pp. 381-384 (1995).

Tzivion, G. et al., "14-3-3 Proteins: Active Cofactors in Cellular Regulation by Serine/Threonine Phosphorylation", The J. of Biological Chemistry, vol. 277(5), pp. 3061-3064 (2002).

Van der Hoeven, P. et al., "Protein kinase C activation by acidic proteins including 14-3-3", Biochem. J., vol. 347, pp. 781-785 (2000).

Walter, M. et al., "Autoreactive Epitopes within the Human α-Enolase and their Recognition by Sera from Patients with Endometriosis", J. of Autoimmunity, vol. 8, pp. 931-945 (1995).

Washburn, M. et al., "Large-scale analysis of the yeast proteome by multidimensional protein identification technology", Nature Biotechnology, vol. 19, pp. 242-247 (2001).

Willuweit, A. et al., "Chronic Inflammation and Protection from Acute Hepatitis in Transgenic Mice Expressing TNF in Endothelial Cells", The J. of Immunology, vol. 167, pp. 3944-3952 (2001).

Yaffe, M. et al., "How do 14-3-3 proteins work?-Gatekeeper phosphorylation and the molecular anvil hypothesis", FEBS Letters, vol. 513, pp. 53-57 (2002).

Yu, W. et al., "Large-Scale Concatenation cDNA Sequencing", Genome Research, vol. 7, pp. 353-358 (1997).

Zhang, H. et al., "Identification and quantification of N-linked glycoproteins using hydrazide chemistry, stable isotope labeling and mass spectrometry", Nature Biotechnology, vol. 21(6), pp. 660-666 (2003).

Zupan, L. et al., "Cloning and Expression of a Human 14-3-3 Protein Mediating Phospholipolysis", The J. of Biological Chemistry, vol. 267(13), pp. 8707-8710 (1992).

Arza, B. et al., "Identification of an Epitope of α-Enolase (a Candidate Plasminogen Receptor) by Phage Display", Thromb. Haemost, vol. 78, pp. 1097-1103 (1997).

Bajorath, J. et al., "Molecular model of the N-terminal receptor-binding domain of the human CD6 ligand ALCAM", Protein Science, vol. 4, pp. 1644-1647 (1995).

Bowen, M. et al., "Cloning, Mapping, and Characterization of Activated Leukocyte-Cell Adhesion Molecule (ALCAM), a CD6 Ligand", J. Exp. Med., vol. 181, pp. 2213-2220 (1995).

Coughlin, P. et al., "Identification and Purification of a Novel Serine Proteinase Inhibitor", The J. of Biological Chemistry, vol. 266 (13), pp. 9541-9547 (1993).

Coughlin, P. et al., "Cloning and Molecular Characterization of a Human Intracellular Serine Proteinase Inhibitor", PNAS, vol. 90, pp. 9417-9421 (1993).

Dawson. S. et al., "Treatment of *Haemophilus aphrophilus* endocarditis with ciprofloxacin", J. of Infection, vol. 24, pp. 317-320 (1992).

NCBI Entrez Accession No. AF021819 (gi:2460317) Beaudon, R. et al., Apr. 7, 1998.

NCBI Entrez Accession No. AF058913 (gi:7212866) Perl, A. et al., Mar. 10, 2000.

NCBI Entrez Accession No. AJ344101 (gi:15216174) Schmidt, T., Aug. 18, 2001.

NCBI Entrez Accession No. AK022710 (gi:10434264) Ota, T. et al., Sep. 12, 2006.

NCBI Entrez Accession No. BC001394 (gi:12655086) Strausberg, R., Jul. 12, 2001.
NCBI Entrez Accession No. BC001829 (gi:12804776) Strausberg, R. et al., Sep. 1, 2006.
NCBI Entrez Accession No. BC010039 (gi:14603146) Srausberg, R. et al., Apr. 22, 2003.
NCBI Entrez Accession No. BC024895 (gi:19354169) Strausberg, R. et al., Dec. 2, 2006.
NCBI Entrez Accession No. BT007148 (gi:30583134) Kalnine, N. et al., May 13, 2003.
NCBI Entrez Accession No. CD014650 (gi:30331109) Clark, M. et al., May 2, 2003.
NCBI Entrez Accession No. D17615 (gi:402510) Watanabe, M. et al., Feb. 4, 1999.
NCBI Entrez Accession No. D45198 (gi:971271) Nagata, K. et al., Feb. 7, 2003.
NCBI Entrez Accession No. L38608 (gi:886257) Bowen, M. et al., Aug. 7, 1995.
NCBI Entrez Accession No. M14328 (gi:182113) Giallongo, A. et al., Nov. 7, 1994.
NCBI Entrez Accession No. NM_000270 (4557800) Chen, H.W. et al., Jan. 24, 2007.
NCBI Entrez Accession No. NM_000895 (gi:4505028) Qiu, H. et al., Jan. 21, 2007.
NCBI Entrez Accession No. NM_002567 (gi:4505620) Moore, C. et al., Oct. 6, 2003.
NCBI Entrez Accession No. NP_000261 (GI:4557801) Chen, H.W. et al. Jan. 24, 2007.
NCBI Entrez Accession No. NP_000886 (gi:4505029) Qiu, H. et al., Jan. 21, 2007.
NCBI Entrez Accession No. NP_002558 (gi:4505621) Al-Mulla, F. et al., Jan. 28, 2007.
NCBI Entrez Accession No. P22712 (gi:126792) Ray, R. et al., Mar. 15, 2004.
NCBI Entrez Accession No. P29312 (gi:112695) Zupan, L. A. et al., Oct. 1, 2004.
NCBI Entrez Accession No. P35237 (gi:20141722 Coughlin, P. et al., Jan. 23, 2007.
NCBI Entrez Accession No. Q13740 (gi:2497297) Bowen, M.A. et al., Oct. 17, 2006.
NCBI Entrez Accession No. Q4TUS4 (gi:74762942) Livingston, R.J. et al., Sep. 13, 2005.
NCBI Entrez Accession No. U20999 (gi:694107) Wen, Y. et al., Mar. 4, 1995.
NCBI Entrez Accession No. U79231 (gi:1711129) Sladeczek, F. et al., Jun. 17, 1997.
NCBI Entrez Accession No. AAA62644 (gi:694108) Wen, Y. et al., Mar. 4, 1995.
NCBI Entrez Accession No. AAC12806 (gi:2460318) Beaudoin, R. et al., Apr. 7, 1998.
NCBI Entrez Accession No. AAC53254 (gi:1711130) Sladeczek, F. et al., Jun. 16, 1997.
NCBI Entrez Accession No. AAF40478 (gi:7212867) Perl, A. et al., Mar. 10, 2000.
NCBI Entrez Accession No. AAH10039 (gi:14603147) Strausberg, R.L. et al., Jul. 15, 2006.
NCBI Entrez Accession No. AAH24895 (gi:19354170) Strausberg, R.L. et al., Dec. 2, 2006.
NCBI Entrez Accession No. AAP35812 (gi:30583135) Kalnine, N. et al., May 13, 2003.
NCBI Entrez Accession No. BAA04534 (gi:402511) Watanabe, M. et al., Feb. 4, 1999.
NCBI Entrez Accession No. BAB14194 (gi:10434265) Ota, T. et al., Sep. 12, 2006.
NCBI Entrez Accession No. CAC51435 (gi:15216175) Schmidt, T., Aug. 18, 2001.
NCBI Entrez Accession No. 87368 (gi:87368) Giallongo, A. et al., Jun. 20, 2000.
NCBI Entrez Accession No. 105479 (gi:105479) Ray, R. et al., Jun. 22, 1999.
NCBI Entrez Accession No. 213658 (gi:2136258) Nagata, K. et al., Nov. 5, 1999.
NCBI Entrez Accession No. 65922 (gi:65922) Tsujibo, H. et al., Jan. 28, 2000.
NCBI Entrez Accession No. P06733 (gi:119339) Giallongo, et al., Jan. 23, 2007.
David L. Streiner and Geoffrey R. Norman, Health Measurement Scales (Table of Contents), Second Edition, Oxford University Press, Oxford, 1995.
Aitken, et al., “14-3-3 Proteins in Cell Regulation”, Biochem. Society Transactions, vol. 30, Part 4, pp. 351-360 (2002).
Kaneko, et al., “The alternative role of 14-3-3 zeta as a sweeper of misfolded proteins in disease conditions”, Med. Hypotheses, vol. 67, pp. 169-171 (2006).
Park, et al., “The Role of Metabolic Activation in Drug-Induced Hepatotoxicity”, Annu. Rev. Pharmacol. Toxicol., vol. 45, pp. 177-202 (2005).

* cited by examiner

FIG. 4A

MDKNELVQKAKLAEQAERYDDMAACMKSVTEQGAELSNEERNLLSVAYKNVVGA
RRSSWRVVSSIEQKTEGAEKKQQMAREYREKIETELRDICNDVLSLLEKFLIPNASQ
AESKVFYLKMKGDYYRYLAEVAAGDDKKGIVDQSQQAYQEAFEISKKEMQPTHPIR
LGLALNFSVFYYEILNSPEKACSLAKTAFDEAIAELDTLSEESYKDSTLIMQLLRDNLT
LWTSDTQGDEAEAGEGGEN

FIG. 4B

MPMFIVNTNVPRASVPDGFLSELTQQLAQATGKPPQYIAVHVVPDQLMAFGGSSEP
CALCSLHSIGKIGGAQNRSYSKLLCGLLAERLRISPDRVYINYYDMNAANVGWNNST
FA

FIG. 7A

BMS-PTX-447
MATLKDQLIYNLLKEEQTPQNKITVVGVGAVGMACAISILMKDLADELALVDVIEDKLKG
EMMDLQHGSLFLRTPKIVSGKDYNVTANSKLVIITAGARQQEGESRLNLVQRNVNIFKFI
IPNVVKYSPNCKLLIVSNPVDILTYVAWKISGFPKNRVIGSGCNLDSARFRYLMGERLGV
HPLSCHGWVLGEHGDSSVPVWSGMNVAGVSLKTLHPDLGTDKDKEQWKEVHKQVVESAYE
VIKLKGYTSWAIGLSVADLAESIMKNLRRVHPVSTMIKGLYGIKDDVFLSVPCILGQNGI
SDLVKVTLTSEEEARLKKSADTLWGIQKELQF

BMS-PTX-749
MASKRALVILAKGAEEMETVIPVDVMRRAGIKVTVAGLAGKDPVQCSRDVVICPDASLED
AKKEGPYDVVVLPGGNLGAQNLSESAAVKEILKEQENRKGLIAAICAGPTALLAHEIGFG
SKVTTHPLAKDKMMNGGHYTYSENRVEKDGLILTSRGPGTSFEFALAIVEALNGKEVAAQ
VKAPLVLKD

BMS-PTX-607
MSSSPVKRQRMESALDQLKQFTTVVADTGDFHAIDEYKPQDATTNPSLILAAAQMPAYQE
LVEEAIAYGRKLGGSQEDQIKNAIDKLFVLFGAEILKKIPGRVSTEVDARLSFDKDAMVA
RARRLIELYKEAGISKDRILIKLSSTWEGIQAGKELEEQHGIHCNMTLLFSFAQAVACAE
AGVTLISPFVGRILDWHVANTDKKSYEPLEDPGVKSVTKIYNYYKKFSYKTIVMGASFRN
TGEIKALAGCDFLTISPKLLGELLQDNAKLVPVLSAKAAQASDLEKIHLDEKSFRWLHNE
DQMAVEKLSDGIRKFAADAVKLERMLTERMFNAENGK

BMS-PTX-808
MPEIVDTCSLASPASVCRTKHLHLRCSVDFTRRTLTGTAALTVQSQEDNLRSLVLDTKDL
TIEKVVINGQEVKYALGERQSYKGSPMEISLPIALSKNQEIVIEISFETSPKSSALQWLT
PEQTSGKEHPYLFSQCQAIHCRAILPCQDTPSVKLTYTAEVSVPKELVALMSAIRDGETP
DPEDPSRKIYKFIQKVPIPCYLIALVVGALESRQIGPRTLVWSEKEQVEKSAYEFSETES
MLKIAEDLGGPYVWGQYDLLVLPPSFPYGGMENPCLTFVTPTLLAGDKSLSNVIAHEISH
SWTGNLVTNKTWDHFWLNEGHTVYLERHICGRLFGEKFRHFNALGGWGELQNSVKTFGET
HPFTKLVVDLTDIDPDVAYSSVPYEKGFALLFYLEQLLGGPEIFLGFLKAYVEKFSYKSI
TTDDWKDFLYSYFKDKVDVLNQVDWNAWLYSPGLPPIKPNYDMTLTNACIALSQRWITAK
EDDLNSFNATDLKDLSSHQLNEFLAQTLQRAPLPLGHIKRMQEVYNFNAINNSEIRFRWL
RLCIQSKWEDAIPLALKMATEQGRMKFTRPLFKDLAAFDKSHDQAVRTYQEHKASMHPVT
AMLVGKDLKVD

BMS-PTX-860
MATKIDKEACRAAYNLVRDDGSAVIWVTFKYDGSTIVPGEQGAEYQHFIQQCTDDVRLFA
FVRFTTGDAMSKRSKFALITWIGENVSGLQRAKTGTDKTLVKEVVQNFAKEFVISDRKEL
EEDFIKSELKKAGGANYDAQTE

BMS-PTX-254
MENGYTYEDYKNTAEWLLSHTKHRPQVAIICGSGLGGLTDKLTQAQIFDYGEIPNFPRST
VPGHAGRLVFGFLNGRACVMMQGRFHMYEGYPLWKVTFPVRVFHLLGVDTLVVTNAAGGL
NPKFEVGDIMLIRDHINLPGFSGQNPLRGPNDERFGDRFPAMSDAYDRTMRQRALSTWKQ
MGEQRELQEGTYVMVAGPSFETVAECRVLQKLGADAVGMSTVPEVIVARHCGLRVFGFSL
ITNKVIMDYESLEKANHEEVLAAGKQAAQKLEQFVSILMASIPLPDKAS

FIG. 7B

BMS-PTX-225
MARYEEVSVSGFEEFHRAVEQHNGKTIFAYFTGSKDAGGKSWCPDCVQAEPVVREGLKHISEGC
VFIYCQVGEKPYWKDPNNDFRKNLKVTAVPTLLKYGTPQKLVESECLQANLVEMLFSED

BMS-PTX-147
MESKGASSCRLLFCLLISATVFRPGLGWYTVNSAYGDTIIIPCRLDVPQNLMFGKWKYEK
PDGSPVFIAFRSSTKKSVQYDDVPEYKDRLNLSENYTLSISNARISDEKRFVCMLVTEDN
VFEAPTIVKVFKQPSKPEIVSKALFLETEQLKKLGDCISEDSYPDGNITWYRNGKVLHPL
EGAVVIIFKKEMDPVTQLYTMTSTLEYKTTKADIQMPFTCSVTYYGPSGQKTIHSEQAVF
DIYYPTEQVTIQVLPPKNAIKEGDNITLKCLGNGNPPPEEFLFYLPGQPEGIRSSNTYTL
MDVRRNATGDYKCSLIDKKSMIASTAITVHYLDLSLNPSGEVTRQIGDALPVSCTISASR
NATVVWMKDNIRLRSSPSFSSLHYQDAGNYVCETALQEVEGLKKRESLTLIVEGKPQIKM
TKKTDPSGLSKTIICHVEGFPKPAIQWTITGSGSVINQTEESPYINGRYYSKIIISPEEN
VTLTCTAENQLERTVNSLNVSAISIPEHDEADEISDENREKVNDQAKLIVGIVVGLLLAA
LVAGVVYWLYMKKSKTASKHVNKDLGNMEENKKLEENNHKTEA

BMS-PTX-459
MAPKRQSPLPPQKKKPRPPPALGPEETSASAGLPKKGEKEQQEAIEHIDEVQNEIDRLNE
QASEEILKVEQKYNKLRQPFFQKRSELIAKIPNFWVTTFVNHPQVSALLGEEDEEALHYL
TRVEVTEFEDIKSGYRIDFYFDENPYFENKVLSKEFHLNESGDPSSKSTEIKWKSGKDLT
KRSSQTQNKASRKRQHEEPESFFTWFTDHSDAGADELGEVIKDDIWPNPLQYYLVPDMDD
EEGEGEEDDDDDEEEEGLEDIDEEGDEDEGEEDEDDDEGEEGEEDEGEDD

BMS-PTX-120
WVCVFPSQCAELSASPLSPAPGLPRHSRLHALLGLAMPVDLSKWSGPLSLQEVDEQPQHP
LHVTYAGAAVDELGKVLTPTQVKNRPTSISWDGLDSGKLYTLVLTDPDAPSRKDPKYREW
HHFLVVNMKGNDISSGTVLSDYVGSGPPKGTGLHRYVWLVYEQDRPLKCDEPILSNRSGD
HRGKFKVASFRKKYELRAPVAGTCYQAEWDDYVPKLYEQLSGK

BMS-PTX-062
MSAAEAGGVFHRARGRTLAAFPAEKESEWKGPFYFILGADPQFGLIKAWSTGDCDNGGDE
WEQEIRLTEQAVQAINKLNPKPKFFVLCGDLIHAMPGKPWRTEQTEDLKRVLRAVDRAIP
LVLVSGNHDIGNTPTAETVEEFCRTWGYDYFSFWVGGVLFLVLNSQFYENPSKCPSLKQA
QDQWLDEQLSIARQRHCQHAIVFQHIPLFLESIDEDDDYYFNLSKSTRKKLADKFIHAGV
RVVFSGHYHRNAGGTYQNLDMVVSSAIGCQLGRDPHGLRVVVVTAEKIVHRYYSLDELSE
KGIEDDLMDLIKKK

BMS-PTX-260
RSLPALEYVSGLGAARTRWLGSAIMDVLAEANGTFALNLLKTLGKDNSKNVFFSPMSMSC
ALAMVYMGAKGNTAAQMAQILSFNKSGGGGDIHQGFQSLLTEVNKTGTQYLLRMANRLFG
EKSCDFLSSFRDSCQKFYQAEMEELDFISAVEKSRKHINTWVAEKTEGKIAELLSPGSVD
PLTRLVLVNAVYFRGNWDEQFDKENTEERLFKVSKNEEKPVQMMFKQSTFKKTYIGEIFT
QILVLPYVGKELNMIIMLPDETTDLRTVEKELTYEKFVEWTRLDMMDEEEVEVSLPRFKL
EESYDMESVLRNLGMTDAFELGKADFSGMSQTDLSLSKVVHKSFVEVNEEGTEAAAATAA
IMMMRCARFVPRFCADHPFLFFIQHSKTNGILFCGRFSSP

FIG. 7C

BMS-PTX-147

MSILKIHAREIFDSRGNPTVEVDLFTSKGLFRAAVPSGASTGIYEALELRDNDKTRYMGK
GVSKAVEHINKTIAPALVSKKLNVTEQEKIDKLMIEMDGTENKSKFGANAILGVSLAVCK
AGAVEKGVPLYRHIADLAGNSEVILPVPAFNVINGGSHAGNKLAMQEFMILPVGAANFRE
AMRIGAEVYHNLKNVIKEKYGKDATNVGDEGGFAPNILENKEGLELLKTAIGKAGYTDKV
VIGMDVAASEFFRSGKYDLDFKSPDDPSRYISPDQLADLYKSFIKDYPVVSIEDPFDQDD
WGAWQKFTASAGIQVVGDDLTVTNPKRIAKAVNEKSCNCLLLKVNQIGSVTESLQACKLA
QANGWGVMVSHRSGETEDTFIADLVVGLCTGQIKTGAPCRSERLAKYNQLLRIEEELGSK
AKFAGRNFRNPLAK

FIG. 8A

PRIMERS FOR PTX-265

| OLIGO | start | len | tm | gc% | any | 3' | seq | SEQ ID: |
|---|---|---|---|---|---|---|---|---|
| LEFT PRIMER | 43 | 20 | 59.93 | 50.00 | 5.00 | 2.00 | caggctgagcgatatgatga | 16 |
| RIGHT PRIMER | 244 | 20 | 59.98 | 50.00 | 6.00 | 1.00 | attctcgagccatctgctgt | 17 |

PRODUCT SIZE: 202 nucleotides

PRIMERS FOR PTX-447

| OLIGO | start | len | tm | gc% | any | 3' | seq | SEQ ID: |
|---|---|---|---|---|---|---|---|---|
| LEFT PRIMER | 533 | 20 | 59.93 | 50.00 | 6.00 | 2.00 | tgggagttcacccattaagc | 18 |
| RIGHT PRIMER | 714 | 20 | 60.06 | 55.00 | 4.00 | 2.00 | agcactctcaaccacctgct | 19 |

PRODUCT SIZE: 182 nucleotides

PRIMERS FOR PTX-749

| OLIGO | start | len | tm | gc% | any | 3' | seq | SEQ ID: |
|---|---|---|---|---|---|---|---|---|
| LEFT PRIMER | 136 | 20 | 59.99 | 50.00 | 3.00 | 2.00 | tgtagccgtgatgtggtcat | 20 |
| RIGHT PRIMER | 348 | 20 | 60.14 | 50.00 | 6.00 | 1.00 | ttcatgagccaacagagcag | 21 |

PRODUCT SIZE: 213 nucleotides

PRIMERS FOR PTX-607

| OLIGO | start | len | tm | gc% | any | 3' | seq | SEQ ID: |
|---|---|---|---|---|---|---|---|---|
| LEFT PRIMER | 745 | 20 | 60.12 | 55.00 | 4.00 | 2.00 | ggctgtgacttcctcaccat | 22 |
| RIGHT PRIMER | 894 | 20 | 60.16 | 50.00 | 4.00 | 3.00 | gtgcaaccaacggaaagact | 23 |

PRODUCT SIZE: 150 nucleotides

PRIMERS FOR PTX-808

| OLIGO | start | len | tm | gc% | any | 3' | seq | SEQ ID: |
|---|---|---|---|---|---|---|---|---|
| LEFT PRIMER | 1188 | 20 | 59.99 | 55.00 | 3.00 | 0.00 | actgcttggaggaccagaga | 24 |
| RIGHT PRIMER | 1344 | 20 | 59.93 | 45.00 | 4.00 | 3.00 | ccaggcattccaatcaactt | 25 |

PRODUCT SIZE: 157 nucleotides

PRIMERS FOR PTX-860

| OLIGO | start | len | tm | gc% | any | 3' | seq | SEQ ID: |
|---|---|---|---|---|---|---|---|---|
| LEFT PRIMER | 68 | 20 | 59.97 | 50.00 | 6.00 | 0.00 | Ccgtcatctgggtgactttt | 26 |
| RIGHT PRIMER | 311 | 20 | 59.97 | 55.00 | 4.00 | 0.00 | Acctccttcaccagggtctt | 27 |

PRODUCT SIZE: 244 nucleotides

PRIMERS FOR PTX-254

| OLIGO | start | len | tm | gc% | any | 3' | seq | SEQ ID: |
|---|---|---|---|---|---|---|---|---|
| LEFT PRIMER | 510 | 20 | 59.70 | 60.00 | 6.00 | 2.00 | gaggcagagggctctcagta | 28 |
| RIGHT PRIMER | 712 | 20 | 59.99 | 50.00 | 6.00 | 2.00 | agccaaagactcgaagtcca | 29 |

PRODUCT SIZE: 203 nucleotides

PRIMERS FOR PTX-225

| OLIGO | start | len | tm | gc% | any | 3' | seq | SEQ ID: |
|---|---|---|---|---|---|---|---|---|
| LEFT PRIMER | 162 | 20 | 59.84 | 50.00 | 4.00 | 2.00 | agaggggctgaagcacatta | 30 |
| RIGHT PRIMER | 345 | 20 | 60.30 | 55.00 | 4.00 | 1.00 | caggttggcctgaagacact | 31 |

PRODUCT SIZE: 184 nucleotides

PRIMERS FOR PTX-147

| OLIGO | start | len | tm | gc% | any | 3' | seq | SEQ ID: |
|---|---|---|---|---|---|---|---|---|
| LEFT PRIMER | 913 | 20 | 60.01 | 50.00 | 5.00 | 2.00 | cgcaatgcaacaggagacta | 32 |
| RIGHT PRIMER | 1129 | 20 | 59.94 | 55.00 | 6.00 | 2.00 | ggctagatcgaagcctgatg | 33 |

PRODUCT SIZE: 217 nucleotides

FIG. 8B

PRIMERS FOR PTX-459

| OLIGO | start | len | tm | gc% | any | 3' | seq | SEQ ID: |
|---|---|---|---|---|---|---|---|---|
| LEFT PRIMER | 123 | 20 | 60.00 | 45.00 | 4.00 | 0.00 | gcaagaagcgattgaacaca | 34 |
| RIGHT PRIMER | 352 | 20 | 59.96 | 55.00 | 5.00 | 0.00 | gcagtgcctcttcatcttcc | 35 |

PRODUCT SIZE: 230 nucleotides

PRIMERS FOR PTX-120

| OLIGO | start | len | tm | gc% | any | 3' | seq | SEQ ID: |
|---|---|---|---|---|---|---|---|---|
| LEFT PRIMER | 253 | 20 | 59.96 | 50.00 | 2.00 | 2.00 | atagacccaccagcatttcg | 36 |
| RIGHT PRIMER | 415 | 20 | 59.90 | 55.00 | 5.00 | 2.00 | actgtgccactgctgatgtc | 37 |

PRODUCT SIZE: 163 nucleotides

PRIMERS FOR PTX-837

| OLIGO | start | len | tm | gc% | any | 3' | seq | SEQ ID: |
|---|---|---|---|---|---|---|---|---|
| LEFT PRIMER | 133 | 18 | 59.30 | 61.11 | 4.00 | 2.00 | gaccagctcatggccttc | 38 |
| RIGHT PRIMER | 335 | 20 | 59.97 | 50.00 | 3.00 | 1.00 | gagttgttccagcccacatt | 39 |

PRODUCT SIZE: 203 nucleotides

PRIMERS FOR PTX-062

| OLIGO | start | len | tm | gc% | any | 3' | seq | SEQ ID: |
|---|---|---|---|---|---|---|---|---|
| LEFT PRIMER | 67 | 20 | 59.96 | 45.00 | 2.00 | 0.00 | gcagaaaaggaaagcgaatg | 40 |
| RIGHT PRIMER | 253 | 20 | 60.03 | 45.00 | 4.00 | 0.00 | agaatttgggtttggggttc | 41 |

PRODUCT SIZE: 187 nucleotides

PRIMERS FOR PTX-260

| OLIGO | start | len | tm | gc% | any | 3' | seq | SEQ ID: |
|---|---|---|---|---|---|---|---|---|
| LEFT PRIMER | 648 | 20 | 59.93 | 45.00 | 6.00 | 2.00 | ccaaatcttggtgcttccat | 42 |
| RIGHT PRIMER | 890 | 20 | 59.98 | 50.00 | 4.00 | 3.00 | agctcgaaggcatcagtcat | 43 |

PRODUCT SIZE: 243 nucleotides

PRIMERS FOR PTX-147

| OLIGO | start | len | tm | gc% | any | 3' | seq | SEQ ID: |
|---|---|---|---|---|---|---|---|---|
| LEFT PRIMER | 278 | 20 | 59.96 | 45.00 | 5.00 | 0.00 | tgatgatcgagatggatgga | 44 |
| RIGHT PRIMER | 466 | 20 | 59.93 | 45.00 | 5.00 | 1.00 | cgccattgatgacattgaac | 45 |

PRODUCT SIZE: 189 nucleotides

FIG. 9A

BMS-PTX-265 ttagcccgaccgacagcccgtgaggatcagctgagagccgcggttagcttagctcagacaggaccatc
gttattccccgacactcagctctgagcagccatggacaagagcgagctagtgcaaaaagccaagctgg
ccgagcaggcagagcgctacgacgacatggcagccgctatgaaggctgtcactgagggtgacattgaa
ctgtcgaacgaggagcgcaacctgctctcggtggcttacaagaacgtggtgggtgcccgtcgctcatc
ctggagggtcgtctccagcatcgagcagaagatggagggtagcgacaaaaagcagcaaatggtcaagg
aatatcgggaaaagatcgagaaggagctgaaggagatctgcaatgacgtactggttcttctggacaag
tatctcatccccaaagcgaccccggctgaaagcagagtcttctatctgaaaatgaaaggcgattgctt
tcgctacttagcagaggtggctgtgggagaggagaaaaactctatcattggcaattcgcaggaggcct
acaaggatgcgtttgaaat

BMS-PTX-837 atgccgatgttcatcgtaaacaccaacgtgccccgcgcctccgtgccggacgggttcctctccgagct
cacccagcagctggcgcaggccaccggcaagcccccccagtacatcgcggtgcacgtggtcccggacc
agctcatggccttcggcggctccagcgagccgtgcgcgctctgcagcctgcacagcatcggcaagatc
ggcggcgcgcagaaccgctcctacagcaagctgctgtgcggcctgctggccgagcgcctgcgcatcag
cccggacagggtctacatcaactattacgacatgaacgcggccaatgtgggctggaacaactccacct
tcgcctag

FIG. 9B

BMS-PTX-447 ggcacgagggagagagaacctggagcaggccggctgccaccttctgggctcctggggccctgcccacc
acaagcgctgagatgcgtctggagagccagagggcctgcctgaaggaatcacctgagcctgtccgtcc
accaggagtggggagatgcccccatccagtcctggaggacccgctgctcctgctgctcccggggatgg
agcaaggccaaggctgcgggaggctgggagccctgccctgcccatccctcctgcaccagcgctgtccc
tgcacatcttggcaggggcacgattccggatctcattgccacgcgcccccgacgaccgcccgacgtgc
attcccgattccttttggttccaagtccaatatggcaactctaaaggatcagctgatttataatcttc
taaaggaagaacagacccccagaataagattacagttgttggggttggtgctgttggcatggcctgt
gccatcagtatcttaatgaaggacttggcagatgaacttgctcttgttgatgtcatcgaagacaaatt
gaagggagagatgatggatctccaacatggcagccttttccttagaacaccaaagattgtctctggca
aagactataatgtaactgcaaactccaagctggtcattatcacggctggggcacgtcagcaagaggga
gaaagccgtcttaatttggtccagcgtaacgtgaacatctttaaattcatcattcctaatgttgtaaa
atacagcccgaactgcaagttgcttattgtttcaaatccagtggatatcttgacctacgtggcttgga
agataagtggttttcccaaaaaccgtgttattggaagtggttgcaatctggattcagcccgattccgt
tacctgatgggggaaaggctgggagttcacccattaagctgtcatgggtgggtccttggggaacatgg
agattccagtgtgcctgtatggagtggaatgaatgttgctggtgtctctctgaagactctgcacccag
atttagggactgataaagataaggaacagtggaaagaggttcacaagcaggtggttgagagtgcttat
gaggtgatcaaactcaaaggctacacatcctgggctattggactctctgtagcagatttggcagagag
tataatgaagaatcttaggcgggtgcacccagtttccaccatgattaagggtctttacggaataaagg
atgatgtcttccttagtgttccttgcattttgggacagaatggaatctcagaccttgtgaaggtgact
ctgacttctgaggaagaggcccgtttgaagaagagtgcagatacactttggggggatccaaaaggagct
gcaattttaaagtcttctgatgtcatatcatttcactgtctaggctacaacaggattctaggtggagg
ttgtgcatgttgtcctttttatctgatctgtgattaaagcagtaatattttaagatggactgggaaaa
acatcaactcctgaagttagaaataagaatggtttgtaaaatccacagctatatcctgatgctggatg
gtattaatcttgtgtagtcttcaactggttagtgtgaaatagttctgccacctctgacgcaccactgc
caatgctgtacgtactgcatttgccccttgagccaggtggatgtttaccgtgtgttatataacttcct
ggctccttcactgaacatgcctagtccaacatttttcccagtgagtcacatcctgggatccagtgta
taaatccaatatcatgtcttgtgcataattcttccaaaggatcttattttgtgaactatatcagtagt
gtacattaccatataatgtaaaaagatctacatacaaacaatgcaaccaactatccaagtgttatacc
aactaaacccccaataaaccttgaacagtgaaaaaaaaaaaaaaaaaaaaaaaaaaaaaaaaaa
aaaaaaaaaaaa

BMS-PTX-749 atggcttccaaaagagctctggtcatcctggctaaaggagcagaggaaatggagacggtcatccctgt
agatgtcatgaggcgagctgggattaaggtcaccgttgcaggcctggctggaaaagacccagtacagt
gtagccgtgatgtggtcatttgtcctgatgccagccttgaagatgcaaaaaaagagggaccatatgat
gtggtggttctaccaggaggtaatctgggcgcacagaatttatctgagtctgctgctgtgaaggagat
actgaaggagcaggaaaaccggaagggcctgatagccgccatctgtgcaggtcctactgctctgttgg
ctcatgaaataggttttggaagtaaagttacaacacaccctcttgctaaagacaaaatgatgaatgga
ggtcattacacctactctgagaatcgtgtggaaaaagacggcctgattcttacaagccgggggcctgg
gaccagcttcgagtttgcgcttgcaattgttgaagccctgaatggcaaggaggtggcggctcaagtga
aggctccacttgttcttaaagactag

FIG. 9C

BMS-PTX-607 atgtcgagctcacccgtgaagcgtcagaggatggagtccgcgctggaccagctcaagcagttcaccac
cgtggtggccgacacgggcgacttccacgccatcgacgagtacaagccccaggatgctaccaccaacc
cgtccctgatcctggccgcagcacagatgcccgcttaccaggagctggtggaggaggcgattgcctat
ggccggaagctgggcgggtcacaagaggaccagattaaaatgctattgataaactttttgtgttgtt
tggagcagaaatactaaagaagattccgggccgagtatccacagaagtagacgcaaggctctcctttg
ataaagatgcgatggtggccagagccaggcggctcatcgagctctacaaggaagctgggatcagcaag
gaccgaattcttataaagctgtcatcaacctgggaaggaattcaggctggaaaggagctcgaggagca
gcacggcatccactgcaacatgacgttactcttctccttcgcccaggctgtggcctgtgccgaggcgg
gtgtgaccctcatctccccatttgttgggcgcatccttgattggcatgtggcaaacaccgacaagaaa
tcctatgagcccctggaagaccctggggtaaagagtgtcactaaaatctacaactactacaagaagtt
tagctacaaaaccattgtcatgggcgcctccttccgcaacacgggcgagatcaaagcactggccggct
gtgacttcctcaccatctcacccaagctcctgggagagctgctgcaggacaacgccaagctggtgcct
gtgctctcagccaaggcggcccaagccagtgacctggaaaaaatccacctggatgagaagtctttccg
ttggttgcacaacgaggaccagatggctgtggagaagctctctgacgggatccgcaagtttgccgctg
atgcagtgaagctggagcggatgctgacagaacgaatgttcaatgcagagaatggaaagtag

BMS-PTX-808 atgcccgagatagtggatacctgttcgttggcctctccggcttccgtctgccggaccaagcacctgca
cctgcgctgcagcgtcgactttactcgccggacgctgaccgggactgctgctctcacggtccagtctc
aggaggacaatctgcgcagcctggttttggatacaaaggaccttacaatagaaaaagtagtgatcaat
ggacaagaagtcaaatatgctcttggagaaagacaaagttacaagggatcgccaatggaaatctctct
tcctatcgctttgagcaaaaatcaagaaattgttatagaaatttcttttgagacctctccaaaatctt
ctgctctccagtggctcactcctgaacagacttctgggaaggaacacccatatctctttagtcagtgc
caggccatccactgcagagcaatccttccttgtcaggacactccttctgtgaaattaacctatactgc
agaggtgtctgtccctaaagaactggtggcacttatgagtgctattcgtgatggagaaacacctgacc
cagaagacccaagcaggaaaatatacaaattcatccaaaaagttccaataccctgctacctgattgct
ttagttgttggagctttagaaagcaggcaaattggcccaagaactttggtgtggtctgagaaagagca
ggtggaaaagtctgcttatgagttttctgagactgaatctatgcttaaaatagcagaagatctgggag
gaccgtatgtatggggacagtatgacctattggtcctgccaccatccttcccttatggtggcatggag
aatccttgccttacttttgtaactcctactctactggcaggcgacaagtcactctccaatgtcattgc
acatgaaatatctcatagctggacagggaatctagtgaccaacaaaacttgggatcacttttggttaa
atgagggacatactgtgtacttggaacgccacatttgcggacgattgtttggtgaaaagttcagacat
tttaatgctctgggaggatggggagaactacagaattcggtaaagacatttggggagacacatccttt
caccaaacttgtggttgatctgacagatatagaccctgatgtagcttattcttcagttccctatgaga
agggctttgctttactttttaccttgaacaactgcttggaggaccagagattttcctaggattctta
aaagcttatgttgagaagttttcctataagagcataactactgatgactggaaggatttcctgtattc
ctattttaaagataaggttgatgttctcaatcaagttgattggaatgcctggctctactctcctggac
tgcctcccataaagcccaattatgatatgactctgacaaatgcttgtattgccttaagtcaaagatgg
attactgccaaagaagatgatttaaattcattcaatgccacagacctgaaggatctctcttctcatca
attgaatgagttttagcacagacgctccagagggcacctcttccattggggcacataaagcgaatgc
aagaggtgtacaacttcaatgccattaacaattctgaaatacgattcagatggctgcggctctgcatt
caatccaagtgggaggacgcaattcctttggcgctaaagatggcaactgaacaaggaagaatgaagtt
tacccggcccttattcaaggatcttgctgcctttgacaaatcccatgatcaagctgtccgaacctacc
aagagcacaaagcaagcatgcatcccgtgactgcaatgctggtggggaaagacttaaaagtggattaa

FIG. 9D

BMS-PTX-860
atggccaccaagatcgacaaagaggcttgccgggcggcgtacaacctggtgcgcgacgacggctcggc
cgtcatctgggtgacttttaaatatgacggctccaccatcgtccccggcgagcagggagcggagtacc
agcacttcatccagcagtgcacagatgacgtccggttgtttgccttcgtgcgcttcaccaccggggat
gccatgagcaagaggtccaagtttgccctcatcacgtggatcggtgagaacgtcagcgggctgcagcg
cgccaaaaccgggacggacaagaccctggtgaaggaggtcgtacagaatttcgctaaggagtttgtga
tcagtgatcggaaggagctggaggaagatttcatcaagagcgagctgaagaaggcgggggggagccaat
tacgacgcccagacggagtaa

BMS-PTX-254
atggagaacggatacacctatgaagattataagaacactgcagaatggcttctgtctcatactaagca
ccgacctcaagttgcaataatctgtggttctggattaggaggtctgactgataaattaactcaggccc
agatctttgactacagtgaaatccccaactttcctcgaagtacagtgccaggtcatgctggccgactg
gtgtttgggttcctgaatggcagggcctgtgtgatgatgcagggcaggttccacatgtatgaagggta
cccactctggaaggtgacattcccagtgagggttttccaccttctgggtgtggacaccctggtagtca
ccaatgcagcaggagggctgaaccccaagtttgaggttggagatatcatgctgatccgtgaccatatc
aacctacctggtttcagtggtcagaaccctctcagagggcccaatgatgaaaggtttggagatcgttt
ccctgccatgtctgatgcctacgaccggactatgaggcagagggctctcagtacctggaaacaaatgg
gggagcaacgtgagctacaggaaggcacctatgtgatggtggcaggccccagctttgagactgtggca
gaatgtcgtgtgctgcagaagctgggagcagacgctgttggcatgagtacagtaccagaagttatcgt
tgcacggcactgtggacttcgagtctttggcttctcactcatcactaacaaggtcatcatggattatg
aaagcctggagaaggccaaccatgaagaagtcttagcagctggcaaacaagctgcacagaaattggaa
cagtttgtctccattcttatggccagcattccactccctgacaaagccagttga

BMS-PTX-225
atggcccgctatgaggaggtgagcgtgtccggcttcgaggagttccaccgggccgtggaacagcacaa
tggcaagaccattttcgcctactttacgggttctaaggacgccggggggaaaagctggtgccccgact
gcgtgcaggctgaaccagtcgtacgagaggggctgaagcacattagtgaaggatgtgtgttcatctac
tgccaagtaggagaaaagccttattggaaagatccaaataatgacttcagaaaaaacttgaaagtaac
agcagtgcctacactacttaagtatggaacacctcaaaaactggtagaatctgagtgtcttcaggcca
acctggtggaaatgttgttctctgaagattaa

FIG. 9E

BMS-PTX-(39)147
cgggacgacgccccctcctgcggcgtggactccgtcagtggcccaccaagaaggaggaggaatatgga
atccaagggggccagttcctgccgtctgctcttctgcctcttgatctccgccaccgtcttcaggccag
gccttggatggtatactgtaaattcagcatatggagataccattatcataccttgccgacttgacgta
cctcagaatctcatgtttggcaaatggaaatatgaaaagcccgatggctccccagtatttattgcctt
cagatcctctacaaagaaaagtgtgcagtacgacgatgtaccagaatacaaagacagattgaacctct
cagaaaactacactttgtctatcagtaatgcaaggatcagtgatgaaagagatttgtgtgcatgcta
gtaactgaggacaacgtgtttgaggcacctacaatagtcaaggtgttcaagcaaccatctaaacctga
aattgtaagcaaagcactgtttctcgaaacagagcagctaaaaaagttgggtgactgcatttcagaag
acagttatccagatggcaatatcacatggtacaggaatggaaaagtgctacatcccttgaaggagcg
gtggtcataattttttaaaaaggaaatggacccagtgactcagctctataccatgacttccaccctgga
gtacaagacaaccaaggctgacatacaaatgccattcacctgctcggtgacatattatggaccatctg
gccagaaaacaattcattctgaacaggcagtatttgatatttactatcctacagagcaggtgacaata
caagtgctgccaccaaaaaatgccatcaaagaaggggataacatcactcttaaatgcttagggaatgg
caaccctcccccagaggaattttttgttttacttaccaggacagcccgaaggaataagaagctcaaata
cttacacactgatggatgtgaggcgcaatgcaacaggagactacaagtgttccctgatagacaaaaaa
agcatgattgcttcaacagccatcacagttcactatttggatttgtccttaaacccaagtggagaagt
gactagacagattggtgatgccctacccgtgtcatgcacaatatctgctagcaggaatgcaactgtgg
tatggatgaaagataacatcaggcttcgatctagcccgtcatttctagtcttcattatcaggatgct
ggaaactatgtctgcgaaactgctctgcaggaggttgaaggactaaagaaaagagagtcattgactct
cattgtagaaggcaaacctcaaataaaaatgacaaagaaaactgatcccagtggactatctaaaacaa
taatctgccatgtggaaggttttccaaagccagccattcagtggacaattactggcagtggaagcgtc
ataaaccaaacagaggaatctccttatattaatggcaggtattatagtaaaattatcatttcccctga
agagaatgttacattaacttgcacagcagaaaaccaactggagagaacagtaaactccttgaatgtct
ctgctataagtattccagaacacgatgaggcagacgagataagtgatgaaaacagagaaaaggtgaat
gaccaggcaaaactaattgtgggaatcgttgttggtctcctccttgctgcccttgttgctggtgtcgt
ctactggctgtacatgaagaagtcaaagactgcatcaaaacatgtaaacaaggacctcggtaatatgg
aagaaaacaaaagttagaagaaaacaatcacaaaactgaagcctaagagagaaactgtcctagttgt
ccagagataaaaatcatatagaccaattgaagcatgaacgtggattgtatttaagacataaacaaaga
cattgacagcaattcatggttcaagtattaagcagttcattctaccaagctgtcacaggttttcagag
aattatctcaagtaaaacaaatgaaatttaattacaaacaataagaacaagttttggcagccatgata
ataggtcatatgttgtgtttggttcaattttttttccgtaaatgtctgcactgaggatttcttttttgg
tttgccttttatgtaaattttttacgtagctatttttatacactgtaagctttgttctgggagttgct
gttaatctgatgtataatgtaatgttttttatttcaattgtttatatggataatctgagcaggtacatt
tctgattctgattgctatcagcaatgccccaaactttctcataagcacctaaaacccaaaggtggcag
cttgtgaagattggggacactcatattgccctaattaaaaactgtgatttttatcacaagggagggga
ggccgagagtcagactgatagacaccataggagccgactctttgatatgccaccagcgaactctcaga
aataaatcacagatgcatatagacacacatacataatggtactcccaaactgacaattttacctattc
tgaaaaagacataaaacagaatt

FIG. 9F

BMS-PTX-459 cccggctgggacttccctaacagcatggcccctaaacgccagtctccactcccgcctcaaaagaagaa
accaagaccacctcctgctctgggaccggaggagacatcggcctctgcaggcttgccgaagaagggag
aaaaagaacagcaagaagcgattgaacacattgatgaagtacaaaatgaaatagacagacttaatgaa
caagccagtgaggagattttgaaagtagaacagaaatataacaaactccgccaaccatttttcagaa
gaggtcagaattgatcgccaaaatcccaaattttgggtaacaacatttgtcaaccatccacaagtgt
ctgcactgcttggggaggaagatgaagaggcactgcattatttgaccagagttgaagtgacagaattt
gaagatattaaatcaggttacagaatagattttattttgatgaaaatccttactttgaaaataaagt
tctctccaaagaatttcatctgaatgagagtggtgatccatcttcgaagtccaccgaaatcaaatgga
aatctggaaaggatttgacgaaacgttcgagtcaaacgcagaataaagccagcaggaagaggcagcat
gaggaaccagagagcttctttacctggtttactgaccattctgatgcaggtgctgatgagttaggaga
ggtcatcaaagatgatatttggccaaacccattacagtactacttggttcccgatatggatgatgaag
aaggagaaggagaagaagatgatgatgatgatgaagaggaggaaggattagaagatattgacgaagaa
ggggatgaggatgaaggtgaagaagatgaagatgatgatgaaggggaggaaggagaggaggatgaagg
agaagatgactaaatagaacactgatggattccaaccttcctttttttaaatttctccagtccctgg
gagcaagttgcagtctttttttttttttttccctcttgtgctcagtcgccctgttcttga
ggtctcttttctctactccatggttctcaatttatttgggggaaataccttgagcagaatacaatgg
gaaaagagtctctacccctttctgttcgaagttcatttttatcccttcctgtctgaacaaaaactgta
tggaatcaacaccaccgagctctgtgggaaaaagaaaaacctgctccctttgctctgctggaagctg
gagggtgctaggcccctgtgtagtagtgtatagaattc

BMS-PTX-120 atgccggtggacctcagcaagtggtccgggcccttgagcctgcaagaagtggacgagcagccgcagca
cccgctgcatgtcacctacgccggggcggcggtggacgagctgggcaaagtgctgacgcccacccagg
ttaagaatagacccaccagcatttcgtgggatggtcttgattcagggaagctctacaccttggtcctg
acagacccggatgctcccagcaggaaggatcccaaatacagagaatggcatcatttcctggtggtcaa
catgaagggcaatgacatcagcagtggcacagtcctctccgattatgtgggctcggggcctcccaagg
gcacaggcctccaccgctatgtctggctggtttacgagcaggacaggccgctaaagtgtgacgagccc
atcctcagcaaccgatctggagaccaccgtggcaaattcaaggtggcgtccttccgtaaaagtatga
gctcagggccccggtggctggcacgtgttaccaggccgagtgggatgactatgtgcccaaactgtacg
agcagctgtctgggaagtag

FIG. 9G

BMS-PTX-062
atgtcggctgcagaggcggggggtgttttccacagagccaggggcaggaccctggccgcgtttcccgc
agaaaaggaaagcgaatggaaaggcccattctacttcatcctgggcgcagacccacagtttgggctga
tcaaggcctggtccactggggactgtgacaatggcggtgacgaatgggaacaggagatccgtctaact
gagcaagccgtccaggccatcaacaagctgaaccccaaacccaaattcttcgttctgtgcggcgacct
catccacgccatgccagggaagccgtggcggacggagcagacggaggacctgaagcgagtgcttaggg
cagtggacagggccatcccactggtccttgtcagcggcaaccatgacattggcaacacccccacggcc
gagaccgtcgaggagttctgccggacttggggatatgactacttcagcttctgggtcgggggcgtcct
gttcctggtcctcaactcccagttctacgagaacccctccaaatgccccagcctgaagcaggctcagg
accagtggctggacgagcagctgagcatcgcgaggcagcggcactgccagcatgccatcgtcttccag
cacatcccgctgttcctggagagcatcgacgaggacgacgactactacttcaacctcagcaagtccac
tcggaagaagttggcagacaagttcatccacgcaggtgtcagagtcgtgttctcaggccactaccaca
ggaatgccgggggtacctaccagaacctcgacatggtggtgtcatctgccattggatgccagctgggc
agagacccccacgggctccgagtcgtggtggtcaccgccgagaaaattgttcaccgatactacagtct
agatgagctgagtgagaaaggaatagaagacgatctcatggatttgatcaagaaaaaatga BMS-PTX-260
ggcacgagggattctccgggatattaccggagacggagtgttttattattagcctttcttaggtggac
atttccatttgaattacaagtcctttaggctgggcgtggtgcatggctgtaatctcagcaccttggga
ggctgaggcaggaagatcacttgaggccaggcgttggagagcagcctgggcaaggtggcaagaacctt
gtctctacaaaaaaaaaagcgtctgccatcatggatgttctcgcagaagcaaatggcacctttgcctt
aaaccttttgaaaacgctgggtaaagacaactcgaagaatgtgtttttctcacccatgagcatgtcct
gtgccctggccatggtctacatggggggcaaagggaaacaccgctgcacagatggcccagatactttct
ttcaataaaagtggcggtggtggagacatccaccagggcttccagtctcttctcaccgaagtgaacaa
gactggcacgcagtacttgcttagggtggccaacaggctctttggggaaaagtcttgtgatttcctct
catcttttagagattcctgccaaaaattctaccaagcagagatggaggagcttgactttatcagcgcc
gtagagaagtccagaaaacacataaacacctgggtagctgaaaagacagaaggtaaaattgcggagtt
gctctctccgggctcagtggatccattgacaaggctggttctggtgaatgctgtctatttcagaggaa
actgggatgaacagtttgacaaggagaacaccgaggagagactgtttaaagtcagcaagaatgaggag
aaacctgtgcaaatgatgtttaagcaatctacttttaagaagacctatataggagaaatatttaccca
aatcttggtgcttccatatgttggcaaggaactgaatatgatcatcatgcttccggacgagaccactg
acttgagaacggtggagaaagaactcacttacgagaagttcgtagaatggacgaggctggacatgatg
gatgaagaggaggtggaagtgtccctcccgcggtttaaactagaggaaagctacgacatggagagtgt
cctgcgcaacctgggcatgactgatgccttcgagctgggcaaggcagacttctctggaatgtcccaga
cagacctgtctctgtccaaggtcgtgcacaagtcttttgtggaggtcaatgaggaaggcacggaggct
gcagccgccacagctgccatcatgatgatgcggtgtgccagattcgtcccccgcttctgcgccgacca
ccccttcctttttcttcatccagcacagcaagaccaacgggattctcttctgcggccgcttttcctctc
cgtgaggacagggcagtcttggtgtgcagcccctctcctctctgtcccctgacactccacagtgtgcc
tgcaacccaagtggccttatccgtgcagtggtggcagttcagaaataaagggcccatttgtgggatgc
cgcattcaaaaaaaaaaaaaaaaaaa

FIG. 9H

BMS-PTX-(29)147 acggagatctcgccggctttacgttcacctcggtgtctgcagcaccctccgcttcctctcctaggcga
cgagacccagtggctagaagttcaccatgtctattctcaagatccatgccagggagatctttgactct
cgcgggaatcccactgttgaggttgatctcttcacctcaaaggtctcttcagagctgctgtgcccag
tggtgcttcaactggtatctatgaggccctagagctccgggacaatgataagactcgctatatgggga
agggtgtctcaaaggctgttgagcacatcaataaaactattgcgcctgccctggttagcaagaaactg
aacgtcacagaacaagagaagattgacaaactgatgatcgagatggatggaacagaaaataaatctaa
gtttggtgcgaacgccattctgggggtgtcccttgccgtctgcaaagctggtgccgttgagaagggggg
tccccctgtaccgccacatcgctgacttggctggcaactctgaagtcatcctgccagtcccggcgttc
aatgtcatcaatggcggttctcatgctggcaacaagctggccatgcaggagttcatgatcctcccagt
cggtgcagcaaacttcagggaagccatgcgcattggagcagaggtttaccacaacctgaagaatgtca
tcaaggagaaatatgggaaagatgccaccaatgtgggggatgaaggcgggtttgctcccaacatcctg
gagaataaagaaggcctggagctgctgaagactgctattgggaaagctggctacactgataaggtggt
catcggcatggacgtagcggcctccgagttcttcaggtctgggaagtatgacctggacttcaagtctc
ccgatgaccccagcaggtacatctcgcctgaccagctggctgacctgtacaagtccttcatcaaggac
tacccagtggtgtctatcgaagatccctttgaccaggatgactggggagcttggcagaagttcacagc
cagtgcaggaatccaggtagtgggggatgatctcacagtgaccaacccaaagaggatcgccaaggccg
tgaacgagaagtcctgcaactgcctcctgctcaaagtcaaccagattggctccgtgaccgagtctctt
caggcgtgcaagctggcccaggccaatggttggggcgtcatggtgtctcatcgttcgggggagactga
agataccttcatcgctgacctggttgtggggctgtgcactgggcagatcaagactggtgccccttgcc
gatctgagcgcttggccaagtacaaccagctcctcagaattgaagaggagctgggcagcaaggctaag
tttgccggcaggaacttcagaaaccccttggccaagtaagctgtgggcaggcaagccttcggtcacct
gttggctacacagacccctcccctcgtgtcagctcaggcagctcgaggcccccgaccaacacttgcag
gggtccctgctagttagcgccccaccgccgtggagttcgtaccgcttccttagaacttctacagaagc
caagctccctggagccctgttggcagctctagcttttgcagtcgtgtaatgggcccaagtcattgttt
ttctcgcctcactttccaccaagtgtctagagtcatgtgagcctcgtgtcatctccggggtggccaca
ggctagatccccggtggttttgtgctcaaataaaaagcctcagtgacccatgag

| Analyte | Detected Human Plasma Range | Method(s) |
|---|---|---|
| 14-3-3 ZETA | 10 – 600 ng/ml | ELISA, Western |
| MIF | 200 – 3500 pg/ml | ELISA |

FIG. 16A

>gi|1711130|gb|AAC53254.1| 14-3-3 zeta protein [Mus musculus]
MDKNELVQKAKLAEQAERYDDMAACMKSVTEQGAELSNEERNLLSVAYKNVVGARRSSWRVVSSIEQKTE
GAEKKQQMAREYREKIETELRDICNDVLSLLEKFLIPNASQPESKVFYLKMKGDYYRYLAEVAAGDDKKG
IVDQSQQAYQEAFEISKKEMQPTHPIRLGLALNFSVFYYEILNSPEKACSLAKTAFDEAIAELDTLSEES
YKDSTLIMQLLRDNLTLWTSDTQGDEAEAGEGGEN

FIG. 16B

>gi|19354170|gb|AAH24895.1| Macrophage migration inhibitory factor [Mus musculus]
MPMFIVNTNVPRASVPEGFLSELTQQLAQATGKPAQYIAVHVVPDQLMTFSGTNDPCALCSLHSIGKIGG
AQNRNYSKLLCGLLSDRLHISPDRVYINYYDMNAANVGWNGSTFA

FIG. 16C

>gi|402511|dbj|BAA04534.1| 14-3-3 protein zeta-subtype [Rattus norvegicus]
MDKNELVQKAKLAEQAERYDDMAACMKSVTEQGAELSNEERNLLSVAYKNVVGARRSSWRVVSSIEQKTE
GAEKKQQMAREYREKIETELRDICNDVLSLLEKFLIPNASQPESKVFYLKMKGDYYRYLAEVAAGDDKKG
IVDQSQQAYQEAFEISKKEMQPTHPIRLGLALNFSVFYYEILNSPEKACSLAKTAFDEAIAELDTLSEES
YKDSTLIMQLLRDNLTLWTSDTQGDEAEAGEGGEN

FIG. 16D

>gi|694108|gb|AAA62644.1| macrophage migration inhibitory factor
MPMFIVNTNVPRASVPEGFLSELTQQLAQATGKPAQYIAVHVVPDQLMTFRGTSDPCALCSLHSIGKIGG
AQNRNYSKLLCGLLSDRLHISPDRVYINYYDMNAANVGWNGSTFA

FIG. 17A

>gi|1711129:1-738 Mus musculus 14-3-3 zeta protein mRNA, complete cds
ATGGATAAAAATGAGCTGGTGCAGAAGGCCAAGCTGGCCGAGCAGGCAGAGCGATATGATGACATGGCAG
CCTGCATGAAGTCTGTCACTGAGCAGGGAGCTGAGCTGTCGAATGAGGAGAGAAACCTTCTCTCTGTTGC
TTATAAAAACGTTGTAGGAGCCCGTAGGTCATCGTGGAGGGTCGTCTCAAGTATTGAGCAGAAGACGGAA
GGTGCTGAGAAAAAGCAGCAGATGGCTCGAGAATACAGAGAGAAGATCGAGACGGAGCTGCGTGACATCT
GCAACGATGTACTGTCTCTTTTGGAAAAGTTCTTGATCCCCAATGCTTCGCAACCAGAAAGCAAAGTCTT
CTATTTGAAAATGAAGGGTGACTACTACCGTTACTTGGCCGAGGTTGCTGCTGGTGATGACAAGAAAGGA
ATTGTGGACCAGTCACAGCAAGCATACCAAGAAGCATTTGAAATCAGCAAAAAGGAGATGCAGCCGACAC
ACCCCATCAGACTGGGTCTGGCCCTCAACTTCTCTGTGTTCTATTACGAGATCCTGAACTCCCCAGAGAA
AGCCTGCTCTCTTGCAAAAACAGCTTTCGATGAAGCCATTGCTGAACTTGATACATTAAGTGAAGAGTCG
TACAAAGACAGCACGCTAATAATGCAGTTACTGAGAGACAACTTAACATTGTGGACATCGGATACCCAAG
GAGATGAAGCAGAAGCAGGAGAAGGAGGGGAAAATTAA

FIG. 17B

>gi|19354169:63-410 Mus musculus macrophage migration inhibitory factor, mRNA (cDNA clone MGC:18483 IMAGE:3978685), complete cds
ATGCCTATGTTCATCGTGAACACCAATGTTCCCCGCGCCTCCGTGCCAGAGGGGTTTCTGTCGGAGCTCA
CCCAGCAGCTGGCGCAGGCCACCGGCAAGCCCGCACAGTACATCGCAGTGCACGTGGTCCCGGACCAGCT
CATGACTTTTAGCGGCACGAACGATCCCTGCGCCCTCTGCAGCCTGCACAGCATCGGCAAGATCGGTGGT
GCCCAGAACCGCAACTACAGTAAGCTGCTGTGTGGCCTGCTGTCCGATCGCCTGCACATCAGCCCGGACC
GGGTCTACATCAACTATTACGACATGAACGCTGCCAACGTGGGCTGGAACGGTTCCACCTTCGCTTGA

FIG. 17C

>gi|402510:129-866 Rattus norvegicus mRNA for 14-3-3 protein zeta-subtype, complete cds
ATGGATAAAAATGAGCTGGTGCAGAAGGCCAAGCTGGCCGAGCAGGCAGAGCGATACGATGACATGGCAG
CCTGCATGAAGTCTGTCACTGAGCAAGGAGCCGAGCTGTCTAACGAGGAGAGGAACCTTCTCTCTGTTGC
TTATAAAAACGTTGTAGGAGCCCGTAGGTCATCTTGGAGGGTCGTCTCGAGTATTGAGCAGAAGACGGAA
GGTGCTGAGAAAAAGCAGCAGATGGCTCGAGAATACAGAGAGAAGATCGAGACGGAGCTGAGGGACATCT
GCAACGACGTACTGTCTCTTTTGGAAAAGTTCTTGATCCCCAATGCTTCGCAGCCAGAAAGCAAAGTCTT
CTATTTGAAAATGAAGGGTGACTACTACCGCTACTTGGCTGAGGTTGCTGCTGGTGATGACAAGAAAGGA
ATTGTGGACCAGTCACAGCAAGCATACCAAGAAGCATTTGAAATCAGCAAAAAGGAGATGCAGCCGACAC
ACCCCATCAGACTGGGTCTGGCCCTCAACTTCTCTGTGTTCTACTATGAGATCCTGAACTCCCCAGAGAA
AGCCTGCTCTCTTGCAAAAACAGCTTTTGATGAAGCCATTGCTGAACTTGATACATTAAGTGAAGAGTCG
TACAAAGACAGCACGCTAATAATGCAGTTACTGAGAGACAACTTGACATTGTGGACATCGGATACCCAAG
GAGACGAAGCAGAAGCGGGAGAAGGAGGGGAAAATTAA

FIG. 17D

>gi|694107:55-402 Rattus norvegicus macrophage migration inhibitory factor mRNA, complete cds
ATGCCTATGTTCATCGTGAACACCAATGTTCCCCGCGCCTCCGTGCCAGAGGGGTTTCTCTCCGAGCTCA
CCCAGCAGCTGGCGCAGGCCACCGGCAAGCCGGCACAGTACATCGCAGTGCACGTGGTCCCGGACCAGCT
CATGACTTTTAGAGGCACGAGCGACCCCTGCGCCCTCTGCAGCCTGCACAGCATCGGCAAGATCGGTGGC
GCCCAGAACCGCAACTACAGCAAGCTGCTGTGCGGCCTGCTGTCCGATCGCCTGCACATCAGCCCGGACC
GGGTCTACATCAACTATTACGACATGAACGCAGCCAACGTGGGCTGGAACGGTTCCACCTTCGCTTGA

FIG. 18

PRIMERS FOR MOUSE PTX-265

| OLIGO | start | len | tm | gc% | sequence |
|---|---|---|---|---|---|
| LEFT PRIMER | 41 | 20 | 59.97 | 50.00 | AGCAGGCAGAGCGATATGAT |
| RIGHT PRIMER | 238 | 20 | 60.10 | 50.00 | GAGCCATCTGCTGCTTTTTC |

PRODUCT SIZE: 198 nucleotides

PRIMERS FOR MOUSE PTX-837

| OLIGO | start | len | tm | gc% | sequence |
|---|---|---|---|---|---|
| LEFT PRIMER | 43 | 19 | 60.10 | 57.89 | GTGCCAGAGGGGTTTCTGT |
| RIGHT PRIMER | 248 | 20 | 60.08 | 55.00 | AGGCCACACAGCAGCTTACT |

PRODUCT SIZE: 206 nucleotides

PRIMERS FOR RAT PTX-265

| OLIGO | start | len | tm | gc% | sequence |
|---|---|---|---|---|---|
| LEFT PRIMER | 194 | 20 | 59.99 | 50.00 | TTGAGCAGAAGACGGAAGGT |
| RIGHT PRIMER | 394 | 20 | 60.03 | 60.00 | CCTCAGCCAAGTAGCGGTAG |

PRODUCT SIZE: 201 nucleotides

PRIMERS FOR RAT PTX-837

| OLIGO | start | len | tm | gc% | sequence |
|---|---|---|---|---|---|
| LEFT PRIMER | 43 | 20 | 61.17 | 60.00 | GTGCCAGAGGGGTTTCTCTC |
| RIGHT PRIMER | 240 | 20 | 59.96 | 55.00 | CAGCAGCTTGCTGTAGTTGC |

PRODUCT SIZE: 198 nucleotides

IDENTIFICATION OF BIOMARKERS FOR LIVER TOXICITY

This application claims benefit to provisional application U.S. Ser. No. 60/480,964 filed Jun. 24, 2003; and to provisional application U.S. Ser. No. 60/529,806, filed Dec. 16, 2003; under 35 U.S.C. 119(e). The entire teachings of the referenced applications are incorporated herein by reference.

FIELD OF THE INVENTION

The present invention relates generally to the fields of proteomics, liquid chromatography, mass spectrometry, and the screening of chemical and biological compounds. More specifically, the invention relates to newly developed methods for predicting in vitro and/or in vivo hepatic toxicity based on screening for levels of specific biomarker polypeptides or polynucleotides. Such methods allow the development of therapeutic compounds having increased efficacy and safety, and can be used to prevent injury caused by the administration of hepatotoxic compounds.

BACKGROUND OF THE INVENTION

Idiosyncratic hepatotoxicity occurs in a particular subgroup of the population for which the pathogenesis is unknown. Such toxicity is not predicted by either pre-clinical animal models or pre-marketing clinical trials. While inherently toxic compounds are readily identified and removed from the development pipeline, idiosyncratic compounds are put on the market, only to wreak havoc on the larger patient population. The effects of idiosyncratic compounds on the general public include varying degrees of hepatic injury, which can lead to liver failure, transplantation, and even death. Idiosyncratic hepatotoxicity arises too frequently in the population (2.7%; In *Energy and Commerce,* 107th Congress, Second Session ed.; FDA: Washington, D.C., 2002, pp. 1), and is therefore a major cause for concern in the pharmaceutical industry (Meadows, M., 2002*, FDA Consumer Magazine* 36:1).

Currently, hepatic injury due to medications is one of the most common causes of acute liver disease and jaundice (see, e.g., Hepatotoxicity Clinical Research Network). The mortality rate of hepatic idiosyncratic drug reactions is quite high, and over half of the cases of acute liver failure in the United States are due to medications exhibiting idiosyncratic hepatotoxicity. In fact, the risks of drug induced toxicity are a primary concern of the pharmaceutical industry and accentuate the need for early and reliable predictors of potential adverse events (Frank and Hargreaves. Nature Reviews/Drug Discovery. 2, 566-580 (2003)). It is therefore clear that the current pre-clinical safety assessment systems are inadequate for the complete and comprehensive evaluation of new therapeutic entities. Yet, elucidation of the mechanisms of hepatic drug injury is often difficult.

Drug-induced liver disease is typically unpredictable and rare. Most of the medications that cause acute liver injury in humans do not produce injury in experimental models, and patients exhibiting hepatotoxicity often have multiple risk factors for liver disease (see, e.g., Hepatotoxicity Clinical Research Network).

Drug-induced liver injury is also quite variable in clinical expression (see, e.g., Hepatotoxicity Clinical Research Network). Patterns of hepatotoxic injury can mimic most other forms of liver disease, including acute viral hepatitis, autoimmune liver disease, bland cholestasis, mixed cholestatic-hepatic syndromes, acute cholangitis, microvesicular steatosis with lactic acidosis, alcohol-like steatohepatitis, and venoocclusive disease. In addition, drugs that cause hepatotoxicity are often withdrawn from use, and their mechanisms of injury remain unknown.

The majority of preliminary compound screening in the pharmaceutical industry is currently conducted using in vitro cell based assays (Lin et al., Current Topics in Med. Chem. 3, 1125 (2003)). These assays typically measure cell viability and metabolism, apoptosis or rely on the measurement of general toxicity indicators that are not applicable to preclinical animal studies. Conversely, traditional in vivo biomarker measurements are typically not suitable for use in high throughput cell based assays (Streiner and Norman., Health Measurement Scales: A practical Guide to Their Development and Use (Oxford University Press, Oxford, 1995); Swanson., Dis. Markers. 18, 47-56 (2002)).

A common set of analytes that could be used both to predict toxicity in vitro and gauge toxic effects in vivo would therefore be of great value. A single set of reagents and standards could be used to evaluate compounds from initial screening, through testing in pre-clinical species, and potentially in clinical trials. Such universal indicators of toxicity should meet several criteria. First, they should correctly identify toxic compounds with diverse mechanisms of action, including various chemical classes/chemotypes. Second, changes in these biomarkers should be consistent, quantifiable and reflect the degree of toxic insult. Third, assays should be adaptable to high throughput technologies without becoming prohibitively expensive. Fourth, in vivo sample collection should be non or minimally invasive, i.e. urine or blood. Fifth, since there may be a need to analyze archival samples, the biomarker needs to be stable.

Despite the clinical significance of hepatic idiosyncratic injury, this form of liver injury is a relatively unstudied area of medicine. Therefore, there is a substantial need in the art to identify and characterize biomarkers useful for predicting in vivo hepatic toxicity. The inventors describe herein the identification of several idiosyncratic hepatotoxicity biomarkers that are capable of predicting the incidence of idiosyncratic hepatotoxicity for a particular compound both in vitro as well as in vivo that meets each of the five criteria described supra.

SUMMARY OF THE INVENTION

In accordance with the present invention, proteomic and immunological techniques were employed to identify biomarker polypeptides (SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64), which show increased levels in the media obtained from modified hepatocyte cell lines treated with toxic drugs as compared to media obtained from cells treated with non-toxic drugs or vehicle alone. Such biomarker polypeptides are particularly useful for pre- or post-clinical screening, which can be used to identify compounds or combinations of compounds that cause hepatic injury and thereby prevent medical complications from hepatotoxicity, e.g., idiosyncratic hepatotoxicity.

Accordingly, the present invention encompasses biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64), that have utility in predicting in vivo hepatotoxicity of a wide range of test substances, including PPAR agonists, anti-inflammatory drugs, neurological drugs, estrogenic and anti-estrogenic drugs, anti-angina drugs, muscle relaxants, and antihistamines, among others. Such biomarker polypeptides can be used in the screening methods of the invention to predict toxic effects of treatment with one or more drugs, compounds, or other therapeutic agents before, after, or concurrently with clinical testing.

The present invention also encompasses antibodies (e.g., polyclonal or monoclonal antibodies, or fragments thereof) specifically directed against one or more of the biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64). Such antibodies can be used detect and measure the levels of the biomarker polypeptides of the present invention, and can be used in the screening methods of the invention, as described herein. In various aspects of the invention, the screening methods can be manual or automated, can be used in conjunction with one or more kits, and can test for hepatotoxicity in one patient or a patient population (see below).

The present invention additionally encompasses assays that use biomarker polypeptides (e.g., SEQ ID NO:1 to SEQ ID NO:15 and SEQ ID NO:61 to SEQ ID NO:64) to predict prior to treatment if an individual patient will be unable to tolerate one or more drugs, compounds, or other therapeutic agents (i.e., test substances) due to hepatotoxic effects, e.g., idiosyncratic hepatotoxicity. In one aspect of the invention, cells from a patient's liver or liver for transplantation can be modified to overexpress one or more cytochrome P450 enzymes, and then assayed (e.g., by immunoassay) to determine the levels of one or more biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64). The cells can be treated with at least one test substance, and extracellular and/or intracellular levels of the biomarker polypeptide(s) in the presence and absence of the test substance(s) can be compared. The observation of high levels of one or more biomarker polypeptide(s) in the presence of the substance(s) can be used to predict in vivo hepatoxicity. In various aspects of the invention, the test substance(s) can comprise one or more PPAR agonists, anti-inflammatory drugs, neurological drugs, estrogenic or anti-estrogenic drugs, anti-angina drugs, muscle relaxants, antihistamines, or other drugs, compounds, or therapeutic agents.

The present invention further encompasses screening assays that measure levels of one or more biomarker polypeptides (e.g., SEQ ID NO:1 to SEQ ID NO:15 and SEQ ID NO:61 to SEQ ID NO:64) to determine or predict if a drug, compound, or other therapeutic agent will have hepatotoxic effects (e.g., idiosyncratic hepatotoxicity) in a patient population. In one aspect of the invention, hepatic cell lines overexpressing one or more cytochrome P450 enzymes can be assayed (e.g., by immunoassay) to determine the levels of one or more biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64), in the presence and absence of at least one test substance. As examples, the extracellular media, intact cells, and/or cell lysates can be used to measure biomarker polypeptide levels. The observation of elevated levels of one or more biomarker polypeptides in the presence of the test substance(s) can be used to predict the likelihood of in vivo hepatotoxicity. In specific aspects of the invention, the test substances can comprise one or more PPAR agonists, anti-inflammatory drugs, neurological drugs, estrogenic or anti-estrogenic drugs, anti-angina drugs, muscle relaxants, antihistamines, or other drugs, compounds, or therapeutic agents. In an additional aspect, the assays of the invention are automated for high throughput screening.

The present invention likewise encompasses screening assays that measure levels of one or more biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64), to monitor a drug, compound, or other therapeutic agent for hepatotoxic effects (e.g., idiosyncratic hepatotoxicity) during treatment of a patient or patient population. In particular aspects, biological samples (e.g., blood, urine, and/or saliva, etc.) can be obtained from one or more patients prior to treatment with a test substance and at designated intervals during treatment. The levels of at least one biomarker polypeptide can be compared in each sample, and the observation of increased biomarker levels that coincide with the commencement/duration of treatment can be used to predict the likelihood hepatotoxic effects (e.g., idiosyncratic hepatotoxicity). The results of such screening may be used to determine the need to modify or discontinue an existing treatment.

The present invention also encompasses microarrays, e.g., protein, antibody, or cell-based microarrays, which can be used in conjunction with the disclosed screening assays. Such arrays can comprise one or more biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64), antibodies that specifically recognize one or more of these polypeptides, or cells producing one or more of these polypeptides. The protein, antibody, and cell-based microarrays can be used in the manual or automated screening assays of the invention as disclosed herein to test one or more drugs, compounds, or other therapeutic agents. For protein microarrays, polypeptides obtained from hepatic cells (e.g., from extracellular media or cell lysates) incubated in the presence and absence of at least one test substance can be affixed to a support, and then contacted with antibodies that specifically bind to one or more biomarker polypeptides (e.g., SEQ ID NO:1 to SEQ ID NO:15 and SEQ ID NO:61 to SEQ ID NO:64). For antibody microarrays, one or more anti-biomarker antibodies can be affixed to a support, and then contacted with extracellular media or cell lysates obtained from hepatic cells incubated in the presence and absence of at least one test substance. For cell-based microarrays, one or more cells can be affixed to a support, and then incubated in the presence and absence of at least one test substance. The microarrays can then be analyzed (e.g., by immunoassay) to determine elevated levels of at least one biomarker polypeptide in the presence of the test substance (s), which can be used to predict in vivo hepatotoxicity. In specific aspects of the invention, the test substances can comprise one or more PPAR agonists, anti-inflammatory drugs, neurological drugs, estrogenic or anti-estrogenic drugs, anti-angina drugs, muscle relaxants, antihistamines, or other drugs, compounds, or therapeutic agents.

The present invention additionally encompasses kits comprising one or more biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), in addition to their respective mouse and rat orthologues, mouse BMS-PTX-265 (SEQ ID NO:61), rat BMS-PTX-265 (SEQ ID NO:62), mouse BMS-PTX-837 (SEQ ID NO:63), and rat BMS-PTX-837 (SEQ ID NO:64), and anti-biomarker antibodies, which can be used to predict the likelihood of hepatotoxic effects, such as idiosyncratic hepatotoxicity, of one or more drugs, compounds, or other therapeutic agents. Such kits can be used in clinical or pre-clinical settings, and can include one or more biomarker polypeptides (e.g., SEQ ID NO:1 to SEQ ID NO:15 and SEQ ID NO:61 to SEQ ID NO:64) and anti-biomarker antibodies. In specific aspects of the invention, the kits can include one or more microarrays comprising antibodies that specifically bind with these biomarker polypeptides. The kits can be employed in conjunction with the manual and automated screening methods of the invention. In various aspects, the kits can include instructions for use, and reagents and materials for measuring levels of the biomarker polypeptides e.g., in immunoassays, such as enzyme linked immunosorbent assays (ELISAs); Western blotting; direct or indirect immunofluorescence, immunohistochemistry, and the like.

The present invention further encompasses cell culture systems for the identification of polypeptides, in addition to the specified biomarker polypeptides (SEQ ID NO:1 to SEQ ID NO:15 and SEQ ID NO:61 to SEQ ID NO:64), whose levels (e.g., extracellular, intracellular, or cell lysate levels) correlate with hepatic toxicity. In specific aspects of the invention, such systems can comprise hepatic cell lines, which can be incubated in the presence or absence of one or more drugs, compounds, or other therapeutic agents. The biomarker polypeptides identified from these systems can be useful for predicting test substances (or combinations of test substances) that can directly or indirectly cause in vivo hepatic injury, e.g., idiosyncratic hepatotoxicity. Test substances for evaluation can include PPAR agonists, anti-inflammatory drugs, neurological drugs, estrogenic and anti-estrogenic drugs, anti-angina drugs, muscle relaxants, antihistamines, and other drugs, compounds, and therapeutic agents.

The present invention encompasses methods of measuring the levels of polypeptides (e.g., extracellular polypeptides in the media) using mass spectrometer data to determine the number of peptide "hits" for each polypeptide, and comparing the results obtained in the presence and absence of a test substance. In various aspects, the test substance used with these methods comprises a PPAR agonist, anti-inflammatory drug, neurological drug, estrogenic and anti-estrogenic drug, anti-angina drug, muscle relaxant, antihistamines, or other drug, compound, or therapeutic agent.

Also encompassed by the invention are nucleic acids encoding the disclosed biomarker polypeptides (SEQ ID NO:1 to SEQ ID NO:15 and SEQ ID NO:61 to SEQ ID NO:64, and SEQ ID NO:61 to SEQ ID NO:64), e.g., as set forth in SEQ ID NO:46 to SEQ ID NO:60, and SEQ ID NO:65 to SEQ ID NO:68, and fragments, variants, and derivatives thereof, as well as screening assays, kits, microarrays, and cell culture systems employing these nucleic acids. In one aspect of the invention, screening assays (e.g., RT-PCR or in situ assays) that measure levels of one or more biomarker nucleic acids (e.g., SEQ ID NO:46 to SEQ ID NO:60 and SEQ ID NO:65 to SEQ ID NO:68) are used to predict or determine if a drug, compound, or other therapeutic agent will have in vivo hepatotoxic effects, e.g., idiosyncratic hepatotoxicity. In accordance with such assays, levels of at least one biomarker nucleic acid is determined for hepatocytes that have been modified to overexpress one or more cytochrome P450 enzymes and then incubated in the presence and absence of one or more test substances. Elevated levels of one or more biomarker nucleic acids in the presence of the test substance(s) can be used to predict the likelihood of in vivo hepatotoxicity, e.g., idiosyncratic hepatotoxicity.

The present invention also encompasses a method of predicting hepatotoxicity of a test substance comprising the steps of: a) incubating a hepatocyte in the presence and absence of a test substance; and b) comparing levels of at least one biomarker polypeptide selected from the group consisting of SEQ ID NO:1 to SEQ ID NO:15 and SEQ ID NO:61 to SEQ ID NO:64, in the presence and absence of said test substance; wherein an elevated level of said biomarker polypeptide(s) in the presence of the test substance indicates that the substance is predicted to cause hepatotoxicity, and wherein the level of said biomarker polypeptide(s) is measured using single or multi dimensional high performance liquid chromatography coupled to tandem mass spectrometry wherein the number of peptide hits from each protein identification are used to determine the abundance of said biomarker polypeptide(s) in the presence and absence of said test substance.

Further objects, features, and advantages of the present invention will be better understood upon a reading of the detailed description of the invention when considered in connection with the accompanying figures or drawings.

BRIEF DESCRIPTION OF THE FIGURES

FIGS. 4A-4B. The primary amino acid sequences of biomarker polypeptides BMS-PTX-265 (FIG. 4A; SEQ ID NO:1) and BMS-PTX-837 (FIG. 4B; SEQ ID NO:2) as expressed in single letter code. BMS-PTX-265 corresponds to GenBank Identifier No. 112695; BMS-PTX-837 corresponds to GenBank Identifier No. 30583135.

FIG. 5A: Results were derived from densitometric analyses of each protein band and calculated as a percentage of total signal intensity. FIG. 5B: Results are shown as discrete values. The asterisks indicate those data that showed a statistically significant difference compared to the DMSO vehicle ($p<0.05$; Troglitazone, Ciglitazone, and Farglitazar). The solid bars indicate the compounds known to be toxic, based on clinical and post-marketing data.

FIGS. 7A-7C. The primary amino acid sequences of additional biomarker polypeptides (see also Tables 3 and 4). FIG. 7A: BMS-PTX-447; (GenBank Ident. No. 65922; SEQ ID NO:3); BMS-PTX-749 (GenBank Ident. No. 2460318; SEQ ID NO:4); BMS-PTX-607 (GenBank Ident. No. 7212867; SEQ ID NO:5); BMS-PTX-808 (GenBank Ident. No. 4505029; SEQ ID NO:6); BMS-PTX-860 (GenBank Ident. No. 14603147; SEQ ID NO:7); and BMS-PTX-254 (GenBank Ident. No. 4557801; SEQ ID NO:8). FIG. 7B: BMS-PTX-225 (GenBank Ident. No. 15216175; SEQ ID NO:9); BMS-PTX-(39)147 (GenBank Ident. No. 2497297; SEQ ID NO:10); BMS-PTX-459 (GenBank Ident. No. 2136258; SEQ ID NO:11); BMS-PTX-120 (GenBank Ident. No. 4505621; SEQ ID NO:12); BMS-PTX-062 (GenBank Ident. No. 10434265; SEQ ID NO:13); and BMS-PTX-260 (GenBank Ident. No. 20141722; SEQ ID NO:14). FIG. 7C: BMS-PTX-(29)147 (GenBank Ident. No. 119339; SEQ ID NO:15).

FIGS. 8A-8B. Non-limiting examples of primers that can be used for the amplification of biomarker polynucleotide sequences, for example, for RT-PCR analysis. FIG. 8A: BMS-PTX-265 (primers SEQ ID NO:16-SEQ ID NO:17), BMS-PTX-447 (primers SEQ ID NO:18-SEQ ID NO:19), BMS-PTX-749 (primers SEQ ID NO:20-SEQ ID NO:21), BMS-PTX-607 (primers SEQ ID NO:22-SEQ ID NO:23), BMS-PTX-808 (primers SEQ ID NO:24-SEQ ID NO:25), BMS-PTX-860 (primers SEQ ID NO:26-SEQ ID NO:27), BMS-PTX-254 (primers SEQ ID NO:28-SEQ ID NO:29), BMS-PTX-225 (primers SEQ ID NO:30-SEQ ID NO:31), and BMS-PTX-(39)147 (primers SEQ ID NO:32-SEQ ID NO:33). FIG. 8B: BMS-PTX-459 (primers SEQ ID NO:34-SEQ ID NO:35), BMS-PTX-120 (primers SEQ ID NO:36-SEQ ID NO:37), BMS-PTX-837 (primers SEQ ID NO:38-SEQ ID NO:39), BMS-PTX-062 (primers SEQ ID NO:40-SEQ ID NO:41), BMS-PTX-260 (primers SEQ ID NO:42-SEQ ID NO:43), and BMS-PTX-(29)147 (primers SEQ ID NO:44-SEQ ID NO:45). Key for FIGS. 8A-8B: start=nucleotide position in cDNA where primer sequence begins; len=length of primer; gc %=percent guanine and cytosine content of the primer; tm=melting temperature of the hybrid; any=a measure of internal complementarity to predict hybridization of the primer; 3'=a measure of 3' complementarity of the primer; seq=sequence of primer.

FIGS. 9A-9H. The nucleotide sequences encoding the biomarker polypeptides. FIG. 9A: BMS-PTX-265 (SEQ ID NO:46; GenBank Ident. No. 30331109) and BMS-PTX-837 (SEQ ID NO:47; GenBank Ident. No. 30583134). FIG. 9B: BMS-PTX-447 (SEQ ID NO:48; GenBank Ident. No. 12804776) and BMS-PTX-749 (SEQ ID NO:49; GenBank Ident. No. 2460317). FIG. 9C: BMS-PTX-607 (SEQ ID NO:50; GenBank Ident. No. 7212866) and BMS-PTX-808 (SEQ ID NO:51; GenBank Ident. No. 4505028). FIG. 9D: BMS-PTX-860 (SEQ ID NO:52; GenBank Ident. No. 14603146), BMS-PTX-254 (SEQ ID NO:53; GenBank Ident. No. 4557800), and BMS-PTX-225 (SEQ ID NO:54; GenBank Ident. No. 15216174). FIG. 9E: BMS-PTX-(39)147 (SEQ ID NO:55; GenBank Ident. No. 886257). FIG. 9F: BMS-PTX-459 (SEQ ID NO:56; GenBank Ident. No. 971271) and BMS-PTX-120 (SEQ ID NO:57; GenBank Ident. No. 4505620). FIG. 9G: BMS-PTX-062 (SEQ ID NO:58; GenBank Ident. No. 10434264) and BMS-PTX-260 (SEQ ID NO:59; GenBank Ident. No. 12655086). FIG. 9H: BMS-PTX-(29)147 (SEQ ID NO:60; GenBank Ident. No. 182113).

FIG. 16A; SEQ ID NO:61) and murine MIF (mouse BMS-PTX-837; FIG. 16B; SEQ ID NO:62) serum levels in mice either prior ("Pre-Treatment") or subsequent ("Post-Treatment") to Compound A exposure at either a dose of 10 mg/kg (FIGS. 10A and 10C) or a dose of 50 mg/kg (FIGS. 10B and 10D). The mouse number is noted on the X-axis. Bars represent relative luminosity as determined by integrated band intensity. Serum levels of were quantified using Quantity One software (Bio-Rad, Hercules, Calif.).

FIG. 16C; SEQ ID NO:63) and MIF (rat BMS-PTX-837; FIG. 16D; SEQ ID NO:64) serum levels in rats following Compound B exposure. Values were determined by Western blot using Quantity One software (Bio-Rad, Hercules, Calif.) and represent the percent increase post-treatment as a percentage over the observed pre-treatment serum levels with either Compound B or vehicle alone ("Vehicle"). Bars represent relative luminosity as determined by integrated band intensity.

FIG. 4A; SEQ ID NO:1) levels as measured by both Western blot and ELISA as described herein.

FIG. 4A; SEQ ID NO:1) and human MIF that was observed in human volunteers using commercially available recombinant MIF and the recombinant 14-3-3 ZETA described herein, as standards.

FIGS. 16A-D. The primary amino acid sequences of the mouse and rat orthologs of the human BMS-PTX-265 and BMS-PTX-837 biomarker polypeptides. FIG. 16A: mouse BMS-PTX-265; (GenBank Ident. No. gi|AAC53254; SEQ ID NO:61); FIG. 16B: mouse BMS-PTX-837 (GenBank Ident. No. gi|AAH24895; SEQ ID NO:62); FIG. 16C: rat BMS-PTX-265 (GenBank Ident. No. gi|BAA04534; SEQ ID NO:63); and FIG. 16D: BMS-PTX-837 (GenBank Ident. No. gi|AAA62644; SEQ ID NO:64).

FIGS. 17A-D. The nucleotide sequences encoding the biomarker polypeptides acid sequences of the mouse and rat orthologs of the human BMS-PTX-265 and BMS-PTX-837 biomarker polypeptides. FIG. 17A: mouse BMS-PTX-265; (GenBank Ident. No. gi|1711129; SEQ ID NO:65); FIG. 17B: mouse BMS-PTX-837 (GenBank Ident. No. gi|19354169; SEQ ID NO:66); FIG. 17C: rat BMS-PTX-265 (GenBank Ident. No. gi|402510; SEQ ID NO:67); and FIG. 17D: BMS-PTX-837 (GenBank Ident. No. gi|694107; SEQ ID NO:68).

FIG. 18. Non-limiting examples of primers that can be used for the amplification of biomarker polynucleotide sequences, for example, for RT-PCR analysis. Mouse BMS-PTX-265 (primers SEQ ID NO:69 and SEQ ID NO:70), Mouse BMS-PTX-837 (primers SEQ ID NO:71 and SEQ ID NO:72), Rat BMS-PTX-265 (primers SEQ ID NO:73 and SEQ ID NO:74), and Rat BMS-PTX-837 (primers SEQ ID NO:75 and SEQ ID NO:76). Key for FIG. 18: start=nucleotide position in cDNA where primer sequence begins; len=length of primer; gc %=percent guanine and cytosine content of the primer; tm=melting temperature of the hybrid; any=a measure of internal complementarity to predict hybridization of the primer; 3'=a measure of 3' complementarity of the primer; seq=sequence of primer.

DETAILED DESCRIPTION OF THE INVENTION

Figure 1:
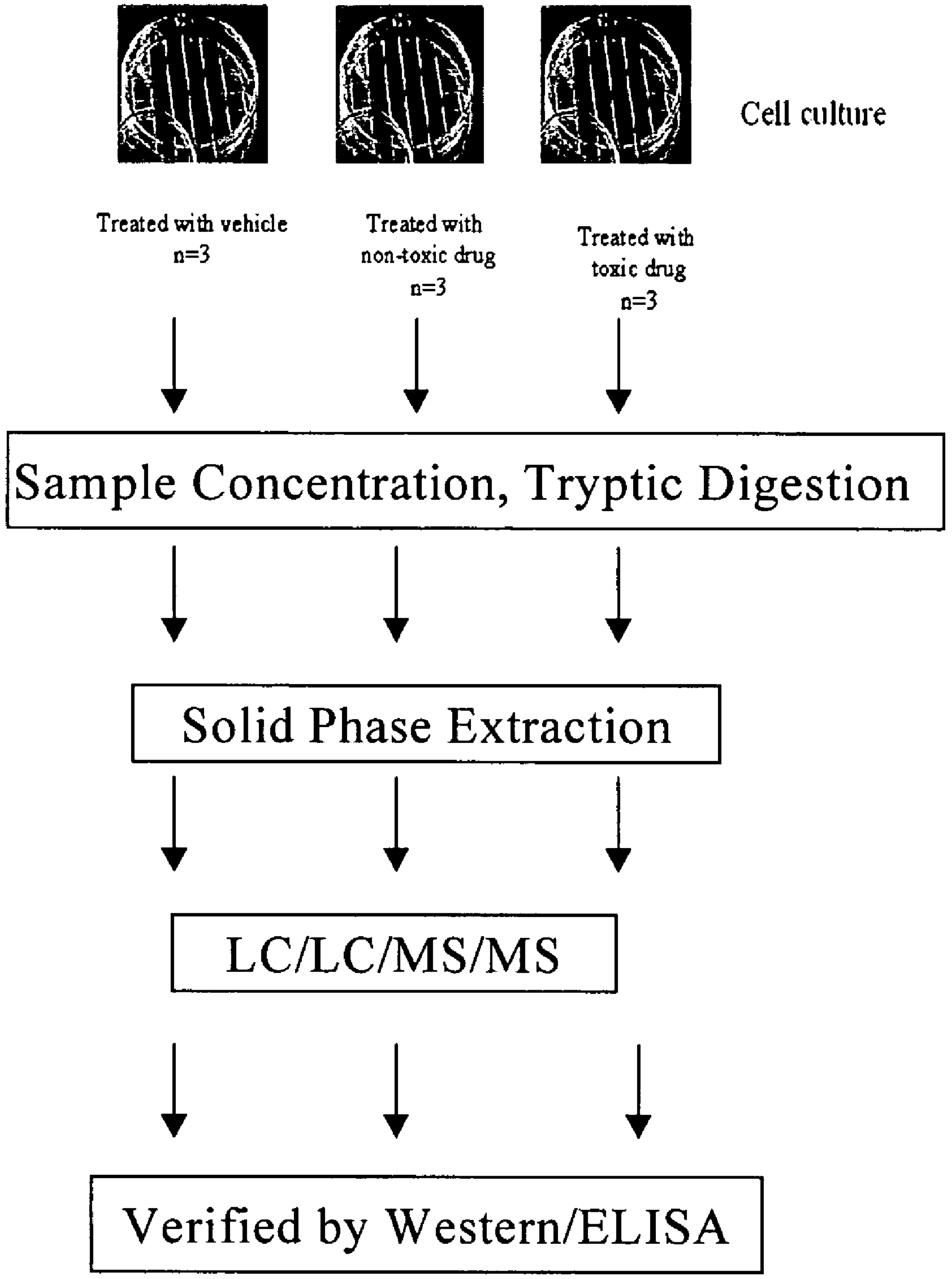
FIG. 1. Flow chart illustrating the sample preparation and bioanalytical steps involved in generating cell supernatants comprising candidate polypeptide biomarkers. Such polypeptides would be expected to be prognostic of the clinical safety profile of the chemical entities tested.

In accordance with the present invention, a combination of proteomic and immunological techniques were employed to identify and verify components of the conditioned culture media from immortalized human hepatocytes overexpressing cytochrome P450 3A4. Cells were treated with several individual compounds, including L-tyrosine PPAR agonists and HIV protease inhibitors, plus a vehicle control, dimethyl sulfoxide. For each drug class, clinically-determined hepatotoxic and non-hepatotoxic compounds were compared. Several polypeptides (SEQ ID NO:1 to SEQ ID NO:15 and SEQ ID NO:61 to SEQ ID NO:64) were identified from this assay, including BMS-PTX-265 (SEQ ID NO:1) and BMS-PTX-837 (SEQ ID NO:2), which were reproducibly and significantly increased in the conditioned media from cells treated with each of the toxic compounds as compared to media from cells treated with the non-toxic compounds or vehicle alone.

The results for BMS-PTX-265 (SEQ ID NO: 1) and BMS-PTX-837 (SEQ ID NO:2) were confirmed using western blots and enzyme linked immunosorbent assays used to measure the response of these two proteins on an expanded set of 20 compounds. For all 20 of the tested drugs, elevations of BMS-PTX-265 correlated exactly with the known safety profile; whereas changes in BMS-PTX-837 correctly predicted the safety profile in 19 of 20 drugs (one false negative was observed). Furthermore, both BMS-PTX-265 and BMS-PTX-837 biomarkers were shown to be readily detectable and quantifiable in the serum and plasma of mice, rats and dogs and that the expression levels of both biomarkers increased with hepatotoxin exposure in a dose dependent manner. These observations indicated that the identified biomarker polypeptides (SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), can be used in pre- or post-clinical screening to identify test substances or combinations of test substances that cause hepatic toxicity. Accordingly, the invention can be used to prevent or decrease the incidence of hepatotoxicity, including idiosyncratic hepatotoxicity.

Definitions

Use of the phrases "SEQ ID NO:1 to SEQ ID NO:15 and SEQ ID NO:61 to SEQ ID NO:64", and "SEQ ID NO:46 to SEQ ID NO:60, and SEQ ID NO:65 to SEQ ID NO:68" etc., is intended, for convenience, to refer to each individual SEQ ID NO. individually, and is not intended to refer to the sequences collectively. The invention encompasses each sequence individually, as well as any combination thereof.

As used herein, the term "test substance" is meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, and the like. A test substance can be assayed in accordance with the methods of the invention at any stage during clinical trials, during pre-trial testing, or following FDA-approval.

A "biomarker polynucleotide" (or nucleic acid) as used herein, refers to a molecule comprising a nucleotide sequence encoding a disclosed polypeptide (e.g., SEQ ID NO:1 to SEQ ID NO:15 and SEQ ID NO:61 to SEQ ID NO:64), for example, as disclosed in FIGS. 9A-9H. Specifically included are DNA and RNA molecules obtained from cellular, cell-free, or synthetic sources, as well as genomic and cDNA sequences, unspliced or partly spliced transcripts, and splicing products. Also included are "protein nucleic acids" (PNAs) formed by conjugating bases to an amino acid backbone. The nucleic acid sequences of the invention may be single- or double-stranded (i.e., DNA-DNA, DNA-RNA and RNA-RNA hybrids), and may represent the sense or antisense strand (i.e., complementary sequences). Nucleic acids (e.g., fragments, variants, and derivatives thereof) encoding functional equivalents of a biomarker polypeptide are also embraced by the present invention.

A "biomarker polypeptide" (or protein) refers to a molecule comprising an amino acid sequence of a disclosed polypeptide (e.g., SEQ ID NO:1 to SEQ ID NO:15 and SEQ ID NO:61 to SEQ ID NO:64), which may be obtained from any species, preferably mammalian, and more preferably, human, and from a variety of sources, including cellular, cell-free, synthetic, semi-synthetic, or recombinant sources. Functional equivalents of a polypeptide (e.g., fragments, variants, and derivatives thereof) are also embraced by the present invention.

"Variant" polynucleotides and polypeptides include molecules containing one or more deletions, insertions and/or substitutions compared to the sequences disclosed in FIGS. 4A-4B, FIGS. 7A-7C, FIGS. 8A-8B, or FIGS. 9A-9H. Variant polynucleotides can encode the same or a functionally-equivalent biomarker polypeptide. Variants and functional equivalents, preferably, retain at least one activity (e.g., correlation with hepatotoxicity) of the original molecules.

"Derivative" polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like. Preferably, a nucleic acid derivative retains at least one activity (e.g., correlation with hepatotoxicity) of the original molecule.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label. Preferably, the polypeptide or peptide retains at least one biological activity (e.g., correlation with hepatotoxicity) of the original molecule.

"Oligonucleotides" or "oligomers" refer to a nucleic acids, preferably comprising contiguous nucleotides, of at least about 6 nucleotides to about 60 nucleotides, preferably at least about 8 to 10 nucleotides in length, more preferably at least about 12 nucleotides in length e.g., about 15 to 35 nucleotides, or about 15 to 25 nucleotides, 18 to 20 nucleotides, or about 20 to 35 nucleotides, which can be typically used in PCR amplification assays, hybridization assays, or in microarrays. It will be understood that the term "oligonucleotide" is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe may comprise at least 20-200 nucleotides, preferably, at least 30-100 nucleotides, more preferably, 50-100 nucleotides.

"Amplification" refers to the production of additional copies of a polynucleotide and is generally carried out using polymerase chain reaction (PCR) technologies, which are well known and practiced in the art (see, D. W. Dieffenbach and G. S. Dveksler, 1995, *PCR Primer, a Laboratory Manual*, Cold Spring Harbor Press, Plainview, N.Y.).

"Microarray" is an array of distinct polynucleotides, oligonucleotides, polypeptides, peptides, or antibodies affixed to a substrate, such as paper, nylon, or other type of membrane; filter; chip; glass slide; or any other type of suitable support.

The term "isolated" refers to polynucleotides, polypeptides, peptides, and antibodies, that are substantially purified or separated, and are at least 60% free, preferably 75% to 85% free, and most preferably 90% or greater free from other components with which they are associated with in a cell, cell extract, or cell-free system.

The term "sample" is meant to be interpreted in its broadest sense. A "sample" refers to a biological sample, such as, for example; one or more cells, tissues, or fluids (including, without limitation, plasma, serum, whole blood, cerebrospinal fluid, lymph, tears, urine, saliva, milk, pus, and tissue exudates and secretions) isolated from an individual or from cell culture constituents, as well as samples obtained from, for example, a laboratory procedure. A biological sample may comprise chromosomes isolated from cells (e.g., a spread of metaphase chromosomes), organelles or membranes isolated from cells, whole cells or tissues, nucleic acid such as genomic DNA in solution or bound to a solid support such as for Southern analysis, RNA in solution or bound to a solid support such as for Northern analysis, cDNA in solution or bound to a solid support, oligonucleotides in solution or bound to a solid support, polypeptides or peptides in solution or bound to a solid support, a tissue, a tissue print and the like.

As used herein, the term "linker" means a chemical moiety which covalently joins the reactive groups already on the substrate and the molecule (e.g., DNA, antibody, or polypeptide) to be eventually immobilized, having a backbone of chemical bonds forming a continuous connection between the reactive groups on the substrate and the binding elements, and having a plurality of freely rotating bonds along that backbone.

The term "antibody" refers to intact molecules as well as fragments thereof, such as Fab, $F(ab')_2$, Fv, which are capable of binding an epitopic or antigenic determinant. This includes immunoglobulin molecules and immunologically active portions or fragments of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class or subclass (e.g., IgG1, IgG2, IgG3, IgG4, IgA1 and IgA2) of immunoglobulin molecule. In a preferred embodiment, the immunoglobulin is an IgG1 isotype. In another preferred embodiment, the immunoglobulin is an IgG2 isotype. In another preferred embodiment, the immunoglobulin is an IgG4 isotype.

The term "monoclonal antibody" as used herein is not limited to antibodies produced through hybridoma technology. The term refers to an antibody that is derived from a single clone, including any eukaryotic, prokaryotic, or phage clone, and not the method by which it is produced.

The term "humanized" antibody refers to antibody molecules in which amino acids have been replaced in the non-antigen binding regions in order to more closely resemble a human antibody, while still retaining the original binding capability, e.g., as described in U.S. Pat. No. 5,585,089 to C. L. Queen et al.

As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example, in U.S. Pat. No. 5,939,598.

The term "epitopes" as used herein, refers to portions of a polypeptide having antigenic or immunogenic activity in an animal, preferably a mammal, and most preferably a human. In a preferred embodiment, the present invention encompasses a polypeptide comprising an epitope, as well as the polynucleotide encoding this polypeptide.

An "immunogenic epitope" as used herein, refers to a portion of a protein that elicits an antibody response in an animal, as determined by any method known in the art, for example, by the methods for generating antibodies described infra. See, for example, Geysen et al., 1983, *Proc. Natl. Acad. Sci. USA,* 81:3998-4002.

The term "antigenic epitope" as used herein refers to a portion of a protein to which an antibody can immunospecifically bind to its antigen as determined by any method well known in the art, for example, by the immunoassays described herein.

The term "antigenic determinant" refers to that portion of a molecule that makes contact with a particular antibody (i.e., an epitope). When a polypeptide, peptide, or fragment thereof is used to immunize a host animal, numerous regions of the sequence may induce the production of antibodies which bind specifically to a given region or three-dimensional structure on the sequence; these regions or structures are referred to an antigenic determinants. An antigenic determinant may compete with the intact antigen (i.e., the immunogen used to elicit the immune response) for binding to an antibody.

The terms "specific binding" or "specifically binding" refer to the interaction between a polypeptide or peptide and a binding molecule, such as an agonist, an antagonist, or an antibody. The interaction is dependent upon the presence of a particular structure (i.e., an antigenic determinant or epitope) of the protein that is recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

In accordance with the present invention, Immunospecific binding excludes non-specific binding, but does not necessarily exclude cross-reactivity with other antigens. Antigenic epitopes need not necessarily be immunogenic.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such methodologies include the following: McDonald W H, Yates J R 3rd., 2002, Shotgun proteomics and biomarker discovery, *Dis. Markers.* 18(2):99-105; Link A J, 2002, Multidimensional peptide separations in proteomics, *Trends Biotechnol. December;* 20(12 Suppl):S8-13. Additional publications outlining the application of such proteomic methods is set forth in the following: J. Gao et al, "Identification of In Vitro Protein Biomarkers of Idiosyncratic Liver Toxicity," Toxicology In Vitro, 18(4), 533-541 (2004); J. Gao et al, "Changes in the Protein Expression of Yeast as a Function of Carbon Source," Journal of Proteome Research, 2(6), 643-649 (2003); J. X. Pang et al, "Biomarker Discovery in Urine by Proteomics," Journal of Proteome Research, 1(2), 161-169 (2002). All of these publications are incorporated by reference herein in their entirety.

An additional embodiment of the present invention relates to a method of predicting hepatotoxicity of a test substance comprising the steps of: a) incubating a hepatocyte in the presence and absence of a test substance; and b) comparing levels of at least one biomarker polypeptide selected from the group consisting of SEQ ID NO:1 to SEQ ID NO:15 and SEQ ID NO:61 to SEQ ID NO:64, in the presence and absence of said test substance; wherein an elevated level of said biomarker polypeptide(s) in the presence of the test substance indicates that the substance is predicted to cause hepatotoxicity, and wherein the level of said biomarker polypeptide(s) is measured using single or multi dimensional high performance liquid chromatography coupled to tandem mass spectrometry wherein the number of peptide hits from each protein identification are used to determine the abundance of said biomarker polypeptide(s) in the presence and absence of said test substance.

The application of single or multi dimensional high performance liquid chromatography coupled to tandem mass spectrometry is a novel means of identifying the relative quantitation of the biomarker polypeptide(s). The method takes into account the fact that an increased number of fragments of an identified protein isolated using single or multi dimensional high performance liquid chromatography coupled to tandem mass spectrometry directly correlates with the level of the protein present in the sample. Applicants invention represents the first application of single or multi dimensional high performance liquid chromatography coupled to tandem mass spectrometry as a means of quantifying the level of protein in a sample. Other applications of this method were simply limited to the task of identifying and/or cataloging the proteins within a sample, and were not directed to quantifying the proteins within that sample.

Polynucleotides

The present invention encompasses isolated polynucleotides that encode biomarker polypeptides (e.g., SEQ ID NO:1 to SEQ ID NO:15 and SEQ ID NO:61 to SEQ ID NO:64), as well as complementary sequences, fragments, variants, and derivatives thereof, and can be used to predict hepatotoxicity, e.g., idiosyncratic hepatotoxicity. Any polynucleotide that encodes an amino acid sequence of a biomarker polypeptide or peptide, or complementary sequences, or related fragments or variants, is included in the invention. In specific aspects, the present invention encompasses polynucleotides comprising one or more of the biomarker nucleotide sequences (SEQ ID NO:46 to SEQ ID NO:60 and SEQ ID NO:65 to SEQ ID NO:68), and complementary sequences, fragments, variants, and derivatives thereof. Polynucleotide variants of the present invention include, but are not limited to, variants that share at least 40%, 50%, 60%, 70%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% nucleotide sequence identity with any one of the sequences of SEQ ID NO:46 to SEQ ID NO:60, and SEQ ID NO:65 to SEQ ID NO:68, or sequences complementary thereto. Preferred are variants that share at least 45%, 51%, or 56% identity with any one of the sequences of SEQ ID NO:46 to SEQ ID NO:60 and SEQ ID NO:65 to SEQ ID NO:68, or sequences complementary thereto. In various embodiments, the invention encompasses polynucleotide fragments, which include, but are not limited to, fragments comprising at least 8, 10, 12, 15, 18, 20, 25, 30, 35, 36, 40, 45 contiguous nucleotides of any one of the sequences of SEQ ID NO:46 to SEQ ID NO:60 and SEQ ID NO:65 to SEQ ID NO:68, or corresponding complementary sequences. Preferably, fragments comprise at least 18, 19, 20, or 21 contiguous nucleotides of any one of the sequences of SEQ ID NO:46 to SEQ ID NO:60 and SEQ ID NO:65 to SEQ ID NO:68, or sequences complementary thereto.

Also encompassed by the invention are polynucleotides that are capable of hybridizing to the nucleotide sequences of SEQ ID NO:46 to SEQ ID NO:60 and SEQ ID NO:65 to SEQ ID NO:68 under various conditions of stringency. Hybridization conditions are typically based on the melting temperature ($T_m$) of the nucleic acid binding complex or probe (see, G. M. Wahl and S. L. Berger, 1987; *Methods Enzymol.,* 152:399-407 and A. R. Kimmel, 1987; *Methods of Enzymol.,* 152:507-511), and may be used at a defined stringency. For example, included in the present invention are sequences capable of hybridizing under moderately stringent conditions to any one of the sequences of SEQ ID NO:46 to SEQ ID NO:60 and SEQ ID NO:65 to SEQ ID NO:68, and other sequences that are degenerate to those which encode a biomarker polypeptide. As a non-limiting example, moderate stringency conditions comprise a prewashing solution of 2×SSC, 0.5% SDS, 1.0 mM EDTA, pH 8.0, and hybridization conditions of 50° C., 5×SSC, and overnight incubation.

As will be appreciated by the skilled practitioner in the art, the degeneracy of the genetic code results in the production of a multitude of nucleotide sequences encoding a biomarker polypeptide (e.g., SEQ ID NO:1 to SEQ ID NO:15 and SEQ ID NO:61 to SEQ ID NO:64). Some of the degenerate sequences may bear minimal homology to the nucleotide sequences of the identified biomarkers (e.g., see SEQ ID NO:46 to SEQ ID NO:60 and SEQ ID NO:65 to SEQ ID NO:68). Accordingly, the present invention contemplates each and every possible variation of nucleotide sequence that could be made by selecting combinations based on possible codon choices. These combinations are made in accordance with the standard triplet genetic code as applied to the nucleotide sequence of the originally identified biomarker polypeptides, and all such variations are to be considered as being specifically disclosed.

For some purposes, it may be advantageous to produce polynucleotides encoding a biomarker polypeptide (e.g., SEQ ID NO:1 to SEQ ID NO:15 and SEQ ID NO:61 to SEQ ID NO:64), or its fragments, variants, or derivatives, which possess a substantially different codon usage. Codons may be selected to increase the rate at which expression of the peptide/polypeptide occurs in a particular prokaryotic or eukaryotic host in accordance with the frequency with which particular codons are utilized by the host. Alterations in codon usage can also be used to produce RNA transcripts having more desirable properties, such as a greater half-life, than transcripts produced from the naturally occurring sequence. In particular, RNA molecules may be modified to increase intracellular stability and half-life. Possible modifications include, but are not limited to, the addition of flanking sequences at the 5' and/or 3' ends of the molecule, or the use of phosphorothioate or 2' O-methyl, rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytosine, guanine, thymine, and uridine which are not as easily recognized by endogenous endonucleases.

The biomarker polynucleotides (e.g., SEQ ID NO:46 to SEQ ID NO:60 and SEQ ID NO:65 to SEQ ID NO:68), and complementary sequences, and fragments thereof, can be engineered using methods generally known in the art in order to alter the sequences for a variety of reasons, including, but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and the like.

Also encompassed by the invention derivatives of the biomarker polynucleotides (e.g., SEQ ID NO:46 to SEQ ID NO:60 and SEQ ID NO:65 to SEQ ID NO:68), and complementary sequences, and fragments thereof, which comprise one or more chemical modification, for example, replacement of hydrogen by an alkyl, acyl, or amino group. Alternatively, derivative polynucleotides may comprise non-naturally-occurring portions, such as altered sugar moieties or inter-sugar linkages. Exemplary among these are phosphorothioate and other sulfur containing species which are known in the art. Derivative polynucleotides may also contain detection labels, including radionucleotides (e.g., $^{32}P$, $^{3}H$, and $^{35}S$), enzymes, fluorescent (e.g., rhodamine, fluorescein, and Cy™3, Cy™5), chemiluminescent, or chromogenic, and other labels (e.g., DNP, digoxigenin, and biotin) such as substrates, cofactors, inhibitors, magnetic particles, and the like.

A wide variety of labels and conjugation techniques are known and employed by those skilled in the art. Nucleic acid labeling can be achieved by oligo-labeling, nick translation, end-labeling, or PCR amplification using a labeled primer. Alternatively, polynucleotides, or any portions or fragments thereof, may be cloned into a vector for the production of labeled mRNA sequences. Such vectors are known in the art, are commercially available, and may be used to synthesize labeled RNA in vitro by addition of an appropriate RNA polymerase, such as T7, T3, or SP(6) and labeled nucleotides. These procedures may be conducted using a variety of commercially available kits (e.g., from Amersham-Pharmacia; Promega Corp.; and U.S. Biochemical Corp., Cleveland, Ohio).

The present invention also encompasses the production of polynucleotides, or portions thereof, which encode a biomarker polypeptide (e.g., SEQ ID NO:1 to SEQ ID NO:15 and SEQ ID NO:61 to SEQ ID NO:64), and its fragments, and derivatives, entirely by synthetic chemistry (see, for example, M. H. Caruthers et al., 1980, *Nucl. Acids Res. Symp. Ser.,* 215-223 and T. Horn et al., 1980, *Nucl. Acids Res. Symp. Ser.,* 225-232). After production, the synthetic sequence may be inserted into any of the many available expression vectors and cell systems using reagents that are well known to those in the art. Moreover, synthetic chemistry may be used to introduce mutations into a sequence encoding a biomarker polypeptide, or any fragment, variant, or derivative thereof. Alternatively, the polynucleotides of the invention can be produced by PCR amplification of the cloned sequences. In addition, the polynucleotides may be produced by recombinant systems, including cell-based and cell-free systems.

Polynucleotides that encode a biomarker polypeptide, or fragments, variants, or derivatives thereof, may be used in recombinant DNA molecules to direct the expression of a biomarker, or fragments or functional equivalents thereof, in appropriate host cells. Because of the inherent degeneracy of the genetic code, other DNA sequences, which encode substantially the same or a functionally equivalent amino acid sequence, may be produced and these sequences may be used to clone and express a biomarker polypeptide. For expression in recombinant systems, a start and stop codons may be added to the nucleic acid sequence of a biomarker polypeptide. In addition, nucleotide sequences encoding epitopes or protein tags can be added to the nucleic acid sequence of the biomarker polypeptide, as described in detail herein. Methods of cloning and expression are well known to those skilled in the art and are described in numerous publication's, for example, Sambrook, Fritsch, and Maniatis, *Molecular Cloning: a Laboratory Manual,* $2^{nd}$ Edition, Cold Spring Harbor Laboratory Press, USA, (1989).

Polypeptides

The present invention encompasses isolated biomarker polypeptides (e.g., SEQ ID NO:1 to SEQ ID NO:15 and SEQ ID NO:61 to SEQ ID NO:64), including BMS-PTX-265 (SEQ ID NO:1) and BMS-PTX-837 (SEQ ID NO:2), peptides, and fragments, variants, and derivatives thereof, that can be used to predict in vivo hepatotoxicity, e.g., idiosyncratic hepatotoxicity, as well as polynucleotides (e.g., SEQ ID NO:46 to SEQ ID NO:60 and SEQ ID NO:65 to SEQ ID NO:68) encoding these peptides or polypeptides. In accordance with the invention, biomarker peptides can range in size from 5 amino acid residues to all but one residue of the entire sequence. Accordingly, peptides include, but are not limited to, fragments comprising at least 5, 6, 7, 8, 9, 10, 11, 12, 13, 14, or 15 contiguous amino acids of any one of SEQ ID NO:1 to SEQ ID NO:15 and SEQ ID NO:61 to SEQ ID NO:64. Preferably, biomarker peptides comprise antigenic fragments of any one of SEQ ID NO:1 to SEQ ID NO:15 and SEQ ID NO:61 to SEQ ID NO:64.

The biomarker polypeptides, peptides, or fragments or variants thereof, may be linked to short tags, e.g., epitope tags such as HA and the like, or to other proteins, such as GST, GFP (e.g., GFP Y66F, GFP Y66H, GFP Y66W, wild type GFP, GFP S65A, GFP S65L, GFP S65T, ECFP, EYFP, DsRed; BD Biosciences CLONTECH, Palo Alto, Calif.), thioredoxin, maltose binding protein, etc. Also provided by the invention are chemically modified derivatives of the peptides and polypeptides of the invention that may provide additional advantages such as increased solubility, stability, and circulating time of the polypeptide. The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

In addition, amino acid sequence variants of the present invention include, but are not limited to, variants that share at least 40%, 50%, 60%, 61%, 67%, 70%, 74%, 76%, 80%, 81%, 84%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% nucleotide sequence identity with any one of SEQ ID NO:1 to SEQ ID NO:15 and SEQ ID NO:61 to SEQ ID NO:64. For variants that are functional equivalents, the percent amino acid sequence identity is at least 61% or 67%. More preferably, the percent amino acid sequence identity is at least 74% or 76%, still more preferably, at least 81% or 84%, and even more preferably, at least 90% to any one of SEQ ID NO:1 to SEQ ID NO:15 and SEQ ID NO:61 to SEQ ID NO:64. However, as will be appreciated by the skilled practitioner, biological function per se need not be maintained where a biomarker peptide comprises an antigenic epitope.

Polypeptide and peptide variants include variants differing by the addition, deletion, or substitution of one or more amino acid residues. For example, to isolate biomarker polypeptides or peptides, it may be useful to encode a tagged biomarker peptide or polypeptide that can be recognized by a commercially available antibody. In particular, a peptide or polypeptide can be fused or linked to epitope tags (e.g., FLAG, HA, GST, thioredoxin, maltose binding protein, etc.), or affinity tags such as biotin and/or streptavidin. As one example, a system for the ready purification of non-denatured fusion proteins expressed in human cell lines has been described by Janknecht et al., (1991, *Proc. Natl. Acad. Sci. USA,* 88:8972-8976). In this system, the gene of interest is subcloned into a vaccinia recombination plasmid such that the open reading frame of the gene is translationally fused to an amino-terminal tag having six histidine residues. The tag serves as a matrix-binding domain for the fusion protein. Extracts from cells infected with the recombinant vaccinia virus are loaded onto an $Ni^{2+}$ nitriloacetic acid-agarose column and histidine-tagged proteins are selectively eluted with imidazole-containing buffers.

A peptide or polypeptide tagged with an epitope or protein may also be engineered to contain a cleavage site located between the binder coding sequence and the tag coding sequence. This can be used to remove the tag, and isolate the biomarker peptide or polypeptide. The biomarker peptides or polypeptides of the invention can be covalently attached to chemical moieties via the amino acid backbone. For these purposes, the peptides or polypeptides may be modified by N- or C-terminal processing of the sequences (e.g., proteolytic processing), deletion of the N-terminal methionine residue, etc. The polypeptides may also be modified with a detectable label, such as an enzymatic, fluorescent, isotopic or affinity label to allow for detection and isolation of the protein, as described in detail herein.

Also included are modified polypeptides and peptides in which one or more residues are modified, and mutants comprising one or more modified residues. Amino acid variants of the invention can be generated by employing the techniques of gene-shuffling, motif-shuffling, exon-shuffling, and/or codon-shuffling (collectively referred to as "DNA shuffling") . DNA shuffling can be employed to generate peptides or polypeptides with altered activity. See, generally, U.S. Pat. Nos. 5,605,793; 5,811,238; 5,830,721; 5,834,252; and 5,837,458, and Patten et al., 1997, *Curr. Opinion Biotechnol.,* 8:724-33; Harayama, 1998, *Trends Biotechnol.,* 16(2):76-82; Hansson, et al., 1999, *J. Mol. Biol.,* 287:265-76; and Lorenzo and Blasco, 1998, *Biotechniques,* 24(2):308-313, the contents of each of which are hereby incorporated by reference in its entirety.

In one embodiment of the invention, alteration of one or more of the biomarker polypeptide sequences as set forth in SEQ ID NO:1 to SEQ ID NO:15 and SEQ ID NO:61 to SEQ ID NO:64 can be achieved by DNA shuffling. DNA shuffling involves the assembly of two or more DNA segments by homologous or site-specific recombination to generate variation in the protein-coding sequence. In another embodiment, the encoded peptides or polypeptides, may be altered by subjecting the coding sequences to random mutapolynucleotides and polypeptidesis by error-prone PCR, random nucleotide insertion, or other methods, prior to recombination. In another embodiment, one or more components, motifs, sections, parts, domains, fragments, etc., of a polynucleotide encoding a peptide or polypeptide of this invention may be recombined with one or more components, motifs, sections, parts, domains, fragments, etc. of one or more heterologous molecules.

The peptides and polypeptides may be differentially modified during or after translation, e.g., by derivatization with known protecting/blocking groups, proteolytic cleavage, linkage to an antibody molecule or other cellular ligand, etc. Useful modifications may include glycosylation, amidation, phosphorylation, sulfation, reduction/alkylation (Tarr, 1986, *Methods of Protein Microcharacterization*, J. E. Silver, Ed., Humana Press, Clifton, N.J., pp. 155-194); acylation (Tarr, supra); chemical coupling (Mishell and Shiigi (Eds), 1980, *Selected Methods in Cellular Immunology*, W H Freeman, San Francisco, Calif.; U.S. Pat. No. 4,939,239); and mild formalin treatment (Marsh, 1971, *Int. Arch. of Allergy and Appl. Immunol.* 41:199-215). Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc. Additional post-translational modifications encompassed by the invention include, for example, e.g., attachment of N-linked or O-linked carbohydrate chains, processing of N-terminal or C-terminal ends, chemical modifications of N-linked or O-linked carbohydrate chains, and addition or deletion of an N-terminal methionine residue as a result of prokaryotic host cell expression.

Additionally, D-amino acids, non-natural amino acids, or non-amino acid analogs can be substituted or added to produce a modified polypeptide. Furthermore, the polypeptides disclosed herein can be modified using polyethylene glycol (PEG) according to known methods (S. I. Wie et al., 1981, *Int. Arch. Allergy Appl. Immunol.* 64(1):84-99) to produce a protein conjugated with PEG. In addition, PEG can be added during chemical synthesis of the protein. Modifications or sequence variations may occur at the amino- or carboxy-terminal positions of the reference polypeptide sequence or anywhere between those terminal positions, interspersed either individually among the amino acids in the reference sequence or in one or more contiguous groups within the reference sequence. The polypeptides and peptides of this invention can be isolated, synthetic, or recombinant. The amino acid sequences may be obtained as individual polypeptides or peptides, or part of a complex.

Polypeptides or peptides may also be modified with a label capable of providing a detectable signal, either directly or indirectly, including, but not limited to, radioisotope, fluorescent, and enzyme labels. Fluorescent labels include, for example, Coumarin (e.g., Hydroxycoumarin, Aminocoumarin, Methoxycoumarin), R-Phycoerythrin (PE), Fluorescein, FITC, Fluor X, DTAF, Auramine, Alexa (e.g., Alexa Fluor® 350, -430, -488, -532, -546, -555, -568, -594, -633, -647, -660, -680, -700, -750), BODIPY-FL, Sulforhodamine (e.g., Texas Red®), Carbocyanine (e.g., Cy2, Cy™3, Cy3.5, Cy™5, Cy5.5, Cy7), Rhodamine, XRITC, TRITC, Lissamine Rhodamine B, Peridinin Chlorphyll Protein (PerCP), Allophycocyanin (APC), PE-Cy5 conjugates (e.g., Cychrome, Tri-Color®, Quantum Red®), PE-Cy5.5 conjugates, PE-Cy7 conjugates, PE-Texas Red conjugates (e.g., Red613), PC5-PE-Cy5 conjugates, PerCP-Cy5.5 conjugates (e.g., TruRed), APC-Cy5.5 conjugates, APC-Cy7 conjugates, ECD-PE-Texas Red conjugates, Sulfonated Pyrene (e.g., Cascade Blue), AMCA Blue, Lucifer Yellow.

Preferred isotope labels include $^{3}H$, $^{14}C$, 32P, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Preferred enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, colloidal gold (e.g., NANOGOLD®), Tyramide Signal Amplification (TSA™), are known in the art, and are commercially available (see, e.g., ABC kit, Vector Laboratories, Inc., Burlingame, Calif.; NEN® Life Science Products, Inc., Boston, Mass.; Nanoprobes, Inc., 95 Horse Block Road, Yaphank, N.Y.).

Biomarker polypeptides (e.g., SEQ ID NO:1 to SEQ ID NO:15 and SEQ ID NO:61 to SEQ ID NO:64), peptides, and fragments, variants, and derivatives thereof) may be produced by direct peptide synthesis using solid-phase techniques (J. Merrifield, 1963, *J. Am. Chem. Soc.,* 85:2149-2154; J. Y. Roberge et al., 1995, *Science,* 269:202-204). Protein or peptide synthesis may be performed using manual techniques or by automation. Automated synthesis may be achieved, for example, using ABI 431A Peptide Synthesizer (PE Biosystems). Various fragments of a biomarker polypeptide or peptide can be chemically synthesized separately and then combined using chemical methods to produce the full-length molecule. The newly synthesized peptide can be substantially purified by preparative high performance liquid chromatography (e.g., T. Creighton, 1983, *Proteins, Structures and Molecular Principles*, W. H. Freeman and Co., New York, N.Y.), by reversed-phase high performance liquid chromatography, or other purification methods as are known in the art. The composition of the synthetic peptides may be confirmed by amino acid analysis or sequencing (e.g., the Edman degradation procedure; Creighton, supra). In addition, the amino acid sequence of biomarker peptide or polypeptide or any portion thereof, may be altered during direct synthesis and/or combined using chemical methods with sequences from other proteins, or any part thereof, to produce a variant peptide or polypeptide.

In Vitro Validation

It was previously hypothesized that existing pre-clinical in vitro models could be employed to identify molecules that could subsequently be used to predict the likelihood of hepatotoxicity (Fabre, G.; Combalbert, J.; Berger, Y.; Cano, J. P., 1990, *Eur. J. Drug Metab. Pharmacokinet.* 15:165-171). Such molecules could be assayed using traditional immunological assays, and thereafter be incorporated in a standard protocol for compound evaluation prior to entering the clinical testing. Thus, the goal of the disclosed experiments was to obtain protein biomarkers that showed altered levels in an in vitro hepatocyte system in response to hepatotoxic drugs.

As shown herein, a set of biomarker polypeptides was successfully identified using proteomics, i.e., multidimensional separations coupled to tandem mass spectrometry, and subsequent immunological in vitro assays. The disclosed results demonstrate that levels of biomarker polypeptides (e.g., SEQ ID NO:1 to SEQ ID NO:15), including BMS-PTX-265 (SEQ ID NO:1) and BMS-PTX-837 (SEQ ID NO:2), can be used to correctly predict in vivo hepatotoxicity. The biomarkers of the invention are useful for predicting toxicity of a test substance prior or subsequent to clinical trials. In addition, the disclosed assay systems can be employed with relatively low costs and ease of use, and can be routinely utilized for pre- or post-clinical evaluations of chemical entities.

There were some differences in the results observed for BMS-PTX-265 and BMS-PTX-837, suggesting that each biomarker may involve separate mechanisms. Yet, BMS-PTX-265 and BMS-PTX-837 were used to correctly predict 18 of the 19 toxicity responses in experiments employing a single dose (50 μM; perhexelene at 20 μM), and a single time point (20 hr). The assays of the invention thereby provide the basis for a very simple and robust analytical system that can greatly aid the evaluation of pre- or post-clinical compounds.

The characteristics of BMS-PTX-265 and BMS-PTX-837 make them ideal biomarkers for use in in vitro experiments for predicting in vivo toxicity. The observations made for BMS-PTX-265 indicate that it may be the more sensitive of the two biomarkers, based on the qualified toxic classification of Dantrolene and the larger overall difference between the two classes of compounds. The BMS-PTX-837 biomarker appeared less sensitive, but was also less variable, based on the compressed dynamic range of its results. Both BMS-PTX-265 and BMS-PTX-837 proteins are small and soluble; they both lack significant hydrophobicity, and possess substantial immunogenicity and specificity in the disclosed assays.

While not wishing to be bound by theory, it is possible that both BMS-PTX-265 and BMS-PTX-837 proteins are leaked from the cells upon treatment, and are not actively induced or secreted. For example, cells may undergo a drug-induced morphological change as observed in the case of carcinoembryonic antigen (Babia, T.; Veldman, R. J.; Hoekstra, D.; Kok, J. W., 1998, *Eur. J. Biochem.* 258:233-242) or aspartate aminotransferase (Pappas, N. J., Jr., 1986, *Clin. Chim. Acta* 154: 181-189). Notably, biomarkers that exhibit a more general response would have certain advantages for the screening of compounds in a pre- or post-clinical candidate optimization setting where a wide variety of compound classes are routinely observed.

The proteomics technology platform disclosed herein provides a practical means for surveying a complex mixture of proteins to identify biomarker candidates and measure relative changes in their abundance. The immunoassays used for verification (see above) demonstrate the validity of the semi-quantitative LC/LC/MS/MS approach. As a result, future experiments can rely on LC/LC/MS/MS data alone, and only progress to immunoassays when large numbers of samples are ready for testing. In future experiments, it may also be useful to vary the criteria for selecting candidate biomarkers from the LC/LC/MS/MS data for further evaluation. The disclosed experiments evaluated candidate biomarkers based on several factors, including the filters of Pearson product-moment correlation coefficient, the data set template, commercial availability of antibodies, and correspondence to peer-reviewed literature. It would also be possible to pursue only biomarkers showing the most sensitivity, i.e., those with the largest relative change between toxic and non-toxic treatments.

In Vivo Validation

Two of the hepatotoxicity biomarkers of the present invention, BMS-PTX-265 (FIG. 4A; SEQ ID NO:1) and BMS-PTX-837 (FIG. 4B; SEQ ID NO:2), were analyzed to confirm that they could be used in pre-clinical species as 'bridging' biomarkers of liver toxicity.

The levels of BMS-PTX-265 (FIG. 4A; SEQ ID NO:1) and BMS-PTX-837 (FIG. 4B; SEQ ID NO:2) were examined in considerable detail following hepatocyte exposure to multiple classes of toxic compounds (Gao et al. In press), some of which are described herein. The experiments were designed to evaluate these two proteins for their ability to detect drug induced hepatotoxic effects in mice, rats and dogs.

Rodent and canine models of toxicity are routinely and extensively used by the pharmaceutical industry for new drug safety evaluation. Therefore, the serum from mice, rats, and dogs treated with toxic doses of different classes of compounds were examine for the presence of BMS-PTX-265 (FIG. 4A; SEQ ID NO:1) and BMS-PTX-837 (FIG. 4B; SEQ ID NO:2).

Animals were administered either an immunomodulatory molecule (biologic, Compound A) or an exploratory cell cycle inhibitor (small molecule, Compound B). These drugs were selected on the basis that high doses of each were known to induce multiple organ toxicity, including liver, for which the markers were initially identified.

Quantification of relative serum levels of the mouse orthologue of BMS-PTX-265 (also referred to as 14-3-3 ZETA; SEQ ID NO:61) in mice exposed to compound A for four weeks showed an overall increase when compared to pre-dose concentrations (FIG. 10 panels A and B). At the lower 10 mg/kg dose, five of eight animals had elevated mouse BMS-PTX-265 (see FIG. 10A) while all eight mice exposed to the higher 50 mg/kg dose had increased serum levels (see FIG. 10B). Of the three animals not exhibiting higher levels after 10 mg/kg treatment, two remained constant (FIG. 10A; M2201, M2203) and one demonstrated decreased levels (FIG. 10A; M2202). The overall increase in mouse BMS-PTX-265 in the 50 mg/kg ranged from 75% (FIG. 10B; M3101) to greater than 3800% (FIG. 10B; M3102).

Analyses of the mouse orthologue of BMS-PTX-837 (also referred to as MIF; SEQ ID NO:62) levels in aliquots of the same samples as the mouse BMS-PTX-265 samples above gave a less definitive dose-response (FIG. 10 panels C and D). At the low 10 mg/kg dose, four had increased mouse BMS-PTX-837 concentrations (FIG. 10C; M2101, M2102, M2104, M2204) and three were decreased after treatment (FIG. 10C; M2201, M2202, M2203). Exposure to the higher 50 mg/kg levels of Compound A resulted in decreased mouse BMS-PTX-837 for one animal (FIG. 10D; M3103), minimal or no change for three animals (FIG. 10D; M3101, M3102, M3104) and increased levels for three mice (FIG. 10D; M3201, M3202, M3203). The magnitude of change was also not as dramatic for the mouse BMS-PTX-837 as for the mouse BMS-PTX-265 (compare FIG. 10 panels A and B vs. panels C and D).

Figure 11A:
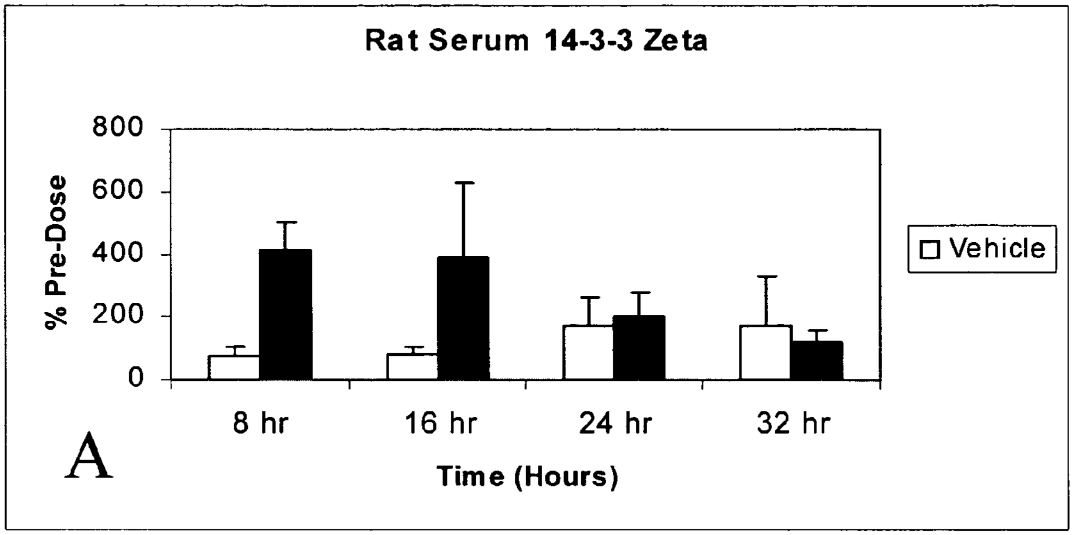
FIGS. 11A-B. Time course of rat 14-3-3 ZETA (rat BMS-PTX-265.
Figure 11B:
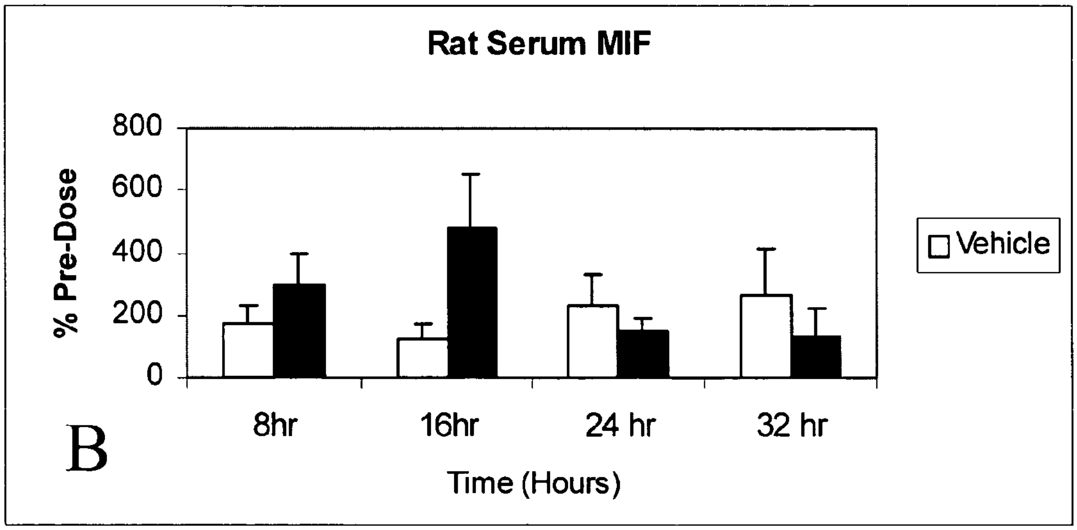

Treatment of rats with Compound B at an acutely toxic dose of 22 mg/kg also caused an elevation in serum levels of both of the rat orthologues of BMS-PTX-265 (SEQ ID NO:63) and BMS-PTX-837 (SEQ ID NO:64) as shown in FIG. 11. BMS-PTX-265 was already significantly increased by eight hours post exposure and remained high through 16 hours, after which levels fell to roughly those of vehicle (FIG. 11A). Serum levels of the rat BMS-PTX-837 also showed an early increase followed by a tapering off to levels lower than control by 24 hours (FIG. 11B). In contrast to the rat BMS-PTX-265, the rat BMS-PTX-837 appeared to have a more gradual induction or release into the serum (compare FIGS. 11A and B at 8 and 16 hours). However, both reach approximately the same relative level of 400% versus either pre-dose or vehicle at 16 hours.

Figure 12A:
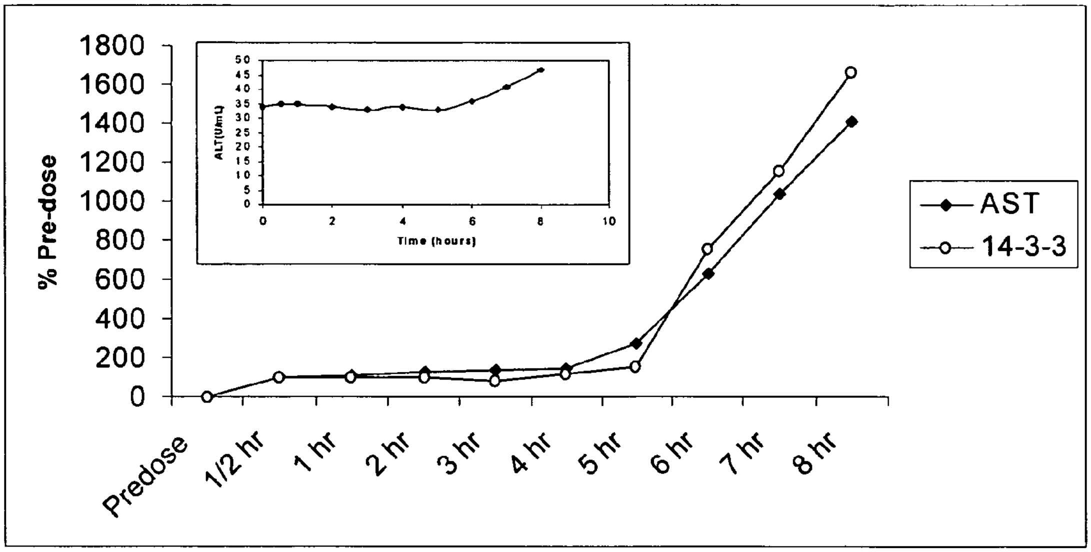
FIGS. 12A-B. Time course of canine 14-3-3 ZETA (canine BMS-PTX-265), in addition to the traditional toxicity markers AST and ALT (inset) following Compound B exposure in two canine subjects (FIG. 12A and FIG. 12B). Canine 14-3-3 ZETA levels were determined by Western blot analyses using Quantity One software (Bio-Rad, Hercules, Calif.). For comparison, all values were normalized to percent of pre-dose.
Figure 12B:
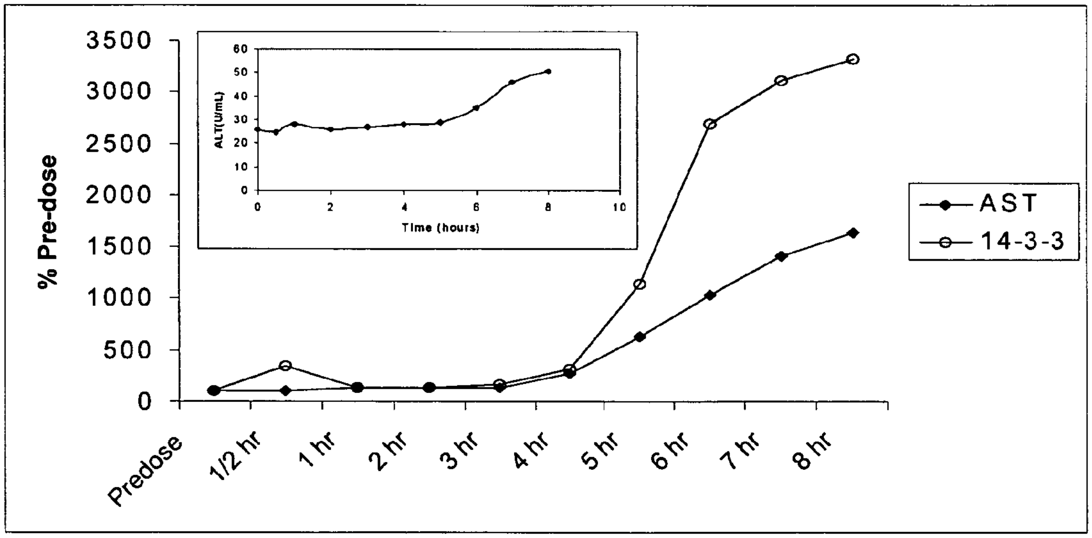

A corresponding study in dogs with Compound B also produced a marked effect on serum levels of the canine BMS-PTX-265. A dramatic increase in canine BMS-PTX-265 was observed following acute toxin exposure (FIG. 12). Both animals had substantially elevated canine BMS-PTX-265 at the eight hour conclusion of the study. This rise began, in both cases, between four and five hours post-treatment. Canine BMS-PTX-265 increased approximately 1600% (FIG. 12A) or 3200% (FIG. 12B) over pre-dose levels and outpaced both of the traditional toxicity markers ALT (FIGS. 12A and B inset) and AST. The canine BMS-PTX-837 was unable to be evaluated in the canine model due to the fact that neither the anti-human nor anti-rodent reagents cross reacted with the dog samples. Additionally, since the sequence of the canine BMS-PTX-837 has yet to be determined in dogs, custom antibodies were not able to be generated.

Figure 13:
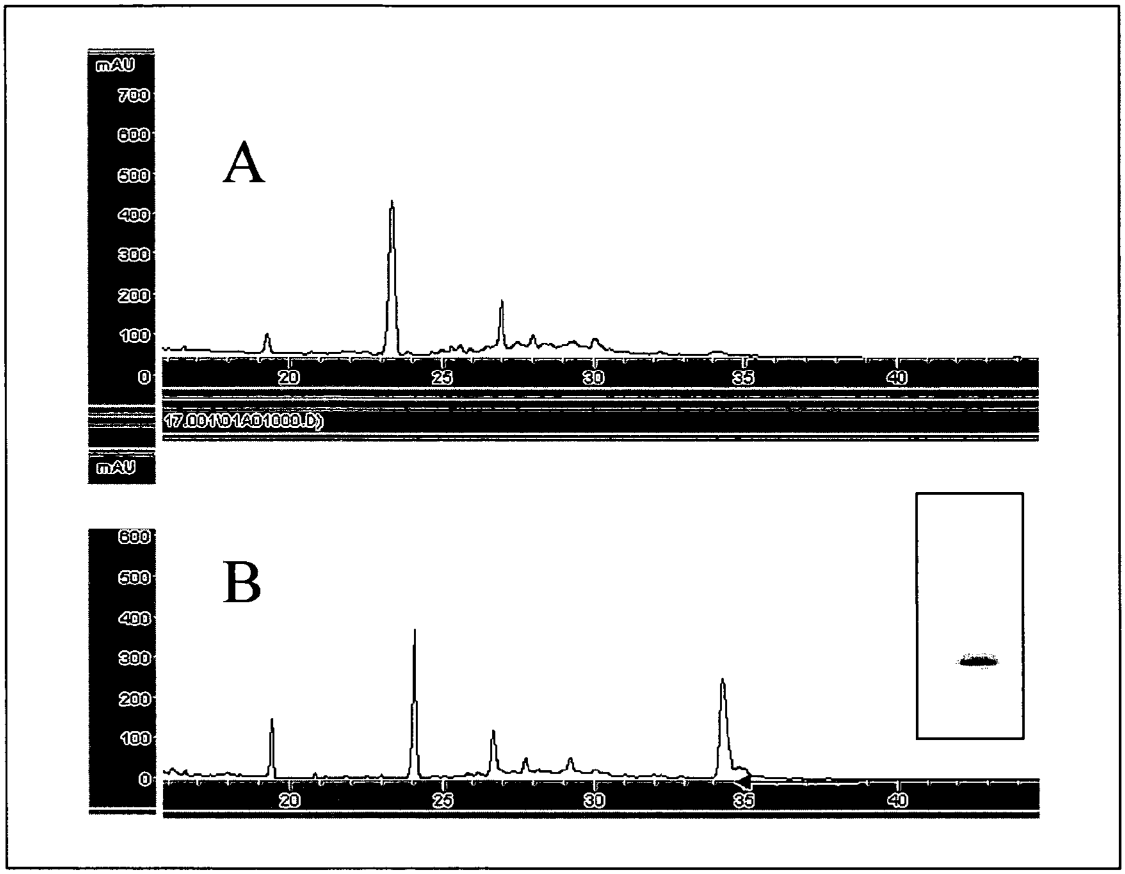
FIGS. 13A-B. HPLC chromatograms of *E. coli* lysates from cells transformed with vector control (A) or recombinant full length human 14-3-3 ZETA (B). Inset shows anti-human-14-3-3 ZETA specific Western band from peak indicated by arrow in (B).

Nonetheless, a wild type recombinant human BMS-PTX-265 was successfully created and isolated for use as a quantification standard. Corresponding chromatograms (FIG. 13) from cell lysates of *E. coli* transformed with vector alone (A) or a full length recombinant human BMS-PTX-265 expression construct (B) show marked differences. Comparison of the HPLC traces revealed a prominent peak specific to the human BMS-PTX-265 expressing cells (FIG. 13B arrow). This fraction was isolated and compared to the parallel fraction from vector control cells by Western blot. A single strongly immunoreactive band of the predicted molecular weight (28 kDa) was detected in the human BMS-PTX-265 expressing cells (FIG. 13B inset), while no bands were detectable in the vector control lysates. The immunoreactive fraction was estimated to be greater than 90% pure based on subsequent HPLC analyses (data not shown). This purified standard was then used in the development of a human BMS-PTX-265 ELISA.

Figures 14, 15:
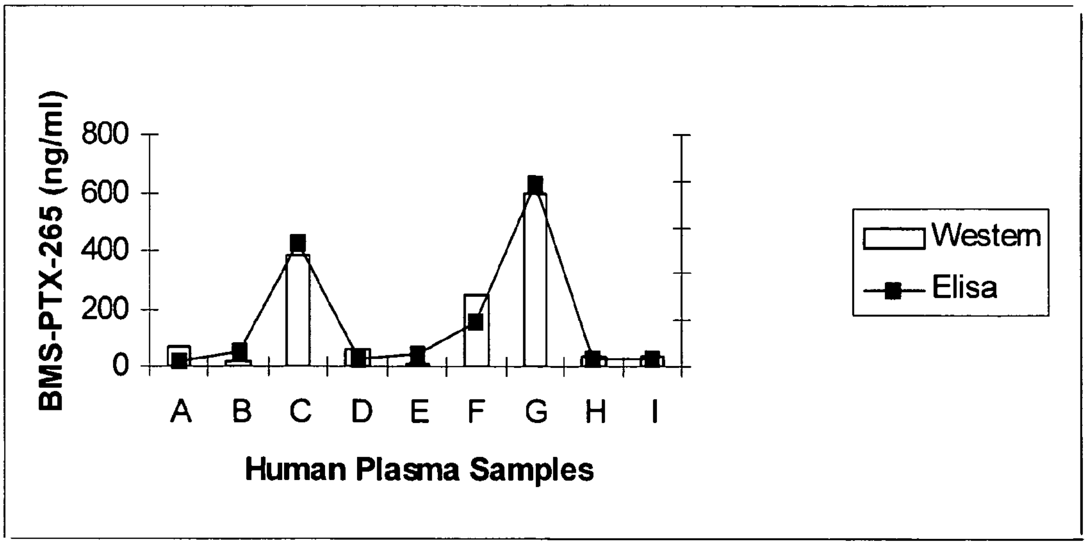
FIG. 14. Comparison of human 14-3-3 ZETA (BMS-PTX-265.
FIG. 15. Provides the range of circulating plasma levels of human 14-3-3 ZETA (BMS-PTX-265.

Human BMS-PTX-265 (SEQ ID NO:1) was readily detectable in human plasma by both Western blot and ELISA. Matching aliquots of frozen reference samples were tested by each method to cross validate the assays. There was an excellent correlation (FIG. 14) between relative human BMS-PTX-265 levels as measured by Western and ELISA. The values not only closely tracked, but did so over a broad range (>30 fold). The range of circulating plasma levels of human BMS-PTX-265 and human BMS-PTX-837 (SEQ ID NO:2) that we have been able to detect in human volunteers using commercially available recombinant human BMS-PTX-837 and the recombinant human BMS-PTX-265, described herein, as standards are shown in FIG. 15.

The results demonstrated consistent and reproducible associations between levels of two serum proteins, BMS-PTX-265 (SEQ ID NO:1) and BMS-PTX-837 (SEQ ID NO:2), and drug induced toxicity in three pre-clinical animal models. These proteins are quite different in structure (Yaffe., FEBS 513(1):53-7 (2002); Bernhagen et al., J. Mol. Med. 76, 151-161 (1998)) and presumed function (Tzivion and Avruch. JBC 277(Gao et al. In press):3061-4 (2002); Lue et al, Microbes and Infection. 4, 449-460 (2002)). BMS-PTX-265

(also referred to as 14-3-3 ZETA) is an individual isoform of a family of conserved proteins with multiple functions including signal transduction, cell cycle regulation and stress response (Tzivion and Avruch. JBC 277 (Gao et al. In press): 3061-4 (2002); Takahashi, Neurochemical Research 8, 1265-1273 (2003)). Specificity of response can be achieved by expression of particular combinations of isoforms (Aitken et al, Biochem Soc Trans. 4, Streiner and Norman., Health Measurement Scales: A practical Guide to Their Development and Use (Oxford University Press, Oxford, 1995)51-60 (2002)). While other family members have been described in cerebrospinal fluid as indicators of Creutzfeld-Jacobs disease (Green et al., Neuroscience letters. 324, 57-60 (2002); Green, Neuropathology and Applied Neurobiology. 28, 427-440 (2002)), BMS-PTX-265 has not been identified in mammalian extracellular fluid.

BMS-PTX-837 (also referred to as MIF) is a cytokine that is expressed by both immune and non-immune cells (Calandra et al., Critical Reviews in Immunology. 17, 77-88 (1997)). It has both tautomerase and oxidoreductase activity and regulates macrophages and lymhpocytes (reviewed in Tzivion and Avruch. JBC 277 (Gao et al. In press):3061-4 (2002)). BMS-PTX-837 has also been implicated in chronic inflammation and endotoxic shock (Bernhagen et al., Nature 365, 756-759 (1993); Donnelly and Bucala., Mol. Med. Today. 3, 502-507 (1998)). It has further been shown to play a role in halothane induced liver toxicity in rodents (Willuweit et al. J. Immunol. 3944-3952 (2001)) and to be readily detectable in mammalian serum (Bourdi et al. BBRC. 294, 225-230 (2002)). In our models, both BMS-PTX-265 and BMS-PTX-837 were consistently up-regulated in animal serum following acute toxin exposure. These models represented not only different animal systems, but compounds with quite different structures, modes of operation and targets.

The mouse model represents chronic, intermittent toxin exposure and produced BMS-PTX-265 serum levels that varied from animal to animal, but showed a dose dependent increase with 100% of animals having levels elevated by at least 50% in the 50 mg/kg dose group. In contrast, 62.5% of the mice in the 10 mg/kg group had elevated BMS-PTX-265. On the other hand, BMS-PTX-837 did not show a consistent increase after either high or low exposure. These proteins were identified as acute toxicity markers in vitro, and the mouse data are consistent with a more acute response in vivo. Transiently elevated BMS-PTX-265 could result from the more recent dosing, while BMS-PTX-837 no longer responds. Long term repeated exposure might also account for the high degree of inter-animal variability since, even with an inbred strain, small variations in acute response early on may be magnified over the course of eight successive rounds of toxin exposure.

Data from our rat model system using a different class of compound (Compound B) provides further evidence that BMS-PTX-265 and BMS-PTX-837 may be acute markers of toxicity. In these experiments (FIG. 11) animals were given a single dose and serum measured at eight hour intervals out to 32 hours. Both biomarkers showed an early increase, followed by a decrease to below control levels by 24 hours, and remained low at 32 hours. BMS-PTX-265 was already maximally elevated by eight hours and remained high through 16 hours, while BMS-PTX-837 was increased at eight hours but continued to rise to a maximum at 16 hours. These data indicate that while both BMS-PTX-265 and BMS-PTX-837 are effective acute markers of toxicity, they likely work through different mechanisms, and therefore, in combination may detect a broader range of toxins than either alone.

This acute response of BMS-PTX-265 after high Compound B inhibitor exposure was further explored using a dog model. The magnitude of increase was additionally compared to two traditional markers of toxicity, AST and ALT. BMS-PTX-265 was clearly elevated after five hours and continued to climb dramatically to eight hours (FIG. 12). A similar pattern occurred with ALT and AST, but to a lesser degree. While BMS-PTX-265 increased to 1600 or 3200% of pretreatment levels, AST rose 1400 or 1500% and ALT increased less than 100% (FIGS. 12A and B respectively). The animal studies, taken in toto, demonstrate these markers of in vitro toxicity to be effective serum biomarkers of acute toxicity in vivo.

A fundamental, and often overlooked, consideration in the development of new protein markers is the generation of consistent and quantifiable standards. This is of even more importance if the same potential markers are to be used to bridge the gap from in vitro cell based assays to examination of in vivo biological samples. Full length BMS-PTX-837 is currently commercially available, however, no such reagents were previously available for BMS-PTX-265 analyses. To address this need we generated and purified full length, recombinant, immunoreactive BMS-PTX-265 (FIG. 13). This allowed us to produce an unlimited supply of pure (>90%) protein to standardize our high throughput assays. This, in combination with our in-house development of accurate and sensitive ELISAs for both BMS-PTX-265 and BMS-PTX-837, has opened the door for large scale screening. Ultimately, these standards will be of clinical value when used to define patient thresholds for toxin exposure.

An examination of human plasma samples for the presence and quantification of both biomarkers using reference samples collected by Biological Specialties Inc has been initiated. In addition to sensitivity (FIG. 15), and consistency between different methods of detection (FIG. 14), these markers have several other positive advantages that make them well suited for examination of clinical samples. Minimal sample volume (10 μl) is required, no enzymatic or time course measurements are needed, and rapid reproducible results are obtained using standard ELISA techniques. These properties imply that BMS-PTX-265 and BMS-PTX-837 could be of immense value as early predictors of human toxic responses. Since small volumes are required, running conventional assays in conjunction with BMS-PTX-265 and/or BMS-PTX-837 would be practical. Long term stability enables accurate evaluation of archival samples, and the simple detection method should allow any laboratory with standard ELISA capability to generate consistent results. In addition, combining the ease of measurement with rigorous standards will allow analogous data to be generated between laboratories. The inventors have clearly demonstrated the utility of measuring both biomarkers in human samples to identify compounds that are subject to inducing toxicity, and in particular, liver toxicity, both in vitro, and in vivo.

The discovery of toxicity biomarkers that are able to bridge the gaps from in vitro screening to pre-clinical animal studies to human trials may ultimately impact how candidates are evaluated throughout the drug development pipeline. Using validated, common tools from in vitro discovery screening platforms, through clinical trials, and potentially beyond into post-marketing studies permits a cross-correlation of data not currently available. The progression of two such markers, identified herein as indicators of toxicity in vitro, through in vivo animal model testing has been demonstrated sufficiently to validate their efficacy in vivo, and in particular their use in tracking toxicity by following their presence in human plasma.

Antibodies

The present invention encompasses antibodies directed to biomarker peptides or polypeptides comprising, or alternatively, consisting of, an epitope of one of the polypeptides set forth in FIGS. 4A-4B, FIGS. 7A-7C, and FIGS. 16A-D which can be used to predict in vivo hepatotoxicity, e.g., idiosyncratic hepatotoxicity. Antibodies directed against the biomarker polypeptides (e.g., SEQ ID NO:1 to SEQ ID NO:15 and SEQ ID NO:61 to SEQ ID NO:64) or peptides of the present invention, or antigenic or immunogenic epitopes thereof, include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. Immunoglobulins may have both a heavy and a light chain. An array of IgG, IgE, IgM, IgD, IgA, and IgY heavy chains can be paired with a light chain of the kappa or lambda types.

Most preferably, the antibodies of the present invention are human antigen-binding antibodies and antibody fragments and include, but are not limited to, Fab, Fab' F.(ab') 2, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of the following: hinge region, and CH1, CH2, and CH3 domains. Also included in connection with the invention are antigen-binding fragments also comprising any combination of variable region(s) with a hinge region, and CH1, CH2, and CH3 domains. Antibodies of the present invention can be described or specified in terms of the epitope(s) or portion(s) of the biomarker polypeptides (e.g., SEQ ID NO:1 to SEQ ID NO:15 and SEQ ID NO:61 to SEQ ID NO:64) or peptides of the present invention which they recognize or specifically bind. The epitope(s) or polypeptide portion(s) can be specified, e.g., by N-terminal and C-terminal positions, by size in contiguous amino acid residues, or as presented in the sequences defined in FIGS. 4A-4B, FIGS. 7A-7C, and FIGS. 16A-D.

The antibodies of the invention may be from any animal origin including birds and mammals. Preferably, the antibodies are of human, murine (e.g., mouse and rat), donkey, sheep, rabbit, goat, guinea pig, camel, horse, or chicken origin. The antibodies of the present invention can be monospecific, bispecific, trispecific, or of greater multispecificity. Multispecific antibodies can be specific for different epitopes of a polypeptide of the present invention, or can be specific for both a polypeptide of the present invention, and a heterologous epitope, such as a heterologous polypeptide or solid support material. See, e.g., PCT publications WO 93/17715; WO 92/08802; WO 91/00360; WO 92/05793; Tutt et al., 1991, *J. Immunol.,* 147:60-69; U.S. Pat. Nos. 4,474,893; 4,714,681; 4,925,648; 5,573,920; 5,601,819; and Kostelny et al., 1992, *J. Immunol.,* 148:1547-1553.

Various procedures known in the art may be used for the production of such antibodies and antibody fragments. Antibodies generated against the polypeptides or peptides corresponding to one or more of the biomarker sequences of the present invention can be obtained by direct injection of the polypeptides or peptides into an animal, or by administering the polypeptides or peptides to an animal, preferably a non-human animal. For the preparation of monoclonal antibodies, any technique that provides antibodies produced by continuous cell line cultures can be used. Examples include the hybridoma technique (Kohler and Milstein, 1975, *Nature,* 256:495-497), the trioma technique, the human B-cell hybridoma technique (Kozbor et al., 1983, *Immunol. Today,* 4:72), and the EBV-hybridoma technique to produce human monoclonal antibodies (Cole et al., 1985. *In: Monoclonal Antibodies and Cancer Therapy*, Alan R. Liss, Inc., pp. 77-96). Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

Either the full-length protein or an antigenic peptide fragment can be used to produce antibodies. Antibodies are preferably prepared from these regions or from discrete fragments in regions of the biomarker amino acid sequences comprising an epitope. Antibodies can also be prepared from any region of the biomarker polypeptides and peptides, as described herein. A preferred fragment generates the production of an antibody that specifically recognizes a biomarker peptide or polypeptide. In addition, antibodies can be developed against an entire polypeptide or domains of the polypeptide. Antibodies can also be developed against specific functional sites, such as the sites that are glycosylated, phosphorylated, myristylated, or amidated, for example.

Polypeptide or peptide fragments that function as epitopes may be produced by any conventional means (see, e.g., Houghten, 1985, *Proc. Natl. Acad. Sci. USA,* 82:5131-5135; and as described in U.S. Pat. No. 4,631,211). In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof, as well as any combination of two, three, four, five or more of these antigenic epitopes.

Antigenic epitopes are useful, for example, to raise antibodies, including monoclonal antibodies, that specifically bind the epitope. In addition, antigenic epitopes can be used as the target molecules in immunoassays (see, for instance, Wilson et al., 1984, *Cell,* 37:767-778; and Sutcliffe et al., 1983, *Science,* 219:660-666). Such fragments as described herein are not to be construed, however, as encompassing any fragments that may be disclosed prior to the invention. Similarly, immunogenic epitopes can be used, for example, to induce antibodies according to methods well known in the art (see, for instance, Sutcliffe et al., supra; Wilson et al., supra; Chow et al., 1985, *Proc. Natl. Acad. Sci. USA,* 82:910-914; and Bittle et al., 1985, *J. Gen. Virol.* 66:2347-2354). Preferred immunogenic epitopes include the immunogenic epitopes disclosed herein, as well as any combination of two, three, four, five or more of these immunogenic epitopes.

Biomarker polypeptides (e.g., SEQ ID NO:1 to SEQ ID NO:15 and SEQ ID NO:61 to SEQ ID NO:64) or peptides comprising one or more immunogenic epitopes that elicit an antibody response can be introduction together with a carrier protein, such as an albumin, to an animal system (such as rabbit or mouse). Alternatively, if the peptide or polypeptide is of sufficient length (e.g., at least about 25 amino acids), the amino acid sequence can be presented without a carrier. However, immunogenic epitopes comprising as few as 5 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods (see, e.g., Sutcliffe et al., supra; Wilson et al., supra; and Bittle et al., supra). If in vivo immunization is used, animals can be immunized with free peptide; however, the anti-peptide antibody titer may be boosted by coupling the peptide to a macromolecular carrier, such as keyhole limpet hemacyanin (KLH), or tetanus toxoid (TT). For instance, peptides containing cysteine residues can be coupled to a carrier using a linker such as maleimidobenzoyl-N-hydroxysuccinimide ester (MBS), while other peptides may be coupled to carriers using a more general linking agent, such as glutaraldehyde.

Epitope bearing peptides of the invention may also be synthesized as multiple antigen peptides (MAPs), first described by J. P. Tam et al., 1995, *Biomed. Pept, Proteins, Nucleic Acids,* 199, 1(3):123-32; and Calvo, et al., 1993, *J. Immunol.,* 150(4):1403-12), which are hereby incorporated by reference in their entirety herein. MAPs contain multiple copies of a specific peptide attached to a non-immunogenic lysine core. MAP peptides usually contain four or eight copies of the peptide, which are often referred to as MAP4 or MAP8 peptides. By way of non-limiting example, MAPs can be synthesized onto a lysine core matrix attached to a polyethylene glycol-polystyrene (PEG-PS) support. The peptide of interest is synthesized onto the lysine residues using 9-fluorenylmethoxycarbonyl (Fmoc) chemistry. For example, Applied Biosystems (Foster City, Calif.) offers commercially available MAP resins, such as, for example, the Fmoc Resin 4 Branch and the Fmoc Resin 8 Branch, which can be used to synthesize MAPs. Cleavage of MAPs from the resin is performed with standard trifloroacetic acid (TFA)-based cocktails known in the art. Purification of MAPs, except for desalting, is not generally necessary. MAP peptides can be used in immunizing vaccines which elicit antibodies that recognize both the MAP and the native protein from which the peptide was derived.

Epitope-bearing peptides of the invention can also be incorporated into a coat protein of a virus, which can then be used as an immunogen or a vaccine with which to immunize animals, including humans, in order stimulate the production of anti-epitope antibodies. For example, the V3 loop of the gp120 glycoprotein of the human immunodeficiency virus type 1 (HIV-1) has been engineered to be expressed on the surface of rhinovirus. Immunization with rhinovirus displaying the V3 loop peptide yielded apparently effective mimics of the HIV-1 immunogens (as measured by their ability to be neutralized by anti-HIV-1 antibodies as well as by their ability to elicit the production of antibodies capable of neutralizing HIV-1 in cell culture). This techniques of using engineered viral particles as immunogens is described in more detail in Smith et al., 1997, *Behring Inst Mitt Feb,* (98):229-39; Smith et al., 1998, *J. Virol.,* 72:651-659; and Zhang et al., 1999, *Biol. Chem.,* 380:365-74), which are hereby incorporated by reference herein in their entireties.

Epitope bearing polypeptides of the invention can be modified, for example, by the addition of amino acids at the amino- and/or carboxy-terminus of the peptide. Such modifications are performed, for example, to alter the conformation of the epitope bearing polypeptide such that the epitope will have a conformation more closely related to the structure of the epitope in the native protein. An example of a modified epitope-bearing polypeptide of the invention is a polypeptide in which one or more cysteine residues have been added to the polypeptide to allow for the formation of a disulfide bond between two cysteines, thus resulting in a stable loop structure of the epitope-bearing polypeptide under non-reducing conditions. Disulfide bonds can form between a cysteine residue added to the polypeptide and a cysteine residue of the naturally-occurring epitope, or between two cysteines which have both been added to the naturally-occurring epitope-bearing polypeptide.

In addition, it is possible to modify one or more amino acid residues of the naturally-occurring epitope-bearing polypeptide by substitution with cysteines to promote the formation of disulfide bonded loop structures. Cyclic thioether molecules of synthetic peptides can be routinely generated using techniques known in the art, e.g., as described in PCT publication WO 97/46251, incorporated in its entirety by reference herein. Other modifications of epitope-bearing polypeptides contemplated by this invention include biotinylation.

As one having skill in the art will appreciate, and as discussed above, the biomarker polypeptides (e.g., SEQ ID NO:1 to SEQ ID NO:15 and SEQ ID NO:61 to SEQ ID NO:64) or peptides can be fused to other amino acid sequences. For example, the polypeptides of the present invention can be fused with the constant domain of immunoglobulins (IgA, IgE, IgG, IgD, or IgM), or portions thereof, e.g., CH1, CH2, CH3, or any combination thereof, and portions thereof, or with albumin (including, but not limited to, recombinant human albumin, or fragments or variants thereof (see, e.g., U.S. Pat. No. 5,876,969; EP Patent No. 0 413 622; and U.S. Pat. No. 5,766,883, incorporated by reference in their entirety herein), thereby resulting in chimeric polypeptides. Such fusion proteins may facilitate purification and may increase half-life in vivo. This has been shown for chimeric proteins containing the first two domains of the human CD4-polypeptide and various domains of the constant regions of the heavy or light chains of mammalian immunoglobulins. See, e.g., Traunecker et al., 1988, *Nature,* 331:84-86.

Enhanced delivery of an antigen across the epithelial barrier to the immune system has been demonstrated for antigens (e.g., insulin) conjugated to an FcRn binding partner, such as IgG or Fc fragments (see, e.g., PCT Publications WO 96/22024 and WO 99/04813). IgG fusion proteins that have a disulfide-linked dimeric structure due to the IgG portion disulfide bonds have also been found to be more efficient in binding and neutralizing other molecules than are monomeric polypeptides, or fragments thereof, alone. See, e.g., Fountoulakis et al., 1995, *J. Biochem.,* 270:3958-3964.

Another aspect of the present invention relates to antibodies and T-cell antigen receptors (TCRs), which immunospecifically bind to a biomarker polypeptide (e.g., SEQ ID NO:1 to SEQ ID NO:15 and SEQ ID NO:61 to SEQ ID NO:64), peptide, or variant of the present invention as determined by immunoassays well known in the art for assaying specific antibody-antigen binding. Also related are bispecific or bifunctional antibodies, which have two different heavy/light chain pairs and two different binding sites. Bispecific antibodies can be produced by a variety of methods, including fusion of hybridomas or linking of Fab' fragments (see, e.g., Songsivilai & Lachmann, 1990, *Clin. Exp. Immunol.,* 79:315-321; Kostelny et al., 1992, *J. Immunol.,* 148:1547 1553). In addition, bispecific antibodies can be formed as “diabodies” (see, Holliger et al., 1993, *Proc. Natl. Acad. Sci. USA,* 90:6444-6448), or “Janusins” (see, Traunecker et al., 1991, *EMBO J.,* 10:3655-3659 and Traunecker et al., 1992, *Int. J. Cancer Suppl.* 7:51-52-127).

The antibodies of the invention (including molecules comprising, or alternatively consisting of, antibody fragments or variants thereof) can bind immunospecifically to a polypeptide or polypeptide fragment or variant of a human biomarker polypeptide as set forth in SEQ ID NO:1 to SEQ ID NO:15 and SEQ ID NO:61 to SEQ ID NO:64. By way of non-limiting example, an antibody can be considered to bind to a first antigen preferentially if it binds to the first antigen with a dissociation constant (Kd) that is less than the antibody's Kd for the second antigen. In another non-limiting embodiment, an antibody can be considered to bind to a first antigen preferentially if it binds to the first antigen with an affinity that is at least one order of magnitude less than the antibody's Ka for the second antigen. In another non-limiting embodiment, an antibody can be considered to bind to a first antigen preferentially if it binds to the first antigen with an affinity that is at least two orders of magnitude less than the antibody's Kd for the second antigen.

In another nonlimiting embodiment, an antibody may be considered to bind to a first antigen preferentially if it binds to the first antigen with an off rate (koff) that is less than the antibody's koff for the second antigen. In another nonlimiting embodiment, an antibody can be considered to bind to a first antigen preferentially if it binds to the first antigen with an affinity that is at least one order of magnitude less than the antibody's koff for the second antigen. In another nonlimiting embodiment, an antibody can be considered to bind to a first antigen preferentially if it binds to the first antigen with an affinity that is at least two orders of magnitude less than the antibody's koff for the second antigen.

Production of Antibodies

The antibodies of the present invention may be generated by any suitable method known in the art. Polyclonal antibodies directed against an antigen or immunogen of interest can be produced by various procedures. For example, a biomarker polypeptide (e.g., SEQ ID NO:1 to SEQ ID NO:15 and SEQ ID NO:61 to SEQ ID NO:64) or peptide of the invention can be administered to various host animals as elucidated above to induce the production of sera containing polyclonal antibodies specific for the antigen. For the production of antibodies in vivo, host animals, such as rabbits, rats, mice, sheep, or goats, can immunized with either free or carrier-coupled peptides or MAP peptides, for example, by intraperitoneal and/or intradermal injection. Injection material is typically an emulsion containing about 100 μg of peptide or carrier protein and Freund's adjuvant, or any other adjuvant known for stimulating an immune response.

Various adjuvants may be used depending on the host species, including but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of anti-peptide antibody which can be detected, for example, by ELISA assay using free polypeptide or peptide adsorbed to a solid surface. The titer of anti-biomarker antibodies in serum from an immunized animal can be increased by selection of anti-biomarker antibodies, e.g., by adsorption of the biomarker polypeptide or peptide onto a solid support and elution of the selected antibodies according to methods well known in the art.

Monoclonal antibodies can be prepared using a wide variety of techniques known in the art, including the use of hybridoma, recombinant and phage display technologies, or a combination thereof. For example, monoclonal antibodies can be produced using hybridoma techniques as known and practiced in the art and as taught, for example, in Harlow et al., Antibodies: A Laboratory Manual, (Cold Spring Harbor Laboratory Press, 2nd Ed. 1988; Hammerling, et al., In: Monoclonal Antibodies and T-Cell Hybridomas, Elsevier, N.Y., pages 563-681, 1981, the contents of which are incorporated herein by reference in their entireties. Methods for producing and screening for specific antibodies using hybridoma technology are routine and well known in the art.

In a nonlimiting example, mice can be immunized with a biomarker polypeptide (e.g., SEQ ID NO:1 to SEQ ID NO:15 and SEQ ID NO:61 to SEQ ID NO:64) or peptide of the invention, or with a cell expressing the polypeptide or peptide. Once an immune response is detected, e.g., antibodies specific for the antigen are detected in the sera of immunized mice, the spleen is harvested and splenocytes are isolated. The splenocytes are then fused by well known techniques to any suitable myeloma cells, for example cells from cell line SP2/0 or P3×63-AG8.653 available from the ATCC. Hybridomas are selected and cloned by limiting dilution techniques. The hybridoma clones are then assayed by methods known in the art to determine and select those cells that secrete antibodies capable of binding to a polypeptide of the invention. Ascites fluid, which generally contains high levels of antibodies, can be generated by immunizing mice with positive hybridoma clones.

Accordingly, the present invention encompasses methods of generating monoclonal antibodies, as well as the antibodies produced by these methods, comprising culturing a hybridoma cell secreting an antibody of the invention wherein, preferably, the hybridoma is generated by fusing splenocytes isolated from a mouse immunized with a biomarker polypeptide or peptide antigen of the invention with myeloma cells and then screening the hybridomas resulting from the fusion for hybridoma clones that secrete an antibody that binds to a polypeptide of the invention.

Another well known method for producing both polyclonal and monoclonal human B cell lines is transformation using Epstein Barr Virus (EBV). Protocols for generating EBV-transformed B cell lines are commonly known in the art, such as, for example, the protocol outlined in Chapter 7.22 of *Current Protocols in Immunology*, Coligan et al., Eds., 1994, John Wiley & Sons, NY, which is hereby incorporated by reference herein in its entirety. The source of B cells for transformation is commonly human peripheral blood, but B cells for transformation can also be obtained from other sources including, but not limited to, lymph node, tonsil, spleen, tumor tissue, and infected tissues. Tissues are generally prepared as single cell suspensions prior to EBV transformation. In addition, T cells that may be present in the B cell samples can be either physically removed or inactivated (e.g., by treatment with cyclosporin A). The removal of T cells is often advantageous, because T cells from individuals seropositive for anti-EBV antibodies can suppress B cell immortalization by EBV. In general, a sample containing human B cells is innoculated with EBV and cultured for 3-4 weeks. A typical source of EBV is the culture supernatant of the B95-8 cell line (ATCC; VR-1492). Physical signs of EBV transformation can generally be seen toward the end of the 3-4 week culture period.

By phase-contrast microscopy, transformed cells appear large, clear and "hairy"; they tend to aggregate in tight clusters of cells. Initially, EBV lines are generally polyclonal.

However, over prolonged periods of cell culture, EBV lines can become monoclonal as a result of the selective outgrowth of particular B cell clones. Alternatively, polyclonal EBV transformed lines can be subcloned (e.g., by limiting dilution) or fused with a suitable fusion partner and plated at limiting dilution to obtain monoclonal B cell lines. Suitable fusion partners for EBV transformed cell lines include mouse myeloma cell lines (e.g., SP2/0, X63-Ag8.653), heteromyeloma cell lines (human×mouse; e.g., SPAM-8, SBC-H20, and CB-F7), and human cell lines (e.g., GM 1500, SKO-007, RPMI 8226, and KR-4). Thus, the present invention also includes a method of generating polyclonal or monoclonal human antibodies against polypeptides of the invention or fragments thereof, comprising EBV-transformation of human B cells.

Antibody fragments that recognize specific epitopes can be generated by known techniques. For example, Fab and F(ab')2 fragments of the invention may be produced by proteolytic cleavage of immunoglobulin molecules, using enzymes such as papain (to produce Fab fragments) or pepsin (to produce F (ab')2 fragments). F(ab')2 fragments contain the variable region, the light chain constant region and the CH1 domain of the heavy chain.

Antibodies encompassed by the present invention can also be generated using various phage display methods known in the art. In phage display methods, functional antibody domains are displayed on the surface of phage particles that carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds to the antigen of interest can be selected or identified with antigen, e.g., using labeled antigen or antigen bound or captured onto a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein.

Non-limiting examples of phage display methods that can be used to make the antibodies of the present invention include those disclosed in Brinkman et al., 1995, *J. Immunol. Methods,* 182:41-50; Ames et al., 1995, *J. Immunol. Methods,* 184:177-186; Kettleborough et al., 1994, *Eur. J. Immunol.,* 24:952-958; Persic et al., 1997, *Gene,* 187:9-18; Burton et al., 1994, *Advances in Immunology,* 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., 1992, *BioTechniques,* 12(6):864-869; Sawai et al., 1995, *AJRI,* 34:2634; and Better et al., 1988, *Science,* 240:1041-1043, which are hereby incorporated by reference herein in their entireties.

Examples of techniques that can be used to produce single-chain Fvs and antibodies include those described in U.S. Pat. Nos. 4,946,778 and 5,258,498; Huston et al., 1991, *Methods in Enzymology,* 203:46-88; Shu et al., 1993, *Proc. Natl. Acad. Sci. USA,* 90:7995-7999; and Skerra et al., 1988, *Science,* 240:1038-1040. For some uses, including the in vivo use of antibodies in humans and in in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, 1985, *Science,* 229:1202; Oi et al., 1986, *BioTechniques,* 4:214; Gillies et al., 1989, *J. Immunol. Methods,* 125:191-202; and U.S. Pat. Nos. 5,807,715; 4,816,567; and 4,816,397, which are incorporated herein by reference in their entirety.

Standard techniques known to those of skill in the art can be used to introduce mutations in the nucleotide sequence encoding a an antibody molecule of the invention, including, for example, site-directed mutapolynucleotides and polypeptidesis and PCR-mediated mutapolynucleotides and polypeptidesis which result in amino acid substitutions. Preferably the molecules are immunoglobulin molecules. Also, preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, relative to the reference $V_H$ domain, $V_H$ CDR1, $V_H$ CDR2, $V_H$ CDR3, $V_L$ domain, $V_L$ CDR1, $V_L$ CDR2, or $V_L$ CDR3.

Antibody variants may comprise one or more conservative amino acid substitutions, such that amino acid residues are replaced with residues having a side chains with a similar properties. Families of amino acid residues having side chains with similar properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutapolynucleotides and polypeptidesis. The resultant mutants can be screened for biological activity to identify mutants that retain activity.

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or to improve hybridoma antibody production. Alternatively, non-neutral missense mutations can alter an antibody's ability to bind antigen. The location of most silent and neutral missense mutations is likely to be in the framework regions, while the location of most non-neutral missense mutations is likely to be in the CDRs, although this is not an absolute requirement. One of skill in the art is able to design and test mutant molecules with desired properties, such as no alteration in antigen binding activity or alteration in binding activity (e.g., improvements in antigen binding activity or change in antibody specificity). Following mutapolynucleotides and polypeptidesis, the encoded protein may routinely be expressed and the functional and/or biological activity of the encoded protein can be determined using techniques described herein or by routinely modifying techniques known and practiced in the art.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that immunospecifically binds to a biomarker polypeptide (e.g., SEQ ID NO:1 to SEQ ID NO:15 and SEQ ID NO:61 to SEQ ID NO:64) or fragments or variants of a biomarker polypeptide, comprises, or alternatively consists of, a $V_H$ domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a $V_H$ domain of a heavy chain expressed by an anti-biomarker polypeptide antibody-expressing cell line of the invention.

In another embodiment, an antibody, including a molecule comprising, or alternatively consisting of, an antibody fragment or variant thereof, that immunospecifically binds to a biomarker polypeptide or fragments or variants of a biomarker polypeptide, comprises, or alternatively consists of, a $V_L$ domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a $V_L$ domain of a light chain expressed by an anti-biomarker polypeptide antibody-expressing cell line of the invention.

Antibodies of the invention may be chemically synthesized or produced through the use of recombinant expression systems. Accordingly, the invention further embraces polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, an antibody that specifically binds to a polypeptide of the invention, preferably, an antibody that binds to a polypeptide having the amino acid sequence of one or more of the biomarker sequences as set forth in SEQ ID NO:1 to SEQ ID NO:15 and SEQ ID NO:61 to SEQ ID NO:64.

If the nucleotide sequence of the antibody is known, a polynucleotide encoding the antibody can be assembled from chemically synthesized oligonucleotides (e.g., as described in Kutmeier et al., 1994, *BioTechniques,* 17:242), which, briefly, involves the synthesis of overlapping oligonucleotides containing portions of the sequence encoding the antibody, the annealing and ligating of those oligonucleotides, and then the amplification of the ligated oligonucleotides by PCR. Alternatively, a polynucleotide encoding an antibody can be generated from nucleic acid from a suitable source. For example, if the sequence of the antibody molecule is known, a nucleic acid encoding the immunoglobulin can be chemically synthesized or obtained from a suitable source, e.g., an antibody cDNA library, or a cDNA library generated from, or a nucleic acid, preferably poly A+ RNA, isolated from, any tissue or cells expressing the antibody, such as hybridoma cells selected to express an antibody of the invention by PCR amplification using synthetic primers hybridizable to the 3' and 5' ends of the sequence. Alternatively, the sequence can be cloned using an oligonucleotide probe specific for the particular gene sequence to identify, for example, a cDNA clone from a cDNA library. Amplified nucleic acids generated by PCR can then be cloned into replicable cloning vectors using any method well known in the art.

Once the nucleotide sequence and corresponding amino acid sequence of the antibody are determined, the nucleotide sequence of the antibody can be manipulated using methods well known in the art for the manipulation of nucleotide sequences, e.g., recombinant DNA techniques, site directed mutapolynucleotides and polypeptidesis, PCR, etc. to generate antibodies having a different amino acid sequence, for example, to create amino acid substitutions, deletions, and/or insertions. See, for example, the techniques described in Sambrook et al., 1990, *Molecular Cloning, A Laboratory Manual,* 2nd Ed., Cold Spring Harbor Laboratory, Cold Spring Harbor, N.Y.; and Ausubel et al., eds., 1998, *Current Protocols in Molecular Biology*, John Wiley & Sons, NY, which are both incorporated by reference herein in their entireties.

A variety of host expression vector systems can be utilized to express the antibody molecules of the invention. Such expression systems represent vehicles by which the coding sequences of interest can be expressed, their encoded products produced and subsequently purified. These systems also represent cells that can, when transformed or transfected with the appropriate nucleotide coding sequences, express an antibody molecule of the invention in situ. Cell expression systems include, but are not limited, to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces* or *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus (CaMV) or tobacco mosaic virus (TMV)), transformed with recombinant plasmid expression vectors (e.g., Ti plasmid) containing antibody coding sequences; or mammalian cell systems (e.g., COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *E. coli*, and more preferably, eukaryotic cells, especially for the expression of whole recombinant antibody molecules, are used for the expression of a recombinant antibody molecule. For example, mammalian cells such as Chinese hamster ovary (CHO) cells, in conjunction with a vector such as the major intermediate early gene promoter element from human cytomegalovirus, is an effective expression system for antibodies (Foecking et al., 1986, *Gene,* 45:101; Cockett et al., 1990, *BioTechnology,* 8:2).

In bacterial systems, a number of expression vectors can be advantageously selected depending upon the use intended for the antibody molecule being expressed. For example, when a large quantity of such a protein is to be produced for the generation of pharmaceutical compositions of an antibody molecule, for example, vectors that direct the expression of high levels of fusion protein products that are readily purified are often desirable. Such vectors include, but are not limited to, the *E. coli* expression vector pUR278 (Ruther et al., 1983, *EMBO J.,* 2:1791), in which the antibody coding sequence can be ligated individually into the vector in-frame with the lacZ coding region so that a fusion protein is produced; pIN vectors (Inouye & Inouye, 1985, *Nucleic Acids Res.,* 13:3101-3109; Van Heeke & Schuster, 1989, *J. Biol. Chem.,* 24:5503-5509; and the like). pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign polynucleotides and polypeptides. The virus grows in *Spodoptera figuriperda* cells. The antibody coding sequence may be cloned individually into non-essential regions (for example the polyhedrin gene) of the virus and placed under control of an AcNPV promoter (for example the polyhedrin promoter). In mammalian host cells, a number of viral based expression systems can be utilized. In cases in which an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) results in a recombinant virus that is viable and capable of expressing the antibody molecule in infected hosts. See, e.g., Logan and Shenk, 1984, *Proc. Natl. Acad. Sci. USA,* 81:355-359. Specific initiation signals can also be required for efficient translation of inserted antibody coding sequences. These signals include the ATG initiation codon and adjacent sequences. Furthermore, the initiation codon must be in-phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, *Methods in Enzymol.,* 153:51-544).

In addition, a host cell strain can be chosen to modulate the expression of the inserted sequences, or to modify and process the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell lines such as, for example, CRL7030 and Hs578Bst.

For long-term, high-yield production of recombinant proteins, stable expression is preferred. For example, cell lines that stably express the antibody molecule can be engineered. Rather than using expression vectors that contain viral origins of replication, host cells can be transformed with DNA controlled by appropriate expression control elements (e.g., promoters, enhancer sequences, transcription terminators, polyadenylation sites, etc.), and a selectable marker. Following the introduction of the foreign DNA, such genetically engineered cells can be allowed to grow for 1-2 days in an enriched medium, and then are typically replated in a selective medium. A selectable marker in the recombinant plasmid confers resistance to the selection and allows cells to stably integrate the plasmid into their chromosomes and grow to form foci which, in turn, can be cloned and expanded into cell lines. This method can advantageously be used to engineer cell lines expressing the antibody molecule. Such engineered cell lines are particularly useful in screening and evaluation of compounds that interact directly or indirectly with the antibody molecule.

A number of selection systems can be used, including but not limited to, herpes simplex virus thymidine kinase (HSV TK), (Wigler et al., 1977, *Cell,* 11:223), hypoxanthine-guanine phosphoribosyltransferase (HGPRT), (Szybalska and Szybalski, 1992, *Proc. Natl. Acad. Sci. USA,* 48:202), and adenine phosphoribosyltransferase (Lowy et al., 1980, *Cell,* 22:817) polynucleotides and polypeptides can be employed in tk-, hgprt-, or aprt-cells (APRT), respectively.

In addition, anti-metabolite resistance can be used as the basis of selection for the following polynucleotides and polypeptides: dhfr, which confers resistance to methotrexate (Wigler et al., 1980, *Proc. Natl. Acad. Sci. USA,* 77:357; and O'Hare et al., 1981, *Proc. Natl. Acad. Sci. USA,* 78:1527); gpt, which confers resistance to mycophenolic acid (Mulligan and Berg, 1981, *Proc. Natl. Acad. Sci. USA,* 78:2072); neo, which confers resistance to the aminoglycoside G418 (*Clinical Pharmacy,* 12:488-505; Wu and Wu, 1991, *Biotherapy,* 3:87-95; Tolstoshev, 1993, *Ann. Rev. Pharmacol. Toxicol.,* 32:573-596; Mulligan, 1993, Science, 260:926-932; Anderson, 1993, *Ann. Rev. Biochem.,* 62:191-21; May, 1993, *TIB TECH,* 11(5):155-215; and hygro, which confers resistance to hygromycin (Santerre et al., 1984, *Gene,* 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, NY (1993); Kriegler, 1990, *Gene Transfer and Expression, A Laboratory Manual*, Stockton Press, NY; in Chapters 12 and 13, Dracopoli et al. (eds), *Current Protocols in Human Genetics*, John Wiley & Sons, NY (1994); Colberre-Garapin et al., 1981. *J. Mol. Biol.,* 150:1, which are incorporated by reference herein in their entireties.

The expression levels of an antibody molecule can be increased by vector amplification (for a review, see Bebbington and Hentschel, The use of vectors based on gene amplification for the expression of cloned polynucleotides and polypeptides in mammalian cells in DNA cloning, Vol. 3. (Academic Press, New York, 1987). When a marker in the vector system expressing an antibody is amplifiable, an increase in the level of inhibitor present in the host cell culture will increase the number of copies of the marker gene. Since the amplified region is associated with the antibody gene, production of the antibody will also increase (Crouse et al., 1983, *Mol. Cell. Biol.,* 3:257).

Vectors that use glutamine synthase (GS) or DHFR as the selectable markers can be amplified in the presence of the drugs methionine sulphoximine or methotrexate, respectively. An advantage of glutamine synthase based vectors is the availability of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene.

Vectors that express glutamine synthase as the selectable marker include, but are not limited to, the pEE6 expression vector described in Stephens and Cockett, 1989, *Nucl. Acids. Res.,* 17:7110. A glutamine synthase expression system and components thereof are detailed in PCT publications: WO87/04462; WO86/05807; WO89/01036; WO89/10404; and WO91/06657, which are incorporated by reference herein in their entireties. In addition, glutamine synthase expression vectors that can be used in accordance with the present invention are commercially available from suppliers, including, for example, Lonza Biologics, Inc. (Portsmouth, N.H.). The expression and production of monoclonal antibodies using a GS expression system in murine myeloma cells is described in Bebbington et al., 1992, *BioTechnology,* 10:169 and in Biblia and Robinson, 1995, *Biotechnol. Prog.,* 11:1, which are incorporated by reference herein in their entireties.

A host cell can be co-transfected with two expression vectors of the invention, the first vector encoding a heavy chain derived polypeptide and the second vector encoding a light chain derived polypeptide. The two vectors can contain identical selectable markers that enable equal expression of heavy and light chain polypeptides. Alternatively, a single vector can be used which encodes, and is capable of expressing, both the heavy and light chain polypeptides. In such situations, the light chain should be placed before the heavy chain to avoid an excess of toxic free heavy chain (Proudfoot, 1986, *Nature,* 322:52; Kohler, 1980, *Proc. Natl. Acad. Sci. USA,* 77:2197). The coding sequences for the heavy and light chains can comprise cDNA or genomic DNA.

Once an antibody molecule of the invention has been produced by an animal, chemically synthesized, or recombinantly expressed, it can be purified by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Moreover, the antibodies or fragments thereof of the present invention can be fused to marker sequences, such as a peptide, to facilitate their purification. In preferred embodiments, the marker amino acid sequence is a hexa-histidine peptide, such as the tag provided in a pQE vector (QIAGEN, Inc., Chatsworth, Calif.), among others, many of which are commercially available. As described in Gentz et al., 1989, *Proc. Natl. Acad. Sci. USA,* 86:821-824, for instance, hexa histidine provides for convenient purification of the fusion protein. Other peptide tags useful for purification include, but are not limited to, the "HA" tag, which corresponds to an epitope derived from the influenza hemagglutinin (HA) protein (Wilson et al., 1984, *Cell,* 37:767) and the "flag" tag.

The present invention encompasses antibodies that are recombinantly fused or chemically conjugated (including both covalently and non-covalently conjugated) to a biomarker polypeptide (e.g., SEQ ID NO:1 to SEQ ID NO:15 and SEQ ID NO:61 to SEQ ID NO:64), or portion thereof, preferably at least 10, 20, 30, 40, 50, 60, 70, 80, 90 or 100 amino acids of the polypeptide, to generate fusion proteins. The fusion does not necessarily need to be direct, but can occur through linker sequences. The antibodies can be specific for antigens other than the biomarker polypeptides, or portions thereof, preferably at least 10, 20, 30, 40, 50, 60, 70, 80, 90 or 100 amino acids of a polypeptide of the present invention. Antibodies fused or conjugated to the polypeptides of the present invention may also be used in in vitro immunoassays and purification methods using methods known in the art. See, e.g., Harbor et al., supra, and PCT publication WO 93/21232; EP 439, 095; Naramura et al., 1994, *Immunol. Lett.,* 39:91-99; U.S. Pat. No. 5,474,981; Gillies et al., 1992, *Proc. Natl. Acad. Sci. USA,* 89:1428-1432; Fell et al., 1991, *J. Immunol.,* 146:2446-2452, which are incorporated by reference herein in their entireties.

Figure 2:
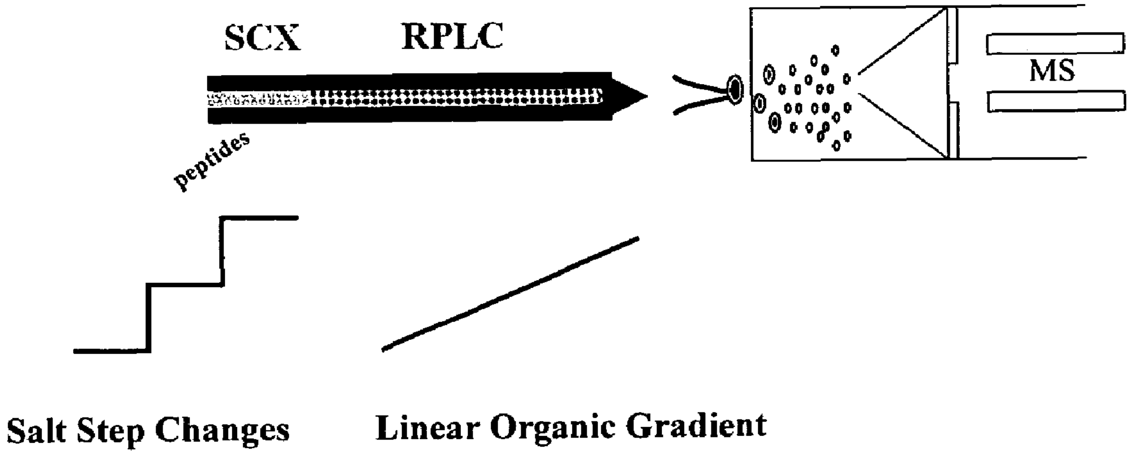
FIG. 2. A diagram of the proteomics apparatus used for the initial discovery phase of this research. The biphasic packed capillary served as a means of separating the peptides created by the proteolysis of the polypeptides found in the cell supernatants. These separated peptides were introduced into the mass spectrometer by electrospray ionization for identification and quantitation analysis.

In various aspects of the invention, antibodies of the present invention (including fragments or variants thereof) can also be fused to albumin (including, but not limited to, recombinant human serum albumin (see, e.g., U.S. Pat. No. 5,876,969, issued Mar. 2, 1999; EP Patent 0 413 622; and U.S. Pat. No. 5,766,883, issued Jun. 16, 1998, incorporated herein by reference in their entirety), resulting in chimeric polypeptides. In a preferred embodiment, antibodies of the present invention (including fragments or variants thereof) are fused with the mature form of human serum albumin (i.e., amino acids 1-585 of human serum albumin as shown in FIGS. 1 and 2 of EP Patent 0 322 094, which is herein incorporated by reference in its entirety). More preferably, antibodies of the present invention, including fragments or variants thereof, are fused with polypeptide fragments comprising, or alternatively consisting of, amino acid residues 1-z of human serum albumin, where z is an integer from 369 to 419, as described in U.S. Pat. No. 5,766,883 incorporated herein by reference in its entirety. Such fusions may, for example, facilitate purification and may increase half-life in vivo.

The present invention further includes compositions comprising the biomarker polypeptides of the present invention (e.g., SEQ ID NO:1 to SEQ ID NO:15 and SEQ ID NO:61 to SEQ ID NO:64) fused or conjugated to antibody domains other than the variable region domain. For example, the polypeptides of the present invention can be fused or conjugated to an antibody Fc region, or portion thereof. The antibody portion fused to a polypeptide of the present invention can comprise the constant region, hinge region, CH1 domain, CH2 domain, CH3 domain, or any combination of whole domains or portions thereof. The polypeptides can also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., 1991, *Proc. Natl. Acad. Sci. USA,* 88:10535-10539; Zheng et al., 1995, *J. Immunol.,* 154:5590-5600; and Vil et al., *Proc. Natl. Acad. Sci. USA,* 89:11337-11341, which are hereby incorporated by reference herein in their entireties.

Such fusions can be used to increase the in vivo half-life of the polypeptides, facilitate purification, or carry out immunoassays using methods known in the art. As guidance, chimeric proteins having the first two domains of the human CD4 polypeptide and various domains of the constant regions of the heavy or light chains of mammalian immunoglobulins have been described (see, e.g., EP 394,827; Traunecker et al., 1988, *Nature,* 331:84-86). The polypeptides of the present invention fused or conjugated to an antibody, or portion thereof, having disulfide-linked dimeric structures due to the IgG, for example, can also be more efficient in binding and neutralizing other molecules, than the monomeric secreted protein or protein fragment alone (Fountoulakis et al., 1995, *J. Biochem.,* 270:3958-3964). In many cases, the Fc portion in a fusion protein is beneficial in therapy, diagnosis, and/or screening methods, and thus can result in, for example, improved pharmacokinetic properties (see, e.g., EP A 232, 262). In drug discovery, for example, the biomarker polypeptides can be fused with Fc domains for the purpose of high-throughput screening assays to identify biomarker antagonists (see, Bennett et al., 1995, *J. Molecular Recognition,* 8:52-58; and Johanson et al., 1995, *J. Biol. Chem.,* 270:9459-9471). Alternatively, the Fc portion can be deleted after the fusion protein has been expressed, detected, and purified. For example, the Fc portion of the fusion protein can be deleted for therapeutic and diagnostic applications.

The present invention further encompasses antibodies or fragments thereof conjugated to a molecule to facilitate detection. Nonlimiting examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. See, for example, U.S. Pat. No. 4,741,900 for metal ions that can be conjugated to antibodies for use as diagnostics according to the present invention. Nonlimiting examples of suitable enzymes include horseradish peroxidase, alkaline phosphatase, beta-galactosidase, or acetylcholinesterase; Nonlimiting examples of suitable prosthetic group complexes include streptavidin/biotin and avidin/biotin; nonlimiting examples of suitable fluorescent materials include umbelliferone, fluorescein, fluorescein isothiocyanate, rhodamine, dichlorotriazinylamine fluorescein, dansyl chloride or phycoerythrin; a nonlimiting example of a luminescent material includes luminol; nonlimiting examples of bioluminescent materials include luciferase, luciferin, and aequorin; and nonlimiting examples of suitable radioactive material include iodine ($^{125}$I, $^{131}$I), carbon ($^{14}$C), sulfur (3sus), tritium ($^{3}$H), indium ($^{111}$In and other radioactive isotopes of inidium), technetium ($^{99}$Tc, $^{99m}$Tc), thallium (20Ti), gallium ($^{68}$Ga, $^{67}$Ga), palladium ($^{103}$Pd), molybdenum ($^{99}$Mo), xenon ($^{133}$Xe), fluorine ($^{19}$F), $^{153}$Sm, $^{177}$Lu, Gd, radioactive Pm, radioactive La, radioactive Yb, $^{166}$Ho, $^{90}$Y, radioactive Sc, radioactive Re, radioactive Re, $^{142}$Pr, $^{105}$Rh, and $^{97}$Ru. Antibodies can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

As nonlimiting examples, antibodies of the present invention can be used to purify, detect, and target the polypeptides of the present invention, including both in vitro and in vivo diagnostic, detection, screening, and/or therapeutic methods. For example, the antibodies have use in immunoassays for qualitatively and quantitatively measuring levels of the biomarker polypeptides of the present invention in biological samples. See, e.g., Harlow et al., *Antibodies: A Laboratory Manual*, Cold Spring Harbor Laboratory Press, 2nd Ed. 1988, which is incorporated by reference herein in its entirety. In specific aspects of the invention, the antibodies can be utilized for typing of drugs, compounds, or other therapeutic agents incubated with cell lines or patients' cells. Antibodies directed against a specific biomarker polypeptide, epitope, or combination of epitopes, allow for the measurement of levels (e.g., extracellular, intracellular, or cell lysate levels) of on or more biomarkers. Various techniques utilizing antibodies can be employed to screen for levels of the biomarker(s), including magnetic separation using antibody-coated magnetic beads, and "panning" with antibody(ies) attached to a solid matrix (i.e., tissue culture plate). These techniques allow for the screening of particular populations of cells, such as cells from individual patients or patient populations.

Antibodies according to this invention can be assayed for immunospecific binding by any method known in the art. The immunoassays which can be used include, but are not limited to, competitive and non-competitive assay systems using techniques such as BIAcore analysis, FACS (Fluorescence Activated Cell Sorter) analysis, immunofluorescence, immunocytochemistry, Western blots, radioimmunoassays (RIAs), ELISAs (enzyme linked immunosorbent assays), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few. Such assays are routine and well known and practiced in the art (see, e.g., Ausubel et al, eds, 1994, *Current Protocols in Molecular Biology*, Vol. 1, John Wiley & Sons, Inc., New York, which is incorporated by reference herein in its entirety). Nonlimiting, exemplary immunoassays are described briefly below.

Immunoprecipitation protocols generally comprise lysing a population of cells in a lysis buffer such as RIPA buffer (i.e., 1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate); adding the antibody of interest to the cell lysate; incubating for a period of time (e.g., 1 to 4 hours) at 4° C.; adding protein A and/or protein G sepharose beads to the cell lysate; incubating for about 60 minutes or more at 4° C.; washing the beads in lysis buffer; and resuspending the beads in SDS/sample buffer. The ability of the antibody of interest to immunoprecipitate a particular antigen can be assessed by, for example, Western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols, see, e.g., Ausubel et al, eds, 1994, *Current Protocols in Molecular Biology*, Vol. 1, John Wiley & Sons, Inc., New York, at 10.16.1.

Western blot analysis generally comprises preparing protein samples; electrophoresis of the protein samples in a polyacrylamide gel (e.g., 8%-20% SDS PAGE depending on the molecular weight of the antigen); transferring the protein sample from the polyacrylamide gel to a membrane such as nitrocellulose, PVDF or nylon; blocking the membrane in blocking solution (e.g., PBS with 3% BSA or nonfat milk); washing the membrane in washing buffer (e.g., PBS-Tween 20); blocking the membrane with primary antibody (the antibody of interest) diluted in blocking buffer; washing the membrane in washing buffer; blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer; washing the membrane in wash buffer; and detecting the presence of the antigen. One of skill in the art would be knowledgeable as to the parameters that can be modified to increase the signal detected and to reduce the background noise. For further discussion regarding Western blot protocols, see, e.g., Ausubel et al, eds, 1994, Current *Protocols in Molecular Biology*, Vol. 1, John Wiley & Sons, Inc., New York, at 10.8.1.

In one embodiment of the invention, ELISAs comprise preparing antigen, coating the wells of a multi-well microtiter plate with antigen, adding to the wells the antibody of interest conjugated to a detectable compound such as an enzymatic substrate (e.g., horseradish peroxidase or alkaline phosphatase), incubating for a period of time; and detecting the presence of the antigen. In ELISAs, the antibody of interest does not have to be conjugated to a detectable compound; instead, a second antibody (which recognizes the antibody of interest) conjugated to a detectable compound can be added to the wells. Further, instead of coating the wells with antigen, the antibody can be first coated onto the well. In this case, a second antibody conjugated to a detectable compound can be added to the antibody-coated wells following the addition of the antigen of interest. One of skill in the art would be knowledgeable as to the parameters that can be modified to increase the signal detected, as well as other variations of ELISAs known in the art. For further discussion regarding ELISAs, see, e.g., Ausubel et al, eds, 1994, *Current Protocols in Molecular Biology*, Vol. 1, John Wiley & Sons, Inc., New York, at 11.2.1.

The binding affinity of an antibody to an antigen and the off-rate of an antibody-antigen interaction can be determined by competitive binding assays. One example of a competitive binding assay is a radioimmunoassay involving the incubation of labeled antigen (e.g., $^{3}H$ or $^{125}I$), or a fragment or variant thereof, with the antibody of interest in the presence of increasing amounts of labeled antigen, and the detection of the antibody bound to the labeled antigen. The affinity of the antibody of interest for a biomarker polypeptide and the binding off rates can be determined from the data by Scatchard plot analysis. Competition with a second antibody can also be determined using radioimmunoassays. In this case, the biomarker polypeptide is incubated with antibody of interest conjugated to a labeled compound (e.g., a compound labeled with $^{3}H$ or $^{125}I$) in the presence of increasing amounts of an unlabeled second antibody. This kind of competitive assay between two antibodies may also be used to determine if two antibodies bind to the same or different epitopes.

In a preferred embodiment, BIAcore kinetic analysis is used to determine the binding on and off rates of antibodies (including antibody fragments or variants thereof) to a biomarker polypeptide, or fragments of a biomarker polypeptide. Kinetic analysis comprises analyzing the binding and dissociation of antibodies from chips with immobilized biomarker polypeptide or peptide on the chip surface.

It is to be further understood that the above-described techniques for the production, expression, isolation, and manipulation of antibody molecules, for example, by recombinant techniques involving molecular biology, as well as by other techniques related to the analysis of polynucleotides and polypeptides and proteins, are applicable to other polypeptide or peptide molecules of the invention as described herein, in particular, the biomarker polypeptides or peptides themselves, as applicable or warranted, in accordance with the various embodiments of this invention.

Treatments

In another embodiment, the present invention embraces the use of one or more biomarker polypeptides (e.g., SEQ ID NO:1 to SEQ ID NO:15 and SEQ ID NO:61 to SEQ ID NO:64) identified herein that can serve as targets for the development of drug therapies for hepatotoxicity, e.g., idiosyncratic hepatotoxicity. Because extracellular levels of these biomarker polypeptides are elevated in the presence of hepatotoxic substances, they may serve as targets for treating hepatotoxicity. As examples, various treatments can be used to decrease extracellular levels of a biomarker polypeptides, including administration of anti-biomarker antibodies such as polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments thereof, as described in detail herein. If expression levels of one or more nucleic acids (e.g., SEQ ID NO:46 to SEQ ID NO:60) encoding the disclosed biomarker polypeptides are also elevated in the presence of hepatotoxic substances, then other treatments may be used to counteract hepatotoxicity, for example, antisense sequences that prevent transcription or translation of the biomarkers of the invention (see, e.g., N. S. Templeton and D. D. Lasic, 2000, *Gene Therapy: Therapeutic Mechanisms and Strategies*, Marcel Dekker).

For antibody-based treatments, it may be preferable to use humanized antibodies, which bind to one or more biomarker polypeptide (e.g., SEQ ID NO:1 to SEQ ID NO:15 and SEQ ID NO:61 to SEQ ID NO:64), and comprise complementarity determining region(s) (CDRs) from a nonhuman species and framework regions from a human immunoglobulin molecule. For such antibodies, framework residues in the human framework regions are often substituted with the corresponding residues from the CDR donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. See, e.g., Queen et al., U.S. Pat. No. 5,585,089; and Riechmann et al., 1988, *Nature,* 332:323, which are incorporated herein by reference in their entireties. Antibodies can be humanized using a variety of techniques known in the art, including, for example, CDR-grafting (EP 239,400; PCT publication WO 91/09967; U.S. Pat. Nos. 5,225,539; 5,530,101; and 5,585,089); veneering or resurfacing (EP 592,106; EP 519,596; Padlan, 1991, *Molecular Immunology,* 28(4/5):489-498; Studnicka et al., 1994, *Protein Engineering,* 7(6):805-814; Roguska et al., 1994, *Proc. Natl. Acad. Sci. USA,* 91:969-973; and chain shuffling (U.S. Pat. No. 5,565,332).

Because humanized (i.e., chimeric) antibodies typically are comprised of a human constant region and a murine variable region, it is expected that certain human anti-chimeric antibody (HACA) responses will be observed, particularly in treatments involving chronic or multi-dose utilizations of the antibody. Thus, it is desirable to provide fully human antibodies against the biomarker polypeptides in order to vitiate concerns and/or effects of human anti-mouse antibody (HAMA) or HACA responses. Completely human antibodies can be made by a variety of established methods, including the phage display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. In addition, completely human antibodies that recognize a selected epitope can be generated using a technique referred to as "guided selection". In this approach, a selected non-human monoclonal antibody, e.g., a mouse antibody, is used to guide the selection of a completely human antibody recognizing the same epitope. (Jespers et al., 1988, *BioTechnology,* 12:899-903). For a detailed discussion of the technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety.

Human antibodies can also be produced using XenoMouse® technology (Abgenix, Fremont, Calif.; Green et al., 1994, *Nature Genetics,* 7:13-21), or similar approaches. See Mendez et al., 1997, *Nature Genetics,* 15:146-156; Green and Jakobovits, 1998, *J. Exp. Med.,* 188:483-495; and Green, 1999, *Journal of Immunological Methods,* 231:11-23, the disclosures of which are hereby incorporated herein by reference. Such methods employ a transgenic mouse that has a substantial portion of the human antibody producing genome inserted, and carries deletions of endogenous antibody producing regions. These mice are capable of producing human immunoglobulin molecules and antibodies, and are deficient in the production of murine immunoglobulin molecules and antibodies. Technologies utilized for achieving the same are disclosed in the patents, applications, and references disclosed herein. Notably, fully human antibodies are expected to minimize the immunogenic and allergic responses intrinsic to mouse or mouse-derivatized monoclonal antibodies and thus to increase the efficacy and safety of the administered antibodies. The use of fully human antibodies can be expected to provide a substantial advantage in the treatment or prevention of hepatotoxicity, which may require repeated antibody administrations.

In specific embodiments, human antibodies can be made by introducing the human heavy and light chain immunoglobulin gene complexes randomly, or by homologous recombination, into mouse embryonic stem cells. Alternatively, the human variable region, constant region, and diversity region may be introduced into mouse embryonic stem cells, in addition to the human heavy and light chain polynucleotides and polypeptides. The mouse heavy and light chain immunoglobulin polynucleotides and polypeptides can then be rendered nonfunctional separately or simultaneously with the introduction of human immunoglobulin loci by homologous recombination. In accordance with these methods, homozygous deletion of the $J_H$ region prevents endogenous antibody production. Following this, the modified embryonic stem cells can be expanded and microinjected into blastocysts to produce chimeric mice. The chimeric mice can then be bred to produce homozygous offspring which express human antibodies, and these offspring can be immunized in the normal fashion with a selected antigen, e.g., all or a portion of a biomarker polypeptide of the invention. Monoclonal antibodies directed against the antigen can be obtained from the immunized transgenic mice using conventional hybridoma technology. The human immunoglobulin transpolynucleotides and polypeptides harbored by the transgenic mice rearrange during B cell differentiation, and subsequently undergo class switching and somatic mutation. Thus, using such a technique, it is possible to produce useful human IgG, IgA, IgM and IgE antibodies. For an overview of the technology for producing human antibodies, see Lonberg and Huszar, 1995, *Intl. Rev. Immunol.* 13:65-93.

Intrabodies directed to one or more biomarker polypeptides (e.g., SEQ ID NO:1 to SEQ ID NO:15 and SEQ ID NO:61 to SEQ ID NO:64) can also be produced in accordance with the invention. Intrabodies are antibodies, often scFvs, that are expressed from a recombinant nucleic acid molecule and are engineered to be retained intracellularly, e.g., retained in the cytoplasm, endoplasmic reticulum, or periplasm of the host cells. Intrabodies can be used, for example, to ablate the function of the biomarker polypeptide to which the intrabody binds. The expression of intrabodies can also be regulated through the use of inducible promoters in the nucleic acid expression vector comprising nucleic acid encoding the intrabody. Intrabodies of the invention can be produced using methods known in the art, such as those disclosed and reviewed in Chen et al., 1994, *Hum. Gene Ther.,* 5:595-601; Marasco, W. A., 1997, *Gene Ther.,* 4:11-15; Rondon and Marasco, 1997, *Annu. Rev. Microbiol.,* 51:257-283; Proba et al., 1998, *J. Mol. Biol.,* 275:245-253; Cohen et al., 1998, *Oncogene,* 17:2445-2456; Ohage and Steipe, 1999, *J. Mol. Biol.,* 291:1119-1128; Ohage et al., 1999, *J. Mol. Biol.,* 291:1129-1134; Wirtz and Steipe, 1999, *Protein Sci.,* 8:2245-2250; Zhu et al., 1999, *J. Immunol. Methods,* 231:207-222.

For some purposes, it may be preferable to conjugate the anti-biomarker antibodies of the invention to one or more other therapeutic moieties for the treatment of hepatotoxicity. Techniques for conjugating therapeutic moieties to antibodies are well known, see, e.g., Hellstrom et al., "Antibodies For Drug Delivery", *In: Controlled Drug Delivery* (2nd Ed.), Robinson et al. (eds.), pp. 623-53, Marcel Deldcer, Inc., 1987. Alternatively, an antibody can be conjugated to a second antibody to form an antibody heteroconjugate, e.g., as described in U.S. Pat. No. 4,676,980 to Segal, which is incorporated herein by reference in its entirety. An antibody, i.e., an antibody specific for a biomarker polypeptide of this invention, with or without a therapeutic moiety conjugated to it, can be administered alone or in combination with other treatments for hepatotoxicity.

Screens

The present invention encompasses methods of determining or predicting if a drug, compound, or other therapeutic agent for use in the treatment for a disease or other medical condition will be likely to have hepatotoxic effects, e.g., idiosyncratic hepatotoxicity, in vivo. Ideally, such methods are performed prior to administration of the test substance (or combination of test substances) to an individual patient or patient population. In accordance with the method of the invention, hepatocyte cell lines or liver cells from a patient are subjected to a screening assay as described herein, to determine levels (e.g., extracellular, intracellular, or cell lysate levels) of one or more biomarker polypeptide (e.g., SEQ ID NO:1 to SEQ ID NO:15 and SEQ ID NO:61 to SEQ ID NO:64) in the presence and absence of one or more test substances. The biomarker polypeptide levels obtained from cells in the presence or absence of the test substance(s) are compared to determine if elevated levels correlate with treatment with the test substance(s). If increased levels of one or more biomarker polypeptides are observed in the presence of the test substance(s), it is highly likely or predicted that substance will cause in vivo hepatotoxicity. By contrast, if comparable levels of one or more biomarker polypeptides are observed in the presence and absence of the test substance(s), it is highly likely or predicted that the substance(s) will not cause in vivo hepatotoxicity. Thus, success or failure of treatment due to hepatotoxic effects can be predicted by measuring levels of the biomarker polypeptides of the invention.

For use with the methods of the present invention, any drug, compound, or other therapeutic agent can be screened for hepatotoxicity. As non-limiting examples, the methods of the invention can be used to test or screen anti-cancer, anti-bacterial, anti-fungal, anti-viral, anti-hypertension, anti-depression, anti-anxiety, and anti-arthritis substances, as well as substances for the treatment of allergies, diabetes, hypercholesteremia, osteoporosis, Alzheimer's disease, Parkinson's disease, and/or other neurodegenerative diseases, and obesity. Specific categories of test substances can include, but are not limited to, PPAR agonists, HIV protease inhibitors, anti-inflammatory drugs, estrogenic drugs, anti-estrogenic drugs, antihistimines, muscle relaxants, anti-anxiety drugs, anti-psychotic drugs, and anti-angina drugs.

Non-limiting examples of PPAR agonists include Pioglitazone, Rosiglitazone, Tesaglitazar, Ragaglitazar, Troglitazone, Farglitazar, Ciglitazone, Azelaoyl PAF, 2-Bromohexadecanoic acid, Clofibrate, 15-Deoxy-d12,14-prostaglandin, Fenofibrate, Fmoc-Leu-OH, GW1929, GW7647, 8(S)-Hydroxy-(5Z,9E,11Z,14Z)-eicosatetraenoic acid (8(S)-HETE), Leukotriene B4, LY-171,883 (Tomelukast), Prostaglandin A2, Prostaglandin J2, Tetradecylthioacetic acid (TTA), WY-14643 (Pirinixic acid), and NN622 (Novo Nordisk, A/S), and related substances. Non-limiting examples of anti-anxiety and anti-psychotic drugs include Hydroxyzine Hydrochloride, Lorazepam, Buspirone Hydrochloride, Pazepam, Chlordiazepoxide, Meprobamate, Oxazepam, Trifluoperazine, Clorazepate Dipotassium, Diazepam, Clozapine, Prochlorperazine, Haloperidol, Thioridazine, Thiothixene, Risperidone, Trifluoperazine Hydrochloride, Chlorpromazine, and related substances. Non-limiting examples of HIV protease inhibitors include Saquinavir, Amprenavir, Ritonavir, Nelfinavir, Indinavir, Atazanavir (BMS232632; Bristol-Myers Squibb), Fosamprenavir (GW433908; GlaxoSmithKline), L-756,423 (Merck), Mozenavir (DMP450; Triangle Pharmaceuticals), Tipranavir (PNU-140690; Boehringer Ingelheim); R0033-4649 (Roche) TMC114 (Tibotec Virco), and related substances.

Non-limiting examples of anti-inflammatory drugs include Diclofenac, Diflunisal, Etodolac, Fenoprofen, Flurbiprofen, Ibuprofen, Indomethacin, Ketoprofen, Ketorolac, Meclofenamate, Mefenamic Acid, Nabumetone, Naproxen, Oxaprozin, Piroxicam, Sulindac, Tolmetin, and related substances. Non-limiting examples of antihistimines include Azelastine (Astelin®), Fexofenadine (e.g., Allegra®), Cetirizine (e.g., Zyrtec®), Desloratadine (e.g., Clarinex®), Loratadine (e.g., Claritin®, Alayert®), Astemizole, Azatadine, Brompheniramine, Chlorpheniramine, Clemastine, Cyproheptadine, Dexchlorpheniramine, Dimenhydrinate, Diphenhydramine, Doxylamine, Hydroxyzine, Phenindamine, Pyrilamine, Terfenadine, Tripelennamine, Triprolidine, Methdilazine, Promethazine, Trimeprazine, Diphenhydramine Liquid, and related substances. Non-limiting examples of muscle relaxants include Dantrolene (e.g., Dantrium®), Baclofen (e.g., Lioresal®), Carisoprodol (e.g., Soma®), Chlorphenesin (e.g., Maolate®), Chlorzoxazone (e.g., Paraflex®), Cisatracurium, Cyclobenzaprine (e.g., Flexeril®), Dantrolene, Diazepam (e.g., Valium®), Metaxalone (e.g., Skelaxin®), Gallamine, Methocarbamol (e.g., Robaxin®), Mivacurium, Orphenadrine (e.g., Norflex®), Pancuronium, Rocuronium, Tizanidine, Suxamethonium, Vecuronium, and related substances.

Non-limiting examples of estrogens and anti-estrogens include conjugated estrogens (e.g., Premarin®), esterified estrogens (e.g., Estratab®, Menest®, Estratest®), synthetic conjugated estrogens (e.g., Cenestin®), Estropipate (e.g., Ogen®, Ortho-Est®), Ethinyl Estradiol (e.g., Estinyl®), Desogestrel, Diethylstilbestrol (e.g., Stilphostrol®), Dienestrol (e.g., Ortho Dienestrol®), Chlorotrianisene (Tace®), Estradiol (e.g., Estrace®, Alora®, Climara®, Vivelle®), Estradiol Cypionate (e.g., Depo-Estradiol®, Depogen®, Dura-Estrin®, Estra-D®, Estro-Cyp®, Estroject-LA®, Estronol-LA®), Estropipate, Ethacrynic Acid, Ethynodiol Diacetate, Levonorgestrel, Medroxyprogesterone, Medroxyprogesterone Acetate, Mestranol, Norethindrone, Norgestimate, Norgestrel, Tamoxifen (e.g., Nolvadex®), Toremifene (e.g., Fareston®), Raloxifene (e.g., Evista®), Megestrol Acetate (Megace®), Aminogluthethimide (e.g., Cytadren®), Anastrozole (e.g., Arimidex®), Letrozole (e.g., Femara®), Exemestane (e.g., Aromasin®), Goserelin (e.g., Zoladex®), Leuprolide (e.g., Lupron®), and related substances. Non-limiting examples of anti-angina drugs include Calan SR, Isoptin, Isoptin SR, Verelan, Nicardipine Hydrochloride, Diltiazem Hydrochloride, Nadolol, Isosorbide Mononitrate, Isosorbide Dinitrate, Metroprolol Tartrate, Nitroglycerin, Amlodipine Besylate, Nifedipine, Atenolol, and related substances.

The methods of the invention can employ available hepatocyte cell lines or liver cells obtained from individual patients. Preferably, the hepatocyte cell lines are human in origin, although mouse, rat, and porcine cell lines may also be used. Non-limiting examples of human hepatocyte cell lines include THLE-5 (Pfeifer, A. M., et al., 1993, *Proc. Natl. Acad. Sci. U.S.A.* 90, 5123-5127; also called THLE-5B), THLE-5B-c15, HH25 (Smalley et al., 1999, *In Vitro Cell. Dev. Biol—Animal* 35:22-32), HH29 (Kono and Roberts, 1996, *Biochem. Biophys. Res. Commun.* Mar 27; 220(3):628-32), HHY41 (Kono et al., 1995, *Exp. Cell. Res.* December; 221(2):478-85), HuH7 (Yamada et al., 1994, *Mol. Carcinog.* July; 10(3): 151-8), Hep3B (Majello et al., 1990, *EMBO J.* February; 9(2):457-65), HepG2 (Schilsky et al., 1989, *J. Clin. Invest.* November; 84(5):1562-8), OUMS-29 (Kobayashi et al., 2000, *Transplantation* January 27;69(2):202-7), ACTIV-Tox® (Amphioxus Cell Technologies, Houston, Tex.), PH5CH (Kato et al., 1996, *Jpn. J. Cancer Res.* 1996 August; 87(8):787-92), HepG2/C3A (ATCC No. CRL-10741), THLE-3 (ATCC No. CRL-11233), DBTRG-05MG (ATCC No. CRL-2020), THLE-2 (ATCC No. CRL-2706), SW 1783 (ATCC No. HTB-13), U-138 MG (ATCC No. HTB-16), SK-LMS-1 (ATCC No. HTB-88). In one aspect of the invention, immortalized but non-tumorigenic hepatic cell lines can be used, for example, HepLiu (Liu et al., 2001, *Artificial Organs* 25(7):539-545; Liu et al., 1999, *Cell Transplantation* 8:219-232; Cascio, 2001, *Artificial Organs* 25(7):529-538). In addition, various constructs can be used for transient or stable transformation of these cell lines, for example, constructs comprising one or more cytochrome P450 enzymes, such as 1A1, 1A2, 2A6, 2B6, 2C8, 2C9, 2C10, 2C19, 2D6, 2E1, 3A4, 3A5, and 3A7 (see, e.g., E. F. Johnson and M. R. Waterman, *Methods in Enzymology Series: Cytochrome P*450, Part C, Volume 357, Academic Press, 2002)

In a specific aspects of the invention, the disclosed methods are employed for predicting and/or determining prior to treatment whether a patient requiring one or more drugs for treatment of a disease (e.g., an anti-cancer drug or anti-HIV drug) will or will not successfully tolerate the drug(s). The methods of the invention can also be used for predicting or monitoring the patient's tolerance of one or more drugs once treatment has commenced. To monitor treatment with a therapeutic substance, for example, levels of biomarker polypeptides (e.g., SEQ ID NO:1 to SEQ ID NO:15 and SEQ ID NO:61 to SEQ ID NO:64) can be measured using biological samples obtained from one or more patients at designated intervals during treatment. In addition, samples can be tested before and after treatment, to determine base-line and post-treatment levels, respectively. As non-limiting examples, biological samples may include blood, urine, and/or saliva samples. In other aspects of the invention, treatments involving a specific combination of drugs (e.g., "drug cocktails" of anti-cancer or anti-HIV drugs) can be screened for hepatotoxic effects before or after administration to a patient. Preferably, the methods of the invention are used to screen a drug, compound, or other therapeutic agent prior to clinical testing. If a prediction of hepatotoxicity is obtained, the drug treatment(s) can be avoided, modified, changed, or discontinued.

Various techniques can be used to measure levels of one or more biomarker polypeptides (e.g., SEQ ID NO:1 to SEQ ID NO:15 and SEQ ID NO:61 to SEQ ID NO:64) found in the presence of absence of at least one drug, compound, or therapeutic agent (see, e.g., R. Seethala and P. Fernandes, 2001, *Handbook of Drug Screening*, Marcel Dekker). Non-limiting detection methods include direct, competitive, and sandwich RIAs and ELISAs, immunoprecipitation, immunofluorescence microscopy, indirect immunofluorescence, immunohistochemistry, western blotting, and other methods disclosed herein. One suitable method involves immunoprecipitation in solution followed by measuring the development of turbidity using a turbidimeter or nephelometer (see, e.g., Deverill and Reeves, 1980, *J. Immunol. Methods.* 38(3-4):191-204; Borque et al., 1995, *J. Clin. Lab. Anal.* 9(5):302-7; E. Diamandis and T. Christopoulus, 1996, *Immunoassay*, Academic Press, San Diego).

In some cases, it may be useful to measure levels of one or more biomarker polypeptides (e.g., SEQ ID NO:1 to SEQ ID NO:15 and SEQ ID NO:61 to SEQ ID NO:64) produced in situ in hepatocytes incubated in the presence or absence of a test substance. For immunofluorescence microscopy, anti-biomarker antibodies can be labeled, for example, with a fluorescent dye (e.g., Cy™3, Cy™5, Alexa, BODIPY, fluorescein, rhodamine, auramine, Texas Red, AMCA Blue, Lucifer Yellow, peridinin chlorophyll protein, and phycoerythrin, or others disclosed herein, or known in the art) and then incubated with the treated and untreated cells. Alternatively, the anti-biomarker antibody can be detected by a fluorescently labeled anti-immunoglobulin, using a technique known as indirect immunofluorescence. The stained cells can be examined in a microscope that exposes them to light to excite the fluorescent dye, which emits light at a characteristic wavelength and is observed through a selective filter (see, e.g., Janeway et al., *Immunobiology.* 5th ed., Garland Publishing, New York and London, 2001). In various aspects of the invention, different biomarker polypeptides can be detected by labeling anti-biomarker antibodies or secondary antibodies with dyes of distinctive color.

As an alternative to immunofluorescence, immunohistochemistry can be used to detecting levels of one or more biomarker polypeptides (e.g., SEQ ID NO:1 to SEQ ID NO:15 and SEQ ID NO:61 to SEQ ID NO:64) in hepatocytes incubated in the presence or absence of a test substance. In this technique, an anti-biomarker antibody is chemically coupled to an enzyme that converts a colorless substrate into a colored reaction product in situ. Alternatively, the anti-biomarker antibody can be detected by an anti-immunoglobulin conjugated to an enzyme label. In both cases, the labeled antibody can be localized by deposits of colored product that can be directly observed under a light microscope. This method is analogous to ELISA, and frequently uses the same coupled enzymes (e.g., horseradish peroxidase, alkaline phosphatase, or other enzymes disclosed herein or known in the art). As with immunofluorescence, the native structure of the biomarker polypeptide being sought usually needs to be preserved, so that it will be recognized by the antibody. Cells are therefore fixed by relatively gentle chemical fixation techniques or frozen samples are used and fixed only after the antibody reaction has been performed (see, e.g., Janeway et al., *Immunobiology.* 5th ed., Garland Publishing, New York and London, 2001).

In some instances the screening process is preferably automated so as to allow screening of suitable numbers of samples. Some examples of widely used types of automated detection systems include densitometric or ELISA readers, fluorescence readers, scintillation counters, and photoluminescence readers (see, e.g., D. Wild, 2001, *Immunoassay Handbook, 2nd ed*, Nature Publishing Group; Fluor-S Max reader, Bio-Rad, Hercules, Calif.). There are a variety of ways to use ELISA/densitometric readers and fluorescence readers to measure biomarker polypeptides in the test samples. Sample treatment varies according to the kind of sample and the type of reader being used. Automated ELISA reader devices are well known in the art (Davis, et al. *Microbiology* 4th. ed., pp. 269-270 (1990)) and are commercially available (see, e.g., Multiskan EX and RC, Komabiotech, Seoul, Republic of Korea; HT3, Anthos Analytical, Durham, N.C.).

In another embodiment, the present invention encompasses methods of classifying whether biological systems comprising hepatic cells will or will not tolerate one or more drugs, compounds, or other therapeutic agents. In a preferred aspect of this invention, cell tolerance to a test agent is determined, e.g., for cells obtained from a hepatic cell line or liver sample. For this method, levels (e.g., extracellular, intracellular, or cell lysate levels) of biomarker polypeptide are measured in the presence and absence of the test substance, using the protocols disclosed herein. If levels of biomarker polypeptide(s) are elevated in the presence of the test substance, this can predict that the hepatic cells will not tolerate the test substance. If levels of biomarker polypeptide(s) are comparable in the presence or absence of the test substance, this can predict that the hepatic cells will successfully tolerate the test substance. Advantageously, the methods of the invention can be performed using a variety of hepatic cell lines or liver samples, and many different types of test substances, or combinations thereof.

The present invention also embraces kits for determining or predicting in vivo hepatoxicity in a patient or patient population prior to or during administration of a drug, compound, or other therapeutic agent. Such kits are useful in clinical or pre-clinical settings, and can be used concurrently with various stages of patient trials. Provided in the kit are one or more biomarker polypeptides (e.g., SEQ ID NO:1 to SEQ ID NO:15 and SEQ ID NO:61 to SEQ ID NO:64) for use as positive controls, and anti-biomarker antibodies, for example, comprising a microarray, or in suitable containers, for use in testing cells, extracellular media, or cell lysates from hepatocyte cell lines or patient liver samples for toxic effects, and instructions for use. The kits of the invention can encompass a variety of methods and systems by which the levels of the biomarker polypeptides can be assayed and/or monitored, for example, via immunoassays, such as ELISA. In kits for performing immunoassays, e.g. ELISAs, immunoblotting assays, and the like, antibodies, or bindable portions thereof, that specifically bind to biomarker polypeptides (e.g., SEQ ID NO:1 to SEQ ID NO:15 and SEQ ID NO:61 to SEQ ID NO:64), or to antigenic or immunogenic peptides thereof, are supplied, in addition to buffers and reagents as necessary for performing the method.

The present invention also encompasses nucleic acids (e.g., SEQ ID NO:46 to SEQ ID NO:60) encoding the disclosed biomarker polypeptides, or fragments, variants, or derivatives thereof, which can be used as biomarkers for hepatotoxic effects of one or more drugs, compounds, or other therapeutic agents. If expression levels of such nucleic acids are elevated in the presence of hepatotoxic substances, they can be used in screening and detection assays of the invention. Such assays embrace a variety of methods for measuring nucleic acid levels in cells that have been exposed to one or more test substances. Suitable methods include detection and evaluation of gene activation or expression of, for example, DNA, RNA, or mRNA. As non-limiting examples, PCR assays (e.g., RT-PCR), Northern blotting, in situ hybridization, and other assays as known and practiced in the art can be employed to quantify RNA in cells being assayed for tolerance to a drug treatment (see, e.g., J. O'Connell, 2002, *RT-PCR Protocols*, Humana Press, Totowa, N.J.; R. Rapley and D. L. Manning, 1998, *RNA Isolation and Characterization Protocols*, Humana Press; R. Rapley, 2000, *Nucleic Acid Protocols Handbook*, Humana Press). In accordance with such assays, if levels of at least one biomarker nucleic acid are elevated in the presence of one or more test substances, this can predict that the substance(s) will cause in vivo hepatotoxic effects. If levels of at least one biomarker nucleic acids are comparable in the presence or absence of one or more test substance(s), this can predict that the substance(s) will not cause in vivo hepatotoxic effects.

In specific examples, expression of biomarker mRNA in the presence or absence of a test substance can be determined, for example, by Northern blotting or in situ hybridization of labeled DNA or RNA in hepatocytes. Northern blots permit comparison of both the level of expression and the size of mRNAs in treated and untreated cells. Although the sensitivity of in situ hybridization is lower than that of Northern blot analysis, it can be very helpful in identifying an mRNA that is expressed at very high levels in a subclass of cells (see, e.g., Lodish et al., *Molecular Cell Biology*, 4th ed., W H Freeman & Co, New York, 2000). Probes comprising all or a fragment of a biomarker nucleic acid (e.g., SEQ ID NO:46 to SEQ ID NO:60), or complementary sequences thereof, can be modified to include a detectable label (e.g., digoxigenin, fluorescent tag, or radiolabel), and incubated with hepatocytes incubated with or without a drug, compound, or other therapeutic agent. For this technique, the cells are not exposed to a high pH, so the chromosomal DNA remains double-stranded and cannot bind the probe. Instead the cells are gently fixed so that its mRNA is retained in an exposed form that will hybridize when the tissue is incubated with a complementary DNA or RNA probe (see, e.g., Alberts et al., *Molecular Biology of the Cell*, 3rd ed., Garland Publishing, New York and London, 1994). In this way the patterns of biomarker expression can be observed in the treated and untreated cells.

Also encompassed by the invention are kits for determining or predicting in vivo hepatotoxicity of a test substance using nucleic acids (e.g., SEQ ID NO:46 to SEQ ID NO:60) encoding the disclosed biomarker polypeptides, or complementary sequences, fragments, variants, or derivatives thereof. Such kits are useful in a clinical or pre-clinical settings, and preferably, can be used prior to patient trials. Provided in the kit are one or more biomarker polynucleotides whose levels correlate with increasing likelihood of hepatotoxicity, provided as a microarray or in suitable containers, along with instructions for use. Such kits are not limited to the employment of microarrays, but can encompass a variety of methods and systems by which the expression of the biomarker nucleic acids can be assayed and/or monitored, both at the level of mRNA and of protein, for example, via PCR assays such as RT-PCR, Northern analysis, or in situ hybridization. In kits for performing PCR assays or in situ hybridization, for example, nucleic acid primers (see, e.g., FIGS. 8A-8B) or probes comprising fragments of one or more of the biomarker nucleic acids, or complementary sequences, or fragments thereof, are supplied, in addition to buffers and reagents as necessary for performing the method, and, optionally, instructions for use.

Microarrays

The present invention encompasses microarrays, e.g., protein or antibody microarrays, which allow profiling of the extracellular or cell lysate levels of one or more biomarker polypeptides (e.g., SEQ ID NO:1 to SEQ ID NO:15 and SEQ ID NO:61 to SEQ ID NO:64) in the presence or absence of a test substance, which can be used to predict in vivo hepatotoxicity, e.g., idiosyncratic hepatotoxicity. Protein or antibody microarrays can be used to compare the relative abundance of various biomarker polypeptides (e.g., SEQ ID NO:1 to SEQ ID NO:15 and SEQ ID NO:61 to SEQ ID NO:64) in samples of media. For a protein microarrays, extracellular or cell lysate polypeptides or peptides (i.e., sample polypeptides) obtained from cell lines or patients' cells contacted with a test substance can be affixed to a substrate or support. The protein microarrays can then be contacted with labeled anti-biomarker antibodies, and levels of the biomarker polypeptides can be determined.

Protein microarrays can include, but are not limited to, sample polypeptides such as biomarker polypeptides (e.g., SEQ ID NO:1 to SEQ ID NO:15 and SEQ ID NO:61 to SEQ ID NO:64), particularly BMS-PTX-265 (SEQ ID NO:1) and BMS-PTX-837 (SEQ ID NO:2), and peptides and fragments thereof, that can be used to predict in vivo hepatotoxicity, as described in detail herein. For antibody microarrays, anti-biomarker antibodies can be affixed to a substrate or support. The antibody microarrays can then be contacted with labeled extracellular or cell lysate polypeptides (i.e., sample polypeptides) obtained from cell lines or patients' cells incubated with test substances, and levels of the biomarker polypeptides can be determined. Antibody microarrays can include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments thereof, specific for a biomarker polypeptide (e.g., SEQ ID NO:1 to SEQ ID NO:15 and SEQ ID NO:61 to SEQ ID NO:64), as described in detail herein.

As with DNA arrays, protein and antibody microarrays are designed to be used as qualitative analysis tools, allowing determination of the presence, absence, and/or relative abundance of a biomarker polypeptide in samples of interest. See, e.g., BD Biosciences CLONTECH, Palo Alto, Calif.; United States Patent Application No. 2002/0076727, published Jun. 20, 2002; United States Patent Application No. 2003/0044389, published Mar. 6, 2003; Arenkov et al., 2000, *Anal. Biochem.* 278:123-131; United States Patent Application No. 2002/0102617, published Aug. 1, 2002, which are incorporated herein by reference. However, protein and antibody arrays can be used where changes in protein levels do not necessarily correlate with changes in gene expression. In addition, protein and antibody microarrays can be used in tandem with DNA microarrays to compare changes in gene expression with changes in protein expression. In this way, DNA, protein, and antibody microarrays can be employed as complementary techniques.

In preferred embodiments, the entire protein or antibody microarray analysis, from sample prep to data collection, is performed in the same day on the bench-top (see, e.g., BD Biosciences CLONTECH). A complete buffer system is provided for sample labeling and incubation. The buffer system is designed to ensure a consistent representation of sample polypeptides by maintaining sample integrity and solubility. Observed sensitivity is in the low pg/ml range, and the open array-platform design is compatible with commercially available fluorescent scanners commonly used for DNA microarrays. The microarray includes multiple antibodies (e.g., monoclonal antibodies) or proteins covalently bound in an ordered layout to a slide (e.g., standard size, 1 inch×3 inches).

Preferably, the sample polypeptides or anti-biomarker antibodies are labeled (e.g., using Cy™3 or Cy™5) prior to incubation with the appropriate microarray. The microarray is then read using a scanner typically used for DNA microarrays. Ideally, the instrument accommodates a slide and is capable of exciting and detecting the label(s) employed. Examples of scanners include those manufactured by Axon, Packard Biochip, Genomic Solutions and Genetic Microsystems and others. For optimal results, the scanner uses a minimum scanning resolution of 10-15 μm. Once the slides are scanned, the raw intensity values are obtained from each spot on the array using the software supplied with the scanner. The raw intensity values are then downloaded from the software into a spreadsheet (such as Microsoft Excel) for analysis. Specific experimental protocols can be used to normalize for potential differences in labeling and incubation, and obtain the most accurate results.

The protein or antibody microarrays of the present invention can be formed upon any suitable substrate or support. The characteristics of these substrates or supports may vary widely depending upon the intended use, and their form may take essentially any shape. Although it is preferred that the substrate or support has at least one surface which is substantially planar or flat, it may also include indentations, protuberances, steps, ridges, terraces and the like. The substrate or support can be in the form of a sheet, a disc, a tubing, a cone, a sphere, a concave surface, a convex surface, a strand, a string, or a combination of any of these and other geometric forms. Several different substrate or support surfaces can be combined in accordance with the invention. One example would be to sandwich target-containing samples between two flat substrate surfaces with microarrays formed on both surfaces.

Various materials, organic or inorganic or a combination of both, can be used as substrate or support for this invention. Suitable materials include, but are not limited to, glasses, ceramics, plastics, metals, alloys, carbon, papers, agarose, silica, quartz, cellulose, polyacrylamide, polyamide, and gelatin, as well as other polymer supports, other solid-material supports, or flexible membrane supports. Polymers that may be used as substrate include, but are not limited to: polystyrene; poly(tetra)fluoroethylene (PTFE); polyvinylidenedifluoride; polycarbonate; polymethylmethacrylate; polyvinylethylene; polyethyleneimine; polyoxymethylene (POM); polyvinylphenol; polylactides; polymethacrylimide (PMI); polyalkenesulfone (PAS); polypropylene; polyethylene; polyhydroxyethylmethacrylate (HEMA); polydimethylsiloxane; polyacrylamide; polyimide; and various block copolymers. The substrate or support can also comprise a combination of materials, whether water-permeable or not, in multi-layer configurations.

Examples of solid substrates or supports include gels, which allow samples to reside in a three-dimensional environment, while still being completely or partially exposed to potentially immobilized or diffused cues (e.g. collagen gels, matrigels, and ECM gels). In addition, derivitized and coated slides are of particular interest. Such slides are commercially available, or may be produced using conventional methods. For example, SuperAldehyde™ substrates contain primary aldehyde groups attached covalently to a glass surface. Coated-slides include films of nitrocellulose (FastSlides™, Schleicher & Schuell), positively-charged nylon membranes (CastSlides™, Schleicher & Schuell), and a polyacrylamide matrix (HydroGel™, Packard Bioscience), etc. A preferred embodiment of the invention employs a 2.5 cm×7.5 cm glass slide with surface Si—OH functionalities. The substrates or supports can take a variety of configurations, including filters, fibers, membranes, beads, particles, dipsticks, sheets, rods, etc. The materials from which the substrate can be fabricated should ideally exhibit a low level of non-specific binding during binding events, except for cases where some non-specific binding is desired.

In order to allow attachment by a linker or directly by a protein or antibody, the surface of the substrate may need to undergo initial preparation in order to create suitable reactive groups. Such reactive groups could include simple chemical moieties such as amino, hydroxyl, carboxyl, carboxylate, aldehyde, ester, ether (e.g. thio-ether), amide, amine, nitrile, vinyl, sulfide, sulfonyl, phosphoryl, or similarly chemically reactive groups. Alternatively, reactive groups may comprise more complex moieties that include, but are not limited to, maleimide, N-hydroxysuccinimide, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, biotin and avidin. Techniques for placing such reactive groups on a substrate by mechanical, physical, electrical or chemical means are well known in the art, such as those described by U.S. Pat. No. 4,681,870, incorporated herein by reference.

Methods of coupling the sample polypeptides or anti-biomarker antibodies to the reactive end groups on the surface of the substrate or on the linker include reactions that form linkage such as thioether bonds, disulfide bonds, amide bonds, carbamate bonds, urea linkages, ester bonds, carbonate bonds, ether bonds, hydrazone linkages, Schiff-base linkages, and noncovalent linkages mediated by, for example, ionic or hydrophobic interactions. The form of reaction will depend, of course, upon the available reactive groups on both the substrate/linker and the antibodies.

To achieve high-density protein or antibody arrays, it may be necessary to "pack" the support surface with reactive groups to a higher density. One preferred method in the case of a glass surface is to first "strip" the surface with reagents such as a strong acid, and then to apply or reapply reactive groups to the surface. In the case of a glass surface, the reactive groups can be silanes, Si—OH, silicon oxide, silicon nitride, primary amines or aldehyde groups. Slides treated with an aldehyde-containing silane reagent are preferred in immobilizing many binding elements and are commercially available from TeleChem International (Cupertino, Calif.) under the trade name SuperAldehyde Substrates™. The aldehyde groups on the surface of these slides react readily with primary amines on proteins to form a Schiff base linkage. Since typical proteins/antibodies display many lysine residues on their surfaces, as well as the generally more reactive alpha-amines at their N-termini, they can attach to the slide in a variety of orientations, permitting different sides of the protein/antibody to interact with the target(s) in solution. After arraying sample polypeptides or anti-biomarker antibodies onto these aldehyde slides, a buffer containing bovine serum albumin (BSA) may be applied to the slide to block later non-specific binding between targets and unreacted aldehyde groups on the slide.

Once the initial preparation of reactive groups on the substrate is completed, if desired, linker molecules may optionally be added to the surface of the substrate to make it suitable for further attachment chemistry. Linkers may be selected from any suitable class of compounds and may comprise polymers or copolymers of organic acids, aldehydes, alcohols, thiols, amines and the like. For example, polymers or copolymers of hydroxy-, amino-, or di-carboxylic acids, such as glycolic acid, lactic acid, sebacic acid, or sarcosine may be employed. Alternatively, polymers or copolymers of saturated or unsaturated hydrocarbons such as ethylene glycol, propylene glycol, saccharides, and the like may be employed. Preferably, the linker should be of an appropriate length that allows the binding element, which is to be attached, to interact freely with molecules in a sample solution and to form effective binding.

The linker in the present invention may include at least two reactive groups with the first to bind the substrate and the second to bind the sample polypeptide or anti-biomarker antibody. The two reactive groups may be of the same chemical moiety, and may include any of the chemical moieties described above of reactive groups on the substrate. One preferred group comprises a maleimide group. Another preferred group is a vinyl sulfone group. It is believed that the hydrophilicity of these groups helps limit nonspecific binding by analytes such as proteins/antibodies when assays are conducted in aqueous buffers. Methods for binding the linker to the surface of the substrate will vary depending on the reactive groups already on the substrate and the linker selected, and will vary as considered appropriate by one skilled in the art. For example, siloxane bonds may be formed via reactions between the trichlorosilyl or trisalkoxy groups of a linker and the hydroxyl groups on the support surface. The linkers may be either branched or unbranched, but this and other structural attributes of the linker should not interfere stereochemically with relevant functions of the proteins/antibodies, such as a target interaction. Protection groups, known to those skilled in the art, may be used to prevent linker's end groups from undesired or premature reactions. For instance, U.S. Pat. No. 5,412,087, incorporated herein by reference, describes the use of photo-removable protection groups on a linker thiol group.

In a preferred embodiment, the linker comprises a BSA molecule. In particularly preferred embodiments, BSA-NHS slides are used to make protein or antibody microarrays. Although appropriate for some applications, slides functionalized with aldehyde groups and further blocked with BSA are not suitable for arrays of peptides or small proteins. In such cases, the BSA obscures the molecules of interest, and BSA-NHS slides are preferable. For such slides, a molecular monolayer of BSA is attached to the surface of the support. As a non-limiting example, a glass slide with hydroxyl groups can be silanated with aminopropyl triethoxy silane before being activated with N,N'-disuccinimidyl carbonate. The activated amino group on the slide, in turn, can form covalent bonds with a linker such as BSA. Then, the surface of the BSA is activated with N,N'-disuccinimidyl carbonate, resulting in activated carbamate and ester, such as a N-hydroxy succinimide (NHS) group. The activated lysine, aspartate, and glutamate residues on the BSA react readily with the surface amines on the sample polypeptide or anti-biomarker antibody to form covalent urea or amide linkages. Any remaining reactive groups on BSA are subsequently quenched with glycine. The result is a sample polypeptide or anti-biomarker antibody immobilized to a support through a BSA linker molecule. In contrast to the BSA-blocked slides with aldehyde functionality, proteins/antibodies arrayed on BSA-NHS substrates are displayed on top of the BSA monolayer, rendering them accessible to targets in solution.

As will be apparent to those of skill in the art, the sample polypeptides and anti-biomarker antibodies may be modified in order to facilitate attachment, through covalent or non-covalent bonds, to the reactive groups on the surface of the substrate, or to the second reactive groups of a linker attached to the substrate. As examples of such modifications, nucleophilic S-, N- and O-containing groups may be added to facilitate attachment of the binding element to the solid support via a Michael addition reaction to the linker. To preserve binding affinity, it is preferred that the sample polypeptide or anti-biomarker antibody is modified so that it binds to the support substrate at a region separate from the region responsible for interacting with its target. If the anti-biomarker antibody or sample polypeptide binds its target at a first terminus, it may be useful to attach the antibody/polypeptide to the support at a second or opposite terminus, or somewhere in between the termini.

In a preferred embodiment, where the antibody component is an scFv, the present invention provides a modification method such that the scFv can be attached to the surface of a glass slide through binding with an electrophilic linker, such as a maleimide group, without interfering with the scFv's antigen-binding activity. According to this method, an scFv is first engineered so that its carboxy-terminus includes a cysteine residue that can then form a thioether linkage with an electrophilic linker such as the maleimide group. Such methods can be used with other polypeptide moieties that comprise thiol groups. An N-terminus of an antibody can also be engineered to include a reactive group for attachment to the support surface. A Michael addition may be employed to attach compounds to glass slides, and plain glass slides may be derivatized to give surfaces that are densely functionalized with maleimide groups.

The protein or antibody microarrays of the invention may be produced by a number of means, including "spotting" wherein small amounts of the reactants are dispensed to particular positions on the surface of the substrate. Methods for spotting include, but are not limited to, microfluidics printing, microstamping (see, e.g., U.S. Pat. Nos. 5,515,131 and 5,731,152), microcontact printing (see, e.g., PCT Publication WO 96/29629) and inkjet head printing. Of particular interest is the use of an automated spotting device, such as the Beckman Biomek 2000 (Beckman Instruments). A number of contact and non-contact microarray printers are available and may be used to print the binding members on a substrate. For example, non-contact printers are available from Perkin Elmer (BioChip Arrayer™, Packard). Contact printers are commercially available from TeleChem International (ArrayIt™). Non-contact printers are of particular interest because they are more compatible with soft/flexible surfaces. Generally, the dispensing device includes calibrating means for controlling the amount of sample deposition, and may also include a structure for moving and positioning the sample in relation to the support surface.

The volume of fluid to be dispensed for the protein/antibody in an array varies with the intended use of the array, and available equipment. Preferably, a volume formed by one dispensation is less than 100 nl, more preferably less than 10 nl, and most preferably about 1 nl. The amount of protein/antibody present in each spot will be sufficient to provide for adequate binding of targets during the assay in which the array is employed. The spot will usually have an overall circular dimension and the diameter will range from about 10 to 5,000 μm, usually from about 20 to 1000 μm and more usually from about 50 to 500 μm. In preferred embodiments, these spots are about 150-200 μm in diameter, to yield about 1600 spots per square centimeter. The size of a spot in an array corresponding to a single protein/antibody spot may be reduced through the addition of media such as glycerol or trehalose that increase the viscosity of the solution, and thereby inhibit the spreading of the solution. Hydrophobic boundaries on a hydrophilic substrate surface can also serve to limit the size of the spots comprising an array.

Adding a humectant to the solution of the protein/antibody may also effectively prevent the dehydration of the microarrays, once they are created on the surface of the substrate. Because dehydration can result in chemical or stereochemical changes to proteins/antibodies, such as oxidation or denaturation, the addition of a humectant can act to preserve and stabilize the microarray and maintain the functionality of binding elements such as scFv. For example, in some preferred embodiments, scFv are coupled to maleimide-derivatized glass in phosphate-buffered saline (PBS) solutions with 40% glycerol. The glycerol helps maintain continued hydration which, in turn, helps to prevent denaturation. Solutions of blocking agents may be applied to the microarrays to prevent non-specific binding by reactive groups that have not bound to a binding element. Solutions of bovine serum albumin (BSA), casein, or nonfat milk, for example, may be used as blocking agents to reduce background binding in subsequent assays.

In one aspect, the present invention encompasses protein and antibody arrays, including high-density microarrays, of proteins or antibodies immobilized on a substrate directly or via a linker. According to the methods of the present invention, extremely high density microarrays, with a density over 50, 100, 200, preferably over 500, further preferably over 1000, and further preferably over 2000 spots per square centimeter, can be formed by attaching an protein or antibody to a support surface which has been functionalized to create a high density of reactive groups or which has been functionalized by the addition of a high density of linkers bearing reactive groups. The total number of protein/antibody spots on the substrate will vary depending on the number of different tests and conditions to be explored, as well as the number of control spots, calibrating spots and the like, as may be desired. Each distinct microarray composition may be present in duplicate or more (usually, at least 5 replicas) to provide an internal correlation of results. Also, for some tasks it is desirable to replicate blocks, each having several identical spots.

By printing onto the surfaces of multi-well plates (preferably flat-surfaced), this combines the advantages of the array approach with those of the multi-well approach. Since the separation between tips in standard microarrayers is compatible with both 384-well and 96-well plates, one can simultaneously print each load in several wells. Printing into wells can be done using both contact and non-contact technology, where the latter is also compatible with non-flat multi-well plates. The sample polypeptide or anti-biomarker antibody will be present in the solution at a concentration of from about 0.0025 to about 10 μg/ml, and may be diluted in series to determine binding curves, etc.

In preferred embodiments, high-precision, contact-printing robots are used to pick up small volumes of dissolved anti-biomarker antibodies or sample polypeptides from the wells of a microtiter plate and to repetitively deliver approximately 1 nl of the solutions to defined locations on the surfaces of substrates, such as chemically-derivatized glass microscope slides. Examples of such robots include the GMS 417 Arrayer, commercially available from Affymetrix of Santa Clara, Calif., and a split pin arrayer constructed according to instructions downloadable from the web (hypertext transfer protocol://cmgm.stanford.edu/pbrown). The chemically-derivatized glass microscope slides are preferably prepared using custom slide-sized reaction vessels that enable the uniform application of solution to one face of the slide. This results in the formation of microscopic spots of compounds on the slides. It will be appreciated by one of ordinary skill in the art, however, that the current invention is not limited to the delivery of 1 nl volumes of solution, to the use of particular robotic devices, or to the use of chemically derivatized glass slides, and that alternative means of delivery can be used that are capable of delivering microliter, nanoliter, picoliter, or smaller volumes. Hence, in addition to a high precision array robot, other means for delivering the compounds can be used, including, but not limited to, ink jet printers, piezoelectric printers, and small volume pipetting robots.

In forming arrays or microarrays of molecules on the surface of a substrate, in situ photochemistry maybe used in combination with photoactivatable reactive groups, which may be present on the surface of the substrate, on linkers, or on the proteins/antibodies. Such photoactivatable groups are well known in the art. Sample polypeptides or anti-biomarker antibodies may be tagged with fluorescent, radioactive, chromatic and other physical or chemical labels or epitopes as described in detail herein. For certain preferred embodiments where quantified labeling is possible, this yields great advantage for later assays. In a preferred embodiment, a fluorescent dye containing a hydrophilic polymer moiety such as polyethyleneglycol is used.

Upon formation of microarrays of proteins/antibodies on the solid support, large quantities of samples may be incubated with the support surface for binding assays. For protein microarrays, one or more anti-biomarker antibodies can be incubated with the arrays to test for levels of biomarker polypeptides or peptides. For antibody arrays, samples (e.g., extracellular media or cell lysates) can be incubated with the arrays, for example, samples obtained from cell lines or patients' cells incubated with test substances, such as drugs, compounds, or other therapeutic agents. The samples may be derived from cell populations which have been incubated in the presence or absence of compounds or other treatments to be tested for deleteriousness due to hepatoxicity, and differences between the treated and untreated populations may be used to assess the deleterious effects of the treatment, as described in detail herein.

The polypeptides in a given sample may be modified to enable later detection by using techniques known to one of ordinary skill in the art, such as using fluorescent, radioactive, chromatic and other physical or chemical labels. In a preferred embodiment, a fluorescent dye containing a hydrophilic polymer moiety such as polyethyleneglycol (e.g. fluorescin-PEG2000-NHS) is used. Labeling can be accomplished through direct labeling of anti-biomarker antibodies or sample polypeptides, or through labeling of an affinity tag (indirect labeling). Direct labeling of sample peptides or polypeptides with different fluorescent dyes makes it possible to conduct multiple assays from the same spot (e.g., measuring polypeptide levels and phosphorylation levels).

Where direct labeling is used, over-labeling of sample polypeptides can cause aggregation, and result in non-specific staining. Over-labeling can also reduce the specificity of a anti-biomarker antibody for its target, and cause loss of signal. To prevent over-labeling, the labeling reaction time can be shortened or the substrate:label ratio can be increased. To prevent labeling of internal epitopes, sample polypeptides can be digested into peptides, and then the peptides can be labeled at their termini. In a preferred embodiment, sample polypeptides are digested with trypsin before subjected to labeling by a succinimidyl ester dye such as Cy™3, CY™5 or an Alexa dye. A succinimidyle ester dye labels primary amines, such as the one in lysine. Trypsin cleaves after lysines, generating peptides with lysines at their C-terminus and no internal lysines. Thus, a succinimidyl ester dye will only label tryptic peptides at their termini.

In an alternative embodiment, another protease may be used to digest a polypeptide, and succinimidyl ester dye can be used for labeling as long as the resulting peptides do not contain internal lysines. Such peptides may be used as a preferred panning peptides. Ideally, for preferred panning peptides, antibodies are first raised to the peptides. Sample polypeptides, e.g., from media or cell lysates, is digested with a protease or a combination of proteases that will generate the specific panning peptides. These sample peptides are then labeled to completion with a succinimidyl ester dye. A large excess of reactive labeling reagent may be used to ensure complete labeling. Then, the labeled peptides are applied to the microarray for capture. Because the amount of labeling on the preferential panning peptides is known, one can quantify the amount of such peptide in a given sample through the amount of label signals detected after affinity capture. Once the number of such panning peptides resulting from the protease digestion of one target protein is known, that number can be easily translated into the amount of the target protein in the sample. Amino acids other than lysine can also be utilized with this method. For example, proteins with limited number of natural or added cysteine may be selected or constructed to be labeled, via a reduced thiol with maleimide-coupled dye such as maleimide-coupled Alexa 488 (commercially available from Molecular Probes of Eugene, Oreg.).

Indirect labeling of a sample polypeptide or anti-biomarker antibody may be achieved by using a second antibody or antibody fragment that has been labeled for subsequent detection (e.g., with radioactive atoms, fluorescent molecules) in a sandwiched fashion. In a preferred embodiment, a sample polypeptide or peptide that binds to a microarray of antibodies is detected through a second fluorescently labeled antibody to the antigen, obviating the need for labeling the antigen. In a further preferred embodiment, the second antibody is a labeled phage particle that displays an antibody fragment. Standard phage display technology using phages such as M13 may be used to produce phage antibodies including antibody fragments such as scFv. This allows relatively easy and fast production of reagents for sandwich detection from phage display antibody libraries. To ensure that the phage antibodies recognize an epitope different from the one that the immobilized capture antibody recognizes on the antigen, selection from phage display libraries may be carried out. First, tubes are coated with the same antibody that is immobilized in microarray for capture purpose. Next, the tube is blocked and the antigen is added and captured by the coated antibody, and after washing, phage antibody libraries are panned in the tubes. The isolated phage antibodies (or polyclonal phage antibody) will bind only to epitopes distinct from the epitope recognized by the capture antibody, and are therefore ideal for the sandwich detection approach.

Specific binding may be detected and measured in a number of different ways, depending on the way the target molecules in the sample are labeled. A common example is to use the technique of autoradiography to detect binding of molecules pre-labeled with radioactive isotopes. For antibody microarrays, fluorescent dyes (e.g., Cy™5) can be used to label proteins in a given sample before the sample is applied to a slide surface printed with microarrays of functional scFv. After incubation and washes, the slide surface is then dried and imaged on a molecular dynamics STORM or ArrayWorx™ optical reader (Applied Precision of Seattle, Wash.). In another preferred embodiment, secondary antibodies labeled with fluorochromes such as Cy™3 are used for later detection of a primary antibody participating in the binding. Various detection methods known in the art such as mass spectrometry, surface plasmon resonance, and optical spectroscopy, to name a few, can be used in this invention to allow detection of binding even if binding targets are not labeled.

If expression levels of one or more genes encoding the biomarker polypeptides (e.g., SEQ ID NO:1 to SEQ ID NO:15 and SEQ ID NO:61 to SEQ ID NO:64) are elevated in the presence of hepatotoxic substances, then DNA microarrays can also be used with the screening methods of the invention. The present invention therefore contemplates the preparation of one or more specialized microarrays (e.g., oligonucleotide microarrays or cDNA microarrays) comprising one or more of the polynucleotides encoding the biomarker polypeptides (e.g., SEQ ID NO:46 to SEQ ID NO:60, and SEQ ID NO:65 to SEQ ID NO:68), or complementary sequences, or fragments thereof. In accordance with this aspect of the invention, the oligonucleotide sequences or cDNA sequences include any of the disclosed polynucleotides or fragments or combinations thereof, which are highly expressed in resistant or sensitive cells, and are contained on a microarray, e.g., a oligonucleotide microarray or cDNA microarray in association with, or introduced onto, any supporting materials, such as glass slides, nylon membrane filters, glass or polymer beads, or other types of suitable substrate material.

For DNA microarray analysis, cellular nucleic acid, e.g., RNA, can be isolated from cells incubated in the presence and absence of a substance to be tested for hepatotoxic effects. The isolated nucleic acid can be appropriately labeled and applied to one or more of the specialized microarrays. The resulting pattern of gene expression on the specialized microarray can be analyzed as described herein and known in the art. An increase in gene expression correlating with hepatotoxicity of at least one test substance can be determined, e.g., via comparison with the gene expression patterns in the absence of the test substance(s). If levels of biomarker gene expression in the presence of the test substance(s) are elevated relative to controls, then the test substance(s) is/are predicted to have hepatotoxic effects. If levels of biomarker gene expression are comparable in the presence and absence of the test substance(s), then the test substance(s) is/are predicted to have hepatotoxic effects, then the test substance(s) is/are predicted to not have hepatotoxic effects. The latter result would indicate that the test substance(s) are unlikely to produce hepatotoxicity, e.g., idiosyncratic hepatotoxicity.

Methods for producing and using DNA microarrays are well known in the art (see, e.g., J. B. Rampal, 2001, *DNA Arrays: Methods and Protocols*, Humana Press; M. Schena, 2002, *Microarray Analysis*, John Wiley & Sons; M. Schena, 2000, *Microarray Biochip Technology*, Eaton Publishing). Briefly, to determine gene expression using microarray technology, polynucleotides, e.g., RNA, DNA, cDNA, preferably RNA, are isolated from a biological sample, e.g., cells incubated in the presence or absence of a test substance. Such cells can include cells obtained from hepatic cell lines or liver samples. The isolated nucleic acid is detectably labeled, e.g., by fluorescent, enzyme, or chemiluminescent label, and applied to a microarray, e.g., one or more of the specialized DNA microarrays provided by this invention. The array is then washed to remove unbound material and visualized by staining or fluorescence, or other means known in the art depending on the type of label utilized.

In alternate embodiments of the invention, cell-based microarrays can be used in conjunction with the screening methods of the invention. Cell-based microarrays and their uses are well-known in the art (see, e.g., Blagoev and Pandey, 2001, *Trends Biochem. Sci.* 26:639-641; Ziauddin and Sabatini, 2001, *Nature* 411:107-110). As an example, DNA constructs for the expression of one or more cytochrome P450 enzymes can be spotted onto individual wells or a microarray platform in association with, or introduced onto, any supporting materials, such as glass slides, nylon membrane filters, glass or polymer beads, or other types of suitable substrate material. Following this, the spotted DNA can be incubated with a transfection solution, and hepatocytes can be added to the wells or arrays, and allowed to replicate. Next, the transfected cells can be spotted with a test substance, and assayed for biomarker expression levels, for example, levels of biomarker nucleic acids (e.g., SEQ ID NO:46 to SEQ ID NO:60) or proteins (e.g., SEQ ID NO:1 to SEQ ID NO:15 and SEQ ID NO:61 to SEQ ID NO:64), as determined by in situ assays performed on the multi-well or microarray platform.

Embodiments of the Invention

Section 1

A method of predicting hepatotoxicity of a test substance comprising:

a) incubating an hepatocyte in the presence and absence of a test substance; and b) comparing levels of at least one biomarker polypeptide selected from the group consisting of SEQ ID NO:1 to SEQ ID NO:15 and SEQ ID NO:61 to SEQ ID NO:64, which are produced by the hepatocyte in the presence and absence of the test substance;

wherein elevated levels of the biomarker polypeptide in the presence of the test substance indicate that the substance is predicted to cause hepatotoxicity.

A method of predicting hepatotoxicity of a test substance comprising:

a) incubating an hepatocyte in the presence and absence of a test substance; and b) comparing levels of a biomarker polypeptide as set forth in SEQ ID NO:1, which are produced by the hepatocyte in the presence and absence of the test substance;

wherein elevated levels of the biomarker polypeptide in the presence of the test substance indicate that the substance is predicted to cause hepatotoxicity.

A method of predicting hepatotoxicity of a test substance comprising:

a) incubating an hepatocyte in the presence and absence of a test substance; and b) comparing levels of a biomarker polypeptide as set forth in SEQ ID NO:2, which are produced by the hepatocyte in the presence and absence of the test substance;

wherein elevated levels of the biomarker polypeptide in the presence of the test substance indicate that the substance is predicted to cause hepatotoxicity.

The method according to any one of the embodiments of this section, wherein the hepatotoxicity is idiosyncratic hepatotoxicity.

The method according to any one of the embodiments of this section, wherein the extracellular levels of the biomarker polypeptide are measured. In specific embodiments, the extracellular levels of the biomarker polypeptide are measured using a method selected from the group consisting of RIA, ELISA, immunoprecipitation, and immunoblotting.

The method according to any one of the embodiments of this section, wherein the intracellular levels of the biomarker polypeptide are measured. In specific embodiments, the intracellular levels of the biomarker polypeptide are measured using a method selected from the group consisting of immunofluorescence microscopy, indirect immunofluorescence, immunohistochemistry, and immunoblotting.

The method according to any one of the embodiments of this section which is automated.

The method according to any one of the embodiments of this section, wherein the levels of the biomarker polypeptide are measured using a hybridization technology. In specific embodiments, the hybridization technology is selected from the group consisting of microarrays, protein, antibody, and cell-based microarrays, PCR, RT-PCR, southern blots, northern blots, in situ hybridization, etc.

The method according to any one of the embodiments of this section, wherein the hepatocyte is obtained from a liver sample from a patient or from a liver for transplant.

The method according to any one of the embodiments of this section, wherein the hepatocyte is obtained from a hepatic cell line. In specific embodiments, the hepatic cell line is selected from the group consisting of mouse, rat, canine, porcine, and human cell lines. In other specific embodiments, the human hepatic cell line is selected from the group consisting of THLE-5, THLE-5B, THLE-5B-c15, HH25, HH29, HHY41, HuH7, Hep3B, HepG2, OUMS-29, ACTIVTox®, PH5CH, HepG2/C3A, THLE-3, DBTRG-05MG, THLE-2, SW 1783, U-138 MG, and SK-LMS-1.

The method according to any one of the embodiments of this section, wherein the hepatocyte includes an expression construct comprising a human cytochrome P450 enzyme selected from the group consisting of 1A1, 1A2, 2A6, 2B6, 2C8, 2C9, 2C10, 2C19, 2D6, 2E1, 3A4, 3A5, and 3A7.

The method according to any one of the embodiments of this section, wherein the test substance is selected from the group consisting of anti-cancer, anti-bacterial, anti-fungal, anti-viral, anti-hypertension, anti-depression, anti-anxiety, and anti-arthritis substances, and substances for the treatment of allergies, diabetes, hypercholesteremia, osteoporosis, Alzheimer's disease, Parkinson's disease, other neurodegenerative diseases, and obesity. In specific embodiments, test substance is selected from the group consisting of PPAR agonists, HIV protease inhibitors, anti-inflammatory drugs, estrogenic drugs, anti-estrogenic drugs, antihistimines, muscle relaxants, anti-anxiety drugs, anti-psychotic drugs, and anti-angina drugs.

Section 2

A method of predicting in vivo hepatotoxicity of a test substance comprising:

a) incubating an hepatocyte in the presence and absence of a test substance; and b) comparing levels of at least one biomarker polynucleotide that encodes a polypeptide selected from the group consisting of SEQ ID NO:1 to SEQ ID NO:15 and SEQ ID NO:61 to SEQ ID NO:64; which are produced by the hepatocyte in the presence and absence of the test substance;

wherein elevated levels of the biomarker polynucleotide in the presence of the test substance indicate that the substance is predicted to cause hepatotoxicity.

The method according to any one of the embodiments of this section, wherein the biomarker polynucleotide is selected from the group consisting of SEQ ID NO:46 to SEQ ID NO:60.

The method according to any one of the embodiments of this section, wherein the hepatotoxicity is idiosyncratic hepatotoxicity.

The method according to any one of the embodiments of this section, wherein the intracellular levels of the biomarker polynucleotide are measured. In specific embodiments, the intracellular levels are measured using a method selected from the group consisting of RT-PCR, Northern blotting, and in situ hybridization.

The method according to any one of the embodiments of this section which is automated.

The method according to any one of the embodiments of this section, wherein the intracellular levels of the biomarker polynucleotide are measured using a microarray. In specific embodiments, the microarray is selected from the group consisting of cDNA, oligonucleotide, and cell-based microarrays.

The method according to any one of the embodiments of this section, wherein the hepatocyte is obtained from a liver sample from a patient.

The method according to any one of the embodiments of this section, wherein the hepatocyte is obtained from a hepatic cell line. In specific embodiments, the hepatic cell line is selected from the group consisting of mouse, rat, porcine, and human cell lines. In other specific embodiments, the human hepatic cell line is selected from the group consisting of THLE-5, THLE-5B, THLE-5B-c15, HH25, HH29, HHY41, HuH7, Hep3B, HepG2, OUMS-29, ACTIVTox®, PH5CH, HepG2/C3A, THLE-3, DBTRG-05MG, THLE-2, SW 1783, U-138 MG, and SK-LMS-1.

The method according to any one of the embodiments of this section, wherein the hepatocyte includes an expression construct comprising a human cytochrome P450 enzyme selected from the group consisting of 1A1, 1A2, 2A6, 2B6, 2C8, 2C9, 2C10, 2C19, 2D6, 2E1, 3A4, 3A5, and 3A7.

The method according to any one of the embodiments of this section, wherein the test substance is selected from the group consisting of anti-cancer, anti-bacterial, anti-fungal, anti-viral, anti-hypertension, anti-depression, anti-anxiety, and anti-arthritis substances, and substances for the treatment of allergies, diabetes, hypercholesteremia, osteoporosis, Alzheimer's disease, Parkinson's disease, other neurodegenerative diseases, and obesity. In specific embodiments, test substance is selected from the group consisting of PPAR agonists, HIV protease inhibitors, anti-inflammatory drugs, estrogenic drugs, anti-estrogenic drugs, antihistimines, muscle relaxants, anti-anxiety drugs, anti-psychotic drugs, and anti-angina drugs.

Section 3

A kit for predicting in vivo hepatotoxicity of a test substance comprising:

a) an antibody directed to at least one biomarker polypeptide selected from the group consisting of SEQ ID NO:1 to SEQ ID NO:15 and SEQ ID NO:61 to SEQ ID NO:64;

b) at least one reagent for detecting antibody binding to the biomarker polypeptide.

A kit for predicting in vivo hepatotoxicity of a test substance comprising:

a) an antibody directed to a biomarker polypeptide as set forth in SEQ ID NO:1;

b) at least one reagent for detecting antibody binding to the biomarker polypeptide.

A kit for predicting in vivo hepatotoxicity of a test substance comprising:

a) an antibody directed to a biomarker polypeptide as set forth in SEQ ID NO:2;

b) at least one reagent for detecting antibody binding to the biomarker polypeptide.

A kit for predicting in vivo hepatotoxicity of a test substance comprising:

a) a set of two or more antibodies, wherein each antibody binds to a different biomarker polypeptide selected from the group consisting of SEQ ID NO:1 to SEQ ID NO:15 and SEQ ID NO:61 to SEQ ID NO:64;

b) at least one reagent for detecting binding of the antibodies to the biomarker polypeptides.

A kit for predicting in vivo hepatotoxicity of a test substance comprising:

a) a set of two or more antibodies, wherein each antibody binds to a different biomarker polypeptide selected from the group consisting of SEQ ID NO:1 and SEQ ID NO:2;

b) at least one reagent for detecting binding of the antibodies to the biomarker polypeptides.

The kit according to any one of the embodiments of this section, wherein the kit is used to detect intracellular levels of the biomarker polypeptide(s). In specific embodiments, the intracellular levels of the biomarker polypeptide(s) are measured using a method selected from the group consisting of immunofluorescence microscopy, indirect immunofluorescence, immunohistochemistry, and immunoblotting.

The kit according to any one of the embodiments of this section, wherein the kit is used to detect extracellular levels of the biomarker polypeptide(s). In specific embodiments, the extracellular levels of the biomarker polypeptide(s) are measured using a method selected from the group consisting of RIA, ELISA, immunoprecipitation, and immunoblotting.

The kit according to any one of the embodiments of this section, wherein the antibody(ies) is/are labeled with a label selected from the group consisting of fluorescent labels, enzyme labels, and radiolabels. In specific embodiments, the fluorescent labels are selected from the group consisting of Coumarin; Hydroxycoumarin; Aminocoumarin; Methoxycoumarin; R-Phycoerythrin; Fluorescein; FITC; Fluor X; DTAF; Auramine; Alexa Fluor® 350, -430, -488, -532, -546, -555, -568, -594, -633, -647, -660, -680, -700, -750; BODIPY-FL; Sulforhodamine; Texas Red®, Carbocyanine; Cy2; Cy™3; Cy3.5; Cy™5; Cy5.5; Cy7; Rhodamine; XRITC; TRITC; Lissamine Rhodamine B; Peridinin Chlorphyll Protein (PerCP); Allophycocyanin (APC); PE-Cy5 conjugates; Cychrome; Tri-Color®; Quantum Red®; PE-Cy5.5 conjugates; PE-Cy7 conjugates; PE-Texas Red conjugates; Red613; PC5-PE-Cy5 conjugates; PerCP-Cy5.5 conjugates; TruRed; APC-Cy5.5 conjugates; APC-Cy7 conjugates; ECD-PE-Texas Red conjugates; Sulfonated Pyrene; Cascade Blue; AMCA Blue; and Lucifer Yellow. In other specific embodiments, the radiolabels are selected from the group consisting of $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. In further specific embodiments, the enzyme labels are selected from the group consisting of peroxidase, β-glucuronidase, β-D-glucosidase, β-D-galactosidase, urease, glucose oxidase plus peroxidase, and alkaline phosphatase.

The kit according to any one of the embodiments of this section, wherein the antibody(ies) is/are unlabeled, but supplied with a label selected from the group consisting of fluorescent labels, enzyme labels, and radiolabels. In specific embodiments, the fluorescent labels are selected from the group consisting of Cy™3, Cy™5, Alexa, BODIPY, fluorescein, Fluor X, DTAF, FITC, rhodamine, TRITC, auramine, Texas Red, AMCA Blue, peridinin chlorophyll protein, phycoerythrin, ECD-PE-Texas Red tandem conjugate, PC5-PE-Cy5 tandem conjugate, allophycocyanin, and Lucifer Yellow. In other specific embodiments, the radiolabels are selected from the group consisting of $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. In additional specific embodiments, the enzyme labels are selected from the group consisting of peroxidase, β-glucuronidase, β-D-glucosidase, β-D-galactosidase, urease, glucose oxidase plus peroxidase, and alkaline phosphatase.

Section 4

A kit for predicting in vivo hepatotoxicity of a test substance comprising:

a) at least one oligonucleotide that hybridizes with a biomarker polynucleotide that encodes a polypeptide selected from the group consisting of SEQ ID NO:1 to SEQ ID NO:15 and SEQ ID NO:61 to SEQ ID NO:64;

b) at least one reagent for detecting hybridization to the biomarker polynucleotide.

A kit for predicting in vivo hepatotoxicity of a test substance comprising:

a) at least one oligonucleotide that hybridizes with a biomarker polynucleotide selected from the group consisting of SEQ ID NO:46 to SEQ ID NO:60 and SEQ ID NO:65 to SEQ ID NO:68;

b) at least one reagent for detecting hybridization to the biomarker polynucleotide.

A kit for predicting in vivo hepatotoxicity of a test substance comprising:

a) a set of two or more oligonucleotides, wherein each oligonucleotide hybridizes to a different biomarker polynucleotide selected from the group consisting of SEQ ID NO:46 to SEQ ID NO:60 and SEQ ID NO:65 to SEQ ID NO:68;

b) at least one reagent for detecting hybridization to the biomarker polynucleotides.

A kit for predicting in vivo hepatotoxicity of a test substance comprising:

a) a set of two or more oligonucleotides, wherein each oligonucleotide hybridizes to a different biomarker polynucleotide selected from the group consisting of SEQ ID NO:46-SEQ ID NO:47;

b) at least one reagent for detecting hybridization to the biomarker polynucleotides.

A kit for predicting in vivo hepatotoxicity of a test substance comprising:

a) a set of two or more oligonucleotides, wherein each oligonucleotide hybridizes to a different biomarker polynucleotide selected from the group consisting of SEQ ID NO:1 and SEQ ID NO:2;

b) at least one reagent for detecting binding of the antibodies to the biomarker polypeptides.

The kit according to any one of the embodiments of this section, wherein the oligonucleotide(s) is/are labeled with a label selected from the group consisting of radionucleotide, enzyme, fluorescent, chemiluminescent, substrate, cofactor, inhibitor, magnetic particle, and chromogenic labels. In specific embodiments, the label is selected from the group consisting of $^{32}P$, $^{3}H$, $^{35}S$, rhodamine, fluorescein, Cy™3, Cy™5, DNP, digoxigenin, and biotin.

The kit according to any one of the embodiments of this section, wherein the oligonucleotide(s) is/are unlabeled, but supplied with a label selected from the group consisting of radionucleotide, enzyme, fluorescent, chemiluminescent, substrate, cofactor, inhibitor, magnetic particle, and chromogenic labels. In specific embodiments, the label is selected from the group consisting of $^{32}P$, $^{3}H$, $^{35}S$, rhodamine, fluorescein, Cy™3, Cy™5, DNP, digoxigenin, and biotin.

Section 5

A microarray for predicting in vivo hepatotoxicity of a test substance comprising an antibody directed to at least one biomarker polypeptide selected from the group consisting of SEQ ID NO:1 to SEQ ID NO:15 and SEQ ID NO:61 to SEQ ID NO:64.

A microarray for predicting in vivo hepatotoxicity of a test substance comprising an antibody directed a biomarker polypeptide as set forth in SEQ ID NO:1.

A microarray for predicting in vivo hepatotoxicity of a test substance comprising an antibody directed a biomarker polypeptide as set forth in SEQ ID NO:2.

A microarray for predicting in vivo hepatotoxicity of a test substance comprising a set of two or more antibodies, wherein each antibody binds to a different biomarker polypeptide selected from the group consisting of SEQ ID NO:1 to SEQ ID NO:15 and SEQ ID NO:61 to SEQ ID NO:64.

A microarray for predicting in vivo hepatotoxicity of a test substance comprising a set of two or more antibodies, wherein each antibody binds to a different biomarker polypeptide selected from the group consisting of SEQ ID NO:1 and SEQ ID NO:2.

The microarray of any of the embodiments of this section, wherein the antibody(ies) is/are affixed to a support comprising one or more materials selected from the group consisting of glasses, ceramics, plastics, metals, alloys, carbon, papers, agarose, silica, quartz, cellulose, polymers, polyacrylamide, polyamide, gels and gelatin. In specific embodiments, the polymers are selected from the group consisting of polystyrene; poly(tetra)fluoroethylene; polyvinylidenedifluoride; polycarbonate; polymethylmethacrylate; polyvinylethylene; polyethyleneimine; polyoxymethylene; polyvinylphenol; polylactides; polymethacrylimide; polyalkenesulfone; polypropylene; polyethylene; polyhydroxyethylmethacrylate; polydimethylsiloxane; polyacrylamide; polyimide; and various block co-polymers. In other specific embodiments, the gels are selected from the group consisting of collagen gels, matrigels, and ECM gels. In additional specific embodiments, the support may be selected from the group consisting of glass slides coated with primary aldehyde groups, nitrocellulose films, positively charged nylon membranes, and a polyacrylamide matrix.

Section 6

A microarray for predicting in vivo hepatotoxicity of a test substance comprising at least one polynucleotide that hybridizes to a nucleic acid selected from the group consisting of SEQ ID NO:46 to SEQ ID NO:60 and SEQ ID NO:65 to SEQ ID NO:68.

A microarray for predicting in vivo hepatotoxicity of a test substance comprising an antibody directed a biomarker polypeptide as set forth in SEQ ID NO:1.

A microarray for predicting in vivo hepatotoxicity of a test substance comprising an antibody directed a biomarker polypeptide as set forth in SEQ ID NO:2.

A microarray for predicting in vivo hepatotoxicity of a test substance comprising a set of two or more antibodies, wherein each antibody binds to a different biomarker polypeptide selected from the group consisting of SEQ ID NO:1 to SEQ ID NO:15 and SEQ ID NO:61 to SEQ ID NO:64.

A microarray for predicting in vivo hepatotoxicity of a test substance comprising a set of two or more antibodies, wherein each antibody binds to a different biomarker polypeptide selected from the group consisting of SEQ ID NO:1 and SEQ ID NO:2.

The microarray of any of the embodiments of this section, wherein the oligonucleotide(s) is/are affixed to a support comprising one or more materials selected from the group consisting of glasses, ceramics, plastics, metals, alloys, carbon, papers, agarose, silica, quartz, cellulose, polymers, polyacrylamide, polyamide, gels and gelatin. In specific embodiments, the polymers are selected from the group consisting of polystyrene; poly(tetra)fluoroethylene; polyvinylidenedifluoride; polycarbonate; polymethylmethacrylate; polyvinylethylene; polyethyleneimine; polyoxymethylene; polyvinylphenol; polylactides; polymethacrylimide; polyalkenesulfone; polypropylene; polyethylene; polyhydroxyethylmethacrylate; polydimethylsiloxane; polyacrylamide; polyimide; and various block co-polymers. In other specific embodiments, the gels are selected from the group consisting of collagen gels, matrigels, and ECM gels. In additional specific embodiments, the support may be selected from the group consisting of glass slides coated with primary aldehyde groups, nitrocellulose films, positively charged nylon membranes, and a polyacrylamide matrix.

Section 7

A method for identifying a biomarker polypeptide that can be used to predict in vivo hepatotoxicity, comprising:

a) incubating an hepatocyte in medium in the presence and absence of a test substance; and
b) analyzing the medium by dimensional packed capillary high performance liquid chromatography coupled to tandem mass spectrometry identifying at least one polypeptide in the medium and comparing the levels of the identified polypeptide in the presence and absence of the test substance; wherein elevated levels of the polypeptide in the medium in presence of the test substance indicate identification of a biomarker polypeptide that can be used to predict in vivo hepatotoxicity.

The method according to any one of the embodiments of this section, wherein the hepatotoxicity is idiosyncratic hepatotoxicity.

The method according to any one of the embodiments of this section, wherein the levels of the polypeptide are measured using a method selected from the group consisting of RIA, ELISA, immunoprecipitation, and immunoblotting.

The method according to any one of the embodiments of this section which is automated.

The method according to any one of the embodiments of this section, wherein the levels of the polypeptide are measured using a microarray. In specific embodiments, the microarray is selected from the group consisting of protein, antibody, and cell-based microarrays.

The method according to any one of the embodiments of this section, wherein the hepatocyte is obtained from a liver sample from a patient.

The method according to any one of the embodiments of this section, wherein the hepatocyte is obtained from a hepatic cell line. In specific embodiments, the hepatic cell line is selected from the group consisting of mouse, rat, porcine, and human cell lines. In other specific embodiments, the human hepatic cell line is selected from the group consisting of THLE-5, THLE-5B, THLE-5B-c15, HH25, HH29, HHY41, HuH7, Hep3B, HepG2, OUMS-29, ACTIVTox®, PH5CH, HepG2/C3A, THLE-3, DBTRG-05MG, THLE-2, SW 1783, U-138 MG, and SK-LMS-1.

The method according to any one of the embodiments of this section, wherein the hepatocyte includes an expression construct comprising a human cytochrome P450 enzyme selected from the group consisting of 1A1, 1A2, 2A6, 2B6, 2C8, 2C9, 2C10, 2C19, 2D6, 2E1, 3A4, 3A5, and 3A7.

The method according to any one of the embodiments of this section, wherein the levels of a polypeptide selected from the group consisting of SEQ ID NO:1 to SEQ ID NO:15 and SEQ ID NO:61 to SEQ ID NO:64 are also measured in the media in the presence and absence of the test substance as a positive control.

The method according to any one of the embodiments of this section, wherein the test substance is selected from the group consisting of anti-cancer, anti-bacterial, anti-fungal, anti-viral, anti-hypertension, anti-depression, anti-anxiety, and anti-arthritis substances. In other embodiments, the test substance is selected from and substances for the treatment of allergies, diabetes, hypercholesteremia, osteoporosis, Alzheimer's disease, Parkinson's disease, other neurodegenerative diseases, and obesity. In specific embodiments, test substance is selected from the group consisting of PPAR agonists, HIV protease inhibitors, anti-inflammatory drugs, estrogenic drugs, anti-estrogenic drugs, antihistimines, muscle relaxants, anti-anxiety drugs, anti-psychotic drugs, and anti-angina drugs.

EXAMPLES

The Examples herein are meant to exemplify the various aspects of carrying out the invention and are not intended to limit the scope of the invention in any way. The Examples do not include detailed descriptions for conventional methods employed, such as biphasic high performance liquid chromatography, tandem mass spectrometry, western blotting, or enzyme linked immunosorbent assay. Such methods are well known to those skilled in the art and described in numerous publications, for example, 2-*D Proteome Analysis Protocols*, Andrew J. Link, editor, Humana Press, 1999, ISBN: 0896035247; *Mass Spectrometry of Proteins and Peptides*, J. R. Chapman, editor, Humana Press, 2000, ISBN: 089603609X.

Example 1

Cell Culture

The human hepatocyte cell line THLE-5 (CRL-11113, ATCC, Manassas, Va.) has been immortalized by transformation with simian virus 40 large T antigen (Pfeifer, A. M., et al., 1993, *Proc. Natl. Acad. Sci. U.S.A.* 90:5123-5127, hereby incorporated by reference in its entirety). These immortalized cells are reported to be similar to quiescent normal human hepatocytes. In particular, the cells are observed to be non-tumorigenic when injected into nude mice, they have near-diploid karyotypes, they do not express alpha-fetoprotein, and they are free of Hepatitis B or human immunodeficiency virus (Pfeifer et al, 1993, supra). The THLE-5 cell line (also named THLE-5B) was previously deposited under the terms and conditions of the Budapest Treaty at the American Type Culture Collection on Apr. 23, 1992, and has been assigned the accession number CRL-11113. The parent cell line, THLE-5B-c15 (T5-c15), does not express Phase I metabolizing activity, but retains normal expression of most Phase II metabolizing enzymes, such as glutathione S-transferase, epoxide hydrolase, N-acetyl transferase type I, aldehyde reductase, and quinone reductase, as well as detoxification systems, such as superoxide dismutase (SOD) and catalase.

The cell line THLE-5B-3A4, which expresses the 3A4 isoform of cytochrome P450, was derived by transfection of THLE-5B-c15 with a CMV expression vector comprising a human cDNA coding for the specific P450 isoenzyme and a selection marker, using methods known in the art. The construction of this cell line was disclosed in U.S. Ser. No. 10/285,093, "Methods of Screening for Toxicity of Test Compounds" filed Oct. 31, 2002, which is hereby incorporated by reference herein. THLE-5B cell lines expressing 3A4 have been previously described (Krauskopf A, et al., 2002, *Br. J. Pharmacol.* 135(4):977-86; Macé, K., et al., 1997, *Carcinogenesis* 18:1291-1297). The 3A4 isoform was chosen because it is responsible for the metabolism of the largest share of marketed pharmaceutical compounds (Evans, W. E.; Relling, M. V., 1999, Science 286:487-491).

Cells were grown in 150 mm culture dish with 50 ml of 3% fetal bovine serum-containing low calcium medium (PMFR-4, BioSource International, Camarillo, Calif.), supplemented with 1.75 uM insulin, 5 ng/ml epidermal growth factor, 10 ug/ml transferrin, 50 ng/ml triiodothyronine, and 15 ug/ml bovine pituitary extract, as supplied by the manufacturer. When the cells reached confluence, the medium was removed by aspiration, and replaced with 30 ml of serum and transferrin free PMRF-4 medium (SFM) containing either vehicle (0.5% DMSO) or compound in 0.5% DMSO.

TABLE 1

| Compound | Concentration | Class | Toxicity in HHA Cells |
|---|---|---|---|
| DMSO | N/A | Vehicle | Non-Toxic |
| Rosiglitazone | 50 μM | PPAR Agonist | Non-Toxic |
| Tesaglitazar | 50 μM | PPAR Agonist | Non-Toxic |
| Troglitazone | 32.7 μM | PPAR Agonist | Toxic |
| Ciglitazone | 38 μM | PPAR Agonist | Toxic |
| Farglitazar | 8.61 μM | PPAR Agonist | Toxic |
| Indinavir | 50 μM | HIV Protease Inhibitor | Non-Toxic |
| Ritonavir | 39 μM | HIV Protease Inhibitor | Toxic |

Table 1. Names, classes, concentrations, and known toxicities of the 8 compounds used to survey the supernatants of the hepatocytes for possible biomarkers of toxicity by LC/LC/MS/MS and immunological assay.

TABLE 2

| Compound | Concentration | Class | Toxicity in HHA Cells |
|---|---|---|---|
| DMSO | N/A | Vehicle | Non-Toxic |
| Pioglitazone | 50 μM | PPAR Agonist | Non-Toxic |
| Rosiglitazone | 50 μM | PPAR Agonist | Non-Toxic |
| Tesaglitazar | 50 μM | PPAR Agonist | Non-Toxic |
| Ragaglitazar | 50 μM | PPAR Agonist | Non-Toxic |
| Indinavir | 50 μM | HIV Protease Inhibitor | Non-Toxic |
| Ethinyl Estradiol | 50 μM | Synthetic Estrogen | Non-Toxic |
| Diclofenac | 50 μM | Anti-Inflammatory | Non-Toxic |
| Ketoprofen | 50 μM | Anti-Inflammatory | Non-Toxic |
| Ibuprofen | 50 μM | Anti-Inflammatory | Non-Toxic |
| Dantrolene | 50 μM | Skeletal Muscle Relaxant | Toxic |
| Troglitazone | 50 μM | PPAR Agonist | Toxic |
| Farglitazar | 50 μM | PPAR Agonist | Toxic |

TABLE 2-continued

| Compound | Concentration | Class | Toxicity in HHA Cells |
|---|---|---|---|
| Ciglitazone | 50 μM | PPAR Agonist | Toxic |
| Ritonavir | 50 μM | HIV Protease Inhibitor | Toxic |
| Raloxifene | 50 μM | Selective ER Modulator | Toxic |
| Tamoxifen | 50 μM | Non-Steroidal Anti-Estrogen | Toxic |
| Terfenadine | 50 μM | $2^{nd}$ Generation Antihistamine | Toxic |
| Trifluoperazine | 50 μM | Anti-Anxiety/Anti-Psychotic | Toxic |
| Perhexilene | 20 μM | Antiangina | Toxic |

Table 2. Names, classes, concentrations, and known toxicities of the 20 compounds tested to evaluate the specificity of BMS-PTX-265 and BMS-PTX-837 as general predictors of toxicity. ER=estrogen receptor.

Cells were incubated for 20 hr at 37° C. Conditioned media (i.e., media incubated with cells) was collected by decanting, then syringe-filtered through 0.22 μm membrane, and stored at −70° C. before preparation for LC/LC/MS/MS analysis. LC/LC/MS/MS analysis employs multidimensional packed capillary high performance liquid chromatography coupled to tandem mass spectrometry (Link, A. J.; Eng, J.; Schieltz, D. M.; Carmack, E.; Mize, G. J.; Morris, D. R.; Garvik, B. M.; Yates, J. R., $3^{rd}$, 1999, *Nat. Biotechnol.* 17:676-682). This technique has been shown to be useful for the simultaneous identification of large numbers of soluble proteins, both in vivo and in vitro, without the need for antibodies (Washburn, M. P.; Wolters, D.; Yates III, J. R., 2001, *Nature Biotechnol.* 19:242-247). LC/LC/MS/MS analysis has also been shown to be semi-quantitative, and can be used to determine relative changes in protein levels (James X. Pang, N. G., Ashok R. Dongre, Stanley A. Hefta, and Gregory J. Opiteck, 2002, *J. Proteome Res.* 1:161-169; Gao, J.; Friedrichs, M.; Dongre, A. R.; Hefta, S. A.; Opiteck, G. J., 2003, *J. Proteome Research*, submitted.

Hepatotoxic drugs were administered to the cells at their $IC_{50}$ values for cytotoxicity, which was determined in the culture system using inhibition of ATP synthesis as the endpoint (Crouch, S. P. M.; Kozlowski, R.; Slater, K. J.; Fletcher, J., 1993, *J. Immunol. Methods* 160:81-88) via a bioluminescence assay (CellTiter-Glo Luminescent Cell Viability Assay, Promega, Madison, Wis.; Petty, R. D.; Sutherland, L. A.; Hunter, E. M.; Cree, I. A., 1995, *J Biolumin. Chemilumin.* 10:29-34). The clinically non-toxic drugs were confirmed to be non-cytotoxic in this culture system to the limit of their solubility. For the purposes of this study, the non-hepatotoxic drugs were administered at 50 μM (Table 1).

Example 2

Protein Concentration, Proteolysis, and Solid Phase Extraction

Following a single thaw in a 1 L cylinder of water at room temperature, the filtered media were concentrated by centrifugal filtration (10 kDa, Pall Gelman Laboratory, Ann Arbor, Mich.). The resulting samples were chloroform methanol precipitated (Barnidge, D. R.; Dratz, E. A.; Jesaitis, A. J.; Sunner, J., 1999, *Anal. Biochem.* 269:1-9) to further concentrate and remove major organic soluble impurities, and then re-solubilized in 200 μl of 8 M urea/400 mM ammonium bicarbonate (Sigma, St. Louis, Mo.). The samples were then subjected to an assay for total protein by the bicinchoninic acid method (Smith, P. K.; Krohn, R. I.; Hermanson, G. T.; Mallia, A. K.; Gartner, F. H.; Provenzano, M. D.; Fujimoto, E. K.; Goeke, N. M.; Olson, B. J.; Klenk, D. C., 1985, *Anal. Biochem.* 150:76-85), and then normalized to 500 μg of total protein. Following this, 225 nmol of dithiothreitol (Sigma) was added to each sample and then incubated for 30 min at 50° C. After reduction, 500 nmol of iodoacetamide (Sigma) was added to each sample and incubated in the dark at room temperature for an additional 30 min. Finally, samples were diluted four-fold and 20 μg of TPCK-treated porcine trypsin (Promega, Madison, Wis.) was added to each sample prior to incubation for 18 hr at 37° C. Samples were subsequently desalted using separate C18 spin columns (Nest Group, Southboro, Mass.) before injection onto the LC/LC/MS/MS system.

Example 3

Separations and Mass Spectrometry

The digested samples were separated and analyzed using a two dimensional biphasic capillary (100 μm i.d.×365 μm o.d.; Link, A. J.; Eng, J.; Schieltz, D. M.; Carmack, E.; Mize, G. J.; Morris, D. R.; Garvik, B. M.; Yates, J. R., 1999, *Nat. Biotechnol.* 17:676-682), which was pulled with a Model P-2000 laser puller (Sutter Instrument Company, Novato, Calif.). The capillary column was first packed with 10 cm of C18 reversed-phase material (SelfPack Poros 10 R2, ABI, Framingham, Mass.), and this was followed by 5 cm of strong cation exchange material (Poros 20 HS SCX, ABI). A load of 200 μg of digested material, based on the total protein assay, was used for each analysis.

For these experiments, the four buffer solutions included Buffer A: 0.1% acetic acid, 0.2% isopropanol, 0.001% TFA in water; Buffer B: 95% acetonitrile, 0.1% acetic acid, 0.2% isopropanol, 0.001% TFA; Buffer C: 1 M ammonium acetate, 0.1% acetic acid, 0.2% isopropanol, 0.001% TFA; and Buffer D: equal to Buffer A. Fifteen fully automated LC/LC analyses were conducted for each sample. Each analysis included a salt step, followed by buffer wash, then a reversed phase run of increasing organic concentration. Following the completion of each successive reversed phase gradient, the salt concentration was increased, and the cycle was begun again (FIG. 2).

The fifteen salt wash steps (expressed as a ratio of Buffer C to Buffer D), which were used for analyses of each sample, included: 0%, 2.5%, 5%, 7.5%, 10%, 12.5%, 15%, 17.5%, 20%, 22.5%, 25%, 40%, 60%, 80%, 100% Buffer C in Buffer D. After each salt wash, the biphasic capillary column was washed with 100% Buffer D for 10 min followed by reversed phase separation. This separation included a 100 min analysis with a gradient of 0-40% Buffer A to B for 0 to 75 min, 40-100% B for 75-85 min, 100-0% B for 85-90 min, and finally a re-equilibration hold at 0% B for 90-100 min. The aforementioned gradients were delivered by a binary pump (1100, Agilent, Wilmington, Del.), which was split 1:200 prior to connection to the capillary column.

The capillary was interfaced with an ion trap mass spectrometer (LCQDeca, ThermoFinnigan, San Jose) equipped with a nano-LC electrospray source (Gatlin, C. L.; Eng, J. K.; Cross, S. T.; Detter, J. C.; Yates, J. R., 2000, *Analyt. Chem.* 72:757-763). The mass spectrometer's capillary temp was set to 200° C., and the spray voltage was set to 2 kV. In survey scan mode, two microscans were used to acquire $9e^7$ counts, with a maximum acquisition time of 1000 msec. In MS/MS mode, 3 microscans were used to acquire $2e^7$ counts, with a maximum acquisition time of 300 msec. The instrument was set to trigger data dependent fragmentation of the three most intense ions detected during the MS survey scan.

Example 4

Data Analysis

The SEQUEST algorithm (Eng, J. K.; McCormack, A. L.; Yates, J. R., 1994, *J. Am. Soc. Mass Spectrom.* 5:976-989) was used to process all mass spectral data files in conjunction with the non-redundant human protein database downloaded from the National Center for Biotechnology Information (file transfer protocol://file transfer protocol.ncbi.nih.gov). The search results from SEQUEST were filtered (Dongre, A. R.; Opiteck, G. J.; Rios, C.; Friedrichs, M.; Hefta, S. A., 2003, *J. Proteome Res.*, in preparation; Tabb, D. L.; McDonald, W. H.; Yates, J. R. I., 2002, *J. Proteome Research* 1:21-26) based on each data file having met four out of the five acceptance criteria, i.e., Xcorr>2.5, DelCn>0.095, Sp>500, Rsp<5 and % ions >35. The list of tentative protein/peptide identifications from each sample was then compiled and compared using our proprietary ANALYSIS software package, which is similar to publicly available programs (Tabb, D. L.; McDonald, W. H.; Yates, J. R. I., 2002, *J. Proteome Res.* 1:21-26; Eddes, J. S.; Kapp, E. A.; Frecklington, D. F.; Connolly, L. M.; Layton, M. J.; Moritz, R. L.; Simpson, R., 2002, *J. Proteomics* 2:1097-1103) that determine relative changes in protein concentration on the basis of peptide "hits" from a particular protein (Gao, J.; Friedrichs, M.; Dongre, A. R.; Hefta, S. A.; Opiteck, G. 2003, *J. Proteome Research*, submitted; Pang, J. X.; Ginani, N.; Dongre, A. R.; Hefta, S. A.; Opiteck, G. J., 2002, *J. Proteome Res.* 1:161-169). The output file from the ANALYSIS program was then downloaded to desktop spreadsheet programs for further statistical analysis (Excel, Microsoft, Redmond, Wash.).

Example 5

Western Blotting and ELISA Assay of BMS-PTX-265

Aliquots (10 μl) of conditioned medium were diluted in an equal volume of sample buffer under reducing conditions (Nupage LDS, Invitrogen, Carlsbad, Calif.), boiled for 5 min, and resolved using 4-12% Bis Tris Gels and MES Buffer (Invitrogen). Following electrophoresis, the proteins were transferred to PVDF membrane at 30 V for 1 hr. The blots were subsequently blocked with 5% non-fat dry milk in phosphate buffered saline including 0.5% Tween-20 (Sigma), and incubated overnight at 4° C. with gentle shaking. Next, the blots were probed with rabbit anti-BMS-PTX-265 antibody (Santa Cruz Biotechnology, Inc., Santa Cruz, Calif.) for 2 hr at 23° C. Following incubation with an anti-rabbit secondary antibody (1:5000 dilution, Sigma), bands were visualized using an enhanced chemiluminescent detection system (ECL+, Amersham, Piscataway, N.J.) and imaged using a cooled charge-coupled device camera (Fluor S-Max, Bio-Rad, Hercules, Calif.). The signals from the blots were quantified using Quantity One software (Bio-Rad).

Western Blotting and ELISA Assay of BMS-PTX-837

The levels of BMS-PTX-837 in the conditioned media were measured with an ELISA sandwich assay using commercially available antibodies (R&D Systems, Minneapolis, Minn.). Briefly, each well of a 96-well microtiter plate was coated with 100 μl of purified mouse monoclonal antibody at 2 μg/ml and incubated overnight at 25° C. After washing with PBS plus 0.05% Tween 20, the plate was blocked with 250 μl of PBS plus 1% BSA and 5% sucrose. Standards were made (100 μl of a serially diluted sample) and added to each well. Samples were then incubated with a goat polyclonal anti-BMS-PTX-837 antibody conjugated to biotin (R&D Systems) and anti-Streptavidin-HRP (Upstate Biotechnology, Lake Placid, N.Y.). After washing four times with 200 μl of PBS plus 0.05% Tween 20, the mixture was incubated at 25° C. for 30 min in the presence of 3,3,5,5-tetramethylbenzidine. The color reaction was terminated with 2N $H_2SO_4$ (J. T. Baker, Phillipsburg, N.J.) and the optical density was read at 450 nm with wavelength correction set at 570 nm (Rainbow Thermo Reader, Tecan, RTP, NC).

Example 6

Discovery System Results

Eight treatments (including seven distinct drugs and vehicle alone; Table 1) were chosen on the basis of their documented response in humans during clinical trials or post-marketing analyses. Within this set, Rosiglitazone, Tesaglitazar, Troglitazone, Ciglitazone, and Farglitazar were selected from the class of drugs called thiazolidinediones, also known as PPAR agonists. Troglitazone, Ciglitazone, and Farglitazar are known to be toxic, while Rosiglitazone and Tesaglitazar are non-toxic. In addition, a set of hepatotoxic and non-hepatotoxic drugs, Indinavir and Ritonavir, were selected from the class of drugs known as HIV protease inhibitors. These drugs are distinct from the PPAR agonists both structurally and by target class, and were used to gain some understanding as to the selectivity and specificity of the biomarkers for tracking hepatotoxicity.

The time point of 20 hr was chosen based on the established protocol for the in vitro cytotoxicity assay, and because the same cells showed substantial changes in transcription profiles at 20 hr in gene chip array experiments (unpublished observations). It was therefore believed that the release of a variety of proteins into the conditioned media would take place at 20 hr. Altogether, the eight treatments were repeated in triplicate, thereby generating 24 distinct samples for analysis. The multidimensional chromatography and mass spectrometry platform was selected based on its non-discriminatory nature and its use in identifying extracellular proteins without the need for specific antibodies. This system worked remarkably well, identifying more than 1000 proteins in the conditioned media from the eight treatments. Since the goal of this project was to identify a small number of proteins that could be assayed by traditional immunological methods, this number of candidates had to be reduced before any further verification or validation could be performed.

Example 7

Results for Selection of BMS-PTX-265 and BMS-PTX-837

Within the array of possible biomarkers, a "template" was applied to the data set to find proteins that were present at the highest concentration when treated with toxic compounds and at the lowest concentration when treated with non-toxic compounds. The template was applied as a mathematical tool such that an artificial protein entry was listed with a value of 100 for each toxic compound, and a value of 1 for each non-toxic compound. Each of the 1000 proteins on the list were compared to this template entry and examined for closeness of fit using a Pearson product-moment correlation coefficient (Hane, B. G.; Jager, K.; Drexler, H. G., 1993, *Electrophoresis* 14:967-972).

In addition, the list of candidates was also examined for potential biomarkers having commercially available antibodies that would be readily adaptable to a high throughput assay. The list was also searched for polypeptides with publications or published mechanisms, i.e. biological relevance, to explain their association with hepatocellular injury. This generated a subset of approximately 15 biomarkers (Table 3) that were believed to be suitable for hepatotoxicity screening.

TABLE 3

| Protein ID | DMSO | Rosi | Tesa | Trog | Ciglit | Farg | Ind | Rit | Pearson |
|---|---|---|---|---|---|---|---|---|---|
| template | 0 | 0 | 0 | 1000 | 1000 | 1000 | 0 | 1000 | 1.00 |
| BMS-PTX-265 | 26 | 3 | 8 | 66 | 93 | 49 | 19 | 59 | 0.90 |
| BMS-PTX-447 | 7 | 9 | 6 | 33 | 82 | 54 | 4 | 56 | 0.87 |
| BMS-PTX-749 | 6 | 17 | 6 | 60 | 142 | 87 | 34 | 77 | 0.86 |
| BMS-PTX-607 | 3 | 0 | 0 | 7 | 6 | 13 | 5 | 11 | 0.84 |
| BMS-PTX-808 | 5 | 6 | 1 | 10 | 14 | 10 | 2 | 18 | 0.83 |
| BMS-PTX-860 | 2 | 3 | 0 | 4 | 9 | 15 | 1 | 12 | 0.83 |
| BMS-PTX-254 | 0 | 3 | 1 | 7 | 28 | 14 | 2 | 17 | 0.83 |
| BMS-PTX-225 | 0 | 0 | 0 | 11 | 25 | 10 | 0 | 28 | 0.83 |
| BMS-PTX-(39)147 | 2 | 1 | 1 | 19 | 36 | 24 | 0 | 64 | 0.82 |
| BMS-PTX-459 | 6 | 10 | 8 | 14 | 31 | 24 | 12 | 21 | 0.82 |
| BMS-PTX-120 | 5 | 6 | 3 | 12 | 44 | 35 | 0 | 50 | 0.81 |
| BMS-PTX-837 | 1 | 10 | 8 | 17 | 25 | 15 | 4 | 36 | 0.81 |
| BMS-PTX-062 | 0 | 0 | 1 | 4 | 27 | 29 | 1 | 28 | 0.81 |
| BMS-PTX-260 | 3 | 1 | 0 | 4 | 24 | 21 | 4 | 30 | 0.80 |
| BMS-PTX-(29)147 | 11 | 25 | 31 | 67 | 239 | 128 | 32 | 118 | 0.79 |

Table 3. LC/LC/MS/MS data showing the peptide hits for each polypeptide and for a "template" entry. The template was the quantitative response anticipated from the known toxicity of each compound. Below it, the top 15 polypeptides identified are shown in descending order of their Pearson product-moment correlation coefficient to the template.

Figure 3A:
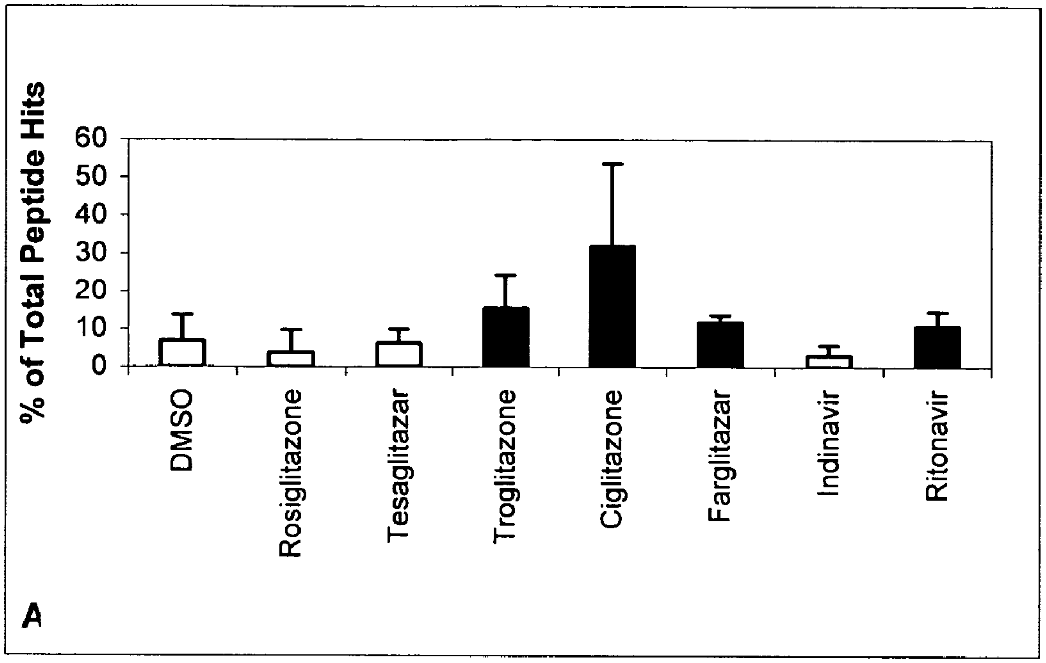
FIGS. 3A-3B. Peptide hits for BMS-PTX-265 (FIG. 3A) and BMS-PTX-837 (FIG. 3B). The number of peptide hits were averaged and normalized from LC/LC/MS/MS data in triplicate experiments and are expressed as the percent of total hits. The solid bars indicate the compounds known to be toxic, based on clinical and post-marketing data.
Figure 3B:
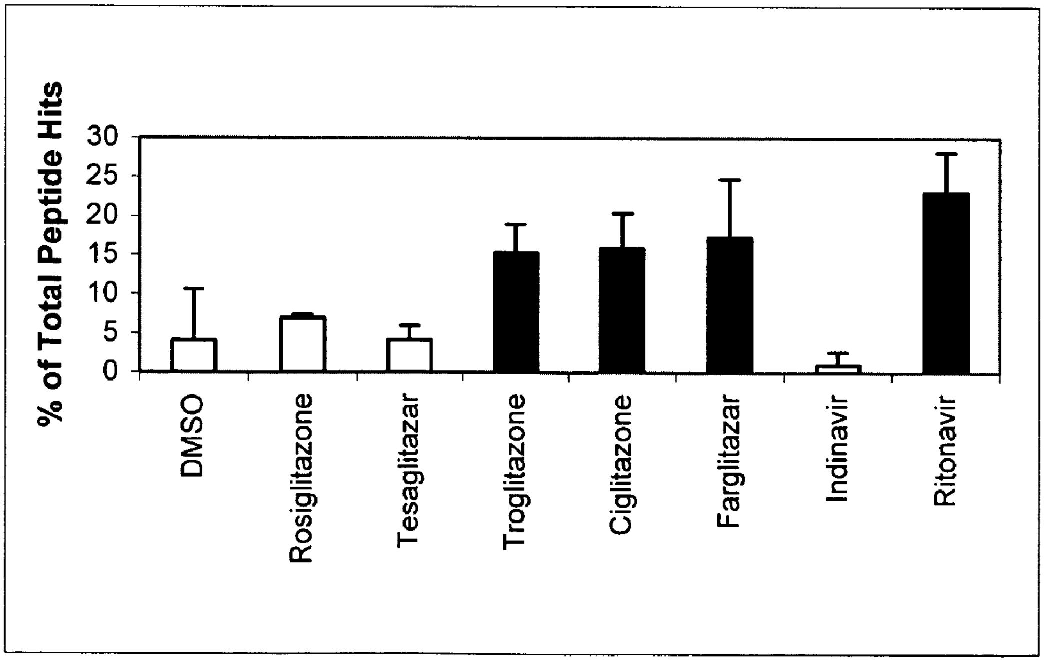

The two polypeptides that had the best match to the template, available publications, and commercially available antibodies, were BMS-PTX-265 and BMS-PTX-837. The LC/LC/MS/MS data for each of these two polypeptides is shown in FIGS. 3A and 3B. Description of the remaining 13 biomarker polypeptides is found in FIGS. 7A-7C and Table 4.

TABLE 4

| BMS Frescobi Acc. No. (abbrev.) | BMS Frescobi Acc. No. (full) | GenBank Identifier No. | Common name |
|---|---|---|---|
| BMS-PTX-447 | P1_7447 | gi\|65922\| | L-lactate dehydrogenase |
| BMS-PTX-749 | P1_246749 | gi\|2460318\| | RNA-binding protein regulatory subunit |
| BMS-PTX-607 | P1_221607 | gi\|7212867\| | transaldolase |
| BMS-PTX-808 | P1_42808 | gi\|4505029\| | leukotriene A4 hydrolase |
| BMS-PTX-860 | P1_165860 | gi\|14603147\| | coactosin-like protein |
| BMS-PTX-254 | P51_11254 | gi\|4557801\| | purine nucleoside phosphorylase |
| BMS-PTX-225 | P4_3225 | gi\|15216175\| | putative 42-9-9 protein |
| BMS-PTX-(39)147 | P1_139147 | gi\|2497297\| | activated leukocyte-cell adhesion molecule (ALCAM) |
| BMS-PTX-459 | P1_144459 | gi\|2136258\| | template activating factor-I |
| BMS-PTX-120 | P2_90120 | gi\|4505621\| | prostatic binding protein |
| BMS-PTX-062 | P2_66062 | gi\|10434265\| | unnamed protein product |
| BMS-PTX-260 | P2_88260 | gi\|20141722\| | serine (or cysteine) proteinase inhibitor, clade B |
| BMS-PTX-(29)147 | P1_29147 | gi\|119339\| | 2-phospho-D-glycerate hydrolyase |

Table 4. GenBank Identifier Numbers and common names for 13 of the biomarker polypeptides. Columns 1 and 2 show BMS Accession information; Column 3 shows GenBank Identifier information; Column 4 shows the common name for each polypeptide. Other names are also available for these polypeptides. The polypeptide sequences of each of these biomarkers, as presented in their respective Genbank Identifier number entries, are hereby incorporated herein by reference in their entirety.

GenBank Identifier Numbers for the polynucleotides encoding the identified biomarker polypeptides, including BMS-PTX-265 and BMS-PTX-837, are shown in Table 5. SEQ ID NOs for each of the biomarker polypeptides (FIGS. 4A-4B and FIGS. 7A-7C), polynucleotides (FIGS. 9A-9H), and exemplary primers (FIGS. 8A-8B) are shown in Table 6.

TABLE 5

| Frescobi Acc. No. (abbrev.) | GenBank Ident. No. | GenBank Acc. No. |
|---|---|---|
| BMS-PTX-265 | gi: 30331109 | CD014650 |
| BMS-PTX-447 | gi: 12804776 | BC001829 |
| BMS-PTX-749 | gi: 2460317 | AF021819 |
| BMS-PTX-607 | gi: 7212866 | AF058913 |
| BMS-PTX-808 | gi: 4505028 | NM_000895 |
| BMS-PTX-860 | gi: 14603146 | BC010039 |
| BMS-PTX-254 | gi: 4557800 | NM_000270 |
| BMS-PTX-225 | gi: 15216174 | AJ344101 |
| BMS-PTX-(39)147 | gi: 886257 | L38608 |
| BMS-PTX-459 | gi: 971271 | D45198 |
| BMS-PTX-120 | gi: 4505620 | NM_002567 |
| BMS-PTX-837 | gi: 30583134 | BT007148 |
| BMS-PTX-062 | gi: 10434264 | AK022710 |
| BMS-PTX-260 | gi: 12655086 | BC001394 |
| BMS-PTX-(29)147 | gi: 182113 | M14328 |

Table 5. GenBank Identifier and Accession Numbers for the nucleotide sequences encoding the biomarker polypeptides of the invention. Columns 1 and 4 show BMS Accession information; Columns 2 and 5 show GenBank Identifier information; Columns 3 and 6 show GenBank Accession information. The polynucleotide sequences of each of these biomarkers, as presented in their respective Genbank Identifier and Accession Number entries, are hereby incorporated herein by reference in their entirety.

TABLE 6

| BMS Frescobi Acc. No. (abbrev.) | Polypeptides SEQ ID NO: | Primers SEQ ID NO: | Polynucleotides SEQ ID NO: |
|---|---|---|---|
| BMS-PTX-265 | 1 | 16, 17 | 46 |
| BMS-PTX-837 | 2 | 38, 39 | 47 |
| BMS-PTX-447 | 3 | 18, 19 | 48 |
| BMS-PTX-749 | 4 | 20, 21 | 49 |
| BMS-PTX-607 | 5 | 22, 23 | 50 |
| BMS-PTX-808 | 6 | 24, 25 | 51 |
| BMS-PTX-860 | 7 | 26, 27 | 52 |
| BMS-PTX-254 | 8 | 28, 29 | 53 |
| BMS-PTX-225 | 9 | 30, 31 | 54 |
| BMS-PTX-(39)147 | 10 | 32, 33 | 55 |
| BMS-PTX-459 | 11 | 34, 35 | 56 |
| BMS-PTX-120 | 12 | 36, 37 | 57 |
| BMS-PTX-062 | 13 | 40, 41 | 58 |
| BMS-PTX-260 | 14 | 42, 43 | 59 |
| BMS-PTX-(29)147 | 15 | 44, 45 | 60 |
| Mouse BMS-PTX-265 | 61 | 69, 70 | 65 |
| Mouse BMS-PTX-837 | 62 | 71, 72 | 66 |
| Rat BMS-PTX-265 | 63 | 73, 74 | 67 |
| Rat e BMS-PTX-837 | 64 | 75, 76 | 68 |

Table 6. Summary of the SEQ ID NOs assigned to the biomarker polypeptide sequences, polynucleotide sequences, and exemplary primer sequences of the invention.

BMS-PTX-265 is a 245 residue homodimer having a mass of 28 kDa and an isoelectric point of 4.7, making it fairly acidic. It is believed to reside in the cytoplasm (Rittinger, K.; Budman, J.; Xu, J.; Volinia, S.; Cantley, L. C.; Smerdon, S. J.; Gamblin, S. J.; Yaffe, M. B., 1999, *Mol. Cell.* 4:153-166) where it activates various hydroxylases and kinases and may regulate cell signaling (Van Der Hoeven, P. C.; Van Der Wal, J. C.; Ruurs, P.; Van Blitterswijk, W. J., 2000, *Biochem. J.* 347:781-785). BMS-PTX-265 exists in several different isoforms (Chaudhri, M.; Scarabel, M.; Aitken, A., 2003, *Biochem. Biophys. Res. Commun.* 300:679-685). It has been reported to have phospholipase A2 activity (Zupan, L. A.; Steffens, D. L.; Berry, C. A.; Landt, M.; Gross, R. W., 1992, *J. Biol. Chem.* 267:8707-8710), and has been used as a biomarker for brain wasting diseases (Green, A. J., 2002, *Neuropathol. Appl. Neurobiol.* 28:427-440). The various names and synonyms for this protein listed on the ExPASy Molecular Biology Server (hypertext transfer protocol://us.expasy.org/) include protein kinase C inhibitor protein-1, KCIP-1, 14-3-3 zeta, 14-3-3 delta, factor activating exoenzyme S, FAS, and the product of gene YWHAZ. The amino acid sequence of BMS-PTX-265 is shown in FIG. 4A (GenBank Ident. No.

112695; GenBank Annotation: 14-3-3-zeta protein; BMS Frescobi Acc. No. (full) P1_18265).

While the LC/LC/MS/MS data for BMS-PTX-837 did not show as tight a correlation to the template as BMS-PTX-265, BMS-PTX-837 did have both commercially available antibodies and a significant number of publications. The BMS-PTX-837 enzyme is a 114 residue homotrimer having a mass of 12 kDa and an isoelectric point of 8.24, making it slightly basic. BMS-PTX-837 is thought to be involved in regulating immune responses (Mitchell, R. A.; Liao, H.; Chesney, J.; Fingerle-Rowson, G.; Baugh, J.; David, J.; Bucala, R., 2002, *Proc. Natl. Acad. Sci. USA* 99:345-350), and may act as phenylpyruvate tautomerase (Lubetsky, J. B.; Dios, A.; Han, J.; Aljabari, B.; Ruzsicska, B.; Mitchell, R.; Lolis, E.; Al-Abed, Y., 2002, *J. Biol. Chem.* 277:24976-24982). The various names and synonyms for this protein listed on the ExPASy Molecular Biology Server include macrophage migration inhibitory factor, MIF, phenylpyruvate tautomerase, glycosylation-inhibiting factor, GIF, and the product of gene MMIF. The amino acid sequence of BMS-PTX-837 is shown in FIG. 4B (GenBank Ident. No. 30583135; GenBank Annotation: macrophage migration inhibitory factor; BMS Frescobi Acc. No. (full) P166_25837).

BMS-PTX-837 was previously reported to be involved in the susceptibility of liver cells to drug induced injury (Bourdi, M.; Reilly, T. P.; Elkahloun, A. G.; George, J. W.; Pohl, L. R., 2002, *Biochem. Biophys. Res. Commun.* 294:225-230). However, the inventors are the first to recognize the usefulness of BMS-PTX-265, BMS-PTX-837, and the other biomarkers of the invention in predicting in vivo liver toxicity for a wide spectrum of test substances. In addition, the inventors are the first to disclose methods of using BMS-PTX-265, BMS-PTX-837, BMS-PTX-447, BMS-PTX-749, BMS-PTX-607, BMS-PTX-808, BMS-PTX-860, BMS-PTX-254, BMS-PTX-225, BMS-PTX-(39) 147, BMS-PTX-459, BMS-PTX-120, BMS-PTX-062, BMS-PTX-260, and BMS-PTX-(29) 147, or any combination thereof, as biomarkers for in vitro screening for hepatotoxicity. More particularly, the inventors are the first to recognize the utility of BMS-PTX-265, BMS-PTX-837, and the other disclosed biomarkers for predicting in vivo idiosyncratic liver toxicity.

Example 8

Figure 5A:
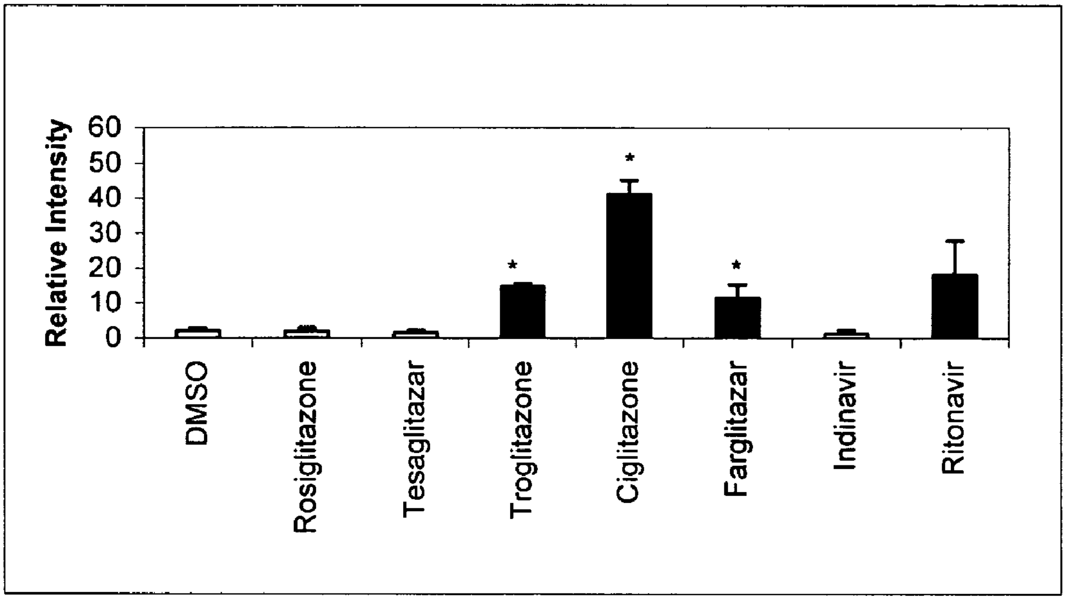
FIGS. 5A-5B. Mean values (+/−SD) of BMS-PTX-265 (FIG. 5A) and BMS-PTX-837 (FIG. 5B) determined from three separate cell culture experiments, as assayed in triplicate.

Results for Verification of BMS-PTX-265 and BMS-PTX-837 by Immunological Assays Antibodies for BMS-PTX-265 were obtained (Santa Cruz Biotechnology, Inc., Santa Cruz, Calif.). Conditioned media samples used to identify the proteins were assayed by blotting to determine presence and relative concentrations of the proteins as a function of each treatment. This was done to verify the accuracy of the mass spectral data (Table 3) and to increase the precision of the quantitative measurements. The blotting experiments mirrored the mass spectral results (see Table 3 and FIG. 5A). In addition, the increased quantitative precision of the blotting technique allowed use of a Student's t-test. This revealed a statistically significant ($p<0.05$) increase in levels of BMS-PTX-265 following treatment with each of the toxic PPAR agonists (Troglitazone, Ciglitazone, and Farglitazar), as compared to the non-toxic treatments. None of the non-toxic PPAR agonists or the non-toxic HIV protease inhibitor produced false positive increases in BMS-PTX-265. A less statistically significant increase in the levels of BMS-PTX-265 was observed after treatment with toxic HIV protease inhibitor Ritonavir (FIG. 5A).

Figure 5B:
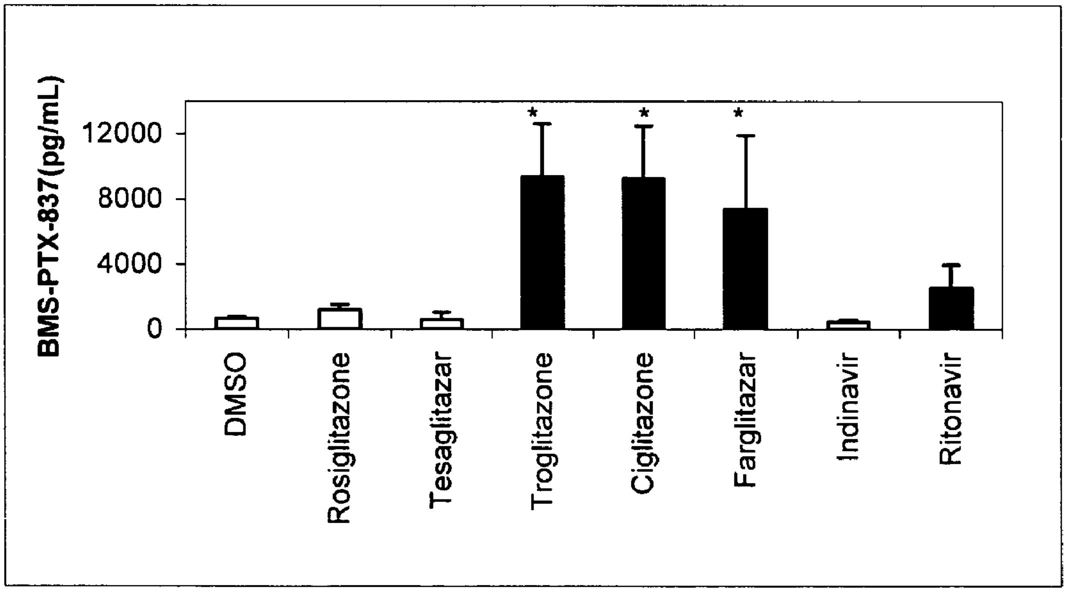

An EIA (enzyme immunoassay) kit for BMS-PTX-837 was obtained (P/N CYT264, Chemicon International, Temecula, Calif.), and the manufacturer's protocol was followed. The same verification paradigm was used to confirm the mass spectral results for BMS-PTX-837 (Table 3). Blotting experiments produced the same pattern of response to the toxic and non-toxic compounds as seen with BMS-PTX-265 (FIG. 5B). The Student's t-test demonstrated that there was a statistically significant ($p<0.05$) increase in BMS-PTX-837 levels following treatment with each of the toxic drugs, as compared to the non-toxic drugs and vehicle. No false positive increases in BMS-PTX-837 were observed in connection with any of the non-toxic compounds. The toxic HIV protease inhibitor Ritonavir caused elevation of BMS-PTX-837 levels, but these were not found to be statistically significant.

Example 9

Results for Evaluation of Hepatotoxic-Specificity of BMS-PTX-265 and BMS-PTX-837

A larger panel of hepatotoxic and non-hepatotoxic compounds was assembled in order to evaluate the specificity of BMS-PTX-265 and BMS-PTX-837 as biomarkers for drug-induced hepatocellular toxicity. The aforementioned immunoassays for the two candidate biomarkers were used for evaluation of this panel of drugs. This larger panel contained 20 total treatments (Table 2), including 19 drugs that were all dosed at 50 μM, except perhexelene, which was dosed at 20 μM due to supply limits. The original seven compounds, Rosiglitazone, Tesaglitazar, Troglitazone, Ciglitazone, Farglitazar, Indinavir, and Ritonavir, were again included in this new and larger panel for comparison to the previous experiments. The 12 new compounds introduced into the experiment included 2 additional PPAR agonists (Ragaglitazar and Pioglitazone), 3 anti-inflammatory agents (Diclofenac, Ketoprofen, and Ibuprofen), 1 neurological drug (Trifluoperazine), 3 estrogenic hormones (Ethinyl Estradiol, Raloxifene, and Tamoxifen), 1 anti-angina drug (Perhexilene), 1 muscle relaxant (Dantrolene), and 1 antihistamine (Terfenadine).

For each of the 19 drugs, a single concentration of administration was used to provide the most realistic scenario for future screening assays. In routine pre-clinic screening, little is typically known about the investigational drugs that are being tested. It was therefore important to design an assay that could predict the potential toxicity of various compounds prior to animal studies or human testing, without requiring knowledge of the final dose to be used. The ability to perform such assays independent of dosage, or with very few doses, drove the selection of the concentration (50 μM) for 18 of the 19 compounds tested.

Figure 6A:
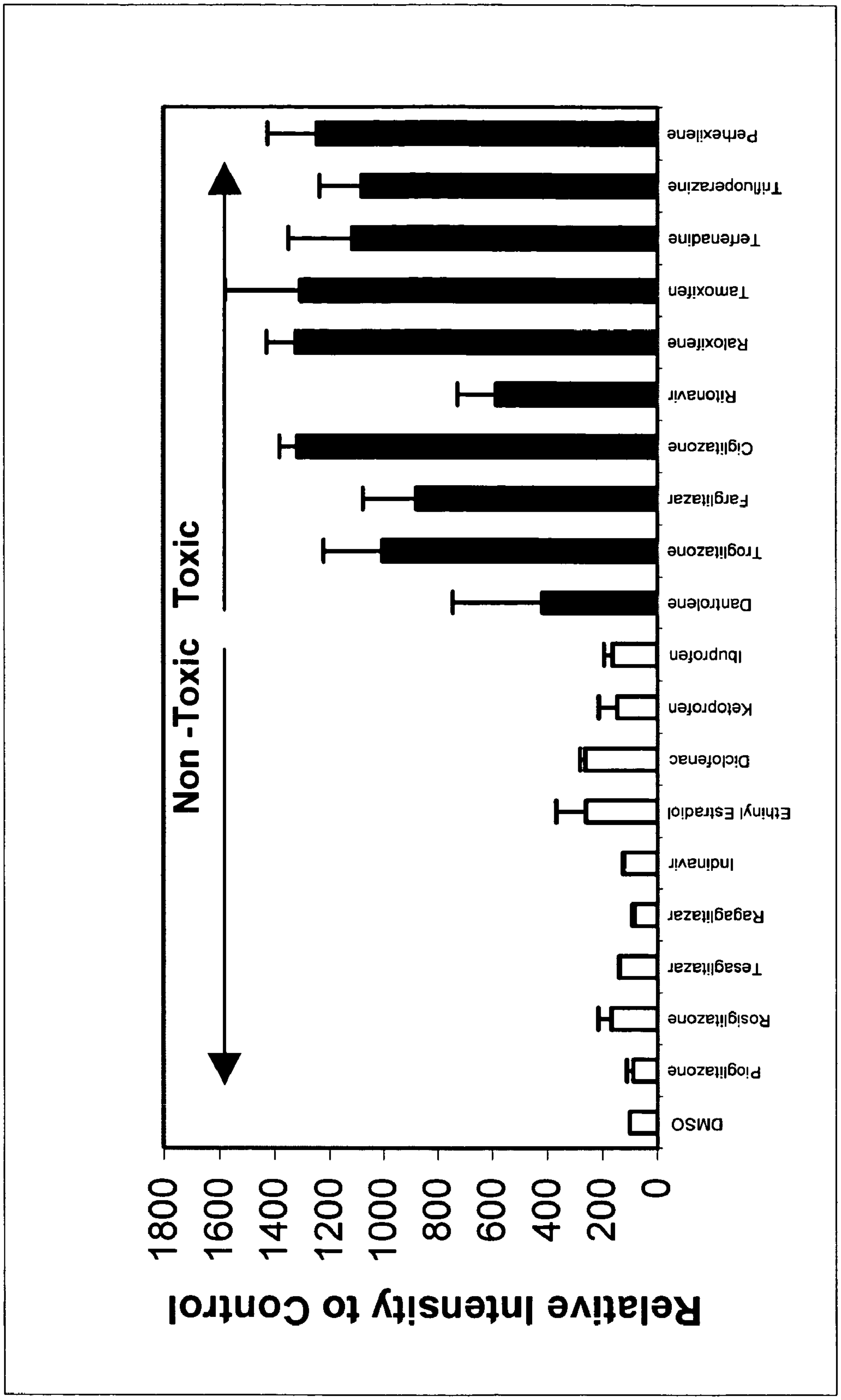
FIGS. 6A-6B. Histograms of the mean densitometry data taken from duplicate western blots of BMS-PTX-265 (FIG. 6A) and the mean colorimetric data taken from duplicate ELISA of BMS-PTX-837 (FIG. 6B). Each is expressed as a function of 20 treatments, as itemized in Table 2 (below). The solid bars indicate the compounds known to be toxic, based on clinical and post-marketing data.

The results of the duplicate experiments for the evaluation of BMS-PTX-265 are shown in FIG. 6A. As before, BMS-PTX-265 levels increased after treatment with the four original toxic compounds, Troglitazone, Ciglitazone, Farglitazar, and Ritonavir. Each of the toxic compounds elicited a large increase in the concentration of BMS-PTX-265, and none of the non-toxic compounds produced a false positive response. Moreover, analysis of the additional 12 compounds showed that increases BMS-PTX-265 levels could be used to correctly predict those drugs that elicit toxic responses in humans. The one exception was Dantrolene, which although hepatotoxic, did not induce a statistically significant increase in BMS-PTX-265 levels.

The mean value of BMS-PTX-265 levels (expressed in units of intensity relative to the vehicle) for the non-toxic compounds was 158 (SD (standard deviation) 34.6), while the mean value for the toxic compounds (omitting Dantrolene) was 1096 (SD 65.1). This represents a ratio of approximately 1:7. The maximum value of a non-toxic compound (Diclofenac) was 262 (SD 18), while the minimum value for a toxic compound (Ritonavir) was 587 (SD 139). This represents a difference of 224%, which did not overlap with any of the non-toxic compounds. The greatest observed difference was between Ragaglitazar (average value=82; SD 9; non-toxic) and Ciglitazone (average value=1317; SD 65; toxic), which represents a 1600% change. The average value of 416 (SD 330) would predict a toxic response for Dantrolene, but the variation in the response makes this compound difficult to predict with a high degree of confidence based on BMS-PTX-265 levels.

Figure 6B:
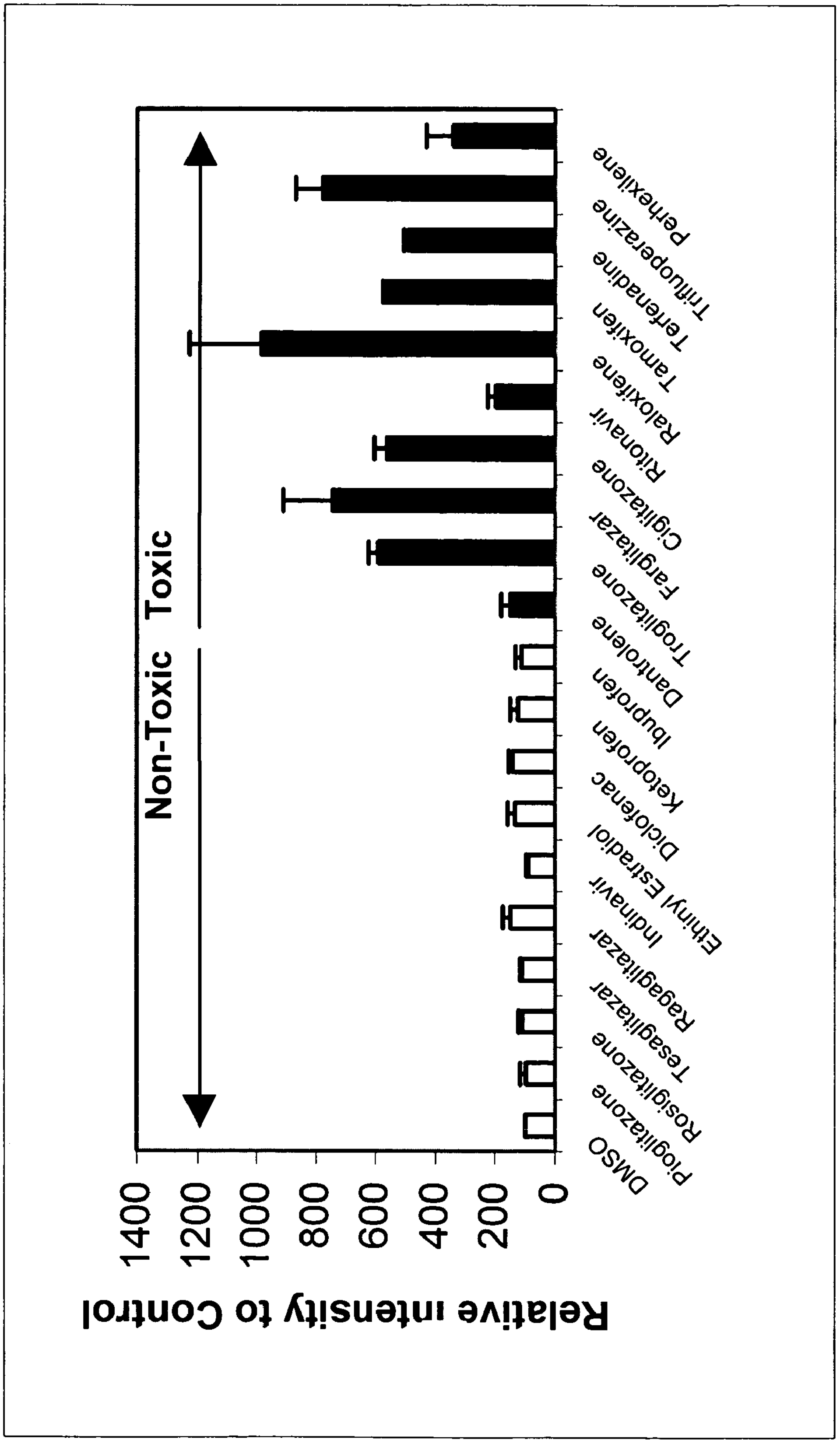
Figure 10A:
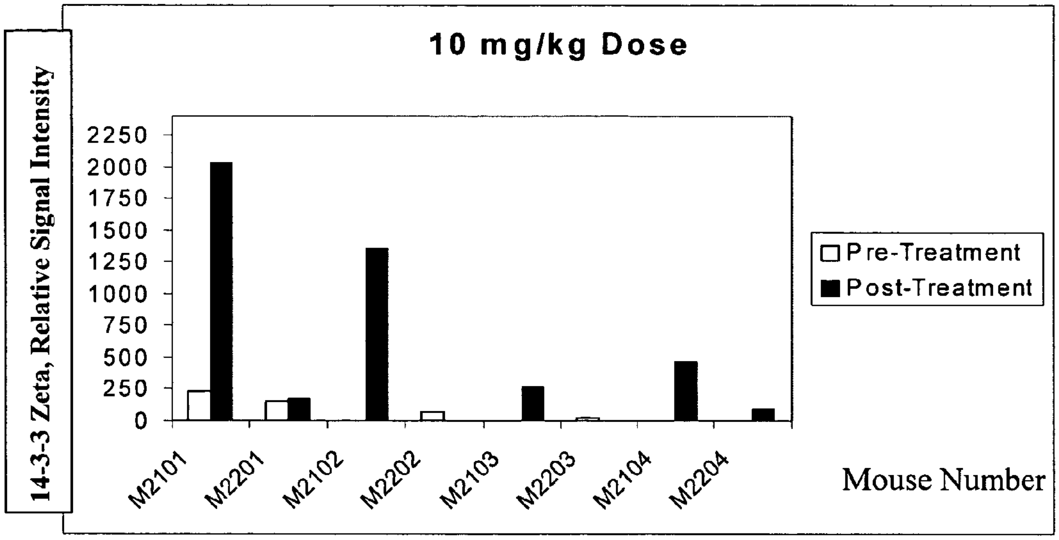
FIGS. 10A-D. Quantified Western analyses of murine 14-3-3 ZETA (mouse BMS-PTX-265.
Figure 10B:
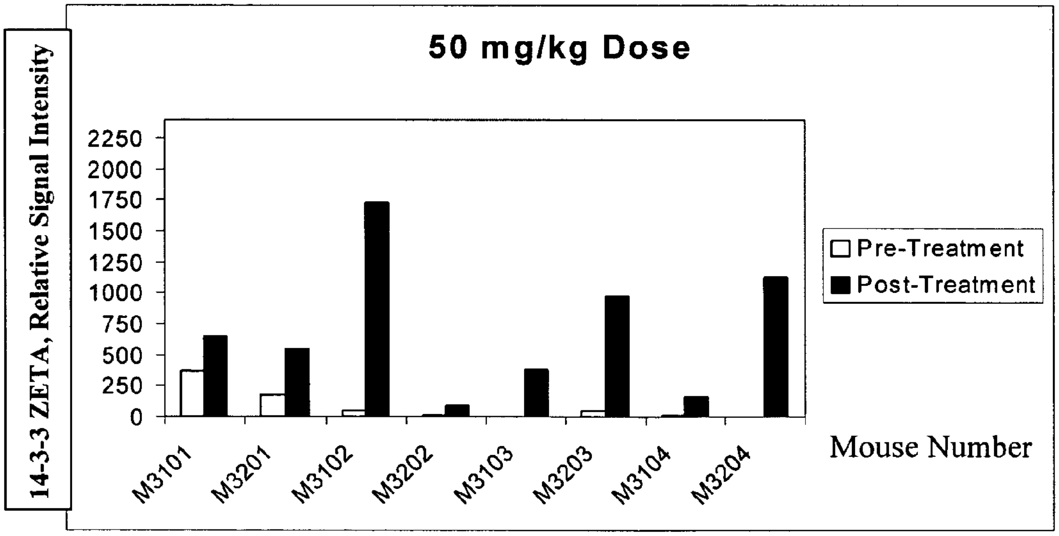
Figure 10C:
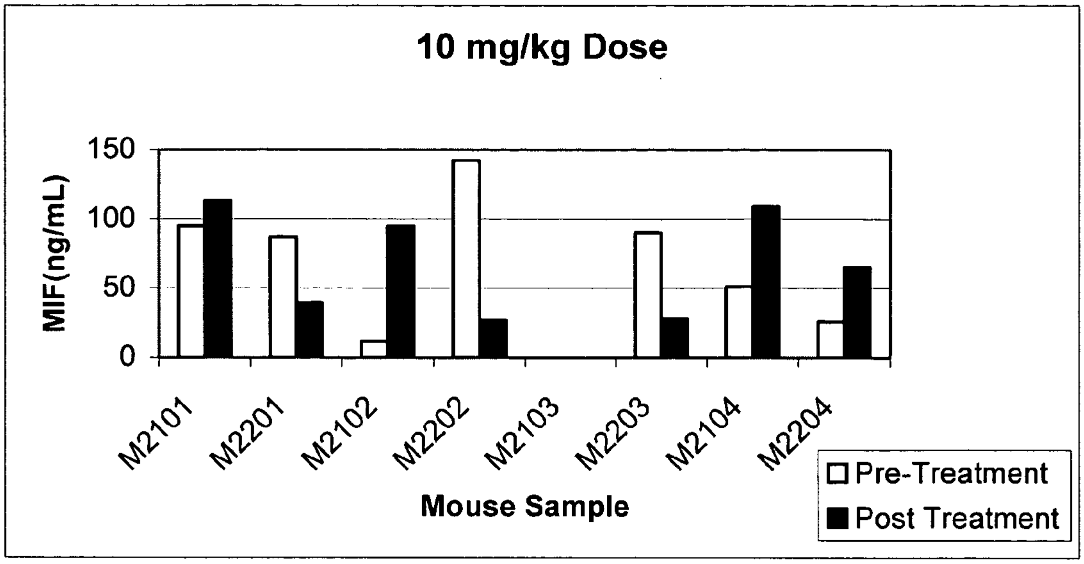
Figure 10D:
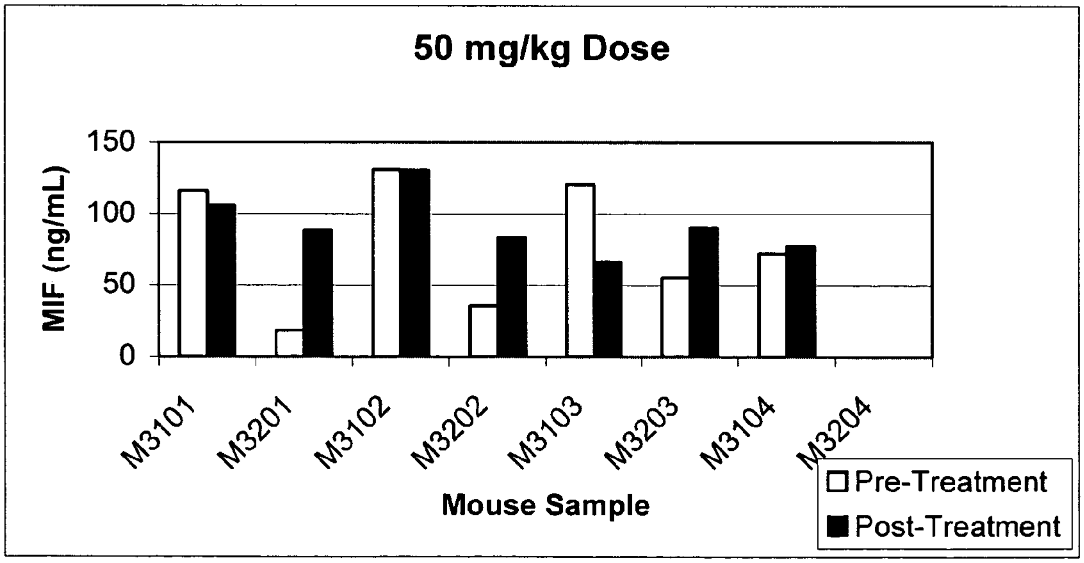

BMS-PTX-837 levels were assessed in conditioned media exposed to the same 20 treatments. The results closely resembled those of the earlier experiments for BMS-PTX-265 (compare FIGS. 6A and 6B). The mean value of BMS-PTX-837 levels in the duplicate assays (expressed in units of intensity relative to the vehicle) for the non-toxic compounds was 118 (SD 8), while the mean value for the toxic compounds (omitting Dantrolene) was 584 (SD 79.5). This represents a difference of 495%. In this assay, the maximum value of a non-toxic compound (Tesaglitazar) was 150 (SD 30), while the minimum value for a toxic compound (Ritonavir) was 198 (SD 25). This represents a difference of 132%, which is significant, but still less than the difference observed for BMS-PTX-265. The greatest observed difference was between Indinavir (average value=90; SD 6; non-toxic) and Raloxifene (average value=986; SD 243; toxic), representing a change of 1100%. In these experiments, Dantrolene produced an average value of 149 (SD 29), which would predict a non-toxic response. Notably, less variability was observed in the results from this assay, as compared to the assay for BMS-PTX-265.

Example 10

Method of Assessing the Expression Profile of the Biomarker Polypeptides

Total RNA from tissues is isolated using the TriZol protocol (Invitrogen) and quantified by determining its absorbance at 260 nM. An assessment of the 18s and 28s ribosomal RNA bands is made by denaturing gel electrophoresis to determine RNA integrity. The specific sequence to be measured is aligned with related genes found in GenBank to identity regions of significant sequence divergence to maximize primer and probe specificity. Gene-specific primers and probes are designed using the ABI primer express software to amplify small amplicons (150 base pairs or less) to maximize the likelihood that the primers function at 100% efficiency. All primer/probe sequences are searched against Public Genbank databases to ensure target specificity. Primers and probes are obtained from ABI. Exemplary primer sequences for amplification of biomarker polynucleotides are shown in FIGS. 8A-8B.

To access the level of contaminating genomic DNA in the RNA, the RNA is divided into 2 aliquots and one half is treated with Rnase-free Dnase (Invitrogen). Samples from both the Dnase-treated and non-treated are then subjected to reverse transcription reactions with (RT+) and without (RT−) the presence of reverse transcriptase. TaqMan assays are carried out with gene-specific primers (see above) and the contribution of genomic DNA to the signal detected is evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If this is not the case, the RNA is not used in further experiments.

In the reverse transcription reaction, 100 ng of Dnase-treated total RNA is annealed to 2.5 μM of the respective gene-specific reverse primers in the presence of 5.5 mM $MgCl_2$ by heating the sample to 72° C. for 2 min and then cooling to 55° C. for 30 min. Next, 1.25 U/μl of MuLv reverse transcriptase and 500 μM of each dNTP is added to the reaction and the tube is incubated at 37° C. for 30 min. The sample is then heated to 90° C. for 5 min to denature enzyme. Quantitative sequence detection is carried out on an ABI PRISM 7700 by adding to the reverse transcribed reaction 2.5 μM forward and reverse primers, 2.0 μM of the TaqMan probe, 500 μM of each dNTP, buffer, and 5 U AmpliTaq Gold™. The PCR reaction is then held at 94° C. for 12 min, followed by 40 cycles of 94° C. for 15 sec and 60° C. for 30 sec. For data handling, the threshold cycle (Ct) of the lowest expressing tissue (the highest Ct value) is used as the baseline of expression and all other tissues are expressed as the relative abundance to that tissue by calculating the difference in Ct value between the baseline and the other tissues and using it as the exponent in $2^{(\Delta Ct)}$

Example 11

Methods of Validating the Hepatotaxity Biomarkers of the Present Invention In Vivo

Pre-Clinical Animal Models

All animal studies were conducted and serum samples collected by the Bristol-Myers Squibb Pharmaceutical Research Institute Departments of Drug Safety Evaluation in Syracuse, N.Y. in accordance with current Standard Operating Procedures and BMS Animal Care and Use Committee guidelines.

Compound A—Mouse

In an intermittent-dose study in mice designed to examine potential toxicity of an immunomodulatory molecule, doses of 10 (low dose) or 50 mg/kg (high dose) were intravenously administered to groups of 12 mice, twice weekly for four weeks. Serum was collected prestudy and at the end of the dosing period. In addition, a third group of mice was given vehicle alone (Dulbeccos's phosphate buffered saline). Western blot analyses and ELISAs were performed on 1 to 10 μl of serum.

Compound B—Rat

In a single-dose study in rats designed to characterize toxicity of an exploratory cell cycle inhibitor, two groups of 20 female rats (Harlan Sprague Dawley, Frederick, Md.) were intravenously administered vehicle (2.1 mM L-tartaric acid in 0.9% NaCl) or compound at 22 mg/kg. This dose was predicted to cause significant, but non-lethal, toxicity over 32 hours. Serum was collected from each animal prior to treatment and from five rats per group at 8, 16, 24, and 32 hours post-treatment. The principal toxicity observed was single cell necrosis of multiple organs including liver. Western blot analyses and ELISAs were performed on 1 to 10 μl of serum.

Compound B—Dog

In a single-dose study designed to investigate toxicity of the same cell cycle inhibitor (Compound B) in dogs, one male and one female (Marshall Farms, North Rose, N.Y.) were intravenously administered 3.6 mg/kg of compound. In a previous study, this dose caused severe toxicity leading to death within 12 to 19 hours. Serum was collected from dogs predose and at 0.5, 1, 2, 3, 4, 5, 6, and 7 hours post dose. Serum was also collected from both dogs prior to euthanasia at 8 hours. As with the rat study of Compound B, the principal toxicity observed was necrosis of multiple organs including liver. A single microliter of serum from each dog was used for Western blot analyses.

Human Reference Plasma Samples

Reference human plasma samples were obtained in 1 ml frozen aliquots (Biological Specialty Corporation, Colmar, Pa.). These were maintained at −80° C. and one microliter was used for Western blot analyses and determination of BMS-PTX-265 levels. From each sample 10 μl of serum was used in BMS-PTX-265 ELISAs.

BMS-PTX-265 Western Blotting

Aliquots of plasma were diluted 10-fold in sample buffer under reducing conditions (Nupage LDS, Invitrogen, Carlsbad, Calif.), boiled for 5 min. and resolved using 4-12% Bis Tris Gels and MES Buffer (Invitrogen). Following electrophoresis, the proteins were transferred to a PVDF membrane at 30 V for 1 hr, and the blots were subsequently blocked with 5% non-fat dry milk in phosphate buffered saline including 0.05% Tween-20 (Sigma) overnight at 4° C. with gentle shaking. The blots were probed with rabbit anti-BMS-PTX-265 antibody (Santa Cruz, Calif.) for 2 hr at 23° C. Following incubation with an anti-rabbit secondary antibody (1:5000 dilution, Sigma), the antibodies were visualized using enhanced chemiluminescent detection (ECL+, Amersham, Piscataway, N.J.) and imaged using a cooled charge-coupled device camera (Fluor S-Max, Bio-Rad, Hercules, Calif.). The signals from the blots were quantified using Quantity One software (Bio-Rad).

BMS-PTX-837 ELISA (Mouse and Rat Samples)

Mouse and rat BMS-PTX-837 were measured using a commercially available kit (Chemicon, Calif.) and the assay was performed per the manufacturers instructions. Samples or standards (5 μl) were added to plates coated with rabbit-anti rodent BMS-PTX-837 and incubated with anti-BMS-PTX-837 conjugated to horseradish peroxidase. After a 30 min incubation with the TMB substrate at 37° C., the reaction was stopped with one half volume of 2N Sulfuric acid and optical density read at 450 nm (Rainbow Thermo Reader, Tecan, RTP, NC).

BMS-PTX-837 ELISA (Human Samples)

The levels of BMS-PTX-837 in the human plasma samples were measured with a ELISA sandwich assay using commercially available antibodies (R&D Systems, Minneapolis, Minn.). Briefly, each well of a 96-well microtiter plate was coated with 100 μl of purified mouse monoclonal antibody at 2 ug/mL overnight at 25° C. After washing with PBS+0.05% Tween 20, the plate was blocked with 250 ul of PBS+1% BSA and 5% sucrose. Standards were made (100 μl of a serially diluted sample) and samples were then added to each well, incubated with a goat polyclonal anti-BMS-PTX-837 antibody conjugated to biotin (R&D Systems) and anti-Streptavidin-HRP. After washing four times with 200 uL of PBS+0.05% Tween 20, the mixture was incubated at 25° C. for 30 min in the presence of 3,3,5,5-tetramethylbenzidine. The color reaction was terminated with one half volume 2N $H_2SO_4$ (J. T. Baker, Phillipsburg, N.J.) and the optical density read at 450 nm with wavelength correction set at 570 nm (Rainbow Thermo Reader).

BMS-PTX-265 ELISA

The protocol for BMS-PTX-265 evaluation used an isoform specific antibody as a capture and pan antibody conjugated to HRP as detection. Briefly, each well of a 96-well microtiter plate was coated with 100 μl of purified rabbit antibody (Santa Cruz, Calif.) at 1 ug/mL overnight at 25° C. After washing with PBS/0.05% Tween 20, the plate was blocked with 250 ul of Superblock (Pierce). Serial dilutions of the standard (100 fold) and human plasma samples (20 fold dilution) were loaded onto the plates for 2 hrs at RT with shaking. The plates were washed and incubated with 100 ul of anti-BMS-PTX-265 conjugated to HRP (Santa Cruz, Calif.) at 1:1000 dilution in PBS/BSA diluent for 45 min. After washing four times with 200 uL of PBS+0.05% Tween 20, the substrate (3,3,5,5-tetramethylbenzidine) was incubated at 25° C. for 15 min. The color reaction was terminated with one volume 2N Sulfuric Acid (J. T. Baker, Phillipsburg, N.J.) and the optical density read at 450 nm with wavelength correction set at 570 nm (Rainbow Thermo Reader).

Generation of Recombinant BMS-PTX-265

An I.M.A.G.E. Consortium clone containing the full length coding sequence of BMS-PTX-265 was obtained (Invitrogen, Carlsbad, Calif.). After PCR and sequence verification, the complete coding sequence was cloned into a Gateway™ entry vector. The construct was created by performing the Gateway™ BP recombination reaction between the PCR product flanked by attB recombination sites and the pDONR201 donor vector containing attP recombination sites. The destination (expression) construct was generated by using an LR recombination reaction between the entry construct above and the pDEST14 vector for native expression in bacteria. The entry construct contained the attL sites and the destination vector contains the attR. The result was a destination construct with the insert flanked by attB recombination sites (pDEST-BMS-PTX-265).

Purification of Recombinant BMS-PTX-265

An HPLC system (1100, Agilent, Wilmington, Del.) was used to purify BMS-PTX-265 from transfected *E. coli* whole cell lysates. Raw material (1 ml) was loaded onto Keystone Hypersil Biobasic C8 4.6×250 mm column. The flow rate was set to 1 mL/min and the gradient was 0-45 min, 0-100% B; 45-50 min, 100% B; 50-51 min, 0% B; 51-60 min, 0% B. Mobile Phase A was 0.1% TFA, 0.2% IPA in $H_2O$; Mobile Phase B was 0.1% TFA, 0.2% IPA in 95% Acetonitrile, 4.7% $H_2O$. Fractions containing BMS-PTX-265 were identified by Western blot and then combined and lyophilized to reduce the volume 10 fold. The sample was dialyzed in 50 mM Tris buffer (Slide-A-Lyzer 7,000 MWCO, Pierce), overnight at 4° C. Final volume was 7.5 mL and the final concentration of the sample was determined using BCA Protein Assay.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the Sequence Listing submitted herewith and the corresponding Computer Readable Form are both incorporated herein by reference in their entireties.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method of predicting idiosyncratic hepatotoxicity of a test substance comprising:

(a) incubating a hepatocyte in the presence and absence of a test substance in media; and (b) comparing measured levels of at least one biomarker polypeptide from the hepatocyte in said media selected from the group consisting of SEQ ID No: 1 and 2, in the presence and absence of said test substance;

wherein an elevated level of said biomarker polypeptide(s) in the presence of the test substance in said media indicates that the substance is predicted to cause idiosyncratic hepatotoxicity.

2. The method according to claim 1, wherein the extracellular levels or intracellular levels of the biomarker polypeptide are measured using a method selected from the group consisting of: RIA, ELISA, immunoprecipitation, immunoblotting, immunofluorescence microscopy, indirect-immunofluorescence, immunohistochemistry, and immunoblotting.

3. The method according to claim 2, which is automated.

4. The method according to claim 1, wherein the level of the biomarker polypeptide(s) is measured using a hybridization technology selected from the group consisting of: microarrays, protein microarrays, antibody microarrays, cell-based microarrays, PCR, RT-PCR, southern blots, northern blots, and in situ hybridization.

5. The method according to claim 1 wherein said method predicts hepatotoxicity of a test substance in vitro or in vivo.

6. The method according to claim 1, wherein the level of said biomarker polypeptide(s) is measured using single or multi dimensional high performance liquid chromatography coupled to tandem mass spectrometry wherein the number of peptide hits from each protein identification are used to determine the abundance of said biomarker polypeptide(s) in the presence and absence of said test substance.

* * * * *

UNITED STATES PATENT AND TRADEMARK OFFICE

CERTIFICATE OF CORRECTION

PATENT NO. : 7,452,678 B2
APPLICATION NO. : 10/873595
DATED : November 18, 2008
INVENTOR(S) : Durham et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 884 days.

Signed and Sealed this

Twenty-eighth Day of September, 2010

David J. Kappos
*Director of the United States Patent and Trademark Office*

```
                              SEQUENCE LISTING

<160> NUMBER OF SEQ ID NOS: 76

<210> SEQ ID NO 1
<211> LENGTH: 245
<212> TYPE: PRT
<213> ORGANISM: Homo sapiens

<400> SEQUENCE: 1

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245


<210> SEQ ID NO 2
<211> LENGTH: 115
<212> TYPE: PRT
<213> ORGANISM: Homo sapiens

<400> SEQUENCE: 2

Met Pro Met Phe Ile Val Asn Thr Asn Val Pro Arg Ala Ser Val Pro
1               5                   10                  15
```

-continued

```
Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser
            100                 105                 110

Thr Phe Ala
        115


<210> SEQ ID NO 3
<211> LENGTH: 332
<212> TYPE: PRT
<213> ORGANISM: Homo sapiens

<400> SEQUENCE: 3

Met Ala Thr Leu Lys Asp Gln Leu Ile Tyr Asn Leu Leu Lys Glu Glu
1               5                   10                  15

Gln Thr Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly
        195                 200                 205

Val Ser Leu Lys Thr Leu His Pro Asp Leu Gly Thr Asp Lys Asp Lys
    210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270
```

-continued

Val Ser Thr Met Ile Lys Gly Leu Tyr Gly Ile Lys Asp Asp Val Phe
275 280 285

Leu Ser Val Pro Cys Ile Leu Gly Gln Asn Gly Ile Ser Asp Leu Val
290 295 300

Lys Val Thr Leu Thr Ser Glu Glu Glu Ala Arg Leu Lys Lys Ser Ala
305 310 315 320

Asp Thr Leu Trp Gly Ile Gln Lys Glu Leu Gln Phe
325 330

<210> SEQ ID NO 4
<211> LENGTH: 189
<212> TYPE: PRT
<213> ORGANISM: Homo sapiens

<400> SEQUENCE: 4

Met Ala Ser Lys Arg Ala Leu Val Ile Leu Ala Lys Gly Ala Glu Glu
1 5 10 15

Met Glu Thr Val Ile Pro Val Asp Val Met Arg Arg Ala Gly Ile Lys
20 25 30

Val Thr Val Ala Gly Leu Ala Gly Lys Asp Pro Val Gln Cys Ser Arg
35 40 45

Asp Val Val Ile Cys Pro Asp Ala Ser Leu Glu Asp Ala Lys Lys Glu
50 55 60

Gly Pro Tyr Asp Val Val Val Leu Pro Gly Gly Asn Leu Gly Ala Gln
65 70 75 80

Asn Leu Ser Glu Ser Ala Ala Val Lys Glu Ile Leu Lys Glu Gln Glu
85 90 95

Asn Arg Lys Gly Leu Ile Ala Ala Ile Cys Ala Gly Pro Thr Ala Leu
100 105 110

Leu Ala His Glu Ile Gly Phe Gly Ser Lys Val Thr Thr His Pro Leu
115 120 125

Ala Lys Asp Lys Met Met Asn Gly Gly His Tyr Thr Tyr Ser Glu Asn
130 135 140

Arg Val Glu Lys Asp Gly Leu Ile Leu Thr Ser Arg Gly Pro Gly Thr
145 150 155 160

Ser Phe Glu Phe Ala Leu Ala Ile Val Glu Ala Leu Asn Gly Lys Glu
165 170 175

Val Ala Ala Gln Val Lys Ala Pro Leu Val Leu Lys Asp
180 185

<210> SEQ ID NO 5
<211> LENGTH: 337
<212> TYPE: PRT
<213> ORGANISM: Homo sapiens

<400> SEQUENCE: 5

Met Ser Ser Ser Pro Val Lys Arg Gln Arg Met Glu Ser Ala Leu Asp
1 5 10 15

Gln Leu Lys Gln Phe Thr Thr Val Val Ala Asp Thr Gly Asp Phe His
20 25 30

Ala Ile Asp Glu Tyr Lys Pro Gln Asp Ala Thr Thr Asn Pro Ser Leu
35 40 45

Ile Leu Ala Ala Ala Gln Met Pro Ala Tyr Gln Glu Leu Val Glu Glu
50 55 60

Ala Ile Ala Tyr Gly Arg Lys Leu Gly Gly Ser Gln Glu Asp Gln Ile
65 70 75 80

-continued

```
Lys Asn Ala Ile Asp Lys Leu Phe Val Leu Phe Gly Ala Glu Ile Leu
                85                  90                  95

Lys Lys Ile Pro Gly Arg Val Ser Thr Glu Val Asp Ala Arg Leu Ser
            100                 105                 110

Phe Asp Lys Asp Ala Met Val Ala Arg Ala Arg Arg Leu Ile Glu Leu
        115                 120                 125

Tyr Lys Glu Ala Gly Ile Ser Lys Asp Arg Ile Leu Ile Lys Leu Ser
    130                 135                 140

Ser Thr Trp Glu Gly Ile Gln Ala Gly Lys Glu Leu Glu Glu Gln His
145                 150                 155                 160

Gly Ile His Cys Asn Met Thr Leu Leu Phe Ser Phe Ala Gln Ala Val
                165                 170                 175

Ala Cys Ala Glu Ala Gly Val Thr Leu Ile Ser Pro Phe Val Gly Arg
            180                 185                 190

Ile Leu Asp Trp His Val Ala Asn Thr Asp Lys Lys Ser Tyr Glu Pro
        195                 200                 205

Leu Glu Asp Pro Gly Val Lys Ser Val Thr Lys Ile Tyr Asn Tyr Tyr
    210                 215                 220

Lys Lys Phe Ser Tyr Lys Thr Ile Val Met Gly Ala Ser Phe Arg Asn
225                 230                 235                 240

Thr Gly Glu Ile Lys Ala Leu Ala Gly Cys Asp Phe Leu Thr Ile Ser
                245                 250                 255

Pro Lys Leu Leu Gly Glu Leu Leu Gln Asp Asn Ala Lys Leu Val Pro
            260                 265                 270

Val Leu Ser Ala Lys Ala Ala Gln Ala Ser Asp Leu Glu Lys Ile His
        275                 280                 285

Leu Asp Glu Lys Ser Phe Arg Trp Leu His Asn Glu Asp Gln Met Ala
    290                 295                 300

Val Glu Lys Leu Ser Asp Gly Ile Arg Lys Phe Ala Ala Asp Ala Val
305                 310                 315                 320

Lys Leu Glu Arg Met Leu Thr Glu Arg Met Phe Asn Ala Glu Asn Gly
                325                 330                 335

Lys
```

<210> SEQ ID NO 6
<211> LENGTH: 611
<212> TYPE: PRT
<213> ORGANISM: Homo sapiens

<400> SEQUENCE: 6

```
Met Pro Glu Ile Val Asp Thr Cys Ser Leu Ala Ser Pro Ala Ser Val
1               5                   10                  15

Cys Arg Thr Lys His Leu His Leu Arg Cys Ser Val Asp Phe Thr Arg
            20                  25                  30

Arg Thr Leu Thr Gly Thr Ala Ala Leu Thr Val Gln Ser Gln Glu Asp
        35                  40                  45

Asn Leu Arg Ser Leu Val Leu Asp Thr Lys Asp Leu Thr Ile Glu Lys
    50                  55                  60

Val Val Ile Asn Gly Gln Glu Val Lys Tyr Ala Leu Gly Glu Arg Gln
65                  70                  75                  80

Ser Tyr Lys Gly Ser Pro Met Glu Ile Ser Leu Pro Ile Ala Leu Ser
                85                  90                  95

Lys Asn Gln Glu Ile Val Ile Glu Ile Ser Phe Glu Thr Ser Pro Lys
            100                 105                 110
```

-continued

```
Ser Ser Ala Leu Gln Trp Leu Thr Pro Glu Gln Thr Ser Gly Lys Glu
        115                 120                 125

His Pro Tyr Leu Phe Ser Gln Cys Gln Ala Ile His Cys Arg Ala Ile
    130                 135                 140

Leu Pro Cys Gln Asp Thr Pro Ser Val Lys Leu Thr Tyr Thr Ala Glu
145                 150                 155                 160

Val Ser Val Pro Lys Glu Leu Val Ala Leu Met Ser Ala Ile Arg Asp
                165                 170                 175

Gly Glu Thr Pro Asp Pro Glu Asp Pro Ser Arg Lys Ile Tyr Lys Phe
            180                 185                 190

Ile Gln Lys Val Pro Ile Pro Cys Tyr Leu Ile Ala Leu Val Val Gly
        195                 200                 205

Ala Leu Glu Ser Arg Gln Ile Gly Pro Arg Thr Leu Val Trp Ser Glu
    210                 215                 220

Lys Glu Gln Val Glu Lys Ser Ala Tyr Glu Phe Ser Glu Thr Glu Ser
225                 230                 235                 240

Met Leu Lys Ile Ala Glu Asp Leu Gly Gly Pro Tyr Val Trp Gly Gln
                245                 250                 255

Tyr Asp Leu Leu Val Leu Pro Pro Ser Phe Pro Tyr Gly Gly Met Glu
            260                 265                 270

Asn Pro Cys Leu Thr Phe Val Thr Pro Thr Leu Leu Ala Gly Asp Lys
        275                 280                 285

Ser Leu Ser Asn Val Ile Ala His Glu Ile Ser His Ser Trp Thr Gly
    290                 295                 300

Asn Leu Val Thr Asn Lys Thr Trp Asp His Phe Trp Leu Asn Glu Gly
305                 310                 315                 320

His Thr Val Tyr Leu Glu Arg His Ile Cys Gly Arg Leu Phe Gly Glu
                325                 330                 335

Lys Phe Arg His Phe Asn Ala Leu Gly Gly Trp Gly Glu Leu Gln Asn
            340                 345                 350

Ser Val Lys Thr Phe Gly Glu Thr His Pro Phe Thr Lys Leu Val Val
        355                 360                 365

Asp Leu Thr Asp Ile Asp Pro Asp Val Ala Tyr Ser Ser Val Pro Tyr
    370                 375                 380

Glu Lys Gly Phe Ala Leu Leu Phe Tyr Leu Glu Gln Leu Leu Gly Gly
385                 390                 395                 400

Pro Glu Ile Phe Leu Gly Phe Leu Lys Ala Tyr Val Glu Lys Phe Ser
                405                 410                 415

Tyr Lys Ser Ile Thr Thr Asp Asp Trp Lys Asp Phe Leu Tyr Ser Tyr
            420                 425                 430

Phe Lys Asp Lys Val Asp Val Leu Asn Gln Val Asp Trp Asn Ala Trp
        435                 440                 445

Leu Tyr Ser Pro Gly Leu Pro Pro Ile Lys Pro Asn Tyr Asp Met Thr
    450                 455                 460

Leu Thr Asn Ala Cys Ile Ala Leu Ser Gln Arg Trp Ile Thr Ala Lys
465                 470                 475                 480

Glu Asp Asp Leu Asn Ser Phe Asn Ala Thr Asp Leu Lys Asp Leu Ser
                485                 490                 495

Ser His Gln Leu Asn Glu Phe Leu Ala Gln Thr Leu Gln Arg Ala Pro
            500                 505                 510

Leu Pro Leu Gly His Ile Lys Arg Met Gln Glu Val Tyr Asn Phe Asn
        515                 520                 525
```

-continued

```
Ala Ile Asn Asn Ser Glu Ile Arg Phe Arg Trp Leu Arg Leu Cys Ile
    530                 535                 540

Gln Ser Lys Trp Glu Asp Ala Ile Pro Leu Ala Leu Lys Met Ala Thr
545                 550                 555                 560

Glu Gln Gly Arg Met Lys Phe Thr Arg Pro Leu Phe Lys Asp Leu Ala
                565                 570                 575

Ala Phe Asp Lys Ser His Asp Gln Ala Val Arg Thr Tyr Gln Glu His
            580                 585                 590

Lys Ala Ser Met His Pro Val Thr Ala Met Leu Val Gly Lys Asp Leu
        595                 600                 605

Lys Val Asp
    610


<210> SEQ ID NO 7
<211> LENGTH: 142
<212> TYPE: PRT
<213> ORGANISM: Homo sapiens

<400> SEQUENCE: 7

Met Ala Thr Lys Ile Asp Lys Glu Ala Cys Arg Ala Ala Tyr Asn Leu
1               5                   10                  15

Val Arg Asp Asp Gly Ser Ala Val Ile Trp Val Thr Phe Lys Tyr Asp
            20                  25                  30

Gly Ser Thr Ile Val Pro Gly Glu Gln Gly Ala Glu Tyr Gln His Phe
        35                  40                  45

Ile Gln Gln Cys Thr Asp Asp Val Arg Leu Phe Ala Phe Val Arg Phe
    50                  55                  60

Thr Thr Gly Asp Ala Met Ser Lys Arg Ser Lys Phe Ala Leu Ile Thr
65                  70                  75                  80

Trp Ile Gly Glu Asn Val Ser Gly Leu Gln Arg Ala Lys Thr Gly Thr
                85                  90                  95

Asp Lys Thr Leu Val Lys Glu Val Val Gln Asn Phe Ala Lys Glu Phe
            100                 105                 110

Val Ile Ser Asp Arg Lys Glu Leu Glu Glu Asp Phe Ile Lys Ser Glu
        115                 120                 125

Leu Lys Lys Ala Gly Gly Ala Asn Tyr Asp Ala Gln Thr Glu
    130                 135                 140


<210> SEQ ID NO 8
<211> LENGTH: 289
<212> TYPE: PRT
<213> ORGANISM: Homo sapiens

<400> SEQUENCE: 8

Met Glu Asn Gly Tyr Thr Tyr Glu Asp Tyr Lys Asn Thr Ala Glu Trp
1               5                   10                  15

Leu Leu Ser His Thr Lys His Arg Pro Gln Val Ala Ile Ile Cys Gly
            20                  25                  30

Ser Gly Leu Gly Gly Leu Thr Asp Lys Leu Thr Gln Ala Gln Ile Phe
        35                  40                  45

Asp Tyr Gly Glu Ile Pro Asn Phe Pro Arg Ser Thr Val Pro Gly His
    50                  55                  60

Ala Gly Arg Leu Val Phe Gly Phe Leu Asn Gly Arg Ala Cys Val Met
65                  70                  75                  80

Met Gln Gly Arg Phe His Met Tyr Glu Gly Tyr Pro Leu Trp Lys Val
                85                  90                  95
```

-continued

```
Thr Phe Pro Val Arg Val Phe His Leu Leu Gly Val Asp Thr Leu Val
            100                 105                 110

Val Thr Asn Ala Ala Gly Gly Leu Asn Pro Lys Phe Glu Val Gly Asp
        115                 120                 125

Ile Met Leu Ile Arg Asp His Ile Asn Leu Pro Gly Phe Ser Gly Gln
    130                 135                 140

Asn Pro Leu Arg Gly Pro Asn Asp Glu Arg Phe Gly Asp Arg Phe Pro
145                 150                 155                 160

Ala Met Ser Asp Ala Tyr Asp Arg Thr Met Arg Gln Arg Ala Leu Ser
                165                 170                 175

Thr Trp Lys Gln Met Gly Glu Gln Arg Glu Leu Gln Glu Gly Thr Tyr
            180                 185                 190

Val Met Val Ala Gly Pro Ser Phe Glu Thr Val Ala Glu Cys Arg Val
        195                 200                 205

Leu Gln Lys Leu Gly Ala Asp Ala Val Gly Met Ser Thr Val Pro Glu
    210                 215                 220

Val Ile Val Ala Arg His Cys Gly Leu Arg Val Phe Gly Phe Ser Leu
225                 230                 235                 240

Ile Thr Asn Lys Val Ile Met Asp Tyr Glu Ser Leu Glu Lys Ala Asn
                245                 250                 255

His Glu Glu Val Leu Ala Ala Gly Lys Gln Ala Ala Gln Lys Leu Glu
            260                 265                 270

Gln Phe Val Ser Ile Leu Met Ala Ser Ile Pro Leu Pro Asp Lys Ala
        275                 280                 285

Ser


<210> SEQ ID NO 9
<211> LENGTH: 123
<212> TYPE: PRT
<213> ORGANISM: Homo sapiens

<400> SEQUENCE: 9

Met Ala Arg Tyr Glu Glu Val Ser Val Ser Gly Phe Glu Glu Phe His
1               5                   10                  15

Arg Ala Val Glu Gln His Asn Gly Lys Thr Ile Phe Ala Tyr Phe Thr
            20                  25                  30

Gly Ser Lys Asp Ala Gly Gly Lys Ser Trp Cys Pro Asp Cys Val Gln
        35                  40                  45

Ala Glu Pro Val Val Arg Glu Gly Leu Lys His Ile Ser Glu Gly Cys
    50                  55                  60

Val Phe Ile Tyr Cys Gln Val Gly Glu Lys Pro Tyr Trp Lys Asp Pro
65                  70                  75                  80

Asn Asn Asp Phe Arg Lys Asn Leu Lys Val Thr Ala Val Pro Thr Leu
                85                  90                  95

Leu Lys Tyr Gly Thr Pro Gln Lys Leu Val Glu Ser Glu Cys Leu Gln
            100                 105                 110

Ala Asn Leu Val Glu Met Leu Phe Ser Glu Asp
        115                 120


<210> SEQ ID NO 10
<211> LENGTH: 583
<212> TYPE: PRT
<213> ORGANISM: Homo sapiens
```

-continued

<400> SEQUENCE: 10

```
Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30

Ser Ala Tyr Gly Asp Thr Ile Ile Ile Pro Cys Arg Leu Asp Val Pro
        35                  40                  45

Gln Asn Leu Met Phe Gly Lys Trp Lys Tyr Glu Lys Pro Asp Gly Ser
    50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
        115                 120                 125

Lys Val Phe Lys Gln Pro Ser Lys Pro Glu Ile Val Ser Lys Ala Leu
    130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Ile Phe Lys Lys Glu Met
            180                 185                 190

Asp Pro Val Thr Gln Leu Tyr Thr Met Thr Ser Thr Leu Glu Tyr Lys
        195                 200                 205

Thr Thr Lys Ala Asp Ile Gln Met Pro Phe Thr Cys Ser Val Thr Tyr
    210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
            260                 265                 270

Asn Gly Asn Pro Pro Pro Glu Glu Phe Leu Phe Tyr Leu Pro Gly Gln
        275                 280                 285

Pro Glu Gly Ile Arg Ser Ser Asn Thr Tyr Thr Leu Met Asp Val Arg
    290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
        355                 360                 365

Asp Asn Ile Arg Leu Arg Ser Ser Pro Ser Phe Ser Ser Leu His Tyr
    370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415
```

-continued

```
Gln Ile Lys Met Thr Lys Lys Thr Asp Pro Ser Gly Leu Ser Lys Thr
            420                 425                 430

Ile Ile Cys His Val Glu Gly Phe Pro Lys Pro Ala Ile Gln Trp Thr
        435                 440                 445

Ile Thr Gly Ser Gly Ser Val Ile Asn Gln Thr Glu Glu Ser Pro Tyr
    450                 455                 460

Ile Asn Gly Arg Tyr Tyr Ser Lys Ile Ile Ile Ser Pro Glu Glu Asn
465                 470                 475                 480

Val Thr Leu Thr Cys Thr Ala Glu Asn Gln Leu Glu Arg Thr Val Asn
                485                 490                 495

Ser Leu Asn Val Ser Ala Ile Ser Ile Pro Glu His Asp Glu Ala Asp
            500                 505                 510

Glu Ile Ser Asp Glu Asn Arg Glu Lys Val Asn Asp Gln Ala Lys Leu
        515                 520                 525

Ile Val Gly Ile Val Val Gly Leu Leu Leu Ala Ala Leu Val Ala Gly
    530                 535                 540

Val Val Tyr Trp Leu Tyr Met Lys Lys Ser Lys Thr Ala Ser Lys His
545                 550                 555                 560

Val Asn Lys Asp Leu Gly Asn Met Glu Glu Asn Lys Lys Leu Glu Glu
                565                 570                 575

Asn Asn His Lys Thr Glu Ala
            580


<210> SEQ ID NO 11
<211> LENGTH: 290
<212> TYPE: PRT
<213> ORGANISM: Homo sapiens

<400> SEQUENCE: 11

Met Ala Pro Lys Arg Gln Ser Pro Leu Pro Pro Gln Lys Lys Lys Pro
1               5                   10                  15

Arg Pro Pro Pro Ala Leu Gly Pro Glu Glu Thr Ser Ala Ser Ala Gly
            20                  25                  30

Leu Pro Lys Lys Gly Glu Lys Glu Gln Gln Glu Ala Ile Glu His Ile
        35                  40                  45

Asp Glu Val Gln Asn Glu Ile Asp Arg Leu Asn Glu Gln Ala Ser Glu
    50                  55                  60

Glu Ile Leu Lys Val Glu Gln Lys Tyr Asn Lys Leu Arg Gln Pro Phe
65                  70                  75                  80

Phe Gln Lys Arg Ser Glu Leu Ile Ala Lys Ile Pro Asn Phe Trp Val
                85                  90                  95

Thr Thr Phe Val Asn His Pro Gln Val Ser Ala Leu Leu Gly Glu Glu
            100                 105                 110

Asp Glu Glu Ala Leu His Tyr Leu Thr Arg Val Glu Val Thr Glu Phe
        115                 120                 125

Glu Asp Ile Lys Ser Gly Tyr Arg Ile Asp Phe Tyr Phe Asp Glu Asn
    130                 135                 140

Pro Tyr Phe Glu Asn Lys Val Leu Ser Lys Glu Phe His Leu Asn Glu
145                 150                 155                 160

Ser Gly Asp Pro Ser Ser Lys Ser Thr Glu Ile Lys Trp Lys Ser Gly
                165                 170                 175

Lys Asp Leu Thr Lys Arg Ser Ser Gln Thr Gln Asn Lys Ala Ser Arg
            180                 185                 190

Lys Arg Gln His Glu Glu Pro Glu Ser Phe Phe Thr Trp Phe Thr Asp
        195                 200                 205
```

-continued

```
His Ser Asp Ala Gly Ala Asp Glu Leu Gly Glu Val Ile Lys Asp Asp
    210                 215                 220

Ile Trp Pro Asn Pro Leu Gln Tyr Tyr Leu Val Pro Asp Met Asp Asp
225                 230                 235                 240

Glu Glu Gly Glu Gly Glu Glu Asp Asp Asp Asp Asp Glu Glu Glu Glu
                245                 250                 255

Gly Leu Glu Asp Ile Asp Glu Glu Gly Asp Glu Asp Glu Gly Glu Glu
            260                 265                 270

Asp Glu Asp Asp Asp Glu Gly Glu Glu Gly Glu Glu Asp Glu Gly Glu
        275                 280                 285

Asp Asp
    290


<210> SEQ ID NO 12
<211> LENGTH: 223
<212> TYPE: PRT
<213> ORGANISM: Homo sapiens

<400> SEQUENCE: 12

Trp Val Cys Val Phe Pro Ser Gln Cys Ala Glu Leu Ser Ala Ser Pro
1               5                   10                  15

Leu Ser Pro Ala Pro Gly Leu Pro Arg His Ser Arg Leu His Ala Leu
            20                  25                  30

Leu Gly Leu Ala Met Pro Val Asp Leu Ser Lys Trp Ser Gly Pro Leu
        35                  40                  45

Ser Leu Gln Glu Val Asp Glu Gln Pro Gln His Pro Leu His Val Thr
    50                  55                  60

Tyr Ala Gly Ala Ala Val Asp Glu Leu Gly Lys Val Leu Thr Pro Thr
65                  70                  75                  80

Gln Val Lys Asn Arg Pro Thr Ser Ile Ser Trp Asp Gly Leu Asp Ser
                85                  90                  95

Gly Lys Leu Tyr Thr Leu Val Leu Thr Asp Pro Asp Ala Pro Ser Arg
            100                 105                 110

Lys Asp Pro Lys Tyr Arg Glu Trp His His Phe Leu Val Val Asn Met
        115                 120                 125

Lys Gly Asn Asp Ile Ser Ser Gly Thr Val Leu Ser Asp Tyr Val Gly
    130                 135                 140

Ser Gly Pro Pro Lys Gly Thr Gly Leu His Arg Tyr Val Trp Leu Val
145                 150                 155                 160

Tyr Glu Gln Asp Arg Pro Leu Lys Cys Asp Glu Pro Ile Leu Ser Asn
                165                 170                 175

Arg Ser Gly Asp His Arg Gly Lys Phe Lys Val Ala Ser Phe Arg Lys
            180                 185                 190

Lys Tyr Glu Leu Arg Ala Pro Val Ala Gly Thr Cys Tyr Gln Ala Glu
        195                 200                 205

Trp Asp Asp Tyr Val Pro Lys Leu Tyr Glu Gln Leu Ser Gly Lys
    210                 215                 220


<210> SEQ ID NO 13
<211> LENGTH: 314
<212> TYPE: PRT
<213> ORGANISM: Homo sapiens

<400> SEQUENCE: 13

Met Ser Ala Ala Glu Ala Gly Gly Val Phe His Arg Ala Arg Gly Arg
1               5                   10                  15
```

-continued

```
Thr Leu Ala Ala Phe Pro Ala Glu Lys Glu Ser Glu Trp Lys Gly Pro
            20                  25                  30

Phe Tyr Phe Ile Leu Gly Ala Asp Pro Gln Phe Gly Leu Ile Lys Ala
        35                  40                  45

Trp Ser Thr Gly Asp Cys Asp Asn Gly Gly Asp Glu Trp Glu Gln Glu
    50                  55                  60

Ile Arg Leu Thr Glu Gln Ala Val Gln Ala Ile Asn Lys Leu Asn Pro
65                  70                  75                  80

Lys Pro Lys Phe Phe Val Leu Cys Gly Asp Leu Ile His Ala Met Pro
                85                  90                  95

Gly Lys Pro Trp Arg Thr Glu Gln Thr Glu Asp Leu Lys Arg Val Leu
            100                 105                 110

Arg Ala Val Asp Arg Ala Ile Pro Leu Val Leu Val Ser Gly Asn His
        115                 120                 125

Asp Ile Gly Asn Thr Pro Thr Ala Glu Thr Val Glu Glu Phe Cys Arg
    130                 135                 140

Thr Trp Gly Tyr Asp Tyr Phe Ser Phe Trp Val Gly Gly Val Leu Phe
145                 150                 155                 160

Leu Val Leu Asn Ser Gln Phe Tyr Glu Asn Pro Ser Lys Cys Pro Ser
                165                 170                 175

Leu Lys Gln Ala Gln Asp Gln Trp Leu Asp Glu Gln Leu Ser Ile Ala
            180                 185                 190

Arg Gln Arg His Cys Gln His Ala Ile Val Phe Gln His Ile Pro Leu
        195                 200                 205

Phe Leu Glu Ser Ile Asp Glu Asp Asp Asp Tyr Tyr Phe Asn Leu Ser
    210                 215                 220

Lys Ser Thr Arg Lys Lys Leu Ala Asp Lys Phe Ile His Ala Gly Val
225                 230                 235                 240

Arg Val Val Phe Ser Gly His Tyr His Arg Asn Ala Gly Gly Thr Tyr
                245                 250                 255

Gln Asn Leu Asp Met Val Val Ser Ser Ala Ile Gly Cys Gln Leu Gly
            260                 265                 270

Arg Asp Pro His Gly Leu Arg Val Val Val Val Thr Ala Glu Lys Ile
        275                 280                 285

Val His Arg Tyr Tyr Ser Leu Asp Glu Leu Ser Glu Lys Gly Ile Glu
    290                 295                 300

Asp Asp Leu Met Asp Leu Ile Lys Lys Lys
305                 310


<210> SEQ ID NO 14
<211> LENGTH: 400
<212> TYPE: PRT
<213> ORGANISM: Homo sapiens

<400> SEQUENCE: 14

Arg Ser Leu Pro Ala Leu Glu Tyr Val Ser Gly Leu Gly Ala Ala Arg
1               5                   10                  15

Thr Arg Trp Leu Gly Ser Ala Ile Met Asp Val Leu Ala Glu Ala Asn
            20                  25                  30

Gly Thr Phe Ala Leu Asn Leu Leu Lys Thr Leu Gly Lys Asp Asn Ser
        35                  40                  45

Lys Asn Val Phe Phe Ser Pro Met Ser Met Ser Cys Ala Leu Ala Met
    50                  55                  60

Val Tyr Met Gly Ala Lys Gly Asn Thr Ala Ala Gln Met Ala Gln Ile
65                  70                  75                  80
```

-continued

```
Leu Ser Phe Asn Lys Ser Gly Gly Gly Gly Asp Ile His Gln Gly Phe
                85                  90                  95

Gln Ser Leu Leu Thr Glu Val Asn Lys Thr Gly Thr Gln Tyr Leu Leu
            100                 105                 110

Arg Met Ala Asn Arg Leu Phe Gly Glu Lys Ser Cys Asp Phe Leu Ser
        115                 120                 125

Ser Phe Arg Asp Ser Cys Gln Lys Phe Tyr Gln Ala Glu Met Glu Glu
    130                 135                 140

Leu Asp Phe Ile Ser Ala Val Glu Lys Ser Arg Lys His Ile Asn Thr
145                 150                 155                 160

Trp Val Ala Glu Lys Thr Glu Gly Lys Ile Ala Glu Leu Leu Ser Pro
                165                 170                 175

Gly Ser Val Asp Pro Leu Thr Arg Leu Val Leu Val Asn Ala Val Tyr
            180                 185                 190

Phe Arg Gly Asn Trp Asp Glu Gln Phe Asp Lys Glu Asn Thr Glu Glu
        195                 200                 205

Arg Leu Phe Lys Val Ser Lys Asn Glu Glu Lys Pro Val Gln Met Met
    210                 215                 220

Phe Lys Gln Ser Thr Phe Lys Lys Thr Tyr Ile Gly Glu Ile Phe Thr
225                 230                 235                 240

Gln Ile Leu Val Leu Pro Tyr Val Gly Lys Glu Leu Asn Met Ile Ile
                245                 250                 255

Met Leu Pro Asp Glu Thr Thr Asp Leu Arg Thr Val Glu Lys Glu Leu
            260                 265                 270

Thr Tyr Glu Lys Phe Val Glu Trp Thr Arg Leu Asp Met Met Asp Glu
        275                 280                 285

Glu Glu Val Glu Val Ser Leu Pro Arg Phe Lys Leu Glu Glu Ser Tyr
    290                 295                 300

Asp Met Glu Ser Val Leu Arg Asn Leu Gly Met Thr Asp Ala Phe Glu
305                 310                 315                 320

Leu Gly Lys Ala Asp Phe Ser Gly Met Ser Gln Thr Asp Leu Ser Leu
                325                 330                 335

Ser Lys Val Val His Lys Ser Phe Val Glu Val Asn Glu Glu Gly Thr
            340                 345                 350

Glu Ala Ala Ala Ala Thr Ala Ala Ile Met Met Met Arg Cys Ala Arg
        355                 360                 365

Phe Val Pro Arg Phe Cys Ala Asp His Pro Phe Leu Phe Phe Ile Gln
    370                 375                 380

His Ser Lys Thr Asn Gly Ile Leu Phe Cys Gly Arg Phe Ser Ser Pro
385                 390                 395                 400
```

<210> SEQ ID NO 15
<211> LENGTH: 434
<212> TYPE: PRT
<213> ORGANISM: Homo sapiens

<400> SEQUENCE: 15

```
Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60
```

-continued

```
Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
    210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
            420                 425                 430

Ala Lys
```

<210> SEQ ID NO 16
<211> LENGTH: 20
<212> TYPE: DNA
<213> ORGANISM: Homo sapiens -continued

<400> SEQUENCE: 16
caggctgagc gatatgatga 20

<210> SEQ ID NO 17
<211> LENGTH: 20
<212> TYPE: DNA
<213> ORGANISM: Homo sapiens

<400> SEQUENCE: 17
attctcgagc catctgctgt 20

<210> SEQ ID NO 18
<211> LENGTH: 20
<212> TYPE: DNA
<213> ORGANISM: Homo sapiens

<400> SEQUENCE: 18
tgggagttca cccattaagc 20

<210> SEQ ID NO 19
<211> LENGTH: 20
<212> TYPE: DNA
<213> ORGANISM: Homo sapiens

<400> SEQUENCE: 19
agcactctca accacctgct 20

<210> SEQ ID NO 20
<211> LENGTH: 20
<212> TYPE: DNA
<213> ORGANISM: Homo sapiens

<400> SEQUENCE: 20
tgtagccgtg atgtggtcat 20

<210> SEQ ID NO 21
<211> LENGTH: 20
<212> TYPE: DNA
<213> ORGANISM: Homo sapiens

<400> SEQUENCE: 21
ttcatgagcc aacagagcag 20

<210> SEQ ID NO 22
<211> LENGTH: 20
<212> TYPE: DNA
<213> ORGANISM: Homo sapiens

<400> SEQUENCE: 22
ggctgtgact tcctcaccat 20

<210> SEQ ID NO 23
<211> LENGTH: 20
<212> TYPE: DNA
<213> ORGANISM: Homo sapiens

<400> SEQUENCE: 23
gtgcaaccaa cggaaagact 20

<210> SEQ ID NO 24
<211> LENGTH: 20
<212> TYPE: DNA
<213> ORGANISM: Homo sapiens

<400> SEQUENCE: 24
actgcttgga ggaccagaga 20

<210> SEQ ID NO 25
<211> LENGTH: 20
<212> TYPE: DNA
<213> ORGANISM: Homo sapiens

<400> SEQUENCE: 25
ccaggcattc caatcaactt 20

<210> SEQ ID NO 26
<211> LENGTH: 20
<212> TYPE: DNA
<213> ORGANISM: Homo sapiens

<400> SEQUENCE: 26
ccgtcatctg ggtgactttt 20

<210> SEQ ID NO 27
<211> LENGTH: 20
<212> TYPE: DNA
<213> ORGANISM: Homo sapiens

<400> SEQUENCE: 27
acctccttca ccagggtctt 20

<210> SEQ ID NO 28
<211> LENGTH: 20
<212> TYPE: DNA
<213> ORGANISM: Homo sapiens

<400> SEQUENCE: 28
gaggcagagg gctctcagta 20

<210> SEQ ID NO 29
<211> LENGTH: 20
<212> TYPE: DNA
<213> ORGANISM: Homo sapiens

<400> SEQUENCE: 29
agccaaagac tcgaagtcca 20

<210> SEQ ID NO 30
<211> LENGTH: 20
<212> TYPE: DNA
<213> ORGANISM: Homo sapiens

<400> SEQUENCE: 30
agaggggctg aagcacatta 20

<210> SEQ ID NO 31
<211> LENGTH: 20
<212> TYPE: DNA
<213> ORGANISM: Homo sapiens

<400> SEQUENCE: 31
caggttggcc tgaagacact 20

<210> SEQ ID NO 32
<211> LENGTH: 20
<212> TYPE: DNA
<213> ORGANISM: Homo sapiens -continued

<400> SEQUENCE: 32
cgcaatgcaa caggagacta 20

<210> SEQ ID NO 33
<211> LENGTH: 20
<212> TYPE: DNA
<213> ORGANISM: Homo sapiens

<400> SEQUENCE: 33
ggctagatcg aagcctgatg 20

<210> SEQ ID NO 34
<211> LENGTH: 20
<212> TYPE: DNA
<213> ORGANISM: Homo sapiens

<400> SEQUENCE: 34
gcaagaagcg attgaacaca 20

<210> SEQ ID NO 35
<211> LENGTH: 20
<212> TYPE: DNA
<213> ORGANISM: Homo sapiens

<400> SEQUENCE: 35
gcagtgcctc ttcatcttcc 20

<210> SEQ ID NO 36
<211> LENGTH: 20
<212> TYPE: DNA
<213> ORGANISM: Homo sapiens

<400> SEQUENCE: 36
atagacccac cagcatttcg 20

<210> SEQ ID NO 37
<211> LENGTH: 20
<212> TYPE: DNA
<213> ORGANISM: Homo sapiens

<400> SEQUENCE: 37
actgtgccac tgctgatgtc 20

<210> SEQ ID NO 38
<211> LENGTH: 18
<212> TYPE: DNA
<213> ORGANISM: Homo sapiens

<400> SEQUENCE: 38
gaccagctca tggccttc 18

<210> SEQ ID NO 39
<211> LENGTH: 20
<212> TYPE: DNA
<213> ORGANISM: Homo sapiens

<400> SEQUENCE: 39
gagttgttcc agcccacatt 20

<210> SEQ ID NO 40
<211> LENGTH: 20
<212> TYPE: DNA
<213> ORGANISM: Homo sapiens -continued

<400> SEQUENCE: 40
gcagaaaagg aaagcgaatg 20

<210> SEQ ID NO 41
<211> LENGTH: 20
<212> TYPE: DNA
<213> ORGANISM: Homo sapiens

<400> SEQUENCE: 41
agaatttggg tttggggttc 20

<210> SEQ ID NO 42
<211> LENGTH: 20
<212> TYPE: DNA
<213> ORGANISM: Homo sapiens

<400> SEQUENCE: 42
ccaaatcttg gtgcttccat 20

<210> SEQ ID NO 43
<211> LENGTH: 20
<212> TYPE: DNA
<213> ORGANISM: Homo sapiens

<400> SEQUENCE: 43
agctcgaagg catcagtcat 20

<210> SEQ ID NO 44
<211> LENGTH: 20
<212> TYPE: DNA
<213> ORGANISM: Homo sapiens

<400> SEQUENCE: 44
tgatgatcga gatggatgga 20

<210> SEQ ID NO 45
<211> LENGTH: 20
<212> TYPE: DNA
<213> ORGANISM: Homo sapiens

<400> SEQUENCE: 45
cgccattgat gacattgaac 20

<210> SEQ ID NO 46
<211> LENGTH: 563
<212> TYPE: DNA
<213> ORGANISM: Homo sapiens

<400> SEQUENCE: 46
ttagcccgac cgacagcccg tgaggatcag ctgagagccg cggttagctt agctcagaca 60
ggaccatcgt tattccccga cactcagctc tgagcagcca tggacaagag cgagctagtg 120
caaaaagcca agctggccga gcaggcagag cgctacgacg acatggcagc cgctatgaag 180
gctgtcactg agggtgacat tgaactgtcg aacgaggagc gcaacctgct ctcggtggct 240
tacaagaacg tggtgggtgc ccgtcgctca tcctggaggg tcgtctccag catcgagcag 300
aagatggagg gtagcgacaa aaagcagcaa atggtcaagg aatatcggga aaagatcgag 360
aaggagctga aggagatctg caatgacgta ctggttcttc tggacaagta tctcatcccc 420
aaagcgaccc cggctgaaag cagagtcttc tatctgaaaa tgaaaggcga ttgctttcgc 480

-continued tacttagcag aggtggctgt gggagaggag aaaaactcta tcattggcaa ttcgcaggag 540
gcctacaagg atgcgtttga aat 563

<210> SEQ ID NO 47
<211> LENGTH: 348
<212> TYPE: DNA
<213> ORGANISM: Homo sapiens

<400> SEQUENCE: 47
atgccgatgt tcatcgtaaa caccaacgtg ccccgcgcct ccgtgccgga cgggttcctc 60
tccgagctca cccagcagct ggcgcaggcc accggcaagc ccccccagta catcgcggtg 120
cacgtggtcc cggaccagct catggccttc ggcggctcca gcgagccgtg cgcgctctgc 180
agcctgcaca gcatcggcaa gatcggcggc gcgcagaacc gctcctacag caagctgctg 240
tgcggcctgc tggccgagcg cctgcgcatc agcccggaca gggtctacat caactattac 300
gacatgaacg cggccaatgt gggctggaac aactccacct tcgcctag 348

<210> SEQ ID NO 48
<211> LENGTH: 1984
<212> TYPE: DNA
<213> ORGANISM: Homo sapiens

<400> SEQUENCE: 48
ggcacgaggg agagagaacc tggagcaggc cggctgccac cttctgggct cctggggccc 60
tgcccaccac aagcgctgag atgcgtctgg agagccagag ggcctgcctg aaggaatcac 120
ctgagcctgt ccgtccacca ggagtgggga gatgccccca tccagtcctg gaggacccgc 180
tgctcctgct gctcccgggg atggagcaag gccaaggctg cgggaggctg ggagccctgc 240
cctgcccatc cctcctgcac cagcgctgtc cctgcacatc ttggcagggg cacgattccg 300
gatctcattg ccacgcgccc ccgacgaccg cccgacgtgc attcccgatt ccttttggtt 360
ccaagtccaa tatggcaact ctaaaggatc agctgattta taatcttcta aaggaagaac 420
agacccccca gaataagatt acagttgttg ggttggtgc tgttggcatg gcctgtgcca 480
tcagtatctt aatgaaggac ttggcagatg aacttgctct tgttgatgtc atcgaagaca 540
aattgaaggg agagatgatg gatctccaac atggcagcct tttccttaga acaccaaaga 600
ttgtctctgg caaagactat aatgtaactg caaactccaa gctggtcatt atcacggctg 660
gggcacgtca gcaagaggga gaaagccgtc ttaatttggt ccagcgtaac gtgaacatct 720
ttaaattcat cattcctaat gttgtaaaat acagcccgaa ctgcaagttg cttattgttt 780
caaatccagt ggatatcttg acctacgtgg cttggaagat aagtggtttt cccaaaaacc 840
gtgttattgg aagtggttgc aatctggatt cagcccgatt ccgttacctg atgggggaaa 900
ggctgggagt tcacccatta agctgtcatg ggtgggtcct tggggaacat ggagattcca 960
gtgtgcctgt atggagtgga atgaatgttg ctggtgtctc tctgaagact ctgcacccag 1020
atttagggac tgataaagat aaggaacagt ggaaagaggt tcacaagcag gtggttgaga 1080
gtgcttatga ggtgatcaaa ctcaaaggct acacatcctg ggctattgga ctctctgtag 1140
cagatttggc agagagtata atgaagaatc ttaggcgggt gcacccagtt tccaccatga 1200
ttaagggtct ttacggaata aaggatgatg tcttccttag tgttccttgc attttgggac 1260
agaatggaat ctcagacctt gtgaaggtga ctctgacttc tgaggaagag gcccgtttga 1320
agaagagtgc agatacactt tgggggatcc aaaaggagct gcaattttaa agtcttctga 1380
tgtcatatca tttcactgtc taggctacaa caggattcta ggtggaggtt gtgcatgttg 1440

-continued

```
tcctttttat ctgatctgtg attaaagcag taatatttta agatggactg ggaaaaacat   1500

caactcctga agttagaaat aagaatggtt tgtaaaatcc acagctatat cctgatgctg   1560

gatggtatta atcttgtgta gtcttcaact ggttagtgtg aaatagttct gccacctctg   1620

acgcaccact gccaatgctg tacgtactgc atttgcccct tgagccaggt ggatgtttac   1680

cgtgtgttat ataacttcct ggctccttca ctgaacatgc ctagtccaac atttttttccc   1740

agtgagtcac atcctgggat ccagtgtata aatccaatat catgtcttgt gcataattct   1800

tccaaaggat cttattttgt gaactatatc agtagtgtac attaccatat aatgtaaaaa   1860

gatctacata caaacaatgc aaccaactat ccaagtgtta taccaactaa aaccccccaat   1920

aaaccttgaa cagtgaaaaa aaaaaaaaaa aaaaaaaaaa aaaaaaaaaa aaaaaaaaaa   1980

aaaa                                                                1984
```

<210> SEQ ID NO 49
<211> LENGTH: 570
<212> TYPE: DNA
<213> ORGANISM: Homo sapiens

<400> SEQUENCE: 49

```
atggcttcca aaagagctct ggtcatcctg gctaaaggag cagaggaaat ggagacggtc     60

atccctgtag atgtcatgag gcgagctggg attaaggtca ccgttgcagg cctggctgga    120

aaagacccag tacagtgtag ccgtgatgtg gtcatttgtc ctgatgccag ccttgaagat    180

gcaaaaaaag agggaccata tgatgtggtg gttctaccag gaggtaatct gggcgcacag    240

aatttatctg agtctgctgc tgtgaaggag atactgaagg agcaggaaaa ccggaagggc    300

ctgatagccg ccatctgtgc aggtcctact gctctgttgg ctcatgaaat aggttttgga    360

agtaaagtta caacacaccc tcttgctaaa gacaaaatga tgaatggagg tcattacacc    420

tactctgaga atcgtgtgga aaaagacggc ctgattctta caagccgggg gcctgggacc    480

agcttcgagt ttgcgcttgc aattgttgaa gccctgaatg gcaaggaggt ggcggctcaa    540

gtgaaggctc cacttgttct taaagactag                                     570
```

<210> SEQ ID NO 50
<211> LENGTH: 1014
<212> TYPE: DNA
<213> ORGANISM: Homo sapiens

<400> SEQUENCE: 50

```
atgtcgagct cacccgtgaa gcgtcagagg atggagtccg cgctggacca gctcaagcag     60

ttcaccaccg tggtggccga cacgggcgac ttccacgcca tcgacgagta caagccccag    120

gatgctacca ccaacccgtc cctgatcctg gccgcagcac agatgcccgc ttaccaggag    180

ctggtggagg aggcgattgc ctatggccgg aagctgggcg ggtcacaaga ggaccagatt    240

aaaaatgcta ttgataaact tttgtgttg tttggagcag aaatactaaa gaagattccg    300

ggccgagtat ccacagaagt agacgcaagg ctctcctttg ataaagatgc gatggtggcc    360

agagccaggc ggctcatcga gctctacaag gaagctggga tcagcaagga ccgaattctt    420

ataaagctgt catcaacctg ggaaggaatt caggctggaa aggagctcga ggagcagcac    480

ggcatccact gcaacatgac gttactcttc tccttcgccc aggctgtggc ctgtgccgag    540

gcgggtgtga ccctcatctc ccatttgtt gggcgcatcc ttgattggca tgtggcaaac    600

accgacaaga aatcctatga gcccctggaa gaccctgggg taaagagtgt cactaaaatc    660

tacaactact acaagaagtt tagctacaaa accattgtca tgggcgcctc cttccgcaac    720
```

-continued acgggcgaga tcaaagcact ggccggctgt gacttcctca ccatctcacc caagctcctg 780
ggagagctgc tgcaggacaa cgccaagctg gtgcctgtgc tctcagccaa ggcggcccaa 840
gccagtgacc tggaaaaaat ccacctggat gagaagtctt tccgttggtt gcacaacgag 900
gaccagatgg ctgtggagaa gctctctgac gggatccgca agtttgccgc tgatgcagtg 960
aagctggagc ggatgctgac agaacgaatg ttcaatgcag agaatggaaa gtag 1014

<210> SEQ ID NO 51
<211> LENGTH: 1836
<212> TYPE: DNA
<213> ORGANISM: Homo sapiens

<400> SEQUENCE: 51
atgcccgaga tagtggatac ctgttcgttg gcctctccgg cttccgtctg ccggaccaag 60
cacctgcacc tgcgctgcag cgtcgacttt actcgccgga cgctgaccgg gactgctgct 120
ctcacggtcc agtctcagga ggacaatctg cgcagcctgg ttttggatac aaaggacctt 180
acaatagaaa aagtagtgat caatggacaa gaagtcaaat atgctcttgg agaaagacaa 240
agttacaagg gatcgccaat ggaaatctct cttcctatcg ctttgagcaa aaatcaagaa 300
attgttatag aaatttcttt tgagacctct ccaaaatctt ctgctctcca gtggctcact 360
cctgaacaga cttctgggaa ggaacaccca tatctcttta gtcagtgcca ggccatccac 420
tgcagagcaa tccttccttg tcaggacact ccttctgtga aattaaccta tactgcagag 480
gtgtctgtcc ctaaagaact ggtggcactt atgagtgcta ttcgtgatgg agaaacacct 540
gacccagaag acccaagcag gaaaatatac aaattcatcc aaaaagttcc aatacctgc 600 tacctgattg ctttagttgt tggagcttta gaaagcaggc aaattggccc aagaactttg 660
gtgtggtctg agaaagagca ggtggaaaag tctgcttatg agttttctga gactgaatct 720
atgcttaaaa tagcagaaga tctgggagga ccgtatgtat ggggacagta tgacctattg 780
gtcctgccac catccttccc ttatggtggc atggagaatc cttgccttac ttttgtaact 840
cctactctac tggcaggcga caagtcactc tccaatgtca ttgcacatga aatatctcat 900
agctggacag ggaatctagt gaccaacaaa acttgggatc acttttggtt aaatgaggga 960
catactgtgt acttggaacg ccacatttgc ggacgattgt ttggtgaaaa gttcagacat 1020
tttaatgctc tgggaggatg gggagaacta cagaattcgg taaagacatt tggggagaca 1080
catcctttca ccaaacttgt ggttgatctg acagatatag accctgatgt agcttattct 1140
tcagttccct atgagaaggg ctttgcttta ctttttttacc ttgaacaact gcttggagga 1200
ccagagattt tcctaggatt cttaaaagct tatgttgaga agttttccta taagagcata 1260
actactgatg actggaagga tttcctgtat tcctatttta aagataaggt tgatgttctc 1320
aatcaagttg attggaatgc ctggctctac tctcctggac tgcctcccat aaagcccaat 1380
tatgatatga ctctgacaaa tgcttgtatt gccttaagtc aaagatggat tactgccaaa 1440
gaagatgatt taaattcatt caatgccaca gacctgaagg atctctcttc tcatcaattg 1500
aatgagtttt tagcacagac gctccagagg gcacctcttc cattggggca cataaagcga 1560
atgcaagagg tgtacaactt caatgccatt aacaattctg aaatacgatt cagatggctg 1620
cggctctgca ttcaatccaa gtgggaggac gcaattcctt tggcgctaaa gatggcaact 1680
gaacaaggaa gaatgaagtt tacccggccc ttattcaagg atcttgctgc ctttgacaaa 1740
tcccatgatc aagctgtccg aacctaccaa gagcacaaag caagcatgca tcccgtgact 1800
gcaatgctgg tggggaaaga cttaaaagtg gattaa 1836

-continued

<210> SEQ ID NO 52
<211> LENGTH: 429
<212> TYPE: DNA
<213> ORGANISM: Homo sapiens

<400> SEQUENCE: 52
atggccacca agatcgacaa agaggcttgc cgggcggcgt acaacctggt gcgcgacgac 60
ggctcggccg tcatctgggt gacttttaaa tatgacggct ccaccatcgt ccccggcgag 120
cagggagcgg agtaccagca cttcatccag cagtgcacag atgacgtccg gttgtttgcc 180
ttcgtgcgct tcaccaccgg ggatgccatg agcaagaggt ccaagtttgc cctcatcacg 240
tggatcggtg agaacgtcag cgggctgcag cgcgccaaaa ccgggacgga caagaccctg 300
gtgaaggagg tcgtacagaa tttcgctaag gagtttgtga tcagtgatcg gaaggagctg 360
gaggaagatt tcatcaagag cgagctgaag aaggcggggg gagccaatta cgacgcccag 420
acggagtaa 429

<210> SEQ ID NO 53
<211> LENGTH: 870
<212> TYPE: DNA
<213> ORGANISM: Homo sapiens

<400> SEQUENCE: 53
atggagaacg gatacaccta tgaagattat aagaacactg cagaatggct tctgtctcat 60
actaagcacc gacctcaagt tgcaataatc tgtggttctg gattaggagg tctgactgat 120
aaattaactc aggcccagat ctttgactac agtgaaatcc ccaactttcc tcgaagtaca 180
gtgccaggtc atgctggccg actggtgttt gggttcctga atggcagggc ctgtgtgatg 240
atgcagggca ggttccacat gtatgaaggg tacccactct ggaaggtgac attcccagtg 300
agggttttcc accttctggg tgtggacacc ctggtagtca ccaatgcagc aggagggctg 360
aaccccaagt ttgaggttgg agatatcatg ctgatccgtg accatatcaa cctacctggt 420
ttcagtggtc agaaccctct cagagggccc aatgatgaaa ggtttggaga tcgtttccct 480
gccatgtctg atgcctacga ccggactatg aggcagaggg ctctcagtac ctggaaacaa 540
atgggggagc aacgtgagct acaggaaggc acctatgtga tggtggcagg ccccagcttt 600
gagactgtgg cagaatgtcg tgtgctgcag aagctgggag cagacgctgt tggcatgagt 660
acagtaccag aagttatcgt tgcacggcac tgtggacttc gagtctttgg cttctcactc 720
atcactaaca aggtcatcat ggattatgaa agcctggaga aggccaacca tgaagaagtc 780
ttagcagctg gcaaacaagc tgcacagaaa ttggaacagt ttgtctccat tcttatggcc 840
agcattccac tccctgacaa agccagttga 870

<210> SEQ ID NO 54
<211> LENGTH: 372
<212> TYPE: DNA
<213> ORGANISM: Homo sapiens

<400> SEQUENCE: 54
atggcccgct atgaggaggt gagcgtgtcc ggcttcgagg agttccaccg ggccgtggaa 60
cagcacaatg gcaagaccat tttcgcctac tttacgggtt ctaaggacgc cggggggaaa 120
agctggtgcc ccgactgcgt gcaggctgaa ccagtcgtac gagaggggct gaagcacatt 180
agtgaaggat gtgtgttcat ctactgccaa gtaggagaaa agccttattg gaaagatcca 240
aataatgact tcagaaaaaa cttgaaagta acagcagtgc ctacactact taagtatgga 300

-continued

```
acacctcaaa aactggtaga atctgagtgt cttcaggcca acctggtgga aatgttgttc    360

tctgaagatt aa                                                        372
```

<210> SEQ ID NO 55
<211> LENGTH: 2539
<212> TYPE: DNA
<213> ORGANISM: Homo sapiens

<400> SEQUENCE: 55

```
cgggacgacg ccccctcctg cggcgtggac tccgtcagtg gcccaccaag aaggaggagg     60

aatatggaat ccaaggggc cagttcctgc cgtctgctct tctgcctctt gatctccgcc     120

accgtcttca ggccaggcct tggatggtat actgtaaatt cagcatatgg agataccatt    180

atcatacctt gccgacttga cgtacctcag aatctcatgt ttggcaaatg gaaatatgaa    240

aagcccgatg gctccccagt atttattgcc ttcagatcct ctacaaagaa aagtgtgcag    300

tacgacgatg taccagaata caaagacaga ttgaacctct cagaaaacta cactttgtct    360

atcagtaatg caaggatcag tgatgaaaag agatttgtgt gcatgctagt aactgaggac    420

aacgtgtttg aggcacctac aatagtcaag gtgttcaagc aaccatctaa acctgaaatt    480

gtaagcaaag cactgtttct cgaaacagag cagctaaaaa agttgggtga ctgcatttca    540

gaagacagtt atccagatgg caatatcaca tggtacagga atggaaaagt gctacatccc    600

cttgaaggag cggtggtcat aatttttaaa aaggaaatgg acccagtgac tcagctctat    660

accatgactt ccaccctgga gtacaagaca accaaggctg acatacaaat gccattcacc    720

tgctcggtga catattatgg accatctggc cagaaaacaa ttcattctga acaggcagta    780

tttgatattt actatcctac agagcaggtg acaatacaag tgctgccacc aaaaaatgcc    840

atcaaagaag ggataacat cactcttaaa tgcttaggga atggcaaccc tcccccagag     900

gaatttttgt tttacttacc aggacagccc gaaggaataa gaagctcaaa tacttacaca    960

ctgatggatg tgaggcgcaa tgcaacagga gactacaagt gttccctgat agacaaaaaa   1020

agcatgattg cttcaacagc catcacagtt cactatttgg atttgtcctt aaacccaagt   1080

ggagaagtga ctagacagat tggtgatgcc ctacccgtgt catgcacaat atctgctagc   1140

aggaatgcaa ctgtggtatg gatgaaagat aacatcaggc ttcgatctag cccgtcattt   1200

tctagtcttc attatcagga tgctggaaac tatgtctgcg aaactgctct gcaggaggtt   1260

gaaggactaa agaaaagaga gtcattgact ctcattgtag aaggcaaacc tcaaataaaa   1320

atgacaaaga aaactgatcc cagtggacta tctaaaacaa taatctgcca tgtggaaggt   1380

tttccaaagc cagccattca gtggacaatt actggcagtg gaagcgtcat aaaccaaaca   1440

gaggaatctc cttatattaa tggcaggtat tatagtaaaa ttatcatttc ccctgaagag   1500

aatgttacat taacttgcac agcagaaaac caactggaga gaacagtaaa ctccttgaat   1560

gtctctgcta taagtattcc agaacacgat gaggcagacg agataagtga tgaaaacaga   1620

gaaaaggtga atgaccaggc aaaactaatt gtgggaatcg ttgttggtct cctccttgct   1680

gcccttgttg ctggtgtcgt ctactggctg tacatgaaga agtcaaagac tgcatcaaaa   1740

catgtaaaca aggacctcgg taatatggaa gaaaacaaaa agttagaaga aaacaatcac   1800

aaaactgaag cctaagagag aaactgtcct agttgtccag agataaaaat catatagacc   1860

aattgaagca tgaacgtgga ttgtatttaa gacataaaca aagacattga cagcaattca   1920

tggttcaagt attaagcagt tcattctacc aagctgtcac aggttttcag agaattatct   1980

caagtaaaac aaatgaaatt taattacaaa caataagaac aagttttggc agccatgata   2040
```

-continued

```
ataggtcata tgttgtgttt ggttcaattt tttttccgta aatgtctgca ctgaggattt   2100

ctttttggtt tgccttttat gtaaattttt tacgtagcta tttttataca ctgtaagctt   2160

tgttctggga gttgctgtta atctgatgta taatgtaatg tttttatttc aattgtttat   2220

atggataatc tgagcaggta catttctgat tctgattgct atcagcaatg ccccaaactt   2280

tctcataagc acctaaaacc caaaggtggc agcttgtgaa gattggggac actcatattg   2340

ccctaattaa aaactgtgat ttttatcaca agggagggga ggccgagagt cagactgata   2400

gacaccatag gagccgactc tttgatatgc caccagcgaa ctctcagaaa taaatcacag   2460

atgcatatag acacacatac ataatggtac tcccaaactg acaattttac ctattctgaa   2520

aaagacataa aacagaatt                                                2539
```

<210> SEQ ID NO 56
<211> LENGTH: 1262
<212> TYPE: DNA
<213> ORGANISM: Homo sapiens

<400> SEQUENCE: 56

```
cccggctggg acttccctaa cagcatggcc cctaaacgcc agtctccact cccgcctcaa     60

aagaagaaac caagaccacc tcctgctctg ggaccggagg agacatcggc ctctgcaggc    120

ttgccgaaga agggagaaaa agaacagcaa gaagcgattg aacacattga tgaagtacaa    180

aatgaaatag acagacttaa tgaacaagcc agtgaggaga ttttgaaagt agaacagaaa    240

tataacaaac tccgccaacc atttttttcag aagaggtcag aattgatcgc caaaatccca    300

aatttttggg taacaacatt tgtcaaccat ccacaagtgt ctgcactgct tggggaggaa    360

gatgaagagg cactgcatta tttgaccaga gttgaagtga cagaatttga agatattaaa    420

tcaggttaca gaatagattt ttattttgat gaaaatcctt actttgaaaa taaagttctc    480

tccaaagaat ttcatctgaa tgagagtggt gatccatctt cgaagtccac cgaaatcaaa    540

tggaaatctg gaaaggattt gacgaaacgt tcgagtcaaa cgcagaataa agccagcagg    600

aagaggcagc atgaggaacc agagagcttc tttacctggt ttactgacca ttctgatgca    660

ggtgctgatg agttaggaga ggtcatcaaa gatgatattt ggccaaaccc attacagtac    720

tacttggttc ccgatatgga tgatgaagaa ggagaaggag aagaagatga tgatgatgat    780

gaagaggagg aaggattaga agatattgac gaagaagggg atgaggatga aggtgaagaa    840

gatgaagatg atgatgaagg ggaggaagga gaggaggatg aaggagaaga tgactaaata    900

gaacactgat ggattccaac cttccttttt ttaaattttc tccagtccct gggagcaagt    960

tgcagtcttt tttttttttt ttttttttt ccctcttgtg ctcagtcgcc ctgttcttga   1020

ggtctctttt ctctactcca tggttctcaa tttatttggg gggaaatacc ttgagcagaa   1080

tacaatggga aaagagtctc taccccttc tgttcgaagt tcatttttat cccttcctgt   1140

ctgaacaaaa actgtatgga atcaacacca ccgagctctg tgggaaaaaa gaaaaacctg   1200

ctccctttgc tctgctggaa gctggagggt gctaggcccc tgtgtagtag tgtatagaat   1260

tc                                                                  1262
```

<210> SEQ ID NO 57
<211> LENGTH: 564
<212> TYPE: DNA
<213> ORGANISM: Homo sapiens -continued

<400> SEQUENCE: 57
atgccggtgg acctcagcaa gtggtccggg cccttgagcc tgcaagaagt ggacgagcag 60
ccgcagcacc cgctgcatgt cacctacgcc ggggcggcgg tggacgagct gggcaaagtg 120
ctgacgccca cccaggttaa gaatagaccc accagcattt cgtgggatgg tcttgattca 180
gggaagctct acaccttggt cctgacagac ccggatgctc ccagcaggaa ggatcccaaa 240
tacagagaat ggcatcattt cctggtggtc aacatgaagg gcaatgacat cagcagtggc 300
acagtcctct ccgattatgt gggctcgggg cctcccaagg gcacaggcct ccaccgctat 360
gtctggctgg tttacgagca ggacaggccg ctaaagtgtg acgagcccat cctcagcaac 420
cgatctggag accaccgtgg caaattcaag gtggcgtcct tccgtaaaaa gtatgagctc 480
agggccccgg tggctggcac gtgttaccag gccgagtggg atgactatgt gcccaaactg 540
tacgagcagc tgtctgggaa gtag 564

<210> SEQ ID NO 58
<211> LENGTH: 945
<212> TYPE: DNA
<213> ORGANISM: Homo sapiens

<400> SEQUENCE: 58
atgtcggctg cagaggcggg gggtgttttc cacagagcca ggggcaggac cctggccgcg 60
tttcccgcag aaaaggaaag cgaatggaaa ggcccattct acttcatcct gggcgcagac 120
ccacagtttg ggctgatcaa ggcctggtcc actggggact gtgacaatgg cggtgacgaa 180
tgggaacagg agatccgtct aactgagcaa gccgtccagg ccatcaacaa gctgaacccc 240
aaacccaaat tcttcgttct gtgcggcgac ctcatccacg ccatgccagg gaagccgtgg 300
cggacggagc agacggagga cctgaagcga gtgcttaggg cagtggacag ggccatccca 360
ctggtccttg tcagcggcaa ccatgacatt ggcaacaccc ccacggccga gaccgtcgag 420
gagttctgcc ggacttgggg atatgactac ttcagcttct gggtcggggg cgtcctgttc 480
ctggtcctca actcccagtt ctacgagaac ccctccaaat gccccagcct gaagcaggct 540
caggaccagt ggctggacga gcagctgagc atcgcgaggc agcggcactg ccagcatgcc 600
atcgtcttcc agcacatccc gctgttcctg gagagcatcg acgaggacga cgactactac 660
ttcaacctca gcaagtccac tcggaagaag ttggcagaca agttcatcca cgcaggtgtc 720
agagtcgtgt tctcaggcca ctaccacagg aatgccgggg gtacctacca gaacctcgac 780
atggtggtgt catctgccat tggatgccag ctgggcagag acccccacgg gctccgagtc 840
gtggtggtca ccgccgagaa aattgttcac cgatactaca gtctagatga gctgagtgag 900
aaaggaatag aagacgatct catggatttg atcaagaaaa aatga 945

<210> SEQ ID NO 59
<211> LENGTH: 1523
<212> TYPE: DNA
<213> ORGANISM: Homo sapiens

<400> SEQUENCE: 59
ggcacgaggg attctccggg atattaccgg agacggagtg ttttattatt agcctttctt 60
aggtggacat ttccatttga attacaagtc ctttaggctg ggcgtggtgc atggctgtaa 120
tctcagcacc ttgggaggct gaggcaggaa gatcacttga ggccaggcgt tggagagcag 180
cctgggcaag gtggcaagaa ccttgtctct acaaaaaaaa aagcgtctgc catcatggat 240
gttctcgcag aagcaaatgg cacctttgcc ttaaaccttt tgaaaacgct gggtaaagac 300

-continued aactcgaaga atgtgttttt ctcacccatg agcatgtcct gtgccctggc catggtctac 360
atgggggcaa agggaaacac cgctgcacag atggcccaga tactttcttt caataaaagt 420
ggcggtggtg gagacatcca ccagggcttc cagtctcttc tcaccgaagt gaacaagact 480
ggcacgcagt acttgcttag ggtggccaac aggctctttg gggaaaagtc ttgtgatttc 540
ctctcatctt ttagagattc ctgccaaaaa ttctaccaag cagagatgga ggagcttgac 600
tttatcagcg ccgtagagaa gtccagaaaa cacataaaca cctgggtagc tgaaaagaca 660
gaaggtaaaa ttgcggagtt gctctctccg ggctcagtgg atccattgac aaggctggtt 720
ctggtgaatg ctgtctattt cagaggaaac tgggatgaac agtttgacaa ggagaacacc 780
gaggagagac tgtttaaagt cagcaagaat gaggagaaac ctgtgcaaat gatgtttaag 840
caatctactt ttaagaagac ctatatagga gaaatattta cccaaatctt ggtgcttcca 900
tatgttggca aggaactgaa tatgatcatc atgcttccgg acgagaccac tgacttgaga 960
acggtggaga aagaactcac ttacgagaag ttcgtagaat ggacgaggct ggacatgatg 1020
gatgaagagg aggtggaagt gtccctcccg cggtttaaac tagaggaaag ctacgacatg 1080
gagagtgtcc tgcgcaacct gggcatgact gatgccttcg agctgggcaa ggcagacttc 1140
tctggaatgt cccagacaga cctgtctctg tccaaggtcg tgcacaagtc ttttgtggag 1200
gtcaatgagg aaggcacgga ggctgcagcc gccacagctg ccatcatgat gatgcggtgt 1260
gccagattcg tcccccgctt ctgcgccgac caccccttcc ttttcttcat ccagcacagc 1320
aagaccaacg ggattctctt ctgcggccgc ttttcctctc cgtgaggaca gggcagtctt 1380
ggtgtgcagc ccctctcctc tctgtcccct gacactccac agtgtgcctg caacccaagt 1440
ggccttatcc gtgcagtggt ggcagttcag aaataaaggg cccatttgtg ggatgccgca 1500
ttcaaaaaaa aaaaaaaaaa aaa 1523

<210> SEQ ID NO 60
<211> LENGTH: 1755
<212> TYPE: DNA
<213> ORGANISM: Homo sapiens

<400> SEQUENCE: 60
acggagatct cgccggcttt acgttcacct cggtgtctgc agcaccctcc gcttcctctc 60
ctaggcgacg agacccagtg gctagaagtt caccatgtct attctcaaga tccatgccag 120
ggagatcttt gactctcgcg ggaatcccac tgttgaggtt gatctcttca cctcaaaagg 180
tctcttcaga gctgctgtgc ccagtggtgc ttcaactggt atctatgagg ccctagagct 240
ccgggacaat gataagactc gctatatggg gaagggtgtc tcaaaggctg ttgagcacat 300
caataaaact attgcgcctg ccctggttag caagaaactg aacgtcacag aacaagagaa 360
gattgacaaa ctgatgatcg agatggatgg aacagaaaat aaatctaagt ttggtgcgaa 420
cgccattctg gggggtgtcc ttgccgtctg caaagctggt gccgttgaga agggggtccc 480
cctgtaccgc cacatcgctg acttggctgg caactctgaa gtcatcctgc cagtcccggc 540
gttcaatgtc atcaatggcg gttctcatgc tggcaacaag ctggccatgc aggagttcat 600
gatcctccca gtcggtgcag caaacttcag ggaagccatg cgcattggag cagaggttta 660
ccacaacctg aagaatgtca tcaaggagaa atatgggaaa gatgccacca atgtgggga 720 tgaaggcggg tttgctccca acatcctgga gaataaagaa ggcctggagc tgctgaagac 780
tgctattggg aaagctggct acactgataa ggtggtcatc ggcatggacg tagcggcctc 840
cgagttcttc aggtctggga agtatgacct ggacttcaag tctcccgatg accccagcag 900

-continued

```
gtacatctcg cctgaccagc tggctgacct gtacaagtcc ttcatcaagg actacccagt    960

ggtgtctatc gaagatccct ttgaccagga tgactgggga gcttggcaga agttcacagc   1020

cagtgcagga atccaggtag tgggggatga tctcacagtg accaacccaa agaggatcgc   1080

caaggccgtg aacgagaagt cctgcaactg cctcctgctc aaagtcaacc agattggctc   1140

cgtgaccgag tctcttcagg cgtgcaagct ggcccaggcc aatggttggg gcgtcatggt   1200

gtctcatcgt tcgggggaga ctgaagatac cttcatcgct gacctggttg tggggctgtg   1260

cactgggcag atcaagactg gtgccccttg ccgatctgag cgcttggcca agtacaacca   1320

gctcctcaga attgaagagg agctgggcag caaggctaag tttgccggca ggaacttcag   1380

aaacccccttg gccaagtaag ctgtgggcag gcaagccttc ggtcacctgt tggctacaca   1440

gacccctccc ctcgtgtcag ctcaggcagc tcgaggcccc cgaccaacac ttgcaggggt   1500

ccctgctagt tagcgcccca ccgccgtgga gttcgtaccg cttccttaga acttctacag   1560

aagccaagct ccctggagcc ctgttggcag ctctagcttt tgcagtcgtg taatgggccc   1620

aagtcattgt ttttctcgcc tcactttcca ccaagtgtct agagtcatgt gagcctcgtg   1680

tcatctccgg ggtggccaca ggctagatcc ccggtggttt tgtgctcaaa ataaaaagcc   1740

tcagtgaccc atgag                                                    1755
```

<210> SEQ ID NO 61
<211> LENGTH: 245
<212> TYPE: PRT
<213> ORGANISM: Mus musculus

<400> SEQUENCE: 61

```
Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Pro
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205
```

-continued

```
Glu Ser Tyr Lys Asp Ser Thr Leu Ile Met Gln Leu Leu Arg Asp Asn
    210                215                220

Leu Thr Leu Trp Thr Ser Asp Thr Gln Gly Asp Glu Ala Glu Ala Gly
225                230                235                240

Glu Gly Gly Glu Asn
                245


<210> SEQ ID NO 62
<211> LENGTH: 115
<212> TYPE: PRT
<213> ORGANISM: Mus musculus

<400> SEQUENCE: 62

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Ser Gly Thr Asn Asp Pro Cys Ala Leu Cys Ser Leu His Ser
    50                  55                  60

Ile Gly Lys Ile Gly Gly Ala Gln Asn Arg Asn Tyr Ser Lys Leu Leu
65                  70                  75                  80

Cys Gly Leu Leu Ser Asp Arg Leu His Ile Ser Pro Asp Arg Val Tyr
                85                  90                  95

Ile Asn Tyr Tyr Asp Met Asn Ala Ala Asn Val Gly Trp Asn Gly Ser
            100                 105                 110

Thr Phe Ala
        115


<210> SEQ ID NO 63
<211> LENGTH: 245
<212> TYPE: PRT
<213> ORGANISM: Rattus norvegicus

<400> SEQUENCE: 63

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Pro
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160
```

-continued

```
Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245


<210> SEQ ID NO 64
<211> LENGTH: 115
<212> TYPE: PRT
<213> ORGANISM: Rattus norvegicus

<400> SEQUENCE: 64

Met Pro Met Phe Ile Val Asn Thr Asn Val Pro Arg Ala Ser Val Pro
1               5                   10                  15

Glu Gly Phe Leu Ser Glu Leu Thr Gln Gln Leu Ala Gln Ala Thr Gly
            20                  25                  30

Lys Pro Ala Gln Tyr Ile Ala Val His Val Val Pro Asp Gln Leu Met
        35                  40                  45

Thr Phe Arg Gly Thr Ser Asp Pro Cys Ala Leu Cys Ser Leu His Ser
    50                  55                  60

Ile Gly Lys Ile Gly Gly Ala Gln Asn Arg Asn Tyr Ser Lys Leu Leu
65                  70                  75                  80

Cys Gly Leu Leu Ser Asp Arg Leu His Ile Ser Pro Asp Arg Val Tyr
                85                  90                  95

Ile Asn Tyr Tyr Asp Met Asn Ala Ala Asn Val Gly Trp Asn Gly Ser
            100                 105                 110

Thr Phe Ala
        115


<210> SEQ ID NO 65
<211> LENGTH: 738
<212> TYPE: DNA
<213> ORGANISM: Mus musculus

<400> SEQUENCE: 65

atggataaaa atgagctggt gcagaaggcc aagctggccg agcaggcaga gcgatatgat      60

gacatggcag cctgcatgaa gtctgtcact gagcagggag ctgagctgtc gaatgaggag     120

agaaaccttc tctctgttgc ttataaaaac gttgtaggag cccgtaggtc atcgtggagg     180

gtcgtctcaa gtattgagca gaagacggaa ggtgctgaga aaaagcagca gatggctcga     240

gaatacagag agaagatcga gacggagctg cgtgacatct gcaacgatgt actgtctctt     300

ttggaaaagt tcttgatccc caatgcttcg caaccagaaa gcaaagtctt ctatttgaaa     360

atgaagggtg actactaccg ttacttggcc gaggttgctg ctggtgatga caagaaagga     420

attgtggacc agtcacagca agcataccaa gaagcatttg aaatcagcaa aaaggagatg     480

cagccgacac accccatcag actgggtctg gccctcaact tctctgtgtt ctattacgag     540

atcctgaact ccccagagaa agcctgctct cttgcaaaaa cagctttcga tgaagccatt     600

gctgaacttg atacattaag tgaagagtcg tacaaagaca gcacgctaat aatgcagtta     660
```

-continued

```
ctgagagaca acttaacatt gtggacatcg gatacccaag gagatgaagc agaagcagga    720

gaaggagggg aaaattaa                                                  738


<210> SEQ ID NO 66
<211> LENGTH: 348
<212> TYPE: DNA
<213> ORGANISM: Mus musculus

<400> SEQUENCE: 66

atgcctatgt tcatcgtgaa caccaatgtt ccccgcgcct ccgtgccaga ggggtttctg     60

tcggagctca cccagcagct ggcgcaggcc accggcaagc ccgcacagta catcgcagtg    120

cacgtggtcc cggaccagct catgactttt agcggcacga acgatccctg cgccctctgc    180

agcctgcaca gcatcggcaa gatcggtggt gcccagaacc gcaactacag taagctgctg    240

tgtggcctgc tgtccgatcg cctgcacatc agcccggacc gggtctacat caactattac    300

gacatgaacg ctgccaacgt gggctggaac ggttccacct tcgcttga                 348


<210> SEQ ID NO 67
<211> LENGTH: 738
<212> TYPE: DNA
<213> ORGANISM: Rattus norvegicus

<400> SEQUENCE: 67

atggataaaa atgagctggt gcagaaggcc aagctggccg agcaggcaga gcgatacgat     60

gacatggcag cctgcatgaa gtctgtcact gagcaaggag ccgagctgtc taacgaggag    120

aggaaccttc tctctgttgc ttataaaaac gttgtaggag cccgtaggtc atcttggagg    180

gtcgtctcga gtattgagca gaagacggaa ggtgctgaga aaaagcagca gatggctcga    240

gaatacagag agaagatcga gacggagctg agggacatct gcaacgacgt actgtctctt    300

ttggaaaagt tcttgatccc caatgcttcg cagccagaaa gcaaagtctt ctatttgaaa    360

atgaagggtg actactaccg ctacttggct gaggttgctg ctggtgatga caagaaagga    420

attgtggacc agtcacagca agcataccaa gaagcatttg aaatcagcaa aaaggagatg    480

cagccgacac accccatcag actgggtctg gccctcaact tctctgtgtt ctactatgag    540

atcctgaact ccccagagaa agcctgctct cttgcaaaaa cagcttttga tgaagccatt    600

gctgaacttg atacattaag tgaagagtcg tacaaagaca gcacgctaat aatgcagtta    660

ctgagagaca acttgacatt gtggacatcg gatacccaag gagacgaagc agaagcggga    720

gaaggagggg aaaattaa                                                  738


<210> SEQ ID NO 68
<211> LENGTH: 348
<212> TYPE: DNA
<213> ORGANISM: Rattus norvegicus

<400> SEQUENCE: 68

atgcctatgt tcatcgtgaa caccaatgtt ccccgcgcct ccgtgccaga ggggtttctc     60

tccgagctca cccagcagct ggcgcaggcc accggcaagc cggcacagta catcgcagtg    120

cacgtggtcc cggaccagct catgactttt agaggcacga gcgacccctg cgccctctgc    180

agcctgcaca gcatcggcaa gatcggtggc gcccagaacc gcaactacag caagctgctg    240

tgcggcctgc tgtccgatcg cctgcacatc agcccggacc gggtctacat caactattac    300

gacatgaacg cagccaacgt gggctggaac ggttccacct tcgcttga                 348
```

-continued

<210> SEQ ID NO 69
<211> LENGTH: 20
<212> TYPE: DNA
<213> ORGANISM: Mus musculus

<400> SEQUENCE: 69
agcaggcaga gcgatatgat 20

<210> SEQ ID NO 70
<211> LENGTH: 20
<212> TYPE: DNA
<213> ORGANISM: Mus musculus

<400> SEQUENCE: 70
gagccatctg ctgctttttc 20

<210> SEQ ID NO 71
<211> LENGTH: 19
<212> TYPE: DNA
<213> ORGANISM: Mus musculus

<400> SEQUENCE: 71
gtgccagagg ggtttctgt 19

<210> SEQ ID NO 72
<211> LENGTH: 20
<212> TYPE: DNA
<213> ORGANISM: Mus musculus

<400> SEQUENCE: 72
aggccacaca gcagcttact 20

<210> SEQ ID NO 73
<211> LENGTH: 20
<212> TYPE: DNA
<213> ORGANISM: Rattus norvegicus

<400> SEQUENCE: 73
ttgagcagaa gacggaaggt 20

<210> SEQ ID NO 74
<211> LENGTH: 20
<212> TYPE: DNA
<213> ORGANISM: Rattus norvegicus

<400> SEQUENCE: 74
cctcagccaa gtagcggtag 20

<210> SEQ ID NO 75
<211> LENGTH: 20
<212> TYPE: DNA
<213> ORGANISM: Rattus norvegicus

<400> SEQUENCE: 75
gtgccagagg ggtttctctc 20

<210> SEQ ID NO 76
<211> LENGTH: 20
<212> TYPE: DNA
<213> ORGANISM: Rattus norvegicus

<400> SEQUENCE: 76
cagcagcttg ctgtagttgc 20